US007442783B2

(12) United States Patent
Carroll et al.

(10) Patent No.: US 7,442,783 B2
(45) Date of Patent: Oct. 28, 2008

(54) NATURAL IGM ANTIBODIES AND INHIBITORS THEREOF

(75) Inventors: Michael C. Carroll, Wellesley, MA (US); Francis D. Moore, Jr., Medfield, MA (US); Herbert B. Hechtman, Chestnut Hill, MA (US)

(73) Assignees: The CBR Institute for Biomedical Research, Inc., Boston, MA (US); President and Fellows of Harvard College, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 11/069,834

(22) Filed: Mar. 1, 2005

(65) Prior Publication Data

US 2005/0276811 A1 Dec. 15, 2005

Related U.S. Application Data

(60) Provisional application No. 60/588,648, filed on Jul. 16, 2004, provisional application No. 60/549,123, filed on Mar. 1, 2004.

(51) Int. Cl.
*C07H 21/02* (2006.01)
*C07H 21/04* (2006.01)
*C12N 15/00* (2006.01)
*C12N 5/02* (2006.01)
*A61K 38/00* (2006.01)

(52) U.S. Cl. .................... 536/23.1; 536/23.5; 530/324; 435/320.1; 435/325

(58) Field of Classification Search ............. 435/320.1, 435/325; 536/23.1, 23.5; 530/324

See application file for complete search history.

(56) References Cited

U.S. PATENT DOCUMENTS 6,753,314 B1 * 6/2004 Giot et al. .................... 514/12

FOREIGN PATENT DOCUMENTS

| | | | |
|---|---|---|---|
| WO | WO 00/42210 | | 7/2000 |
| WO | WO200175067 A2 | * | 10/2001 |
| WO | WO-01/93892 | | 12/2001 |
| WO | WO2003055982 | * | 7/2003 |

OTHER PUBLICATIONS

Guo et al., Protein tolerance to random amino acid change.Proc Natl Acad Sci U S A. Jun. 22, 2004;101(25):9205-10. Epub Jun. 14, 2004.*

Sryer, Biochemistry Third Edition W.H. Freeman and Company pp. 36-40.*

Veronese FM. Peptide and protein PEGylation: a review of problems and solutions. Biomaterials. Mar. 2001;22(5):405-17.*

Ahearn et al., "Disruption of the Cr2 locus results in a reduction in B-1a cells and in an impaired B cell response to T-dependent antigen," Immunity 4:251-262 (1996).

Arnold et al., "Development of B-1 Cells: Segregation of Phosphatidyl Choline-specific B Cells to the B-1 Population Occurs After Immunoglobulin Gene Expression," J. Exp. Med. 179:1585-1595 (1994).

Borodovsky et al., "Chemistry-based functional proteomics reveals novel members of the deubiquitinating enzyme family," Chem. Biol. 9:1149-1159 (2002).

Carroll, M.C., "The role of complement and complement receptors in induction and regulation of immunity," Ann. Rev. Immunol. 16:545-568 (1998).

Clarke, J., "B-1 Cell Development: Evidence for an Uncommityed Immunoglobulin (Ig)M+ B Cell Precursor in B-1 Cell Differentiation," Exp. Med. 187:1325-1334 (1998).

Epstein et al., "The collections in innate immunity," Immunol. 8:29-35 (1996).

Fearon et al., "The CD19/CR2/TAPA-1 complex of B lymphocytes: linking natural to acquired immunity," Annu. Rev. Immunol. 13:127-149 (1995).

Feeney, J., "Lack of N Regions in Fetal and Neonatal Mouse Immunoglobulin V-D-J Junctional Sequences," Exp. Med. 172:1377-1390 (1990).

Golomb et al., "Identification and Characterization of Nonmuscle Myosin II-C, a New Member of the Myosin II Family," J. Biol. Chem. 279:2800-2808 (2004).

Gu et al., "Sequence homologies, N sequence insertion and $J_h$ gene utilization in $V_HDJ_H$joining: implications for the joining mechanism and the ontogenetic timing of Lyl B cell and B-CLL progenitor generation," EMBO J 9:2133-2140 (1990).

Hardy et al., "Distinctive Development Origins and Specificities of Murine CD5+ B Cells," Immunol. Rev. 137:91-118 (1994).

Hayakawa et al., "Immunoglobulin-bearing B cells reconstitute and maintain the murine Ly-1 B cell lineage," Eur. J. Immunol. 16:1313-1316 (1986).

Herzenberg et al., "B-cell lineages exist in the mouse," Immunol. Today 14:79-83, discussion 88-90 (1993).

Kantor et al., "Origin of murine B cell lineages," Annu. Rev. Immunol. 11:501-538 (1993).

Kelley et al., "Xenopus Nonmuscle Myosin Heavy Chain Isoforms Have Different Subcellular Localizations and Enzymatic Activites," J. Cell Biol. 134:675-687 (1996).

Molina et al., "Markedly impaired humoral immune response in mice deficient in complement receptors 1 and 2," Proc. Natl. Acad. Sci. USA 93:3357-3361 (1996).

Muller-Eberhard, H.J., "Molecular organization and function of the complement system," Ann. Rev. Biochem. 57:321-347 (1988).

O'Keefe et al., "Hyperresponsive B cells in CD22-deficient mice," Science 274:798-801 (1996).

Reid et al., "Functional Activity of Natural Antibody is Altered in Cr2-Deficient Mice[1]," J. Immunol. 5433-5440 (2002).

Shinkai et al., "RAG-2-deficient mice lack mature lymphocytes owing to inability to initiate V(D)J rearrangement," Cell, 68:855-867 (1992).

(Continued)

*Primary Examiner*—Anne Marie Wehbe
*Assistant Examiner*—Maria Leavitt
(74) *Attorney, Agent, or Firm*—Foley Hoag LLP

(57) ABSTRACT

The invention provides natural IgM antibody inhibitors that may be used to treat various inflammatory diseases or disorders.

16 Claims, 33 Drawing Sheets

OTHER PUBLICATIONS

Shultz et al., "Mutations at the Murine Motheaten Locus Are within the Hematopoietic Cell Protein-Tyrosine Phosphatase (Hcph) Gene," Cell 73:1445-1454 (1993).

Vorup-Jensen et al., "Structure and allosteric regulation of the αXβ2 integrin I domain," PNAS USA 100:1873-1878 (2003).

Weiser et al., "Reperfusion Injury of Ischemic Skeletal Muscle Is Mediated by Natural Antibody and Complement," J. Exp. Med., 183:2343-2348 (1996).

Williams et al., "Intestinal reperfusion injury is mediated by IgM and complement," J. Appl. Physiol. 86:938-42 (1999).

Wortis, H.H., "Surface Markers, Heavy Chain Sequences and B Cell Lineages," Int. Rev. Immunol., 8:235-246 (1992).

Zhang et al., "Identification of a specific self-reactive IgM antibody that initiates intestinal ischemia/reperfusion injury," PNAS USA 101:3886-91 (2004).

Database EMBL "*Arabidopsis thaliana* unknown protein (At3g57990) mRNA, complete cds," XP-002343885; Database Accession No. AY122933.

Database EMBL "*Aspergillus nidulans* GFSC A4 chromosome I ANcontigl.116, whole genome shotgun sequence," XP-002343886; Database Accession No. AACD01000116.

Database EMBL "*Ruminococcus albus* xynC gene for xylanase C, hypothetical proteins, complete and partial cds," XP-002343887; Database Accession No. AB957589.

Austen et al., "Murine hindlimb reperfusion injury can be initiated by a self-reactive monoclonal IgM," Surgery, 136(2):401-406.

XP002462307; "*Xenopus laevis* cDNA clone Image:4889191, partial cds."; Sep. 18, 2003 (retrieved from EBI accession No. EMBL: BC057729 Database accession No. BC057729).

XP002462308; "*Homo sapiens* mRNA; cDNA DKFZp451J0218 (from clone DKFZp451J0218); complete cds" Jul. 10, 2002; (retrieved from EBI accession No. EMBL:AL832639).

XP002462309; "*Homo sapiens*, Similar to myosin, heavy polypeptide 9, non-muscle, clone Image: 5563109, mRNA partial cds"; Apr. 2, 2003; (retrieved from EBI accession No. EMBL:BC049849).

XP002462310; "*Oryctolagus cuniculus* mRNA for myosin heavy chain, partial cds"; May 10, 2001 (retrieved from EBI accession No. EMBL:D63694).

XP002462311; "*Bos taurus* nonmuscle myosin heavy chain B mRNA fragment II, partial cds"; Oct. 6, 1995; (retrieved from EBI acccession No. EMBL:U15693).

EP 05 72 3931 Search Report dated Dec. 13, 2007.

* cited by examiner

FIGURE 1A

```
<---------------------------------- FWR1 -------------------------------------
CAG GTT CAG CTG CAG CAG TCT GGG GCT GAG CTG GTG AAG CCT GGG GCC TCA GTG AAG ATT TCC

---------------------------------> ________CDR1_______ <------------------------
TGC AAA GCT TCT GGC TAC GCA TTC AGT AGC TAC TGG ATG AAC TGG GTG AAG CAG AGG CCT GGA

---FWR2------------------> ____________________ CDR2_________________________
AAG GGT CTT GAG TGG ATT GGA CAG ATT TAT CCT GGA GAT GGT GAT ACT AAC TAC AAC GGA

_______________ <---------------------------- FWR3 ----------------------------
AAG TTC AAG GGC AAG GCC ACA CTG ACT GCA GAC AAA TCC TCC AGC ACA GCC TAC ATG CAG CTC

--------------------------------------------------------> _________D ________
AGC AGC CTG ACC TCT GAG GAC TCT GCG GTC TAT TTC TGT GCA AGA GAA GAT TAC TAC GGT AGT

<------------------------- J --------------------------------->
GAC TGG TAC TTC GAT GTC TGG GGC ACA GGG ACC ACG GTC ACC GTC TCC TCA GGT AAG CTG GCT

                                *
TTT TTC TTT CTG CAC ATT CCA TTC TGA (SEQ ID NO:1)
```

FIGURE 1B

--------------FWR1-----------> <CDR1> <----FWR2---->
QVQLQQSGAELVKPGASVKISCKASGYAFS SYWMN WVKQRPGKGLEWIG

<----CDR2-------> <-------------FWR3------------->
QIYPGDGDTNYNGKFKG KATLTADKSSSTAYMQLSSLTSEDSAVYFCAR

<-D--> <-------J------->
EDYYGS DWYFDVWGTGTTVTVSSGKLAFFFLHIPF*(SEQ ID NO:2)

FIGURE 2A

```
<------------------------------------- FWR1------------------------------------------>
ATT GTG ATG ACC CAG TCT GCT GCT TCC TTA GCT GTA TCT CTG GGG CAG AGG GCC ACC ATC TCA TAC

 __________________________ CDR1 ___________________________ <------------------------
AGG GCC AGC AAA AGT GTC AGT ACA TCT GGC TAT AGT TAT ATG CAC TGG AAC CAA CAG AAA CCA GGA

FWR2-------------------------> ___________CDR2____________ <--------------------------
CAG CCA CCC AGA CTC CTC ATC TAT CTT GTA TCC AAC CTA GAA TCT GGG GTC CCT GCC AGG TTC AGT

---------------- ----------------------- FWR3-----------------------------------------
GGC AGT GGG TCT GGG ACA GAC TTC ACC CTC AAC ATC CAT CCT GTG GAG GAG GAG GAT GCT GCA ACC

---------->                            ___________________J ___________________________*
TAT TAC TGT CAG CAC ATT AGG GAG CTT ACA CGT TCG GAG GGG GGA CCA AGC TGG AAA TAA (SEQ ID NO:7)
```

FIGURE 2B

```
--------FWR1--------->   <-----CDR1----->   <-----FWR2----->
IVMTQSAASLAVSLGQRATISY   RASKSVSTSGYSYMH   WNQQKPGQPPRLLIY

<-CDR2->  <-----------------FWR3----------->
LVSNLES   GVPARFSGSGSGTDFTLNIHPVEEEDAATYYC QHIRE

 <----J--->
LTRSEGGPSWK*  (SEQ ID NO:8)
```

```
   1 tgggcagggc acggaaggct caagaacctg acctgctgca gcttccagtc tcgcgttcgc
  61 cccaccccgc cgcgccgccc gagcgctcga gaaagtccac tcggaagaac cagcgcctgt
 121 tccccgggca gacccaggtt caggtcctgg ccgcaagtca ccatggctca gcaggctgca
 181 gacaagtacc tctatgtgga taaaaacttc atcaataacc cgctggccca agctgactgg
 241 gctgccaaga agttggtatg ggtgccttcc agcaagaatg gctttgaacc agctagcctc
 301 aaggaggagg tgggagaaga ggccattgta gagctggtag agaatgggaa gaaggtgaag
 361 gtgaacaagg acgacatcca gaagatgaac ccacccaagt tctccaaggt ggaggacatg
 421 gcagagctca cgtgcctcaa cgaagcttcg gtgctgcaca acctcaagga gcgatactac
 481 tcagggctta tctacaccta ttcaggcctg ttctgtgtgg tcatcaaccc ttataagaac
 541 ctgcccatct actcagagga gatcgtggag atgtacaagg gcaagaagag gcacgagatg
 601 ccaccccaca tctacgccat cacagatact gcctaccgga gcatgatgca ggaccgggaa
 661 gatcagtcca tcctgtgcac gggggagtct ggagcaggga agacagagaa caccaagaaa
 721 gtcatccagt acctggcaca tgtggcctcc tcacacaaga gcaagaagga ccagggggag
 781 ttggagcggc agctgctaca ggccaaccct atcctagagg cctttggaaa cgccaagacg
 841 gtgaagaatg acaactcctc tcgattcggt aaattcattc gtatcaactt tgatgtcaat
 901 ggctacattg ttggtgccaa cattgagact tatcttctgg agaaatctcg tgctatccgc
 961 caagccaaag aggagcggac cttccacatc ttctactacc tgctgtctgg ggccggagaa
1021 cacctgaaga ctgatctcct gttggagcca tacaacaaat accgcttcct gtccaacggg
1081 cacgtcacca tccctgggca gcaggacaag gacatgttcc aggagacaat ggaggccatg
1141 agaattatgg gtatcccaga ggatgagcag atgggcttgc tgcgggtcat ctctggggtc
1201 cttcagcttg gcaacattgc cttcaagaag gagcggaaca ctgaccaggc gtccatgccg
1261 gacaacacag ctgctcaaaa ggtgtcccac ctcctgggga tcaatgtgac cgacttcacc
1321 agaggcatcc tcaccccacg catcaaggtg ggcagagact atgtgcagaa ggcgcagact
1381 aaagagcagg ctgactttgc cattgaggcc ttggccaagg ctacctatga gcggatgttc
1441 cgctggctgg tgcttcgcat caacaaagct ctggacaaga ccaagaggca gggcgcctca
1501 tttatcggga tcctggacat cgctggcttt gagatctttg atctgaactc cttcgagcag
1561 ctgtgcatca actacaccaa cgagaagctg cagcagctgt tcaaccacac catgttcatc
1621 ctggagcagg aggagtacca gcgagagggc atcgagtgga acttcatcga cttcggcctg
1681 gacctgcagc cctgcatcga cctcattgag aagccggcgg gtcccccagg catcctggcc
1741 ctgctagatg aggagtgctg gtttcctaag gccactgaca agagcttcgt ggagaaggtg
1801 gtgcaggagc agggcaccca ccccaagttc cagaagccca agcaactgaa ggacaaggct
1861 gatttctgca ttatccacta tgccggcaag gtggactata aagctgacga gtggctgatg
1921 aagaacatgg acccccttgaa cgacaacatc gccacgctgc ttcaccagtc ctcagacaag
1981 tttgtctctg agctgtggaa ggatgtggat cggatcattg gcttggacca agtggctgga
2041 atgtccgaga cagcactacc tggtgccttc aagacccgga agggcatgtt ccgtactgtc
2101 ggacagctgt acaaggagca gctggccaag ctcatggcca cgttgaggaa taccaacccc
2161 aacttcgtgc gctgcatcat tcccaaccat gagaagaagg ccggcaaact ggacccgcac
2221 ttggtgctgg accagctgcg ctgcaatggc gtccttgagg gcatccggat ctgccgccag
2281 ggctttccca acagggtggt cttccaggag ttccggcaga ggtatgagat cctcaccccc
2341 aactccatcc cgaagggctt catggatggc aagcaagcgt gtgtgctcat gatcaaagcc
2401 ttggagcttg acagcaacct gtaccgcatc ggccagagca aagtgttctt ccgggcagga
2461 gtgctagccc acctggagga agagcgggac ctgaagatca ccgatgtcat cattggcttc
2521 caggcctgct gcaggggcta cctggccagg aaggcctttg ccaagaggca gcaacagctg
2581 accgccatga aggtcctaca gaggaactgt gctgcgtacc tcaggctgcg caactggcag
2641 tggtggaggc tcttcaccaa ggtcaagccc ctgttgaact caataagaca tgaggatgag
2701 ctgttagcca aggaggcgga actgacaaag gttcgagaga aacatctggc tgcagagaac
2761 aggctgacag agatggagac gatgcagtct cagctcatgg cagagaagct gcagcttcag
2821 gagcagctgc aggcggagac agagctgtgt gccgaggctg aggagctccg ggcccgtctg
2881 acagcgaaga agcaggagct ggaggagatc tgccatgacc tggaggccag ggtggaggag
2941 gaggaggagc gctgccagta cctgcaggcc gagaagaaga agatgcagca gaacatccag
3001 gaacttgagg agcagttgga ggaggaggag agcgcccggc agaagctgca gcttgagaag
3061 gtgaccaccg aggccaagct gaagaaactg gaggaggacc agatcatcat ggaggaccag
3121 aactgcaaac tggccaagga gaagaaactg ctggaagaca gagtagctga attcactacc
```

```
3181 aacctcatgg aagaggagga gaagtccaag agcctggcca agctcaagaa caagcacgag
3241 gcaatgatca ccgacctgga agagcgcctc cgtagggagg agaagcagag gcaggagttg
3301 gagaagaccc gtcgcaagct ggagggagac tccacagacc tcagtgacca gattgctgag
3361 ctccaggcgc agatagcaga gctcaagatg cagctggcca agaaggagga ggagttgcag
3421 gctgccttgg ccagagtgga agaagaagct gctcagaaga atatggccct gaagaagatc
3481 cgagaactgg aaactcagat ctctgagctc caggaggacc tggagtcgga gcgagcctcc
3541 aggaataaag ccgagaagca gaaacgggat ctgggagagg agctggaggc gctgaagaca
3601 gagctggagg acacgctgga ctccacggct gcccagcagg agctgaggtc gaagcgtgag
3661 caggaggtga gcatcctgaa gaagactctg gaggacgagg ccaagaccca tgaggcccag
3721 atccaggaga tgaggcagaa gcactcacag gctgtggagg agctggcaga tcagttggag
3781 cagacgaagc gggtaaaagc taccccttgag aaggcgaagc agaccctgga gaatgagcgg
3841 ggagagctgg ccaatgaggt gaaggccctg ctgcaaggca agggcgactc agagcacaag
3901 cgcaagaagg tggaggcgca gctgcaagaa ctgcaggtca agttcagcga gggagagcgc
3961 gtgcgaaccg aactggccga caaggtcacc aagctgcagg ttgaactgga cagtgtgacc
4021 ggtctcctta gccagtctga cagcaagtcc agcaagctta cgaaggactt ctctgcgctg
4081 gagtcccagc ttcaggacac acaggagttg ctccaggagg agaaccggca gaagctgagc
4141 ctgagcacca agctcaagca gatggaggat gagaaaaact ccttcaggga gcagctggag
4201 gaggaggagg aggccaagcg caacttggag aagcagatcg ccacgctcca tgcccaggtg
4261 accgacatga agaagaagat ggaggacggt gtagggtgcc tggagactgc agaggaggcg
4321 aagcggaggc ttcagaagga cttggaaggc ctgagccagc ggcttgagga gaaggtggct
4381 gcctacgata agctggagaa gaccaagaca cggctgcagc aggagctgga cgacctgctg
4441 gttgacctgg accaccagcg gcagagcgtc tccaacctgg aaaagaagca gaagaagttc
4501 gaccagctcc tagccgagga gaagaccatc tcggccaagt atgcagagga gcgtgaccga
4561 gctgaggctg aggcccgtga gaaggagaca aaggcgctat cactggcccg ggcgcttgag
4621 gaggccatgg agcagaaggc agagctggag cggctcaaca agcagttccg cacggagatg
4681 gaggacctca tgagctccaa ggatgacgtg ggcaagagtg tccacgagct ggagaagtcc
4741 aagcgggcct tggagcagca ggtggaggag atgaagaccc agctggagga gctggaggat
4801 gagctgcagg ccacggagga tgccaagctc cgcctggagg tgaacctgca ggccatgaag
4861 gcccagtttg agcgggatct gcagggccgg gatgaacaga gcgaggagaa gaagaagcag
4921 ctggtcagac aggtgcggga gatggaggcg gagctggagg atgagaggaa gcagcgctcc
4981 atggccatgg ccgcacgcaa gaaactggag atggatctga aggacctgga ggcacacatt
5041 gacacagcca ataagaaccg ggaagaggcc atcaaacagc tgcggaagct tcaggcccag
5101 atgaaggact gcatgcggga gctggacgac acgcgcgcct cccgggagga gatcctggcg
5161 caggccaagg agaatgagaa gaagctgaag agcatggagg ccgagatgat tcagctgcag
5221 gaggaactgg cagctgctga gcgtgctaag cgtcaggccc aacaggaacg ggacgagctg
5281 gctgatgaga tcgccaacag cagtggcaaa ggggccctag cattagagga gaagcggcga
5341 ctggaggccc gcattgccct gctggaggag gagctggagg aggaacaggg caacacggag
5401 ctgatcaacg atcggctgaa gaaggccaac ctgcagatcg accaaataaa caccgacctg
5461 aacctggaac gcagccacgc acagaagaat gagaatgcgc gacagcagct ggaacgccag
5521 aacaaggagc tcaaggccaa gctgcaggaa atggagagtg ctgtcaagtc caaatacaag
5581 gcctccatcg cggccttgga ggccaaaatt gcacagctgg aggaacagct ggacaacgag
5641 accaaggagc gccaggcagc ctccaagcag gtgcgccgga cggagaagaa gctgaaggac
5701 gtgctgctgc aggtggagga cgagcggagg aacgcggaac agttcaagga ccaggctgac
5761 aaggcgtcca cccgcctgaa gcagcttaaa cggcagctag aggaggctga agaggaggcc
5821 cagcgggcca atgcctcacg ccggaagctg cagcgtgagc tggaagatgc cacagagacc
5881 gctgatgcta tgaaccgcga ggtcagctcc ctgaagaaca aactgaggcg tggggacctg
5941 ccatttgtcg tgactcgccg aattgttcgg aaaggcactg gcgactgctc agacgaggag
6001 gtcgacggta aagcagatgg ggccgatgcc aaggcagctg aataggagct tctcctgcag
6061 cccaggcgga tggacaaacg gctctgcctc cctcccccaa ccctccacac ccctgccttg
6121 agactgctct gaccatgtcc ccctcctccc aaggccttcc cgagggcatt ggcttcctct
6181 gctgcagccc ttccagtcct ccatacccttt tgagaatctg ataccaaaga gtccaggctg
6241 gctcaggccg gatgacccac agggtcttgt cctccttgcc tgaaagcacg ggtggtgggc
6301 aagaagggcg gccattggag taggcacaag agttttctat gaatctattt tgtcttcaga
6361 taaagatttt gatagctcag gcctctagta gtgttaccct ccccgacctc ggctgtcccc
6421 gtcccccgtc cccctgctg ttggcaatca cacacggtaa cctcatacct gccctatggc
6481 cccccttccct gggccctatt ggtccagaag gagcctctgt ctgggtgcag aacatggggc
6541 actctgggaa tccccccact cccttctggg cagcactggt gcctctgctc ctccgactgt
```

6601 aaaccgtctc aagtgcaatg cccctcccct cccttgccaa ggacagaccg tcctggcacc
6661 ggggcaaacc agacagggca tcagggccac tctagaaagg ccaacagcct tccggtggct
6721 tctcccagca ctctagggga ccaaatatat ttaatggtta agggacttgc agggcctggc
6781 agccagaata tccaagggct ggagcccact gtgcgctctg gtgcctctcc taggactggg
6841 gccaagggtg gtcgagctgt gccacccact ctatagcttc aagtctgcct tccacaagga
6901 tgcttttgaa agaaaaaaaa aggttttatt tttcccttct tgtagtaagt gctctagttc
6961 tgggtgtctt cactgccttg ccctggaact gtgtttagaa gagagtagct tgccctacaa
7021 tgtctacact ggtcgctgag ttccctgcgc actgcacctc actgtttgta aatgctgtga
7081 ttaggttccc ttatggcagg aaggcttttt ttttcttttt ttttttcttt tctttttttt
7141 tttttaaag gaaaaccagt caaatcatga agccacatac gctagagaag ctgaatccag
7201 gtcccaaagg cgctgtcata aaggagcaag tgggacccgc accccttttt ttatataata
7261 caagtgcctt agcatgtgtc gcagctgtca ccactacagt aagctggttt acagatgttt
7321 ccactgagcg tcacaataaa gagtaccatg tccta (SEQ ID NO: 47)

(B)

1 maqqaadkyl yvdknfinnp laqadwaakk lvwvpssskng fepaslkeev geeaivelve
61 ngkkvkvnkd diqkmnppkf skvedmaelt clneasvlhn lkeryysgli ytysglfcvv
121 inpyknlpiy seeivemykg kkrhempphi yaitdtayrs mmqdredqsi lctgesgagk
181 tentkkviqy lahvasshks kkdqgelerq llqanpilea fgnaktvknd nssrfgkfir
241 infdvngyiv ganietylle ksrairqake ertfhifyyl lsgagehlkt dlllepynky
301 rflsnghvti pgqqdkdmfq etmeamrimg ipedeqmgll rvisgvlqlg niafkkernt
361 dqasmpdnta aqkvshllgi nvtdftrgil tprikvgrdy vqkaqtkeqa dfaiealaka
421 tyermfrwlv lrinkaldkt krqgasfigi ldiagfeifd lnsfeqlcin ytneklqqlf
481 nhtmfileqe eyqregiewn fidfgldlqp cidliekpag ppgilallde ecwfpkatdk
541 sfvekvvqeq gthpkfqkpk qlkdkadfci ihyagkvdyk adewlmknmd plndniatll
601 hqssdkfvse lwkdvdriig ldqvagmset alpgafktrk gmfrtvgqly keqlaklmat
661 lrntnpnfvr ciipnhekka gkldphlvld qlrcngvleg iricrqgfpn rvvfqefrqr
721 yeiltpnsip kgfmdgkqac vlmikaleld snlyrigqsk vffragvlah leeerdlkit
781 dviigfqacc rgylarkafa krqqqltamk vlqrncaayl rlrnwqwwrl ftkvkpllns
841 irhedellak eaeltkvrek hlaaenrlte metmqsqlma eklqlqeqlq aetelcaeae
901 elrarltakk qeleeichdl earveeeeer cqylqaekkk mqqniqelee qleeeesarq
961 klqlekvtte aklkkleedq iimedqnckl akekklledr vaefttnlme eeekskslak
1021 lknkheamit dleerlrree kqrqelektr rklegdstdl sdqiaelqaq iaelkmqlak
1081 keeelqaala rveeeaaqkn malkkirele tqiselqedl eserasrnka ekqkrdlgee
1141 lealkteled tldstaaqqe lrskreqevs ilkktledea ktheaqiqem rqkhsqavee
1201 ladqleqtkr vkatlekakq tlenergela nevkallqgk gdsehkrkkv eaqlqelqvk
1261 fsegervrte ladkvtklqv eldsvtglls qsdsksssklt kdfsalesql qdtqellqee
1321 nrqklslstk lkqmedekns freqleeeee akrnlekqia tlhaqvtdmk kkmedgvgcl
1381 etaeeakrrl qkdleglsqr leekvaaydk lektktrlqq elddllvdld hqrqsvsnle
1441 kkqkkfdqll aeektisaky aeerdraeae areketkals laraleeame qkaelerlnk
1501 qfrtemedlm sskddvgksv helekskral eqqveemktq leeledelqa tedaklrlev
1561 nlqamkaqfe rdlqgrdeqs eekkkqlvrq vremeaeled erkqrsmama arkklemdlk
1621 dleahidtan knreeaikql rklqaqmkdc mrelddtras reeilaqake nekklksmea
1681 emiqlqeela aaerakrqaq qerdeladei anssgkgala leekrrlear ialleeelee
1741 eqgntelind rlkkanlqid qintdlnler shaqknenar qqlerqnkel kaklqemesa
1801 vkskykasia aleakiaqle eqldnetker qaaskqvrrt ekklkdvllq vederrnaeq
1861 fkdqadkast rlkqlkrqle eaeeeaqran asrrklqrel edatetadam nrevsslknk
1921 lrrgdlpfvv trrivrkgtg dcsdeevdgk adgadakaae (SEQ ID NO: 48)

```
   1 atacgactca ctatagggcg atcaggtgct ggaaagaagg ctaagcaagg ctgacctgct
  61 gcagctcccg cctcgtgcgc tcgccccacc cggccgccgc ccgagcgctc gagaaagtcc
 121 tctcgggaga agcagcgcct gttcccgggg cagatccagg ttcaggtcct ggctataagt
 181 caccatggca cagcaagctg ccgataagta tctctatgtg gataaaaact tcatcaacaa
 241 tccgctggcc caggccgact gggctgccaa gaagctggta tgggtgcctt ccgacaagag
 301 tggctttgag ccagccagcc tcaaggagga ggtgggcgaa gaggccatcg tggagctggt
 361 ggagaatggg aagaaggtga aggtgaacaa ggatgacatc cagaagatga acccgcccaa
 421 gttctccaag gtggaggaca tggcagagct cacgtgcctc aacgaagcct cggtgctgca
 481 caacctcaag gagcgttact actcagggct catctacacc tattcaggcc tgttctgtgt
 541 ggtcatcaat ccttacaaga acctgcccat ctactctgaa gagattgtgg aaatgtacaa
 601 gggcaagaag aggcacgaga tgccccctca catctatgcc atcacagaca ccgcctacag
 661 gagtatgatg caagaccgag aagatcaatc catcttgtgc actggtgaat ctggagctgg
 721 caagacggag aacaccaaga aggtcatcca gtatctggcg tacgtggcgt cctcgcacaa
 781 gagcaagaag gaccagggcg agctggagcg gcagctgctg caggccaacc ccatcctgga
 841 ggccttcggg aacgccaaga ccgtgaagaa tgacaactcc tcccgcttcg gcaaattcat
 901 tcgcatcaac tttgatgtca atggctacat tgttggagcc aacattgaga cttatctttt
 961 ggagaaatct cgtgctatcc gccaagccaa ggaagaacgg accttccaca tcttctatta
1021 tctcctgtct ggggctggag agcacctgaa gaccgatctc ctgttggagc cgtacaacaa
1081 ataccgcttc ctgtccaatg gacacgtcac catccccggg cagcaggaca aggacatgtt
1141 ccaggagacc atggaggcca tgaggattat gggcatccca gaagaggagc aaatgggcct
1201 gctgcgggtc atctcagggg ttcttcagct cggcaacatc gtcttcaaga aggagcggaa
1261 cactgaccag gcgtccatgc ccgacaacac agctgcccaa aaggtgtccc atctcttggg
1321 tatcaatgtg accgatttca ccagaggaat cctcaccccg cgcatcaagg tgggacggga
1381 ttacgtccag aaggcgcaga ctaaagagca ggctgacttt gccatcgagg ccttggccaa
1441 ggcgacctat gagcggatgt tccgctggct ggtgctgcgc atcaacaagg ctctggacaa
1501 gaccaagagg cagggcgcct ccttcatcgg gatcctggac attgccggct tcgagatctt
1561 tgatctgaac tcgtttgagc agctgtgcat caattacacc aatgagaagc tgcagcagct
1621 cttcaaccac accatgttca tcctggagca ggaggagtac cagcgcgagg gcatcgagtg
1681 gaacttcatc gactttggcc tcgacctgca gccctgcatc gacctcattg agaagccagc
1741 aggcccccg ggcattctgg ccctgctgga cgaggagtgc tggttcccca aagccaccga
1801 caagagcttc gtggagaagg tgatgcagga gcagggcacc caccccaagt tccagaagcc
1861 caagcagctg aaggacaaag ctgatttctg cattatccac tatgccggca aggtggatta
1921 caaagctgac gagtggctga tgaagaacat ggatcccctg aatgacaaca tcgccacact
1981 gctccaccag tcctctgaca agtttgtctc ggagctgtgg aaggatgtgg accgcatcat
2041 cggcctggac caggtggccg gcatgtcgga gaccgcactg cccggggcct tcaagacgcg
2101 gaagggcatg ttccgcactg tggggcagct ttacaaggag cagctggcca agctgatggc
2161 tacgctgagg aacacgaacc ccaactttgt ccgctgcatc atccccaacc acgagaagaa
2221 ggccggcaag ctggacccgc atctcgtgct ggaccagctg cgctgcaacg gtgttctcga
2281 gggcatccgt atctgccgcc agggcttccc caacagggtg gtcttccagg agtttcggca
2341 gagatatgag atcctgactc caaactccat tcccaagggt ttcatggacg ggaagcaggc
2401 gtgcgtgctc atgataaaag ccctggagct cgacagcaat ctgtaccgca ttggccagag
2461 caaagtcttc ttccgtgccg gtgtgctggc ccacctggag gaggagcgag acctgaagat
2521 caccgacgtc atcatagggt tccaggcctg ctgcaggggc tacctggcca ggaaagcatt
2581 tgccaagcgg cagcagcagc ttaccgccat gaaggtcctc cagcggaact gcgctgccta
2641 cctgaagctg cggaactggc agtggtggcg gctcttcacc aaggtcaagc cgctgctgca
2701 ggtgagccgg caggaggagg agatgatggc caaggaggag gagctggtga aggtcagaga
2761 gaagcagctg gctgcggaga acaggctcac ggagatggag acgctgcagt ctcagctcat
2821 ggcagagaaa ttgcagctgc aggagcagct ccaggcagaa accgagctgt gtgccgaggc
2881 tgaggagctc cgggcccgcc tgaccgccaa gaagcaggaa ttagaagaga tctgccatga
2941 cctagaggcc agggtggagg aggaggagga gcgctgccag cacctgcagg cggagaagaa
3001 gaagatgcag cagaacatcc aggagcttga ggagcagctg gaggaggagg agagcgcccg
3061 gcagaagctg cagctggaga aggtgaccac cgaggcgaag ctgaaaaagc tggaggagga
3121 gcagatcatc ctggaggacc agaactgcaa gctggccaag gaaaagaaac tgctggaaga
```

```
3181 cagaatagct gagttcacca ccaacctcac agaagaggag gagaaatcta agagcctcgc
3241 caagctcaag aacaagcatg aggcaatgat cactgacttg gaagagcgcc tccgcaggga
3301 ggagaagcag cgacaggagc tggagaagac ccgccggaag ctggagggag actccacaga
3361 cctcagcgac cagatcgccg agctccaggc ccagatcgcg gagctcaaga tgcagctggc
3421 caagaaagag gaggagctcc aggccgccct ggccagagtg gaagaggaag ctgcccagaa
3481 gaacatggcc ctcaagaaga tccgggagct ggaatctcag atctctgaac tccaggaaga
3541 cctggagtct gagcgtgctt ccaggaataa agctgagaag cagaaacggg accttgggga
3601 agagctagag gcgctgaaaa cagagttgga ggacacgctg gattccacag ctgcccagca
3661 ggagctcagg tcaaaacgtg agcaggaggt gaacatcctg aagaagaccc tggaggagga
3721 ggccaagacc cacgaggccc agatccagga gatgaggcag aagcactcac aggccgtgga
3781 ggagctggcg gagcagctgg agcagacgaa gcgggtgaaa gcaaacctcg agaaggcaaa
3841 gcagactctg gagaacgagc gggggagct ggccaacgag gtgaaggtgc tgctgcaggg
3901 caaaggggac tcggagcaca agcgcaagaa agtggaggcg cagctgcagg agctgcaggt
3961 caagttcaac gagggagagc gcgtgcgcac agagctggcc gacaaggtca ccaagctgca
4021 ggtggagctg gacaacgtga ccgggcttct cagccagtcc gacagcaagt ccagcaagct
4081 caccaaggac ttctccgcgc tggagtccca gctgcaggac actcaggagc tgctgcagga
4141 ggagaaccgg cagaagctga gcctgagcac caagctcaag caggtggagg acgagaagaa
4201 ttccttccgg gagcagctgg aggaggagga ggaggccaag cacaacctgg agaagcagat
4261 cgccaccctc catgcccagg tggccgacat gaaaaagaag atggaggaca gtgtggggtg
4321 cctggaaact gctgaggagg tgaagaggaa gctccagaag gacctggagg gcctgagcca
4381 gcggcacgag gagaaggtgg ccgcctacga caagctggag aagaccaaga cgcggctgca
4441 gcaggagctg gacgacctgc tggtggacct ggaccaccag cgccagagcg cgtgcaacct
4501 ggagaagaag cagaagaagt ttgaccagct cctggcggag gagaagacca tctctgccaa
4561 gtatgcagag gagcgcgacc gggctgaggc ggaggcccga gagaaggaga ccaaggctct
4621 gtcgctggcc cgggccctgg aggaagccat ggagcagaag gcggagctgg agcggctcaa
4681 caagcagttc cgcacggaga tggaggacct tatgagctcc aaggatgatg tgggcaagag
4741 tgtccacgag ctggagaagt ccaagcgggc cctagagcag caggtggagg agatgaagac
4801 gcagctggaa gagctggagg acgagctgca ggccaccgaa gatgccaagc tgcggttgga
4861 ggtcaacctg caggccatga aggcccagtt cgagcgggac ctgcagggcc gggacgagca
4921 gagcgaggag aagaagaagc agctggtcag acaggtgcgg gagatggagg cagagctgga
4981 ggacgagagg aagcagcgct cgatggcagt ggccgcccgg aagaagctgg agatggacct
5041 gaaggacctg gaggcgcaca tcgactcggc caacaagaac cgggacgaag ccatcaaaca
5101 gctgcggaag ctgcaggccc agatgaagga ctgcatgcgc gagctggatg acacccgcgc
5161 ctctcgtgag gagatcctgg cccaggccaa agagaacgag aagaagctga agagcatgga
5221 ggccgagatg atccagttgc aggaggaact ggcagccgcg gagcgtgcca agcgccaggc
5281 ccagcaggag cgggatgagc tggctgacga gatcgccaac agcagcggca aaggagccct
5341 ggcgttagag gagaagcggc gtctggaggc ccgcatcgcc cagctggagg aggagctgga
5401 ggaggagcag ggcaacacgg agctgatcaa cgaccggctg aagaaggcca acctgcagat
5461 cgaccagatc aacaccgacc tgaacctgga gcgcagccac gcccagaaga acgagaatgc
5521 tcggcagcag ctggaacgcc agaacaagga gcttaaggtc aagctgcagg agatggaggg
5581 cactgtcaag tccaagtaca aggcctccat caccgccctc gaggccaaga ttgcacagct
5641 ggaggagcag ctggacaacg agaccaagga gcgccaggca gcctgcaaac aggtgcgtcg
5701 gaccgagaag aagctgaagg atgtgctgct gcaggtggat gacgagcgga ggaacgccga
5761 gcagtacaag gaccaggccg acaaggcatc tacccgcctg aagcagctca agcggcagct
5821 ggaggaggcc gaagaggagg cccagcgggc caacgcctcc cgccggaaac tgcagcgcga
5881 gctggaggac gccactgaga cggccgatgc catgaaccgc gaagtcagct ccctaaagaa
5941 caagctcagg cgcggggacc tgccgtttgt cgtgccccgc cgaatggccc ggaaaggcgc
6001 cggggatggc tccgacgaag aggtagatgg caaagcggat ggggctgagg ccaaacctgc
6061 cgaataagcc tcttctcctg cagcctgaga tggatggaca gacagacacc acagcctccc
6121 cttcccagac cccgcagcac gcctctcccc accttcttgg gactgctgtg aacatgcctc
6181 ctcctgccct ccgccccgtc cccccatccc gtttccctcc aggtgttgtt gagggcattt
6241 ggcttcctct gctgcatccc cttccagctc cctcccctgc tcagaatctg ataccaaaga
6301 gacagggccc gggcccaggc agagagcgac cagcaggctc ctcagccctc tcttgccaaa
6361 aagcacaaga tgttgaggcg agcagggcag gcccccgggg aggggccaga gttttctatg
6421 aatctatttt tcttcagact gaggcctttt ggtagtcgga gcccccgcag tcgtcagcct
6481 ccctgacgtc tgccaccagc gcccccactc ctcctccttt ctttgctgtt tgcaatcaca
6541 cgtggtgacc tcacacacct ctgcccttg ggcctcccac tcccatggct ctgggcggtc
```

```
6601 cagaaggagc aggccctggg cctccacctc tgtgcagggc acagaaggct ggggtggggg
6661 gaggagtgga ttcctcccca ccctgtccca ggcagcgcca ctgtccgctg tctccctcct
6721 gattctaaaa tgtctcaagt gcaatgcccc ctcccctcct ttaccgagga cagcctgcct
6781 ctgccacagc aaggctgtcg ggtcaagct ggaaaggcca gcagccttcc agtggcttct
6841 cccaacactc ttggggacca aatatattta atggttaagg gacttgtccc aagtctgaca
6901 gccagagcgt tagaggggcc agcggccctc ccaggcgatc ttgtgtctac tctaggactg
6961 ggcccgaggg tggtttacct gcaccgttga ctcagtatag tttaaaaatc tgccacctgc
7021 acaggtattt ttgaaagcaa aataaggttt tctttttcc cctttcttgt aataaatgat
7081 aaaattccga gtctttctca ctgcctttgt ttagaagaga gtagctcgtc ctcactggtc
7141 tacactggtt gccgaattta cttgtattcc taactgtttt gtatatgctg cattgagact
7201 tacggcaaga aggcattttt ttttttaaa ggaaacaaac tctcaaatca tgaagtgata
7261 taaaagctgc atatgcctac aaagctctga attcaggtcc cagttgctgt cacaaaggag
7321 tgagtgaaac tcccacccta ccccctttt tatataataa aagtgcctta gcatgtgttg
7381 cagctgtcac cactacagta agctggttta cagatgtttt ccactgagca tcacaataaa
7441 gagaaccatg tgctaaaaaa aaaaaaaaaa aaaa (SEQ ID NO: 49)
```

(B)

```
   1 maqqaadkyl yvdknfinnp laqadwaakk lvwvpsdksg fepaslkeev geeaivelve
  61 ngkkvkvnkd diqkmnppkf skvedmaelt clneasvlhn lkeryysgli ytysglfcvv
 121 inpyknlpiy seeivemykg kkrhempphi yaitdtayrs mmqdredqsi lctgesgagk
 181 tentkkviqy layvasshks kkdqgelerq llqanpilea fgnaktvknd nssrfgkfir
 241 infdvngyiv ganietylle ksrairqake ertfhifyyl lsgagehlkt dlllepynky
 301 rflsnghvti pgqqdkdmfq etmeamrimg ipeeeqmgll rvisgvlqlg nivfkkernt
 361 dqasmpdnta aqkvshllgi nvtdftrgil tprikvgrdy vqkaqtkeqa dfaiealaka
 421 tyermfrwlv lrinkaldkt krqgasfigi ldiagfeifd lnsfeqlcin ytneklqqlf
 481 nhtmfileqe eyqregiewn fidfgldlqp cidliekpag ppgilallde ecwfpkatdk
 541 sfvekvmqeq gthpkfqkpk qlkdkadfci ihyagkvdyk adewlmknmd plndniatll
 601 hqssdkfvse lwkdvdriig ldqvagmset alpgafktrk gmfrtvgqly keqlaklmat
 661 lrntnpnfvr ciipnhekka gkldphlvld qlrcngvleg iricrqgfpn rvvfqefrqr
 721 yeiltpnsip kgfmdgkqac vlmikaleld snlyrigqsk vffragvlah leeerdlkit
 781 dviigfqacc rgylarkafa krqqqltamk vlqrncaayl klrnwqwwrl ftkvkpllqv
 841 srqeeemmak eeelvkvrek qlaaenrlte metlqsqlma eklqlqeqlq aetelcaeae
 901 elrarltakk qeleeichdl earveeeeer cqhlqaekkk mqqniqelee qleeeesarq
 961 klqlekvtte aklkkleeeq iiledqnckl akekklledr iaefttnlte eeekskslak
1021 lknkheamit dleerlrree kqrqelektr rklegdstdl sdqiaelqaq iaelkmqlak
1081 keeelqaala rveeeaaqkn malkkirele sqiselqedl eserasrnka ekqkrdlgee
1141 lealkteled tldstaaqqe lrskreqevn ilkktleeea ktheaqiqem rqkhsqavee
1201 laeqleqtkr vkanlekakq tlenergela nevkvllqgk gdsehkrkkv eaqlqelqvk
1261 fnegervrte ladkvtklqv eldnvtglls qsdskssklt kdfsalesql qdtqellqee
1321 nrqklslstk lkqvedekns freqleeeee akhnlekqia tlhaqvadmk kkmedsvgcl
1381 etaeevkrkl qkdleglsqr heekvaaydk lektktrlqq elddllvdld hqrqsacnle
1441 kkqkkfdqll aeektisaky aeerdraeae areketkals laraleeame qkaelerlnk
1501 qfrtemedlm sskddvgksv helekskral eqqveemktq leeledelqa tedaklrlev
1561 nlqamkaqfe rdlqgrdeqs eekkkqlvrq vremeaeled erkqrsmava arkklemdlk
1621 dleahidsan knrdeaikql rklqaqmkdc mrelddtras reeilaqake nekklksmea
1681 emiqlqeela aaerakrqaq qerdeladei anssgkgala leekrrlear iaqleeelee
1741 eqgntelind rlkkanlqid qintdlnler shaqknenar qqlerqnkel kvklqemegt
1801 vkskykasit aleakiaqle eqldnetker qaackqvrrt ekklkdvllq vdderrnaeq
1861 ykdqadkast rlkqlkrqle eaeeeaqran asrrklqrel edatetadam nrevsslknk
1921 lrrgdlpfvv prrmarkgag dgsdeevdgk adgaeakpae (SEQ ID NO: 50)
```

```
   1 gtctttcctg ggagatgggc gcgcaaaccg accagtgggt ctgggggcgg cagtgatggg
  61 cgtggagatg gcccaatgag ggtgggagtg ggtggggcag gcgcgagcag cagtgctaaa
 121 ggagcccggc ggaggcagcg gtgggtttgg aattgagacg ctggatctgt ggtcgctgct
 181 ggggacgtgt gccggcgcca ccatcttcgg ctgaagaggc aattactttt gggtccttct
 241 gtttacaatg gcccagagaa ctggactgga ggatcccgag aggtatctct ttgtggacag
 301 ggctgtcatc tacaaccctg ccactcaagc tgactggaca gctaaaaagc tggtgtggat
 361 tccatcggaa cgccatggtt ttgaggcagc tagtattaaa gaagagcggg gcgatgaggt
 421 tatggtggag ctggcagaga atgggaagaa agcaatggtc aacaaagatg acattcagaa
 481 gatgaaccca ccaaagttct ccaaggtgga ggatatggca gagctgacat gcttgaacga
 541 agcctctgtc ttacataatt tgaaggaccg ctactattca ggacttatct atacttactc
 601 tggactcttc tgtgtggtga taaatcctta caagaacctt ccaatttact ctgagaatat
 661 tattgaaatg tatagaggga agaaacgcca tgagatgcca ccacacatct acgccatatc
 721 agagtctgct tacagatgca tgcttcaaga tcgtgaggac cagtcaattc tatgcacggg
 781 tgaatcgggt gccgggaaga cagaaaatac caagaaagtc attcagtacc ttgcccacgt
 841 tgcttcttct cacaaaggaa gaaaggacca taatattcct ggggaacttg aacggcagct
 901 tttacaagca aatccaattc tggaatcctt tggaaatgcg aagactgtga aaaatgataa
 961 ctcatctcgc tttggcaagt ttatccggat caactttgat gtaactggct atattgttgg
1021 ggccaacatt gaaacatacc ttctggaaaa gtctcgtgct gttcgtcaag ctaaagatga
1081 gcgtacattt catatctttt atcagttgct ctctggagca ggggaacacc tgaaatccga
1141 cttactcctg gaaggtttca acaactacag attcctctcc aatggctata ttcctattcc
1201 tggacagcaa gacaaggata acttccagga gaccatggaa gccatgcaca tcatgggctt
1261 ctctcacgaa gagatcctct caatgcttaa agtcgtatct tcagtgctgc agtttggaaa
1321 catctctttc aaaaaggaga gaaacactga ccaagcctcc atgccggaga acacagtcgc
1381 acagaagctc tgccacctgc tcgggatgaa tgtgatggag ttcactcggg ctatcctcac
1441 gcccaggatc aaggttggcc gggattacgt acagaaagcc cagaccaaag agcaggctga
1501 ttttgcagtg gaagcattgg caaaagctac ctatgagcgg ttgtttcgct ggctcgttca
1561 ccgcatcaat aaagcgctgg ataggaccaa acgccaggga gcttccttca ttgggatcct
1621 ggatattgct ggttttgaaa tttttgagct gaactccttc gagcagctgt gcatcaacta
1681 caccaacgag aagctgcagc agctgttcaa ccacaccatg ttcatcctgg agcaggagga
1741 gtaccagcga gagggcatcg agtggaactt tatcgacttc ggcctggacc tgcagccctg
1801 catcgacctg atagagagac ctgccaatcc ccctggcgtg ctggccctcc tggatgaaga
1861 atgctggttc cccaaagcta cagataaaac atttgttgaa aagctggttc aggagcaagg
1921 ttcccactcc aagtttcaga agccgcgcca actgaaagac aaagccgact tctgcatcat
1981 ccactacgcg gggaaggtgg actataaggc agatgagtgg ctgatgaaga acatggaccc
2041 gctgaatgac aacgtggcca ccctcctgca ccagtcctcg gacagatttg tggctgagct
2101 ttggaaggac gtggaccgaa ttgtaggtct ggatcaagtc actgggatga ctgagaccgc
2161 gtttggctct gcatacaaaa ccaagaaggg catgttccga accgtcgggc agctctacaa
2221 ggagtctctc accaagctga tggcaactct ccgcaacacc aaccccaact tcgtccgctg
2281 catcattcca aatcacgaga agcgggctgg gaaactggac ccgcacctcg tgctcgatca
2341 gcttcgctgt aacggcgtcc tggaagggat ccggatctgt cgccaggggt tccccaaccg
2401 gatagttttc caggaattca gacagagata tgagatccta actcccaatg ctattcctaa
2461 aggcttcatg gatggcaaac aggcgtgtga gcgaatgatc cgagctttag aactggaccc
2521 aaacctgtat agaattggac agagcaagat atttttccga gctggagttt tggcgcactt
2581 agaagaagaa agagatttaa aaatcactga tatcatcatc tttttccaag ctgtatgcag
2641 aggctacctc gcccgaaagg cctttgccaa gaaacagcaa caactaagtg ccttaaaggt
2701 cttgcagcgg aactgtgcgg cgtacctgaa gctgcgacac tggcagtggt ggcgtgtctt
2761 cacgaaggtg aagcctctcc tccaagtgac ccgccaggag gaagaactcc aggcaaaaga
2821 tgaggagctg ctgaaggtga aagagaagca gacaaaagtg gaaggggagc ttgaggagat
2881 ggagcggaag caccagcagc tgctggaaga gaagaatatc ctggcagaac aactgcaagc
2941 cgagaccgag ctcttcgctg aagcagaaga gatgagagca aggcttgctg ccaaaaagca
3001 ggaactggag gagattctcc atgacctcga gtccagggtg gaggaggagg aagagcggaa
3061 ccagatccta cagaatgaga agaagaagat gcaggcgcac attcaggacc tagaagaaca
3121 actggatgag gaggaggggg cccggcaaaa gctgcagctg gagaaggtga cagcagaggc
```

```
3181 taaaatcaag aagatggaag aggaggttct gcttctcgaa gaccagaatt ccaaatttat
3241 caaagaaaag aaactcatgg aagaccgaat tgctgagtgt tcctctcagc tggctgaaga
3301 ggaagaaaag gcaaaaaact tggccaaaat caggaataag caagaagtga tgatctcgga
3361 cttagaagaa cgcttgaaga aggaggagaa aactcgacag gaactggaaa aggccaaacg
3421 gaagctggat ggggaaacaa ccgatctgca ggaccagatc gctgagctgc aggcacaggt
3481 cgatgagctc aaagtccagt tgaccaagaa ggaggaggag cttcaggggg cgctggccag
3541 aggagatgat gagacactgc acaagaataa tgcacttaaa gttgcacggg agctgcaggc
3601 ccaaatcgca gagctccagg aagactttga gtctgaaaag gcttcaagga acaaggctga
3661 gaaacaaaaa cgggacttga gtgaggagct ggaagctctg aagacagagc tggaggacac
3721 cctagacacc acagcagctc agcaggaact ccgcacaaaa cgtgagcagg aagtggcaga
3781 gctgaagaag gctcttgagg atgaaactaa gaaccacgaa gctcagatcc aggacatgag
3841 acagaggcat gccacagcgc tggaggagct ttccgagcag ctggagcaag cgaaaaggtt
3901 caaagccaac ctggagaaga acaaacaggg cctggagaca gacaacaagg agctggcgtg
3961 tgaggtgaag gtgctgcagc aggtgaaggc ggagtcagag cacaagagga agaagctgga
4021 tgcccaggtc caggagctcc atgccaaggt gtcagagggt gacaggctca gggtagagct
4081 ggccgagaaa gcaaacaagc tacagaatga gctggataat gtgtcaaccc tgctggaaga
4141 agctgagaag aaaggtatta agtttgcgaa ggatgcagct ggtctcgagt ctcaactaca
4201 ggacacacag gagctccttc aggaagagac acggcagaaa ctgaacctga gcagtcggat
4261 ccggcagctg gaggaggaga agaacagcct tcaggagcag caggaggagg aggaggaggc
4321 caggaagaac ctggagaagc aggtgttggc tctgcagtcc cagctggctg acaccaagaa
4381 gaaagtggac gatgacctgg ggacaatcga gagtttggag gaagccaaaa agaaactgct
4441 caaggatgtg gaggcgctga gccagcggct ggaggagaag gtcctggcgt atgacaagct
4501 ggagaagacc aagaaccggc tgcaacaaga actggatgac ctgacggtgg acctggacca
4561 ccagcgccag atcgtctcca acttggagaa gaaacagaag aagttcgacc agctgttggc
4621 agaagaaaag ggcatctctg ctcgctatgc agaagagcgg gaccgggctg aagctgaggc
4681 cagagagaaa gaaaccaaag cgctctccct ggcgcgggcc cttgaggagg ccttggaggc
4741 gaaggaggaa ttcgagaggc agaacaagca gcttcgagca gacatggaag acctgatgag
4801 ctctaaagac gatgtgggga agaacgtcca cgagcttgag aaatccaagc gagccttgga
4861 gcagcaggtg gaggagatgc ggacccagct ggaggagctg gaggacgagc tgcaggccac
4921 tgaggatgcc aagctccgcc tggaagtcaa catgcaggcc atgaaggccc agtttgagag
4981 ggacctgcaa acccgagatg agcagaatga agaaaagaag cggctgctgc ttaagcaggt
5041 gcgggagctc gaggcagagc tggaggatga gcggaaacag cgggcactgg ctgtggcgtc
5101 aaagaagaag atggagatag acctgaagga cctggaggct cagatcgagg ctgcgaacaa
5161 agcccgggat gaagtgatca agcagcttcg caaacttcag gcacagatga aggattacca
5221 gcgtgaacta gaagaggctc gagcatctag agatgagatt tttgctcaat ccaaagaaag
5281 tgaaaagaaa ctgaagagtc tagaagcaga aattcttcag ctgcaagagg agctggcctc
5341 atccgagcga gcccgccgac acgcagagca ggagcgagac gagctggctg atgagatcgc
5401 caacagcgcc tctggaaagt ctgcgctgtt ggatgagaag cggcgcctgg aagcgcggat
5461 cgcacagctg gaagaggagc tggaggagga gcagagcaac atggagctgc tcaatgaccg
5521 cttccgcaag accacgctgc aggtggacac actgaacaca gagctggcag cagagcgcag
5581 cgctgcccag aagagtgaca atgcccgcca gcagctggag cgacaaaaca aggagctgaa
5641 ggccaagctg caggagctgg agggggcagt caagtccaag ttcaaggcta ccatctcagc
5701 cctggaagcc aagattgggc agctggagga gcagcttgag caggaagcca aggagcgagc
5761 agctgccaac aaactagtcc gtcgaacaga gaagaaactg aaagaaatct tcatgcaggt
5821 tgaagacgag cgtcggcatg cggatcagta taaggagcag atggagaagg ctaatgccag
5881 gatgaagcag cttaaacgac agttggaaga ggctgaggaa gaggccacac gtgccaacgc
5941 atctcggcgt aaactccaaa gggagctgga cgacgccact gaggccaatg aaggcctgag
6001 ccgcgaggtc agcactctca agaaccggct caggcggggc ggtccaatca gcttttcttc
6061 aagccgatct ggccggcgcc agctgcacat tgagggggca tcgctagagc tgtcagatga
6121 cgacacagaa agtaagacca gtgatgtcaa tgacacacag ccaccccaat cagaataggc
6181 acaggaggtc agaggtgatg ctgaggacag gccagaactc atcccagcac cagtctgctt
6241 gagccctgca ctcactgctc gggaatggca agctcccaga ttccttccag gaaagtcaac
6301 tgtgtcttaa ggctttgcgg cctgcgcaga ctatatcctg cttcagacta gatacaattg
6361 ccccttttta tatatacacc tccacaagac atgcgtatta aacagattgt ctcatcgttg
6421 catctatttt ccatgtattc atcaagagac cattttatga cacattaaga agaaagaacc
6481 tttttgaaac aaactccagg ccctttgttg ccagtggctg ggcctaaggg ttgccccggg
6541 accgtgctca gctgctctgc atgccctgtc ctactgacag gtaccttagt tctgtgttca
```

```
6601 tgtggccctg acccttcctt caaccacacc tggtctctta gaacattgtg aacctaacct
6661 gcacttgtgt ctctcatttc ctgtgaatag tgatcactgt ctcagtgagc aaactgggag
6721 aggggctttg gcggcttagg ggtgggtttg gattggggaa gcagcatcca tttggggttc
6781 tcctgcccat ctcccaaggg gtgaccctgc ccctcaaatt catggtgtcc ccaccgtctc
6841 aatgtgaata gtctcagagc tctgtgcaca gagaggacag tggccacaac acataaggtg
6901 ccccgggtgg cagccatcac agtaacttcc aggtggtctc ctgagtgtct ggcttgataa
6961 tgccctcaat tcaggagtga gcctctgtga ccccttggggt gctcgcagaa ggcctctcca
7021 agcagtcaag ccctcttgca aattcagcca ctgctttgag cccaaaacgg gaatattagt
7081 tttatgtcgg aggtgtgttc caagtttgtc aatgaggcta tagcctcaag aagatgccat
7141 ctgcctgaat gttgacatgc cagcgggcgt gtgacccttc attttccctt tcccttcctt
7201 tggacagtgt tacaatgaac acttagcatt ctgtttttgg ttgatagttg agcaaactga
7261 cattacagaa agtgccttag acactacagt actaagacaa tgttaaatat attatttgcc
7321 tctataacaa cttaatgtat taagttctga ctgtgcttca tatcatgtac ctctctagtg
7381 aagtagatgc gcaaacattc agtgacagca aatcagtgtt agtgacaagc cccgaccgtg
7441 gcgatgtgct ggaaaacacg gacctttttgg gttaaaagct ttaacatctg tgaggaagaa
7501 ctggtcacat gggtttggaa tctttgattt cccctgtatg aattgtactg gctgttgacc
7561 accagacacc tgactgcaaa tatcttttct tgtattccca tatttctaga caatgatttt
7621 tgtaagacaa taaatttatt cattatagaa aaaaaaaaaa aaaaaa (SEQ ID NO: 51)
```

(B)

```
   1 maqrtgledp erylfvdrav iynpatqadw takklvwips erhgfeaasi keergdevmv
  61 elaengkkam vnkddiqkmn ppkfskvedm aeltclneas vlhnlkdryy sgliytysgl
 121 fcvvinpykn lpiyseniie myrgkkrhem pphiyaises ayrcmlqdre dqsilctges
 181 gagktentkk viqylahvas shkgrkdhni pgelerqllq anpilesfgn aktvkndnss
 241 rfgkfirinf dvtgyivgan ietylleksr avrqakdert fhifyqllsg agehlksdll
 301 legfnnyrfl sngyipipgq qdkdnfqetm eamhimgfsh eeilsmlkvv ssvlqfgnis
 361 fkkerntdqa smpentvaqk lchllgmnvm eftrailtpr ikvgrdyvqk aqtkeqadfa
 421 vealakatye rlfrwlvhri nkaldrtkrq gasfigildi agfeifelns feqlcinytn
 481 eklqqlfnht mfileqeeyq regiewnfid fgldlqpcid lierpanppg vlalldeecw
 541 fpkatdktfv eklvqeqgsh skfqkprqlk dkadfciihy agkvdykade wlmknmdpln
 601 dnvatllhqs sdrfvaelwk dvdrivgldq vtgmtetafg sayktkkgmf rtvgqlykes
 661 ltklmatlrn tnpnfvrcii pnhekragkl dphlvldqlr cngvlegiri crqgfpnriv
 721 fqefrqryei ltpnaipkgf mdgkqacerm iraleldpnl yrigqskiff ragvlahlee
 781 erdlkitdii iffqavcrgy larkafakkq qqlsalkvlq rncaaylklr hwqwwrvftk
 841 vkpllqvtrq eeelqakdee llkvkekqtk vegeleemer khqqlleekn ilaeqlqaet
 901 elfaeaeemr arlaakkqel eeilhdlesr veeeeernqi lqnekkkmqa hiqdleeqld
 961 eeegarqklq lekvtaeaki kkmeeevlll edqnskfike kklmedriae cssqlaeeee
1021 kaknlakirn kqevmisdle erlkkeektr qelekakrkl dgettdlqdq iaelqaqvde
1081 lkvqltkkee elqgalargd detlhknnal kvarelqaqi aelqedfese kasrnkaekq
1141 krdlseelea lkteledtld ttaaqqelrt kreqevaelk kaledetknh eaqiqdmrqr
1201 hataleelse qleqakrfka nleknkqgle tdnkelacev kvlqqvkaes ehkrkkldaq
1261 vqelhakvse gdrlrvelae kanklqneld nvstlleeae kkgikfakda aglesqlqdt
1321 qellqeetrq klnlssrirq leeeknslqe qqeeeeeark nlekqvlalq sqladtkkkv
1381 dddlgtiesl eeakkkllkd vealsqrlee kvlaydklek tknrlqqeld dltvdldhqr
1441 qivsnlekkq kkfdqllaee kgisaryaee rdraeaeare ketkalslar aleealeake
1501 eferqnkqlr admedlmssk ddvgknvhel ekskraleqq veemrtqlee ledelqated
1561 aklrlevnmq amkaqferdl qtrdeqneek krlllkqvre leaelederk qralavaskk
1621 kmeidlkdle aqieaankar devikqlrkl qaqmkdyqre leearasrde ifaqskesek
1681 klksleaeil qlqeelasse rarrhaeqer deladeians asgksallde krrleariaq
1741 leeeleeeqs nmellndrfr kttlqvdtln telaaersaa qksdnarqql erqnkelkak
1801 lqelegavks kfkatisale akigqleeql eqeakeraaa nklvrrtekk lkeifmqved
1861 errhadqyke qmekanarmk qlkrqleeae eeatranasr rklqrelddа teaneglsre
1921 vstlknrlrr ggpisfsssr sgrrqlhieg aslelsdddt esktsdvndt qppqse
(SEQ ID NO: 52)
```

```
   1 actgaggcgc tggatctgtg gtcgcggctg gggacgtgcg cccgcgccac catcttcggc
  61 tgaagaggca attgcttttg gatcgttcca tttacaatgg cgcagagaac tggactcgag
 121 gatccagaga ggtatctctt tgtggacagg gctgtcatct acaaccctgc cactcaagct
 181 gattggacag ctaaaaagct agtgtggatt ccatcagaac gccatggttt tgaggcagct
 241 agtatcaaag aagaacgggg agatgaagtt atggtggagt tggcagagaa tggaaagaaa
 301 gcaatggtca acaaagatga tattcagaag atgaacccac ctaagttttc caaggtggag
 361 gatatggcag aattgacatg cttgaatgaa gcttccgttt tacataatct gaaggatcgc
 421 tactattcag gactaatcta tacttattct ggactcttct gtgtagttat aaacccttac
 481 aagaatcttc caatttactc tgagaatatt attgaaatgt acagagggaa gaagcgtcat
 541 gagatgcctc cacacatcta tgctatatct gaatctgctt acagatgcat gcttcaagat
 601 cgtgaggacc agtcaattct ttgcacgggt gagtcaggtg ctgggaagac agaaaataca
 661 aagaaagtta ttcagtacct tgcccatgtt gcttcttcac ataaaggaag aaaggaccat
 721 aatattcctg gggaacttga acggcagctt ttgcaagcaa atccaattct ggaatcattt
 781 ggaaatgcga agactgtgaa aaatgataac tcatctcgtt ttggcaaatt tattcggatc
 841 aactttgatg taactggcta tatcgttggg gccaacattg aaacatacct tctggaaaag
 901 tctcgtgctg ttcgtcaagc aaaagatgaa cgtacttttc atatctttta ccagttgtta
 961 tctggagcag gagaacacct aaagtctgat ttgcttcttg aaggatttaa taactacagg
1021 tttctctcca atggctatat tcctattccg ggacagcaag acaaagataa tttccaggag
1081 accatggaag caatgcacat aatgggcttc tcccatgaag agattctgtc aatgcttaaa
1141 gtagtatctt cagtgctaca gtttggaaat atttctttca aaaaggagag aaatactgat
1201 caagcttcca tgccagaaaa tacagttgcg cagaagctct gccatcttct tgggatgaat
1261 gtgatggagt ttactcgggc catcctgact ccccggatca aggtcggccg agactatgtg
1321 caaaaagccc agaccaaaga acaggcagat tttgcagtag aagcattggc aaaagctacc
1381 tatgagcggc tctttcgctg gctcgttcat cgcatcaata aagctctgga taggaccaaa
1441 cgtcagggag catctttcat tggaatcctg gatattgctg gatttgaaat ttttgagctg
1501 aactcctttg aacaactttg catcaactac accaatgaga agctgcagca gctgttcaac
1561 cacaccatgt ttatcctaga acaagaggaa taccagcgcg aaggcatcga gtggaacttc
1621 atcgatttcg ggctggatct gcagccatgc atcgacctaa tagagagacc tgcgaaccct
1681 cctggtgtac tggccctttt ggatgaagaa tgctggttcc ctaaagccac agataaaacc
1741 tttgttgaaa aactggttca agagcaaggt tcccactcca agtttcagaa acctcgacaa
1801 ttaaaagaca aagctgattt ttgcattata cattatgcag ggaaggtgga ctataaggca
1861 gatgagtggc tgatgaagaa tatggacccc ctgaatgaca acgtggccac ccttttgcac
1921 cagtcatcag acagatttgt ggcagagctt tggaaagatg tggaccgtat cgtgggtctg
1981 gatcaagtca ctggtatgac tgagacagct tttggctccg catataaaac caagaagggc
2041 atgtttcgta ccgttgggca actctacaaa gaatctctca ccaagctgat ggcaactctc
2101 cgaaacacca accctaactt tgttcgttgt atcattccaa atcacgagaa gagggctgga
2161 aaattggatc cacacctagt cctagatcag cttcgctgta atggtgtcct ggaagggatc
2221 cgaatctgtc gccagggctt ccctaaccga atagttttcc aggaattcag acagagatat
2281 gagatcctaa ctccaaatgc tattcctaaa ggttttatgg atggtaaaca ggcctgtgaa
2341 cgaatgatcc gggctttaga attggaccca aacttgtaca gaattggaca gagcaagata
2401 tttttcagag ctggagttct ggcacactta gaggaagaaa gagatttaaa aatcaccgat
2461 atcattatct tcttccaggc cgtttgcaga ggttacctgg ccagaaaggc ctttgccaag
2521 aagcagcagc aactaagtgc cttaaaggtc ttgcagcgga actgtgccgc gtacctgaaa
2581 ttacggcact ggcagtggtg gcgagtcttc acaaaggtga agccgcttct acaagtgact
2641 cgccaggagg aagaacttca ggccaaagat gaagagctgt tgaaggtgaa ggagaagcag
2701 acgaaggtgg aaggagagct ggaggagatg gagcggaagc accagcagct tttagaagag
2761 aagaatatcc ttgcagaaca actacaagca gagactgagc tctttgctga agcagaagag
2821 atgagggcaa gacttgctgc taaaaagcag gaattagaag agattctaca tgacttggag
2881 tctagggttg aagaagaaga agaaagaaac caaatcctcc aaaatgaaaa gaaaaaaatg
2941 caagcacata ttcaggacct ggaagaacag ctagacgagg aggaaggggc tcggcaaaag
3001 ctgcagctgg aaaaggtgac agcagaggcc aagatcaaga agatggaaga ggagattctg
3061 cttctcgagg accaaaattc caagttcatc aaagaaaaga aactcatgga agatcgcatt
3121 gctgagtgtt cctctcagct ggctgaagag gaagaaaagg cgaaaaactt ggccaaaatc
```

```
3181 aggaataagc aagaagtgat gatctcagat ttagaagaac gcttaaagaa ggaagaaaag
3241 actcgtcagg aactggaaaa ggccaaaaga aaactcgacg gggagacgac cgacctgcag
3301 gaccagatcg cagagctgca ggcgcagatt gatgagctca agctgcagct ggccaagaag
3361 gaggaggagc tgcagggcgc actggccaga ggtgatgatg aaacactcca taagaacaat
3421 gcccttaaag ttgtgcgaga gctacaagcc caaattgctg aacttcagga agactttgaa
3481 tccgagaagg cttcacggaa caaggccgaa aagcagaaaa gggacttgag tgaggaactg
3541 gaagctctga aaacagagct ggaggacacg ctggacacca cggcagccca gcaggaacta
3601 cgtacaaaac gtgaacaaga agtggcagag ctgaagaaag ctcttgagga ggaaactaag
3661 aaccatgaag ctcaaatcca ggacatgaga caaagacacg caacagccct ggaggagctc
3721 tcagagcagc tggaacaggc caagcggttc aaagcaaatc tagagaagaa caagcagggc
3781 ctggagacag ataacaagga gctggcgtgt gaggtgaagg tcctgcagca ggtcaaggct
3841 gagtctgagc acaagaggaa gaagctcgac gcgcaggtcc aggagctcca tgccaaggtc
3901 tctgaaggcg acaggctcag ggtggagctg gcggagaaag caagtaagct gcagaatgag
3961 ctagataatg tctccaccct tctggaagaa gcagagaaga agggtattaa atttgctaag
4021 gatgcagcta gtcttgagtc tcaactacag gatacacagg agcttcttca ggaggagaca
4081 cgccagaaac taaacctgag cagtcggatc cggcagctgg aagaggagaa gaacagtctt
4141 caggagcagc aggaggagga ggaggaggcc aggaagaacc tggagaagca agtgctggcc
4201 ctgcagtccc agttggctga taccaagaag aaagtagatg acgacctggg aacaattgaa
4261 agtctggaag aagccaagaa gaagcttctg aaggacgcgg aggccctgag ccagcgcctg
4321 gaggagaagg cactggcgta tgacaaactg gagaagacca agaaccgcct gcagcaggag
4381 ctggacgacc tcacggtgga cctggaccac cagcgccagg tcgcctccaa cttggagaag
4441 aagcagaaga agtttgacca gctgttagca gaagagaaga gcatctctgc tcgctatgcc
4501 gaagagcggg accgggccga agccgaggcc agagagaaag aaaccaaagc cctgtcactg
4561 gcccgggccc tcgaggaagc cctggaggcc aaggaggagt ttgagaggca gaacaagcag
4621 ctccgagcag acatggaaga cctcatgagc tccaaagatg atgtgggaaa aaacgttcac
4681 gaacttgaaa aatccaaacg ggccctagag cagcaggtgg aggaaatgag gacccagctg
4741 gaggagctgg aagacgaact ccaggccacg gaagatgcca agcttcgtct ggaggtcaac
4801 atgcaggcca tgaaggcgca gttcgagaga gacctgcaaa ccagggatga gcagaatgaa
4861 gagaagaagc ggctgctgat caaacaggtg cgggagctcg aggcggagct ggaggatgag
4921 aggaaacagc gggcgcttgc tgtagcttca aagaaaaaga tggagataga cctgaaggac
4981 ctcgaagccc aaatcgaggc tgcgaacaaa gctcgggatg aggtgattaa gcagctccgc
5041 aagctccagg ctcagatgaa ggattaccaa cgtgaattag aagaagctcg tgcatccaga
5101 gatgagattt ttgctcaatc caaagagagt gaaaagaaat tgaagagtct ggaagcagaa
5161 atccttcaat tgcaggagga acttgcctca tctgagcgag cccgccgaca cgccgagcag
5221 gagagagatg agctggcgga cgagatcacc aacagcgcct ctggcaagtc cgcgctgctg
5281 gatgagaagc ggcgtctgga agctcggatc gcacagctgg aggaggagct ggaagaggag
5341 cagagcaaca tggagctgct caacgaccgc ttccgcaaga ccactctaca ggtggacaca
5401 ctgaacgccg agctagcagc cgagcgcagc gccgcccaga agagtgacaa tgcacgccag
5461 caactggagc ggcagaacaa ggagctgaag gccaagctgc aggaactcga gggtgctgtc
5521 aagtctaagt tcaaggccac catctcagcc ctggaggcca agattgggca gctggaggag
5581 cagcttgagc aggaagccaa ggaacgagca gccgccaaca aattagtccg tcgcactgag
5641 aagaagctga aagaaatctt catgcaggtt gaggatgagc gtcgacacgc ggaccagtat
5701 aaagagcaga tggagaaggc caacgctcgg atgaagcagc ttaaacgcca gctggaggaa
5761 gcagaagaag aagcgacgcg tgccaacgca tctcggcgta aactccagcg ggaactggat
5821 gatgccaccg aggccaacga gggcctgagc cgcgaggtca gcaccctgaa gaaccggctg
5881 aggcggggtg gccccatcag cttctcttcc agccgatctg gccggcgcca gctgcacctt
5941 gaaggagctt ccctggagct ctccgacgat gacacagaaa gtaagaccag tgatgtcaac
6001 gagacgcagc caccccagtc agagtaaagt tgcaggaagc cagaggaggc aatacagtgg
6061 gacagttagg aatgcacccg gggcctcctg cagatttcgg aaattggcaa gctacgggat
6121 tccttcctga aagatcaact gtgtcttaag gctctccagc ctatgcatac tgtatcctgc
6181 ttcagactta ggtacaattg ctcccctttt tatatataga cacacacagg acacatatat
6241 taaacagatt gtttcatcat tgcatctatt ttccatatag tcatcaagag accattttat
6301 aaaacatggt aagacccttt ttaaaacaaa ctccaggccc ttggttgcgg gtcgctgggt
6361 tattggggca gcgccgtggt cgtcactcag tcgctctgca tgctctctgt catacagaca
6421 ggtaacctag ttctgtgttc acgtggcccc cgactcctca gccacatcaa gtctcctaga
6481 ccactgtgga ctctaaactg cacttgtctc tctcatttcc ttcaaataat gatcaatgct
6541 atttcagtga gcaaactgtg aaaggggctt tggaaagagt aggaggggtg ggctggatcg
```

```
6601 gaagcaacac ccatttgggg ttaccatgtc catcccccaa ggggggccct gcccctcgag
6661 tcgatggtgt cccgcatcta ctcatgtgaa ctggccttgg cgagggctgg tctgtgcata
6721 gaagggatag tggccacact gcagctgagg ccccaggtgg cagccatgga tcatgtagac
6781 ttccagatgg tctcccgaac cgcctggctc tgccggcgcc ctcctcacgt caggagcaag
6841 cagccgtgga cccctaagcc gagctggtgg aaggcccctc cctgtcgcca gccgggccct
6901 catgctgacc ttgcaaattc agccgctgct ttgagcccaa aatgggaata ttggttttgt
6961 gtccgaggct tgttccaagt ttgtcaatga ggtttatgga gcctccagaa cagatgccat
7021 cttcctgaat gttgacatgc cagtgggtgt gactccttca tttttccttc tcccttccct
7081 ttggacagtg ttacagtgaa cacttagcat cctgtttttg gttggtagtt aagcaaactg
7141 acattacgga aagtgcctta gacactacag tactaagaca atgttgaata tatcattcgc
7201 ctctataaca atttaatgta ttcagttttg actgtgcttc atatcatgta cctctctagt
7261 caaagtggta ttacagacat tcagtgacaa tgaatcagtg ttaattctaa atccttgatc
7321 ctctgcaatg tgcttgaaaa cacaaacctt ttgggttaaa agctttaaca tctattagga
7381 agaatttgtc ctgtgggttt ggaatcttgg attttccccc tttatgaact gtactggctg
7441 ttgaccacca gacacctgac cgcaaatatc ttttcttgta ttcccatatt tctagacaat
7501 gatttttgta agacaataaa tttattcatt atagatattt gcgcctgctc tgtttacttg
7561 aagaaaaaag cacccgtgga gaataaagag acctcaataa acaagaataa tcatgtgaa
(SEQ ID NO: 53)
```

(B)

```
   1 maqrtgledp erylfvdrav iynpatqadw takklvwips erhgfeaasi keergdevmv
  61 elaengkkam vnkddiqkmn ppkfskvedm aeltclneas vlhnlkdryy sgliytysgl
 121 fcvvinpykn lpiyseniie myrgkkrhem pphiyaises ayrcmlqdre dqsilctges
 181 gagktentkk viqylahvas shkgrkdhni pgelerqllq anpilesfgn aktvkndnss
 241 rfgkfirinf dvtgyivgan ietylleksr avrqakdert fhifyqllsg agehlksdll
 301 legfnnyrfl sngyipipgq qdkdnfqetm eamhimgfsh eeilsmlkvv ssvlqfgnis
 361 fkkerntdqa smpentvaqk lchllgmnvm eftrailtpr ikvgrdyvqk aqtkeqadfa
 421 vealakatye rlfrwlvhri nkaldrtkrq gasfigildi agfeifelns feqlcinytn
 481 eklqqlfnht mfileqeeyq regiewnfid fgldlqpcid lierpanppg vlalldeecw
 541 fpkatdktfv eklvqeqgsh skfqkprqlk dkadfciihy agkvdykade wlmknmdpln
 601 dnvatllhqs sdrfvaelwk dvdrivgldq vtgmtetafg saykt kkgmf rtvgqlykes
 661 ltklmatlrn tnpnfvrcii pnhekragkl dphlvldqlr cngvlegiri crqgfpnriv
 721 fqefrqryei ltpnaipkgf mdgkqacerm iraleldpnl yrigqskiff ragvlahlee
 781 erdlkitdii iffqavcrgy larkafakkq qqlsalkvlq rncaaylklr hwqwwrvftk
 841 vkpllqvtrq eeelqakdee llkvkekqtk vegeleemer khqqlleekn ilaeqlqaet
 901 elfaeaeemr arlaakkqel eeilhdlesr veeeeernqi lqnekkkmqa hiqdleeqld
 961 eeegarqklq lekvtaeaki kkmeeeilll edqnskfike kklmedriae cssqlaeeee
1021 kaknlakirn kqevmisdle erlkkeektr qelekakrkl dgettdlqdq iaelqaqide
1081 lklqlakkee elqgalargd detlhknnal kvvrelqaqi aelqedfese kasrnkaekq
1141 krdlseelea lkteledtld ttaaqqelrt kreqevaelk kaleeetknh eaqiqdmrqr
1201 hataleelse qleqakrfka nleknkqgle tdnkelacev kvlqqvkaes ehkrkkldaq
1261 vqelhakvse gdrlrvelae kasklqneld nvstlleeae kkgikfakda aslesqlqdt
1321 qellqeetrq klnlssrirq leeeknslqe qqeeeeeark nlekqvlalq sqladtkkkv
1381 dddlgtiesl eeakkkllkd aealsqrlee kalaydklek tknrlqqeld dltvdldhqr
1441 qvasnlekkq kkfdqllaee ksisaryaee rdraeaeare ketkalslar aleealeake
1501 eferqnkqlr admedlmssk ddvgknvhel ekskraleqq veemrtqlee ledelqated
1561 aklrlevnmq amkaqferdl qtrdeqneek krllikqvre leaelederk qralavaskk
1621 kmeidlkdle aqieaankar devikqlrkl qaqmkdyqre leearasrde ifaqskesek
1681 klksleaeil qlqeelasse rarrhaeqer deladeitns asgksallde krrleariaq
1741 leeeleeeqs nmellndrfr kttlqvdtln aelaaersaa qksdnarqql erqnkelkak
1801 lqelegavks kfkatisale akigqleeql eqeakeraaa nklvrrtekk lkeifmqved
1861 errhadqyke qmekanarmk qlkrqleeae eeatranasr rklqreldda teaneglsre
1921 vstlknrlrr ggpisfsssr sgrrqlhleg aslelsdddt esktsdvnet qppqse
(SEQ ID NO: 54)
```

```
   1 cctttctgt  ccaggccgag gcctctggac cgccctgggc gccgaccatg gctgcagtga
  61 ccatgtccgt gtctgggagg aaggtagcct ccaggccagg cccggtgcct gaggcagccc
 121 aatcgttcct ctacgcgccc cggacgccaa atgtaggtgg ccctggaggg ccacaggtgg
 181 agtggacagc ccggcgcatg gtgtgggtgc cctcggaact gcatgggttc gaggcagcag
 241 ccctgcggga tgaaggggag gaggaggcag aagtggagct ggcggagagt gggcgccgcc
 301 tgcggctgcc cagggaccag atccagcgca tgaacccacc caagttcagc aaggcagaag
 361 atatggctga gctcacctgc ctcaacgagg cctcggtcct gcacaacctg cgagaacgct
 421 actactccgg gctcatttat acctactctg gcctcttctg tgtggtcatt aacccataca
 481 agcagctgcc catctacacg gaggccattg ttgaaatgta ccggggcaag aagcgccatg
 541 aggtgccacc tcacgtgtat gctgtgacgg agggcgcgta ccgcagcatg cttcaggatc
 601 gtgaggatca atccattctc tgcacgggag agtctggcgc tgggaagacg gagaacacca
 661 agaaggtcat ccagtacctg gcccatgtgg catcatctcc aaagggcagg aaggagcctg
 721 gtgtccctgc ctccgtcagc accatgtctt atggggagct agagcgtcag cttcttcaag
 781 ccaaccccat cctagaggcc tttggcaatg ccaagacagt gaagaacgac aactcttccc
 841 gatttggcaa attcatccgc atcaactttg atattgctgg ctacatcgtg ggagcaaaca
 901 tcgagaccta tctgttggag aagtcccggg ccatcagaca ggccaaggat gaatgcagct
 961 tccatatctt ctaccagctg ctagggggcg ctggggagca gctaaaagct gacctccttc
1021 tggagccctg ttcccattat cgcttcctga ccaatgggcc ctcatcgtcc ccgggccagg
1081 agcgtgagtt attccaggag accctggagt ccctgcgtgt gctgggcctc ctcccagaag
1141 agatcactgc catgctgcgc actgtctctg ctgtcctcca gtttggcaac attgtcctga
1201 agaaagagcg caatacggac caagccacca tgcctgacaa cacagctgcc cagaagcttt
1261 gccgcctctt gggactcgga gtgaccgact tctccagagc ccttctcaca ccccgcatca
1321 aagtgggccg agattatgtt cagaaagcac aaaccaagga gcaggctgac tttgcgctgg
1381 aggctctggc caaagctacc tatgagcgcc tgttccgctg gctggttctg cggctcaacc
1441 gtgccctgga cagaagcccg cggcagggtg cctccttcct gggcatcctg gacatcgcgg
1501 gctttgagat cttccagctg aactccttcg agcagctgtg catcaactac accaacgaga
1561 agctacagca gctattcaac cacaccatgt tcgtgctgga gcaggaggag taccagcgag
1621 agggcatccc ctggaccttc ctagacttcg ggttggacct gcaaccttgc atcgacctca
1681 ttgagcgtcc ggccaaccct ccaggtctcc tggccctgct ggacgaggag tgctggttcc
1741 ccaaggccac ggacaagtct tttgtggaga aggtcgccca ggagcagggc agccacccca
1801 aattccagcg ccccaggaac ctgcgagatc aggccgactt cagcgtcctg cactatgccg
1861 gcaaggttga ctacaaagcc agtgagtggc tgatgaagaa catggaccca ctgaatgaca
1921 atgtggccgc cttgcttcac cagagcacgg atcgtctcac agctgagatc tggaaggatg
1981 tggagggcat cgtggggctg gagcaagtaa gcagccttgg agatggccca ccgggaggcc
2041 gcccccgccg tggaatgttc cggactgtgg ggcagctcta caaagaatcc ctgagccgcc
2101 tcatggccac gctcagcaac accaacccta gttttgtccg ctgcatcgtt cccaatcatg
2161 agaagagggc tggaaagctg gagccgcgcc tggtgctgga ccaactccgt tgtaacgggg
2221 tcctcgaggg tatacgcatc tgtcgccaag gcttccccaa ccgcatcctc ttccaggagt
2281 tccgacagcg ctatgaaatc ctcaccccga acgctattcc caagggcttc atggacggca
2341 aacaggcctg tgagaagatg atccaggccc tggagctaga ccccaacctg taccgtgttg
2401 gccaaagcaa gatcttcttc cgggcagggg tcctggccca gctggaggag gagcgggacc
2461 tgaaagtcac cgacatcata gtgtctttcc aggcagcggc acggggctac ctggcccgta
2521 gggctttcca gagacggcag cagcagcaga gtgctctgag ggtgatgcag agaaactgtg
2581 ctgcctacct caagctcagg aactggcagt ggtggaggct gttcatcaag gtgaagcccc
2641 tgctgcaggt gacacggcag gatgaggtgc tgcaggcgcg cgcccaggag ctgcagaaag
2701 ttcaggagct gcagcagcag agcgctcgtg aagtggggga actgcagggt cgagtggcac
2761 agctagagga ggagcgcacg cgcctggctg agcagcttcg agcagaagcc gagctctgct
2821 ctgaggccga ggagacgcgg gcgcgactgg ctgcccggaa gcaggagctg gagctggtgg
2881 tgacagagct ggaggcacga gtgggcgagg aagaagagtg cagccggcag ctgcagagtg
2941 agaagaagag gctgcagcag catatccagg agctagagag ccacctggaa gctgaggagg
3001 gtgcccggca gaagctacag ctggagaagg tgaccacaga ggccaagatg aagaaatttg
3061 aggaggacct gctgctcctg gaggaccaga attccaagct gagcaaggag cggaggctgc
3121 tggaggagcg gctggctgag ttctcctcac aggcagcaga agaggaagag aaagtcaaaa
```

```
3181 gtctcaacaa gctgaggctc aaatatgaag ccacaatctc agacatggaa gaccggctga
3241 agaaggagga gaagggacgc caggaactag agaagctgaa gcgacggctg gacggggaga
3301 gctcagagct tcaggagcag atggtggagc agaagcagag ggcagaggaa ctgctcgcac
3361 agctgggccg caaggaggat gagctgcagg ccgccctgct cagggcagag gaagagggtg
3421 gtgcccgtgc ccagttgctc aagtccctgc gagaggcaca ggctggcctt gctgaggctc
3481 aggaggacct ggaagctgag cgggtagcca gggccaaggc ggagaagcag cgccgggacc
3541 tgggcgagga gttggaggcc ctacgtgggg agctcgagga cactctggat tccaccaacg
3601 cccagcagga gctgcggtcc aagagggagc aggaggtgac agagctgaag aaagcattgg
3661 aagaggagtc ccgtgcccat gaggtgtcca tgcaggagct gagacagagg catagccagg
3721 cactggtgga gatggccgag cagttggagc aagcccggag gggcaaaggt gtgtgggaga
3781 agactcggct atccctggag gctgaggtgt ccgagctgaa ggccgagctg agcagcctgc
3841 agacctcgag acaggagggt gagcagaaga ggcgccgcct ggagtcccag ctacaggagg
3901 tccagggccg atccagtgat tcggagcggg ctcggtctga ggctgctgag aagctgcaga
3961 gagcccaggc ggaacttgag agcgtgtcca cagccctgag tgaggcggag tccaaagcca
4021 tcaggctggg caaggagctg agcagtgcag agtcccagct gcatgacacc caggaactgc
4081 ttcaggagga gaccagggca aagctggcct tggggtcccg tgtgcgtgcc ctagaggccg
4141 aggcggcggg gcttcgggag cagatggaag aggaggtggt tgccagggaa cgggctggcc
4201 gggagctgca gagcacgcag gcccagctct ctgaatggcg gcgccgccag gaagaagagg
4261 ctgcggtgct ggaggctggg gaggaggctc ggcgccgtgc agcccgggag gcagagaccc
4321 tgacccagcg cctggcagaa aagactgagg ctgtagaacg actggagcga gcccggcgcc
4381 gactgcagca ggagttggac gatgccactg tggatctggg gcagcagaag cagctcctga
4441 gcacactgga gaagaagcag cggaaatttg accagctcct ggcagaggag aaggctgcag
4501 ttctacgggc tgtggaagac cgtgaacgga tagaggccga aggccgggag cgagaggccc
4561 gggccctgtc gctgacccgg gccctggaag aggagcagga ggcccgggag gagctggaga
4621 ggcagaaccg tgctctgagg gctgagctgg aagcactgct gagcagcaag gatgacgtgg
4681 gcaagaacgt gcacgagctg gagcgagccc gtaaggcggc tgaacaggca gccagtgacc
4741 tgcggacaca ggtgacagaa ttggaggatg agctgacagc cgcagaggat gccaagctgc
4801 gcctggaggt gactgtgcag gctctgaagg ctcaacatga acgcgacctg cagggccgcg
4861 atgatgccgg tgaggagagg cggaggcagc tggccaagca gctaagagac gcagaggtag
4921 agcgcgatga ggaacggaag cagagggcac tggctatggc tgcccgcaag aagctggagc
4981 tggaactgga ggagttgaag gcgcagacat ctgctgctgg gcagggcaag gaagaggcag
5041 tgaagcagct gaagaagatg caggtccaga tgaaggagct gtggcgggag gtagaggaga
5101 cgcgtagctc ccgcgacgag atgtttaccc tgagcaggga aaatgagaag aagctcaagg
5161 ggctggaagc tgaggtgctg cgtctgcaag aggaacttgc tgcctcagac cgagcccgga
5221 ggcaggccca gcaagacaga gacgagatgg cagaggaggt ggccagtggc aatcttagca
5281 aggcagccac cctggaggaa aaacggcagc tggaggggcg actgagccag ttggaagagg
5341 agctggagga agaacagaac aactcggagc tgctcaagga ccattaccga aagctagtgc
5401 tacaggtcga gtccctcacc acagaactgt ctgccgaacg aagtttctca gccaaggccg
5461 agagtggacg gcagcagctg gagcggcaga tccaggaact gcgggcccgc ttgggtgaag
5521 aggatgctgg agcccgagcc aggcagaaaa tgctgatcgc tgctctggag tctaaactgg
5581 cccaggcaga ggagcagctg gagcaggaga gcagggagcg catcctctct ggcaagctgg
5641 tacgcagagc tgagaagcgg ctgaaggagg tagttcttca ggtggatgaa gagcgcaggg
5701 tggctgacca ggtccgggac cagctggaga aaagcaacct ccggctgaag cagctcaaga
5761 ggcagctgga ggaggcagag gaggaggcat ctcgggcaca ggctggtcgg aggcggctgc
5821 agcgggagct ggaggacgtc actgagtctg cagaatccat gaaccgggag gtgaccacgc
5881 tgaggaacag gctccggcgt ggcccactta cattcaccac acggactgtg cgccaggtgt
5941 tccggctgga agagggcgtg gcttctgacg aggaagaggc tgaaggagct gaacctggct
6001 ctgcaccagg ccaggagccg gaggctccgc cccctgccac accccaatga tccagtctgt
6061 cctagatgcc ccaaggacag agccctttcc agtgcccctc ctggtttgca ctttgaaatg
6121 gcactgtcct ctggcacttt ctggcattga tgaaccctcc tgggacccca ggacccctgc
6181 ccactggggg ccccaaacca aggagctggg tgggagggag gccatgatgg tctctcttgt
6241 tagagaaaca aaattgaacg tggatgtcaa gaatgtcctg tctgcaccta ttttcagcag
6301 gcctgtcccc tggagagggc aggcagggtg cttccatccc ctctcagtat cttgccctct
6361 tttttggggg gaagtggggt gtctgtgtgc tcatagggta atgctcatgg cccctcatgc
6421 tccagacact aaagaaataa aa (SEQ ID NO: 55)
```

(B)

```
   1 maavtmsvsg rkvasrpgpv peaaqsflya prtpnvggpg gpqvewtarr mvwvpselhg
  61 feaaalrdeg eeeaevelae sgrrlrlprd qiqrmnppkf skaedmaelt clneasvlhn
 121 lreryysgli ytysglfcvv inpykqlpiy teaivemyrg kkrhevpphv yavtegayrs
 181 mlqdredqsi lctgesgagk tentkkviqy lahvasspkg rkepgvpasv stmsygeler
 241 qllqanpile afgnaktvkn dnssrfgkfi rinfdiagyi vganietyll eksrairqak
 301 decsfhifyq llggageqlk adlllepcsh yrfltngpss spgqerelfq etleslrvlg
 361 llpeeitaml rtvsavlqfg nivlkkernt dqatmpdnta aqklcrllgl gvtdfsrall
 421 tprikvgrdy vqkaqtkeqa dfalealaka tyerlfrwlv lrlnraldrs prqgasflgi
 481 ldiagfeifq lnsfeqlcin ytneklqqlf nhtmfvleqe eyqregipwt fldfgldlqp
 541 cidlierpan ppgllallde ecwfpkatdk sfvekvaqeq gshpkfqrpr nlrdqadfsv
 601 lhyagkvdyk asewlmknmd plndnvaall hqstdrltae iwkdvegivg leqvsslgdg
 661 ppggrprrgm frtvgqlyke slsrlmatls ntnpsfvrci vpnhekragk leprlvldql
 721 rcngvlegir icrqgfpnri lfqefrqrye iltpnaipkg fmdgkqacek miqaleldpn
 781 lyrvgqskif fragvlaqle eerdlkvtdi ivsfqaaarg ylarrafqrr qqqqsalrvm
 841 qrncaaylkl rnwqwwrlfi kvkpllqvtr qdevlqaraq elqkvqelqq qsarevgelq
 901 grvaqleeer trlaeqlrae aelcseaeet rarlaarkqe lelvvtelea rvgeeeecsr
 961 qlqsekkrlq qhiqeleshl eaeegarqkl qlekvtteak mkkfeedlll ledqnsklsk
1021 errlleerla efssqaaeee ekvkslnklr lkyeatisdm edrlkkeekg rqeleklkrr
1081 ldgesselqe qmveqkqrae ellaqlgrke delqaallra eeeggaraql lkslreaqag
1141 laeaqedlea ervarakaek qrrdlgeele alrgeledtl dstnaqqelr skreqevtel
1201 kkaleeesra hevsmqelrq rhsqalvema eqleqarrgk gvwektrlsl eaevselkae
1261 lsslqtsrqe geqkrrrles qlqevqgrss dserarseaa eklqraqael esvstalsea
1321 eskairlgke lssaesqlhd tqellqeetr aklalgsrvr aleaeaaglr eqmeeevvar
1381 eragrelqst qaqlsewrrr qeeeaavlea geearrraar eaetltqrla ekteaverle
1441 rarrrlqqel ddatvdlgqq kqllstlekk qrkfdqllae ekaavlrave drerieaegr
1501 erearalslt raleeeqear eelerqnral raeleallss kddvgknvhe lerarkaaeq
1561 aasdlrtqvt eledeltaae daklrlevtv qalkaqherd lqgrddagee rrrqlakqlr
1621 daeverdeer kqralamaar kkleleleel kaqtsaagqg keeavkqlkk mqvqmkelwr
1681 eveetrssrd emftlsrene kklkgleaev lrlqeelaas drarrqaqqd rdemaeevas
1741 gnlskaatle ekrqlegrls qleeeleeeq nnsellkdhy rklvlqvesl ttelsaersf
1801 sakaesgrqq lerqiqelra rlgeedagar arqkmliaal esklaqaeeq leqesreril
1861 sgklvrraek rlkevvlqvd eerrvadqvr dqleksnlrl kqlkrqleea eeeasraqag
1921 rrrlqreled vtesaesmnr evttlrnrlr rgpltfttrt vrqvfrleeg vasdeeeaeg
1981 aepgsapgqe peapppatpq (SEQ ID NO: 56)
```

(C)

```
   1 ccgaccatgg ctgcagtgac catgtccgtg tctgggagga aggtagcctc caggccaggc
  61 ccggtgcctg aggcagccca atcgttcctc tacgcgcccc ggacgccaaa tgtaggtggc
 121 cctggagggc cacaggtgga gtggacagcc cggcgcatgg tgtgggtgcc ctcggaactg
 181 catgggttcg aggcagcagc cctgcgggat gaaggggagg aggaggcaga agtggagctg
 241 gcggagagtg ggcgccgcct gcggctgccc agggaccaga tccagcgcat gaacccaccc
 301 aagttcagca aggcagaaga tatggctgag ctcacctgcc tcaacgaggc ctcggtcctg
 361 cacaacctgc gagaacgcta ctactccggg ctcatttata cctactctgg cctcttctgt
 421 gtggtcatta acccatacaa gcagctgccc atctacacgg aggccattgt tgaaatgtac
 481 cggggcaaga agcgccatga ggtgccacct cacgtgtatg ctgtgacgga gggcgcgtac
 541 cgcagcatgc ttcaggatcg tgaggatcaa tccattctct gcacgggaga gtctggcgct
 601 gggaagacgg agaacaccaa gaaggtcatc cagtacctgg cccatgtggc atcatctcca
 661 aagggcagga aggagcctgg tgtccctggg gagctagagc gtcagcttct tcaagccaac
 721 cccatcctag aggcctttgg caatgccaag acagtgaaga acgacaactc ttccccgattt
 781 ggcaaattca tccgcatcaa ctttgatatt gctggctaca tcgtgggagc aaacatcgag
 841 acctatctgt tggagaagtc ccgggccatc agacaggcca aggatgaatg cagcttccat
 901 atcttctacc agctgctagg gggcgctggg gagcagctaa aagctgacct ccttctggag
```

```
 961 ccctgttccc attatcgctt cctgaccaat gggccctcat cgtccccggg ccaggagcgt
1021 gagttattcc aggagaccct ggagtccctg cgtgtgctgg gcctcctccc agaagagatc
1081 actgccatgc tgcgcactgt ctctgctgtc ctccagtttg gcaacattgt cctgaagaaa
1141 gagcgcaata cggaccaagc caccatgcct gacaacacag ctgcccagaa gctttgccgc
1201 ctcttgggac tcggagtgac cgacttctcc agagcccttc tcacaccccg catcaaagtg
1261 ggccgagatt atgttcagaa agcacaaacc aaggagcagg ctgactttgc gctggaggct
1321 ctggccaaag ctacctatga gcgcctgttc cgctggctgg ttctgcggct caaccgtgcc
1381 ctggacagaa gcccgcggca gggtgcctcc ttcctgggca tcctggacat cgcgggcttt
1441 gagatcttcc agctgaactc cttcgagcag ctgtgcatca actacaccaa cgagaagcta
1501 cagcagctat tcaaccacac catgttcgtg ctggagcagg aggagtacca gcgagagggc
1561 atcccctgga ccttcctaga cttcgggttg gacctgcaac cttgcatcga cctcattgag
1621 cgtccggcca accctccagg tctcctggcc ctgctggacg aggagtgctg gttccccaag
1681 gccacggaca agtcttttgt ggagaaggtc gcccaggagc agggcagcca ccccaaattc
1741 cagcgcccca ggaacctgcg agatcaggcc gacttcagcg tcctgcacta tgccggcaag
1801 gttgactaca aagccagtga gtggctgatg aagaacatgg acccactgaa tgacaatgtg
1861 gccgccttgc ttcaccagag cacggatcgt ctcacagctg agatctggaa ggatgtggag
1921 ggcatcgtgg ggctggagca agtaagcagc cttggagatg gcccaccggg aggccgcccc
1981 cgccgtggaa tgttccggac tgtggggcag ctctacaaag aatccctgag ccgcctcatg
2041 gccacgctca gcaacaccaa ccctagtttt gtccgctgca tcgttcccaa tcatgagaag
2101 agggctggaa agctggagcc gcgcctggtg ctggaccaac tccgttgtaa cggggtcctc
2161 gagggtatac gcatctgtcg ccaaggcttc cccaaccgca tcctcttcca ggagttccga
2221 cagcgctatg aaatcctcac cccgaacgct attcccaagg gcttcatgga cggcaaacag
2281 gcctgtgaga agatgatcca ggccctggag ctagacccca acctgtaccg tgttggccaa
2341 agcaagatct tcttccgggc aggggtcctg gcccagctgg aggaggagcg ggacctgaaa
2401 gtcaccgaca tcatagtgtc tttccaggca gcggcacggg gctacctggc ccgtagggct
2461 ttccagagac ggcagcagca gcagagtgct ctgagggtga tgcagagaaa ctgtgctgcc
2521 tacctcaagc tcaggaactg gcagtggtgg aggctgttca tcaaggtgaa gcccctgctg
2581 caggtgacac ggcaggatga ggtgctgcag gcgcgcgccc aggagctgca gaaagttcag
2641 gagctgcagc agcagagcgc tcgtgaagtg gggaactgcc agggtcgagt ggcacagcta
2701 gaggaggagc gcacgcgcct ggctgagcag cttcgagcag aagccgagct ctgctctgag
2761 gccgaggaga cgcgggcgcg actggctgcc cggaagcagg agctggagct ggtggtgaca
2821 gagctggagg cacgagtggg cgaggaagaa gagtgcagcc ggcagctgca gagtgagaag
2881 aagaggctgc agcagcatat ccaggagcta gagagccacc tggaagctga ggagggtgcc
2941 cggcagaagc tacagctgga gaaggtgacc acagaggcca agatgaagaa atttgaggag
3001 gacctgctgc tcctggagga ccagaattcc aagctgagca aggagcggag gctgctggag
3061 gagcggctgg ctgagttctc ctcacaggca gcagaagagg aagagaaagt caaaagtctc
3121 aacaagctga ggctcaaata tgaagccaca atctcagaca tggaagaccg gctgaagaag
3181 gaggagaagg gacgccagga actagagaag ctgaagcgac ggctggacgg ggagagctca
3241 gagcttcagg agcagatggt ggagcagaag cagagggcag aggaactgct cgcacagctg
3301 ggccgcaagg aggatgagct gcaggccgcc ctgctcaggg cagaggaaga gggtggtgcc
3361 cgtgcccagt tgctcaagtc cctgcgagag gcacaggctg gccttgctga ggctcaggag
3421 gacctggaag ctgagcgggt agccagggcc aaggcggaga agcagcgccg ggacctgggc
3481 gaggagttgg aggccctacg tggggagctc gaggacactc tggattccac caacgcccag
3541 caggagctgc ggtccaagag ggagcaggag gtgacagagc tgaagaaagc attggaagag
3601 gagtcccgtg cccatgaggt gtccatgcag gagctgagac agaggcatag ccaggcactg
3661 gtggagatgg ccgagcagtt ggagcaagcc cggagggggca aggtgtgtg ggagaagact
3721 cggctatccc tggaggctga ggtgtccgag ctgaaggccg agctgagcag cctgcagacc
3781 tcgagacagg agggtgagca gaagaggcgc cgcctggagt cccagctaca ggaggtccag
3841 ggccgatcca gtgattcgga gcgggctcgg tctgaggctg ctgagaagct gcagagagcc
3901 caggcggaac ttgagagcgt gtccacagcc ctgagtgagg cggagtccaa agccatcagg
3961 ctgggcaagg agctgagcag tgcagagtcc cagctgcatg acacccagga actgcttcag
4021 gaggagacca gggcaaagct ggccttgggg tcccgtgtgc gtgccctaga ggccgaggcg
4081 gcggggcttc gggagcagat ggaagaggag gtggttgcca gggaacgggc tggccgggag
4141 ctgcagagca cgcaggccca gctctctgaa tggcggcgcc gccaggaaga agaggccgcg
4201 gtgctggagg ctggggagga ggctcggcgc cgtgcagccc gggaggcaga gaccctgacc
4261 cagcgcctgg cagaaaagac tgaggctgta gaacgactgg agcgagcccg gcgccgactg
4321 cagcaggagt tggacgatgc cactgtggat ctggggcagc agaagcagct cctgagcaca
```

```
4381 ctggagaaga agcagcggaa atttgaccag ctcctggcag aggagaaggc tgcagttcta
4441 cgggctgtgg aagaccgtga acggatagag gccgaaggcc gggagcgaga ggcccgggcc
4501 ctgtcgctga cccgggccct ggaagaggag caggaggccc gggaggagct ggagaggcag
4561 aaccgtgctc tgagggctga gctggaagca ctgctgagca gcaaggatga cgtgggcaag
4621 aacgtgcacg agctggagcg agcccgtaag gcggctgaac aggcagccag tgacctgcgg
4681 acacaggtga cagaattgga ggatgagctg acagccgcag aggatgccaa gctgcgcctg
4741 gaggtgactg tgcaggctct gaaggctcaa catgaacgcg acctgcaggg ccgcgatgat
4801 gccggtgagg agaggcggag gcagctggcc aagcagctaa gagacgcaga ggtagagcgc
4861 gatgaggaac ggaagcagag ggcactggct atggctgccc gcaagaagct ggagctggaa
4921 ctggaggagt tgaaggcgca gacatctgct gctgggcagg gcaaggaaga ggcagtgaag
4981 cagctgaaga agatgcaggt ccagatgaag gagctgtggc gggaggtaga ggagacgcgt
5041 agctcccgcg acgagatgtt taccctgagc agggaaaatg agaagaagct caaggggctg
5101 gaagctgagg tgctgcgtct gcaagaggaa cttgctgcct cagaccgagc ccggaggcag
5161 gcccagcaag acagagacga gatggcagag gaggtggcca gtggcaatct tagcaaggca
5221 gccaccctgg aggaaaaacg gcagctggag ggcgactga gccagttgga agaggagctg
5281 gaggaagaac agaacaactc ggagctgctc aaggaccatt accgaaagct agtgctacag
5341 gtcgagtccc tcaccacaga actgtctgcc gaacgaagtt tctcagccaa ggccgagagt
5401 ggacggcagc agctggagcg gcagatccag gaactgcggg cccgcttggg tgaagaggat
5461 gctggagccc gagccaggca gaaaatgctg atcgctgctc tggagtctaa actggcccag
5521 gcagaggagc agctggagca ggagagcagg gagcgcatcc tctctggcaa gctggtacgc
5581 agagctgaga agcggctgaa ggaggtagtt cttcaggtgg atgaagagcg cagggtggct
5641 gaccaggtcc gggaccagct ggagaaaagc aacctccggc tgaagcagct caagaggcag
5701 ctggaggagg cagaggagga ggcatctcgg gcacaggctg gtcggaggcg gctgcagcgg
5761 gagctggagg acgtcactga gtctgcagaa tccatgaacc gggaggtgac cacgctgagg
5821 aacaggctcc ggcgtggccc acttacattc accacacgga ctgtgcgcca ggtgttccgg
5881 ctggaagagg gcgtggcttc tgacgaggaa gaggctgaag gagctgaacc tggctctgca
5941 ccaggccagg agccggaggc tccgcccccct gccacacccc aatgatccag tctgtcctag
6001 atgccccaag gacagagccc tttccagtgc ccctcctggt ttgcactttg aaatggcact
6061 gtcctctggc actttctggc attgatgaac cctcctggga ccccaggacc cctgccccact
6121 gggggcccca aaccaaggag ctgggtggga gggaggccat gatggtctct cttgttagag
6181 aaacaaaatt gaacgtggat gtcaagaatg tcctgtctgc acctattttc agcaggcctg
6241 tcccctggag agggcaggca gggtgcttcc atcccctctc agtatcttgc cctcttttttt
6301 gggggggaagt ggggtgtctg tgtgctcata gggtaatgct catggcccct catgctccag
6361 acactaaaga aataaaa  (SEQ ID NO: 57)
```

(D)

```
   1 maavtmsvsg rkvasrpgpv peaaqsflya prtpnvggpg gpqvewtarr mvwvpselhg
  61 feaaalrdeg eeeaevelae sgrrlrlprd qiqrmnppkf skaedmaelt clneasvlhn
 121 lreryysgli ytysglfcvv inpykqlpiy teaivemyrg kkrhevpphv yavtegayrs
 181 mlqdredqsi lctgesgagk tentkkviqy lahvasspkg rkepgvpgel erqllqanpi
 241 leafgnaktv kndnssrfgk firinfdiag yivganiety lleksrairq akdecsfhif
 301 yqllggageq lkadlllepc shyrfltngp ssspgqerel fqetleslrv lgllpeeita
 361 mlrtvsavlq fgnivlkker ntdqatmpdn taaqklcrll glgvtdfsra lltprikvgr
 421 dyvqkaqtke qadfaleala katyerlfrw lvlrlnrald rsprqgasfl gildiagfei
 481 fqlnsfeqlc inytneklqq lfnhtmfvle qeeyqregip wtfldfgldl qpcidlierp
 541 anppgllall deecwfpkat dksfvekvaq eqgshpkfqr prnlrdqadf svlhyagkvd
 601 ykasewlmkn mdplndnvaa llhqstdrlt aeiwkdvegi vgleqvsslg dgppggrprr
 661 gmfrtvgqly keslsrlmat lsntnpsfvr civpnhekra gkleprlvld qlrcngvleg
 721 iricrqgfpn rilfqefrqr yeiltpnaip kgfmdgkqac ekmiqaleld pnlyrvgqsk
 781 iffragvlaq leeerdlkvt diivsfqaaa rgylarrafq rrqqqsalr vmqrncaayl
 841 klrnwqwwrl fikvkpllqv trqdevlqar aqelqkvqel qqqsarevge lqgrvaqlee
 901 ertrlaeqlr aeaelcseae etrarlaark qelelvvtel earvgeeeec srqlqsekkr
 961 lqqhiqeles hleaeegarq klqlekvtte akmkkfeedl llledqnskl skerrlleer
1021 laefssqaae eeekvkslnk lrlkyeatis dmedrlkkee kgrqeleklk rrldgessel
```

```
1081 qeqmveqkqr aeellaqlgr kedelqaall raeeeggara qllkslreaq aglaeaqedl
1141 eaervaraka ekqrrdlgee lealrgeled tldstnaqqe lrskreqevt elkkaleees
1201 rahevsmqel rqrhsqalve maeqleqarr gkgvwektrl sleaevselk aelsslqtsr
1261 qegeqkrrrl esqlqevqgr ssdserarse aaeklqraqa elesvstals eaeskairlg
1321 kelssaesql hdtqellqee traklalgsr vraleaeaag lreqmeeevv areragrelq
1381 stqaqlsewr rrqeeeaavl eageearrra areaetltqr laekteaver lerarrrlqq
1441 elddatvdlg qqkqllstle kkqrkfdqll aeekaavlra vedrerieae grerearals
1501 ltraleeeqe areelerqnr alraeleall sskddvgknv helerarkaa eqaasdlrtq
1561 vteledelta aedaklrlev tvqalkaqhe rdlqgrddag eerrrqlakq lrdaeverde
1621 erkqralama arkklelele elkaqtsaag qgkeeavkql kkmqvqmkel wreveetrss
1681 rdemftlsre nekklkglea evlrlqeela asdrarrqaq qdrdemaeev asgnlskaat
1741 leekrqlegr lsqleeelee eqnnsellkd hyrklvlqve slttelsaer sfsakaesgr
1801 qqlerqiqel rarlgeedag ararqkmlia alesklaqae eqleqesrer ilsgklvrra
1861 ekrlkevvlq vdeerrvadq vrdqleksnl rlkqlkrqle eaeeeasraq agrrrlqrel
1921 edvtesaesm nrevttlrnr lrrgpltftt rtvrqvfrle egvasdeeea egaepgsapg
1981 qepeapppat pq (SEQ ID NO: 58)
```

```
   1 ctctttctcc ccaggccgaa gcctcgggac ggccctggaa gccgaccatg gcagccgtga
  61 ccatgtcggt gcccgggcgg aaggcgcccc ccaggccggg cccagtgccc gaggcggccc
 121 agccgttcct gttcacgccc cgcgggccca gcgcgggtgg cgggcctggc tcgggcacct
 181 ccccgcaggt ggagtggacg gcccggcgtc tcgtgtgggt gccttcggag cttcacgggt
 241 tcgaggcggc ggcgctgcgg gacgaaggcg aggaggaggc ggaggtggag ctggcggaga
 301 gcgggaggcg gctgcgactg ccgcgggacc agatccagcg catgaacccg cccaagttca
 361 gcaaggccga ggacatggcc gagctgacct gcctcaacga ggcctcggtc ctgcacaacc
 421 tccgggagcg gtactactcc ggcctcatct acacgtactc cggccttttc tgtgtggtca
 481 tcaacccgta caagcagctt cccatctaca cagaagccat tgtggagatg taccggggca
 541 agaagcgcca cgaggtgcca ccccacgtgt acgcagtgac cgaggggggcc tatcggagca
 601 tgctgcagga tcgtgaggac cagtccattc tctgcactgg agagtctgga gctgggaaga
 661 cggaaaacac caagaaggtc atccagtacc tcgcccacgt ggcatcgtct ccaaagggca
 721 ggaaggagcc gggtgtcccc ggtgagctgg agcggcagct gcttcaggcc aaccccatcc
 781 tagaggcctt tggcaatgcc aagacagtga agaatgacaa ctcctcccga ttcggcaaat
 841 tcatccgcat caactttgat gttgccgggt acatcgtggg cgccaacatt gagacctacc
 901 tgctggagaa gtcgcgggcc atccgccagg ccaaggacga gtgcagcttc cacatcttct
 961 accagctgct ggggggcgct ggagagcagc tcaaagccga cctcctcctc gagccctgct
1021 cccactaccg gttcctgacc aacgggccgt catcctctcc cggccaggag cgggaactct
1081 tccaggagac gctggagtcg ctgcgggtcc tgggattcag ccacgaggaa atcatctcca
1141 tgctgcggat ggtctcagca gttctccagt ttggcaacat tgccttgaag agagaacgga
1201 acaccgatca agccaccatg cctgacaaca cagctgcaca gaagctctgc cgcctcttgg
1261 gactgggggt gacggatttc tcccgagcct tgctcacccc tcgcatcaaa gttggccgag
1321 actatgtgca gaaagcccag actaaggaac aggctgactt cgcgctggag gccctggcca
1381 aggccaccta cgagcgcctc ttccgctggc tggttctgcg cctcaaccgg gccttggacc
1441 gcagcccccg ccaaggcgcc tccttcctgg gcatcctgga catcgcgggc tttgagatct
1501 tccagctgaa ctccttcgag cagctctgca tcaactacac caacgagaag ctgcagcagc
1561 tcttcaacca caccatgttc gtgctggagc aggaggagta ccagcgtgag ggcatcccct
1621 ggaccttcct cgactttggc ctcgacctgc agccctgcat cgacctcatc gagcggccgg
1681 ccaacccccc tggactcctg gccctgctgg atgaggagtg ctggttcccg aaggccacag
1741 acaagtcgtt tgtggagaag gtagcccagg agcagggcgg ccaccccaag ttccagcggc
1801 cgaggcacct gcgggatcag gccgacttca gtgttctcca ctacgcgggc aaggtcgact
1861 acaaggccaa cgagtggctg atgaaaaaca tggaccctct gaatgacaac gtcgcagcct
1921 tgctccacca gagcacagac cggctgacgg cagagatctg gaaagacgtg gagggcatcg
1981 tggggctgga acaggtgagc agcctgggcg acggcccacc aggtggccgc ccccgtcggg
2041 gtatgttccg gacagtggga cagctctaca aggagtccct gagccgcctc atggccacac
2101 tcagcaacac caaccccagt tttgtccggt gcattgtccc caaccacgag aagagggccg
2161 ggaagctgga gccacggctg gtgctggacc agcttcgctg caacggggtc ctggagggca
2221 tccgcatctg tcgccagggc ttccccaacc gcatcctctt ccaggagttc cggcagcgat
2281 acgagatcct gacacccaat gccatcccca agggcttcat ggatgggaag caggcctgtg
2341 aaaagatgat ccaggcgctg gaactggacc ccaacctcta ccgcgtggga cagagcaaga
2401 tcttcttccg ggctggggtc ctggcccagc tggaagagga gcgagacctg aaggtcaccg
2461 acatcatcgt ctccttccag gcagctgccc ggggatacct ggctcgcagg gccttccaga
2521 agcgccagca gcagcagagc gccctgaggg tgatgcagcg gaactgcgcg gcctacctca
2581 agctgagaca ctggcagtgg tggcggctgt ttaccaaggt gaagccactg ctgcaggtga
2641 cgcggcagga tgaggtgctg caggcacggg cccaggagct gcagaaagtg caggagctac
2701 agcagcagag cgcccgcgaa gttggggagc tccagggccg agtggcacag ctggaagagg
2761 agcgcgcccg cctggcagag caattgcgag cagaggcaga actgtgtgca gaggccgagg
2821 agacgcgggg gaggctggca gcccgcaagc aggagctgga gctggtggtg tcagagctgg
2881 aggctcgcgt gggcgaggag gaggagtgca gccgtcaaat gcaaaccgag aagaagaggc
2941 tacagcagca catacaggag ctagaggccc accttgaggc tgaggagggt gcgcggcaga
3001 agctgcagct ggagaaggtg acgacagagg caaaaatgaa gaaatttgaa gaggacctgc
3061 tgctcctgga agaccagaat tccaagctga gcaagagcgg aagctgctgg aagatcgtct
3121 ggccgagttc tcatcccagg cagctgagga ggaggagaag gtcaagagcc tcaataagct
```

```
3181 acggctcaaa tatgaggcca caatcgcaga catggaggga ccgcctacgg aaggaggaga
3241 agggtcgcca ggagctggag aagctgaagc ggaggctgga tggggagagc tcagagctgc
3301 aggagcagat ggtggagcag caacagcggg cagaggagct gcgggcccag ctgggccgga
3361 aggaggagga gctgcaggct gccctggcca gggcagaaga cgagggtggg gcccgggccc
3421 agctgctgaa atccctgcgg gaggctcaag cagccctggc cgaggcccag gaggacctgg
3481 agtctgagcg tgtggccagg accaaggcgg agaagcagcg ccgggacctg ggcgaggagc
3541 tggaggcgct gcggggcgag ctggaggaca cgctggactc caccaacgca cagcaggagc
3601 tccggtccaa gagggaacag gaggtgacgg agctgaagaa gactctggag gaggagactc
3661 gcatccacga ggcggcagtg caggagctga ggcagcgcca cggccaggcc ctgggggagc
3721 tggcggagca gctggagcag gcccggaggg gcaaaggtgc atgggagaag acccggctgg
3781 ccctggaggc cgaggtgtcc gagctgcggg cagaactgag cagcctgcag actgcacgtc
3841 aggagggtga gcagcggagg cgccgcctgg agttacagct gcaggaggtg cagggccggg
3901 ctggtgatgg ggagagggca cgagcggagg ctgctgagaa gctgcagcga gcccaggctg
3961 aactggagaa tgtgtctggg gcgctgaacg aggctgagtc caaaaccatc cgtcttagca
4021 aggagctgag cagcacagaa gcccagctgc acgatgccca ggagctgctg caggaggaga
4081 ccagggcgaa attggccttg ggtcccgggg tgcgagccat ggaggctgag gcagccgggc
4141 tgcgtgagca gctggaggag gaggcagctg ccagggaacg ggcgggccgt gaactgcaga
4201 ctgcccaggc ccagctttcc gagtggcggc ggcgccagga ggaggaggca ggggcactgg
4261 aggcagggga ggaggcacgg cgccgggcag cccgggaggc cgaggccctg acccagcgcc
4321 tggcagaaaa gacagagacc gtggatcggc tggagcgggg ccgccgccgg ctgcagcagg
4381 agctggacga cgccaccatg gacctggagc agcagcggca gcttgtgagc accctggaga
4441 agaagcagcg caagtttgac cagcttctgg cagaggagaa ggcagctgta cttcgggcag
4501 tggaggaacg tgagcgggcc gaggcagagg gccgggagcg tgaggctcgg gccctgtcac
4561 tgacacgggc actggaggag gagcaggagg cacgtgagga gctggagcgg cagaaccggg
4621 ccctgcgggc tgagctggag gcactgctga gcagcaagga tgacgtcggc aagagcgtgc
4681 atgagctgga acgagcctgc cgggtagcag aacaggcagc caatgatctg cgagcacagg
4741 tgacagaact ggaggatgag ctgacagcgg ccgaggatgc caagctgcgt ctggaggtga
4801 ctgtgcaggc tctcaagact cagcatgagc gtgacctgca gggccgtgat gaggctggtg
4861 aagagaggcg gaggcagctg gccaagcagc tgagagatgc agaggtggag cgggatgagg
4921 agcggaagca gcgcactctg gccgtggctg cccgcaagaa gctggaggga gagctggagg
4981 agctgaaggc tcagatggcc tctgccggcc agggcaagga ggaggcggtg aagcagcttc
5041 gcaagatgca ggcccagatg aaggagctat ggcgggaggt ggaggagaca cgcacctccc
5101 gggaggagat cttctcccag aatcgggaaa gtgaaaagcg cctcaagggc ctggaggctg
5161 aggtgctgcg gctgcaggag gaactggccg cctcggaccg tgctcggcgg caggcccagc
5221 aggaccggga tgagatggca gatgaggtgg ccaatggtaa ccttagcaag gcagccattc
5281 tggaggagaa gcgtcagctg gaggggcgcc tggggcagtt ggaggaagag ctggaggagg
5341 agcagagcaa ctcagagctg ctcaatgacc gctaccgcaa gctgctcctg caggtagagt
5401 cactgaccac agagctgtca gctgagcgca gtttctcagc caaggcagag agcgggcggc
5461 agcagctgga acggcagatc caggagctac ggggacgcct gggtgaggag gatgctgggg
5521 cccgtgcccg ccacaagatg accattgctg cccttgagtc taagttggcc caggctgagg
5581 agcagctaga gcaagagacc agagagcgca tcctctctgg aaagctggtg cgcagagctg
5641 agaagcggct taaagaggtg gtgctccagg tggaggagga gcggagggtg gctgaccagc
5701 tccgggacca gctggagaag ggaaaccttc gagtcaagca gctgaagcgg cagctggagg
5761 aggccgagga ggaggcatcc cgggctcagg ctggccgccg gaggctgcag cgtgagctgg
5821 aagatgtcac agagtcggcc gagtccatga accgtgaagt gaccacactg aggaaccggc
5881 ttcgacgcgg cccccctcacc ttcaccaccc gcacggtgcg ccaggtcttc cgactagagg
5941 agggcgtggc atccgacgag gaggcagagg aagcacagcc tgggtctggg ccatccccgg
6001 agcctgaggg gtccccacca gcccaccccc agtgacccta ccctgtcccc agatgcacta
6061 acagatgggg cccagccccc ttcctccctg gaccccacgg gcccctgtcc caggaacccc
6121 gccctctgac ttcttgccct ttggaaatgg tgcagcactc tggcatttat cacccccacc
6181 tgggtcccct gcaacctccc atcaaaggat gacccctaaa cacagaggag cggggcaggc
6241 agggaggcaa ggactggagc taccttgctt gttgggggac tgggtacagt tggcaagctg
6301 tgtttccatc agctccctgt cctcctttct tccctcgtta ttgatctata gacattagga
6361 agggagtgag acggctcctc caccatcctc agccagtgca acccattccc tctgcttctc
6421 tctctctctc tctctctccc tccctctcct tccctaccct ctcaccatct ttcttggcct
6481 ctctgagggt ctctctgtgc atctttttag gaatctcgct ctcactctct acgtagccac
6541 tctccttccc ccatttctgc gtccacccct gaactcctga gcgacagaag ccccaggcct
```

```
6601 ccaccagcct tgaacccttg caaaggggca ggacaagggg acccctctca ctcctgctgc
6661 tgcccatgct ctgccctccc ttctggttgc tctgagggtt cggagcttcc ctctgggact
6721 aaaggagtgt cctttaccct cccagcctcc aggctctggc agaaataaac tccaacccga
6781 ctggac  (SEQ ID NO: 59)
```

(B)

```
   1 maavtmsvpg rkapprpgpv peaaqpflft prgpsagggp gsgtspqvew tarrlvwvps
  61 elhgfeaaal rdegeeeaev elaesgrrlr lprdqiqrmn ppkfskaedm aeltclneas
 121 vlhnlreryy sgliytysgl fcvvinpykq lpiyteaive myrgkkrhev pphvyavteg
 181 ayrsmlqdre dqsilctges gagktentkk viqylahvas spkgrkepgv pgelerqllq
 241 anpileafgn aktvkndnss rfgkfirinf dvagyivgan ietylleksr airqakdecs
 301 fhifyqllgg ageqlkadll lepcshyrfl tngpssspgq erelfqetle slrvlgfshe
 361 eiismlrmvs avlqfgnial krerntdqat mpdntaaqkl crllglgvtd fsralltpri
 421 kvgrdyvqka qtkeqadfal ealakatyer lfrwlvlrln raldrsprqg asflgildia
 481 gfeifqlnsf eqlcinytne klqqlfnhtm fvleqeeyqr egipwtfldf gldlqpcidl
 541 ierpanppgl lalldeecwf pkatdksfve kvaqeqgghp kfqrprhlrd qadfsvlhya
 601 gkvdykanew lmknmdplnd nvaallhqst drltaeiwkd vegivgleqv sslgdgppgg
 661 rprrgmfrtv gqlykeslsr lmatlsntnp sfvrcivpnh ekragklepr lvldqlrcng
 721 vlegiricrq gfpnrilfqe frqryeiltp naipkgfmdg kqacekmiqa leldpnlyrv
 781 gqskiffrag vlaqleeerd lkvtdiivsf qaaargylar rafqkrqqqq salrvmqrnc
 841 aaylklrhwq wwrlftkvkp llqvtrqdev lqaraqelqk vqelqqqsar evgelqgrva
 901 qleeerarla eqlraeaelc aeaeetrgrl aarkqelelv vselearvge eeecsrqmqt
 961 ekkrlqqhiq eleahleaee garqklqlek vtteakmkkf eedlllledq nsklsksgsc
1021 wkivwpsshp rqlrrrrrsr asisygsnmr pqsqtwrdrl rkeekgrqel eklkrrldge
1081 sselqeqmve qqqraeelra qlgrkeeelq aalaraedeg garaqllksl reaqaalaea
1141 qedleserva rtkaekqrrd lgeelealrg eledtldstn aqqelrskre qevtelkktl
1201 eeetriheaa vqelrqrhgq algelaeqle qarrgkgawe ktrlaleaev selraelssl
1261 qtarqegeqr rrrlelqlqe vqgragdger araeaaeklq raqaelenvs galneaeskt
1321 irlskelsst eaqlhdaqel lqeetrakla lgsrvramea eaaglreqle eeaaarerag
1381 relqtaqaql sewrrrqeee agaleageea rrraareaea ltqrlaekte tvdrlergrr
1441 rlqqelddat mdleqqrqlv stlekkqrkf dqllaeekaa vlraveerer aeaegrerea
1501 ralsltrale eeqeareele rqnralrael eallsskddv gksvhelera crvaeqaand
1561 lraqvteled eltaaedakl rlevtvqalk tqherdlqgr deageerrrq lakqlrdaev
1621 erdeerkqrt lavaarkkle geleelkaqm asagqgkeea vkqlrkmqaq mkelwrevee
1681 trtsreeifs qnresekrlk gleaevlrlq eelaasdrar rqaqqdrdem adevangnls
1741 kaaileekrq legrlgqlee eleeeqsnse llndryrkll lqvesltte1 saersfsaka
1801 esgrqqlerq iqelrgrlge edagararhk mtiaaleskl aqaeeqleqe trerilsgkl
1861 vrraekrlke vvlqveeerr vadqlrdqle kgnlrvkqlk rqleeaeeea sraqagrrrl
1921 qreledvtes aesmnrevtt lrnrlrrgpl tfttrtvrqv frleegvasd eeaeeaqpgs
1981 gpspepegsp pahpq  (SEQ ID NO: 60)
```

NATURAL IGM ANTIBODIES AND INHIBITORS THEREOF

1. CROSS-REFERENCE TO RELATED APPLICATIONS

This application claims the benefit of U.S. Provisional Application No. 60/588,648, filed on Jul. 16, 2004 and U.S. Provisional Application No. 60/549,123 filed on Mar. 1, 2004; the content of each provisional application is specifically incorporated by reference herein.

2. GOVERNMENT SUPPORT

This invention was made with government support under grant No. GM52585, GM24891, and GM07560 from the National Institutes of Health. The government has certain rights in the invention.

3. BACKGROUND OF THE INVENTION

Nucleated cells are highly sensitive to hypoxia and even short periods of ischemia in multi-cellular organisms can have dramatic effects on cellular morphology, gene transcription, and enzymatic processes. Mitochondria, as the major site of oxygen metabolism, are particularly sensitive to changes in oxygen levels and during hypoxia release reactive oxygen species that chemically modify intracellular constituents such as lipids and proteins. Clinically these effects manifest as an inflammatory response in the patient. Despite intensive investigations of cellular responses to hypoxia little is known regarding the initiation of acute inflammation.

Acute inflammatory responses can result from a wide range of diseases and naturally occurring events such as stroke and myocardial infarction. Common medical procedures can also lead to localized and systemic inflammation. Left untreated inflammation can result in significant tissue loss and may ultimately lead to multi-system failure and death. Interfering with the inflammatory response after injury may be one method to reduce tissue loss.

Inflammatory diseases and acute inflammatory responses resulting from tissue injury, however, cannot be explained by cellular events alone. Accumulating evidence supports a major role for the serum innate response or complement system in inflammation. Studies to date have looked at tissue injury resulting from ischemia and reperfusion as one type of inflammatory disorder that is complement dependent. For example, in the rat myocardial model of reperfusion injury, pretreatment of the rats with the soluble form of the complement type 1 receptor dramatically reduced injury. Understanding how complement activation contributes to an inflammatory response is an area of active investigation.

Inflammatory diseases or disorders are potentially life-threatening, costly, and affect a large number of people every year. Thus, effective treatments of inflammatory diseases or disorders are needed.

4. SUMMARY OF THE INVENTION

In one aspect, the invention features isolated natural immunoglobulins (IgMs). In one embodiment, the antibody is produced by ATCC Accession Number PTA-3507. In another embodiment, the antibody has a light chain variable region comprising the amino acid sequence shown as SEQ ID NO: 8. In yet another embodiment, the antibody has a heavy chain variable region comprising the amino acid sequence shown as SEQ ID NO: 2.

In another aspect, the invention features IgM inhibitors and pharmaceutical preparations thereof. In one embodiment, the IgM inhibitor is a peptide that specifically binds to a natural IgM and thereby blocks binding to the antigen and/or complement activation. In one embodiment, the peptide includes the following consensus sequence: xNNNxNNxNNNN (SEQ ID NO: 14). Certain inhibitory peptides are provided as SEQ ID NOs: 16, 18, 20, 22, 24, 26, 28, 30, 32, 34, 36, and 38. Inhibitory peptides may be modified, for example to increase in vivo half-life or bioavailability. Inhibitory peptides may also be labeled to facilitate detection.

In another aspect, the invention features nucleic acids encoding peptides that specifically bind to natural IgM antibodies, as well as vectors and host cells for expressing the peptides. Certain nucleic acids are provided as SEQ ID NOs: 13, 15, 17, 19, 21, 23, 25, 27, 29, 31, 33, 35 and 37.

In a further aspect, the invention features methods of treating an inflammatory disease in a subject by administering to the subject a pharmaceutical composition comprising an IgM inhibitor as disclosed herein.

In yet other aspects, the invention features method of detecting, diagnosing or monitoring inflammatory diseases in a subject using labeled inhibitory antibodies.

Other features and advantages of the invention will be apparent based on the following Detailed Description and claims.

5. BRIEF DESCRIPTION OF THE DRAWINGS

FIG. 1 shows an IgM heavy chain sequence of B-1 hybridoma 22A5. (A) shows the $IgM^{CM-22}$ (or 22A5 IgM) heavy chain nucleic acid sequence (SEQ ID NO: 1) and (B) shows the amino acid sequence corresponding to the heavy chain sequence of SEQ ID NO: 1 (SEQ ID NO: 2). Framework regions (FVWR) and complementarity-determining regions (CDR) are indicated above the nucleotides.

FIG. 2 shows an IgM light chain sequence of B-1 hybridoma 22A5. (A) shows the $IgM^{CM-22}$ (or 22A5 IgM) light chain nucleic acid sequence (SEQ ID NO: 7) and (B) shows the amino acid sequence corresponding to the light chain sequence of SEQ ID NO: 7 (SEQ ID NO: 8). Framework-regions (FVWR) and complementarity-determining regions (CDR) are indicated above the nucleotides.

Figure 3:
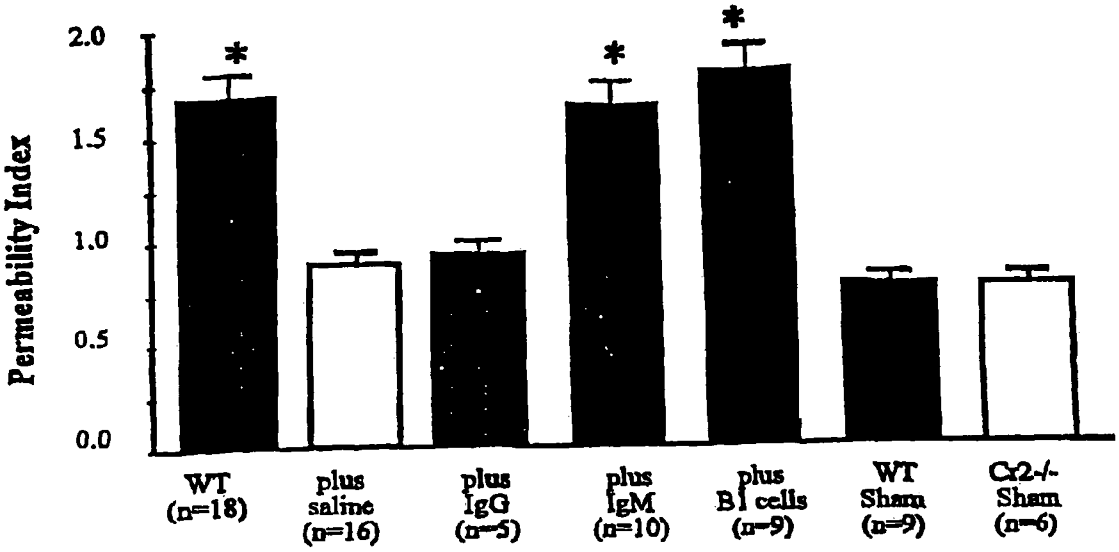

FIG. 3 is a bar graph depicting changes in intestinal permeability of inbred mice after intestinal ischemia and reperfusion or no injury (sham). WT represents parent strain for Cr2−/− mice. Cr2−/− was reconstituted with pooled IgG or IgM or saline control. Pooled IgM or IgG (0.5 mg) was administered intravenously approximately 1 hour before treatment. Values are means+standard error; n equals the number of mice in experimental groups.

Figure 4:
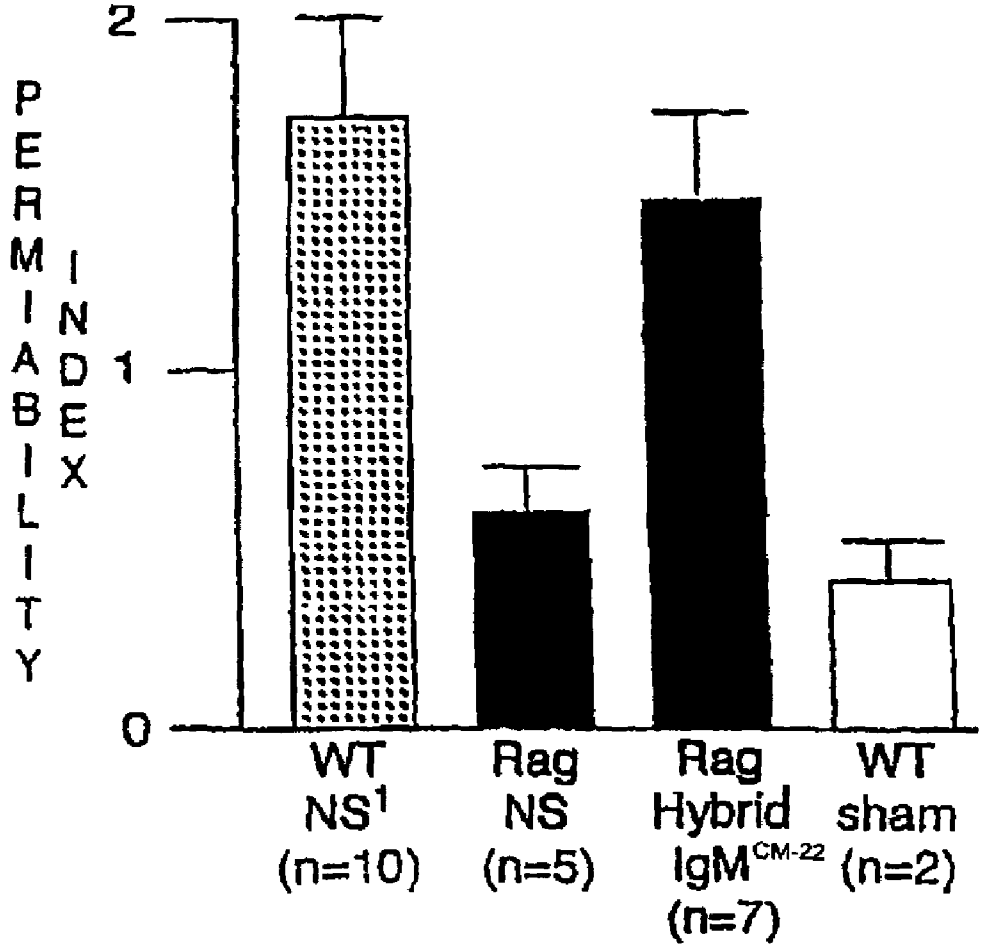

FIG. 4 demonstrates reconstitution of I/R injury in antibody deficient mice (RAG-1) by pooled IgM from a single B-1 cell hybridoma clone. IgM or saline was injected intravenously 30 minutes before initial laparotomy. At the end of reperfusion, blood is obtained and permeability index is calculated as the ratio of $^{125}I$ counts of dried intestine versus that of blood. Values represent means±standard error; n equals the numbers of mice used in experimental groups. 1=WT plus normal saline; 2=RAG plus normal saline; 3=RAG plus IgM hybridoma CM-22; 4=WT sham control.

Figure 5:
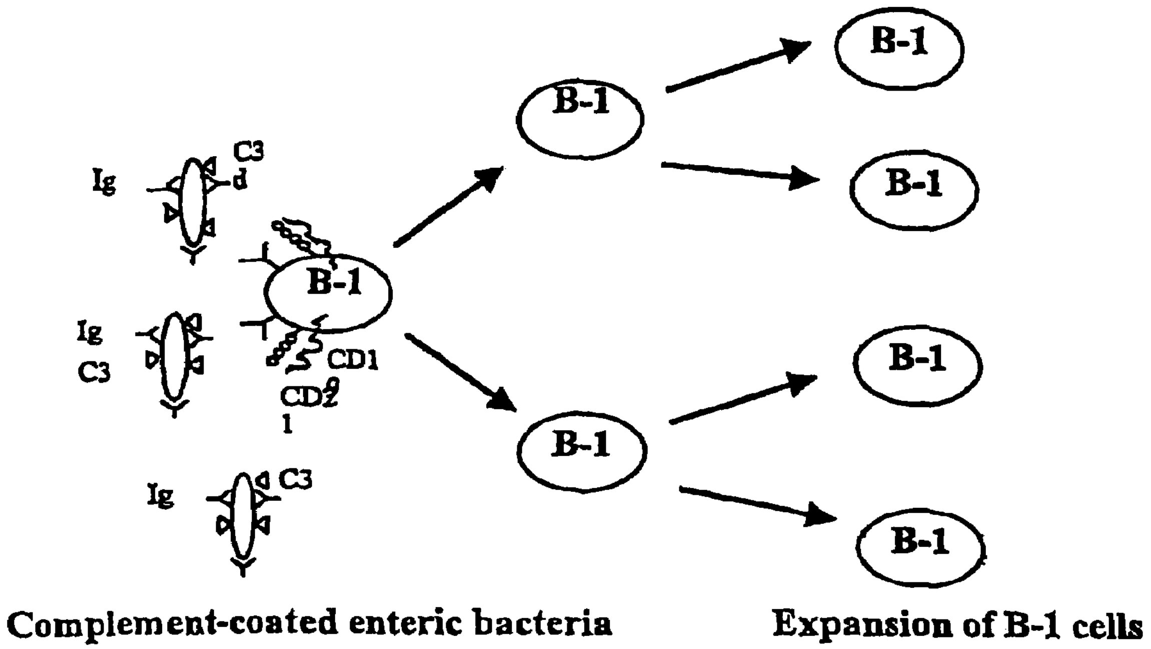

FIG. 5 is a schematic diagram of the proposed role for complement and complement receptors in positive selection of peritoneal B-1 lymphocytes.

Figure 6:
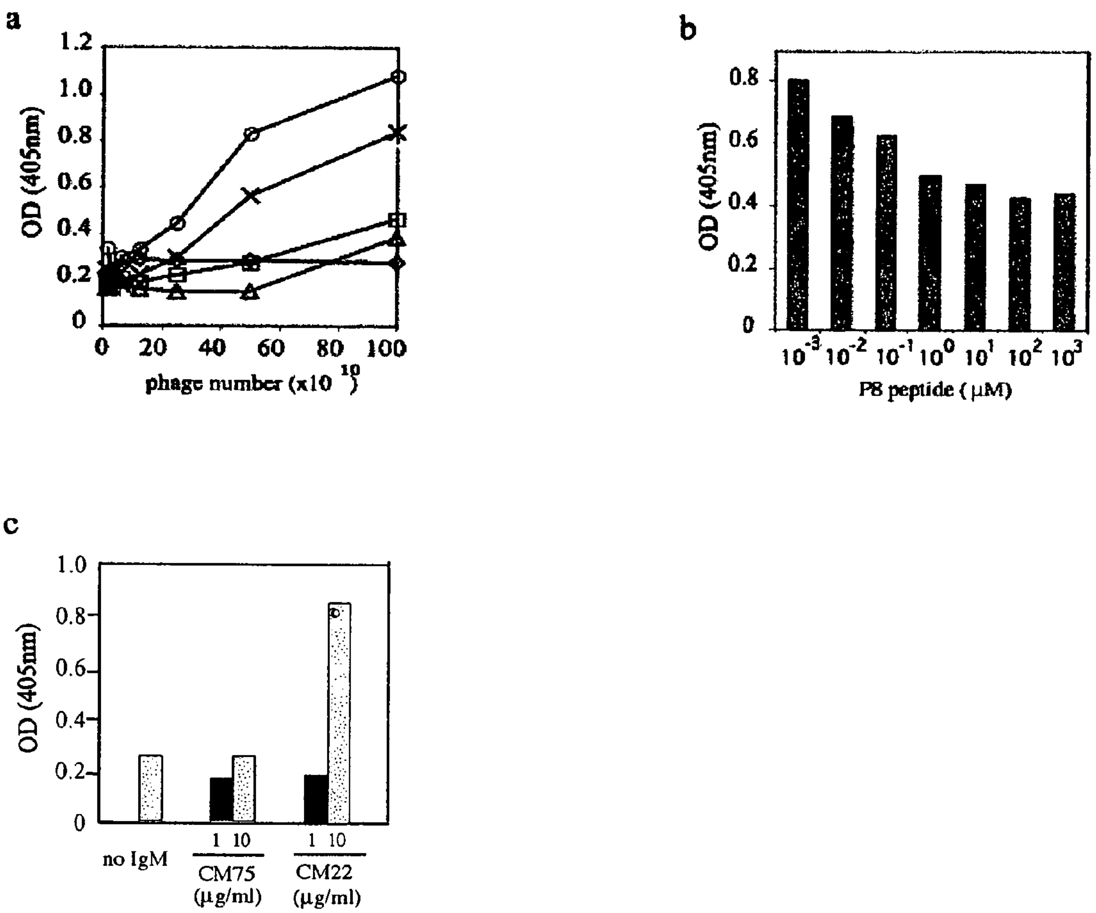

FIG. 6A is a graph showing the ELISA screening of M-13 phage-display library for $IgM^{CM-22}$-specific peptides. Symbols: □-P1 clone; X-P2 clone, ○-P7 clone; ◇-P8 clone. The plate was coated with a solution of $IgM^{CM-22}$ before addition of varying concentrations of phage-clones. The results are representative of at least three independent experiments.

FIG. 6B is a bar graph showing that the synthetic peptide P8 inhibits $IgM^{CM-22}$ binding of phage clone P8. ELISA was performed with varying concentrations of the synthetic peptide P8 added to the $IgM^{CM-22}$-coated plate prior to the addition of $5\times10^{11}$ PFU phage. The results are representative of at least three independent experiments.

FIG. 6C is a bar graph showing specific binding of the P8 peptide to $IgM^{CM-22}$. The ELISA plates were coated with 50 μg/ml solution of P8 peptide, followed by addition of $IgM^{CM-22}$ or $IgM^{CM-75}$ at 1 or 10 μg/ml. IgM binding was detected with a biotinylated rat anti-mouse IgM followed by streptavidin-phosphatase and color reaction. The results are representative of at least three independent experiments.

Figure 7:
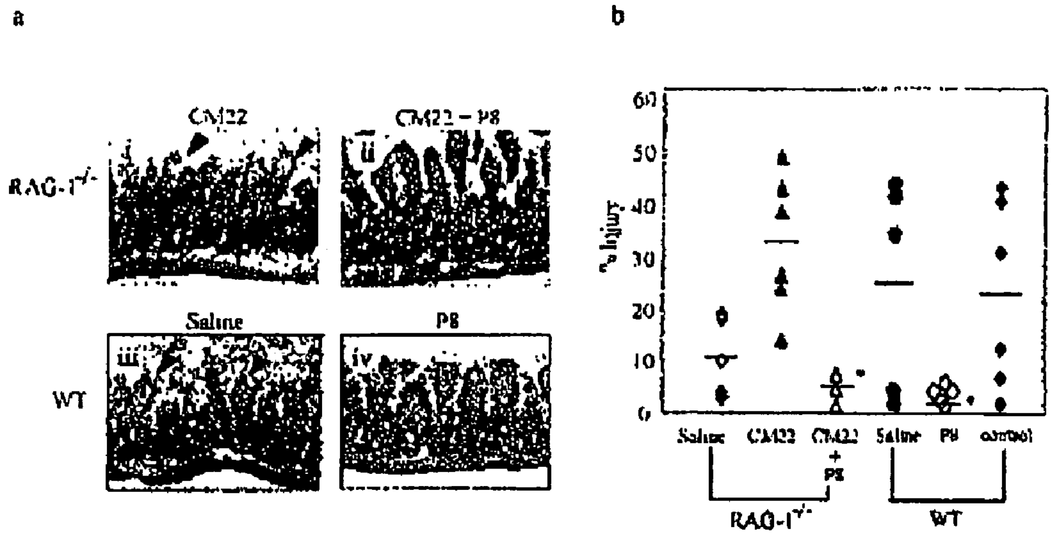

FIG. 7A is a series of photomicrographs showing that the P8 peptide blocked $IgM^{CM-22}$ mediated injury in vivo. Two upper panels (i and ii) are representative sections (stained with Haematoxylin and Eosin) prepared following RI treatment in RAG-$1^{-/-}$ mice with $IgM^{CM-22}$ alone or mixed with P8 peptide, respectively. Two lower panels (iii and iv) are representative sections prepared from wild type mice treated for intestinal reperfusion injury, which received either saline or peptide P8 5 minutes prior to reperfusion. Arrows indicate pathologic features of injury. Magnification 200×.

FIG. 7B is a scatter plot indicating the mean pathology score of each group of treated animals. Each symbol represents the score from one animal. Control group is WT mice pretreated with a control peptide (ACGMPYVRIPTA; SEQ ID NO: 61) at a similar dose as the peptide P8. * indicates statistical significance determined by Student t test of the P8-treated versus untreated groups ($p<0.05$).

Figure 8:
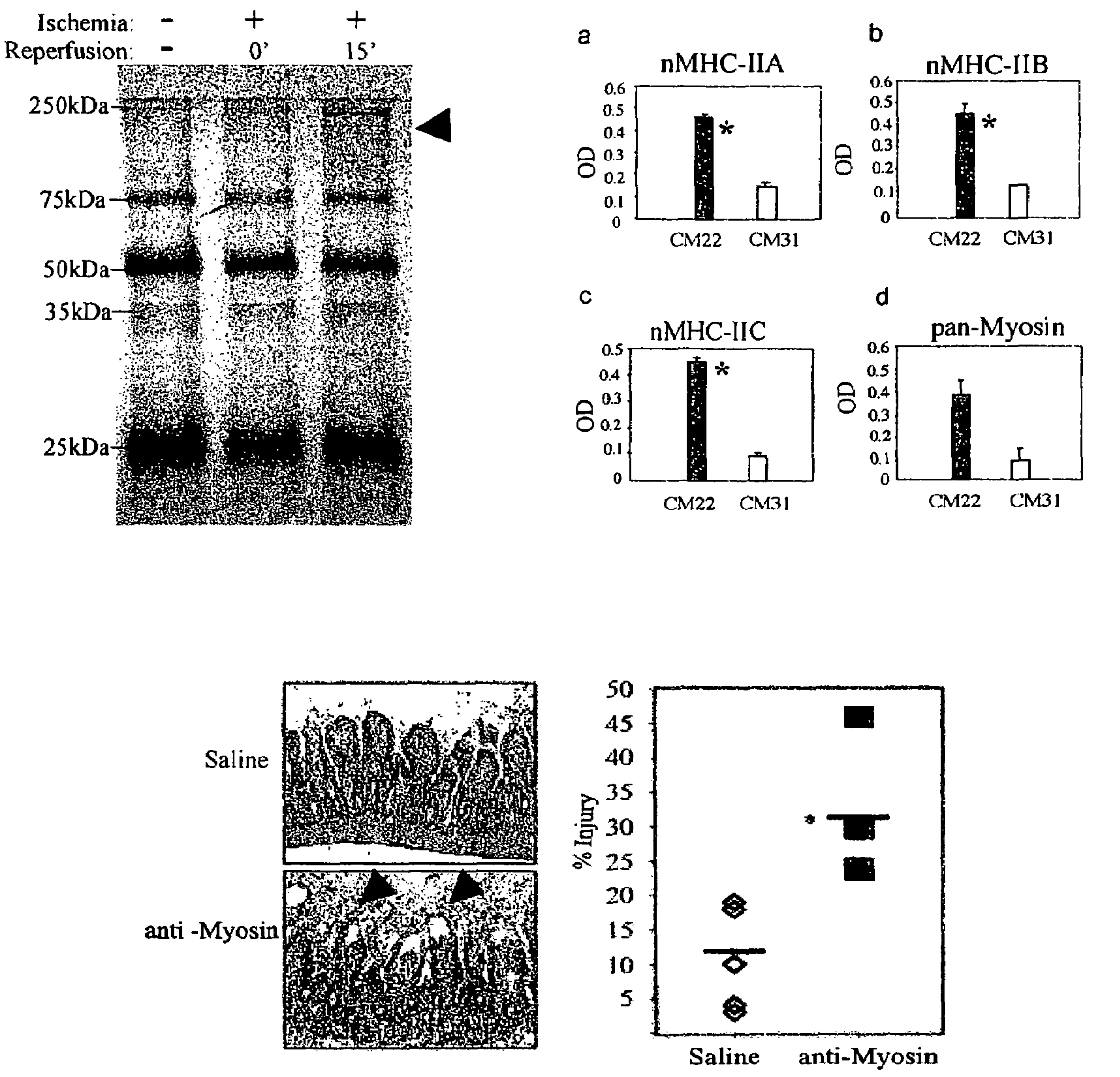

FIG. 8A is an immunoblot showing the immune precipitation of reperfusion injury (RI) specific antigens. Detection of a unique band (arrow) at approximately 250 kDa on a SDS-PAGE (10%). Size markers are indicated on the left. Intestinal lysates were prepared from RAG-$1^{-/-}$ mice reconstituted with $IgM^{CM-22}$ and either sham control (no ischemia) or subjected to ischemia followed by reperfusion for 0 or 15 min.

FIG. 8B is a series of graphs showing results of in vitro binding assays of $IgM^{CM-22}$ to the isoforms of non-muscle myosin heavy chain-II (NMHC-II). ELISA plates were coated with monoclonal antibodies for 3 different isoforms of NMHC-II (upper left: isoform A, upper right: isoform B, lower left: isoform C and lower right: anti-pan myosin antibody). Bound myosin heavy chain from intestinal lysates was detected by $IgM^{CM-22}$ or $IgM^{CM-31}$. The results represent mean±standard error of OD 405 nm units and are representative of triplicate samples.

FIG. 8C is a photomicrograph and a scatter plot showing the restoration of RI injury by anti-pan myosin antibody in RAG-$1^{-/-}$ mice. RAG-$1^{-/-}$ mice were reconstituted with affinity purified anti-pan myosin followed by RI surgery. The left panels represents morphologies of RAG-$1^{-/-}$ animals with saline control and with anti-pan myosin treatment. The right panel is the pathology scores of intestinal injury. The scatter plot (right panel) represents the pathology scores where each symbol represents a single animal.

FIG. 9A is a graph showing the surface plasmon resonance for the self-peptide N2. Binding isotherms for samples of the self-peptide N2 with concentration from 10.5 μM to 120 μM injected over the $IgM^{CM-22}$-coupled surface.

FIG. 9B is a graph showing the surface plasmon resonance for a control peptide. Binding isotherm for a same-length, random-sequence control peptide (AGCMPYVRIPTA; SEQ ID NO: 62), injected at a concentration of 117 μM over the $IgM^{CM-22}$-coupled surface.

FIG. 9C is a graph showing the nonlinear curve fitting with a 1:1 Langmuir binding isotherm to the steady-state response levels for the injection showed in FIG. 9A ($\chi^2=10$).

FIG. 9D is a graph showing the binding isotherm for the injection of the self-peptide N2 at 120 μM over a surface coupled with the control $IgM^{CM-31}$.

Figure 10:
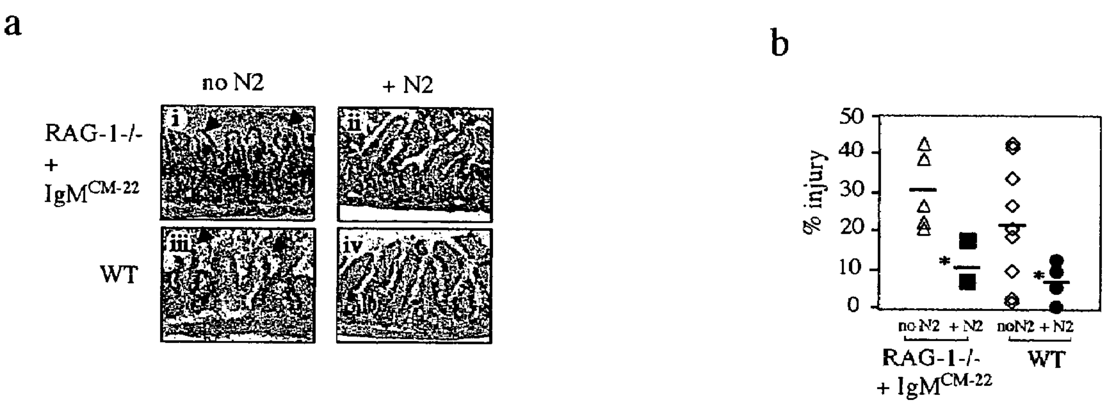
Figure 10:
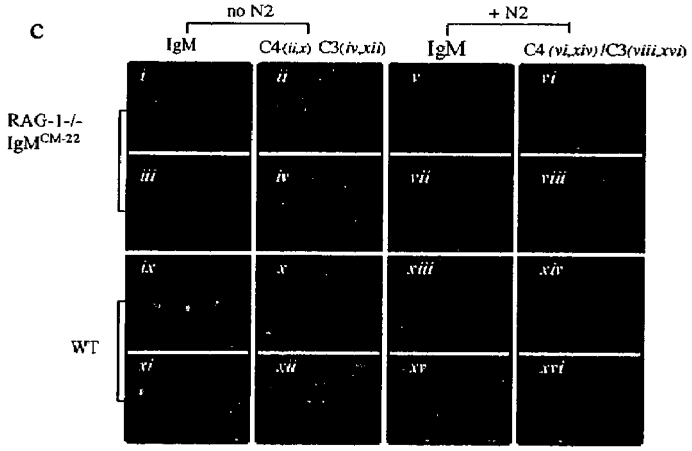

FIG. 10A is a series of photomicrographs showing that the N2 self-peptide blocking RI in RAG-$1^{-/-}$ mice. Two upper panels show representative sections prepared following RI treatment in RAG-$1^{-/-}$ mice with $IgM^{CM-22}$ alone or mixed with N2 self-peptide. Two lower panels are representative sections prepared from WT mice treated for intestinal RI, which received either saline or N2 peptide 5 minutes prior to reperfusion.

FIG. 10B is a scatter plot indicating the mean pathology score of each group of treated animals. Each symbol represents a single mouse. * indicates a statistical significance bases on a Student t test.

FIG. 10C is a series of photomicrographs showing the prevention of the activation of classical pathway of complement in intestinal RI by the self-peptide N2. Representative cryosections of intestinal tissues were harvested following intestinal RI and treated with an antibody specific for the mouse IgM, C4 or C3 (400× magnification). $IgM^{CM-22}$-reconstituted RAG-$1^{-/-}$ mice without pretreatment with the self-peptide N2 are in panels i-iv or with the self-peptide N2 are in panels v-viii. Wild type mice without pretreatment with the self-peptide N2 are in panels ix-xii or with pretreatment with the self-peptide N2 are in panels xiii-xvi. The tissue in panels i, iii, v, vii, ix, xiii, xi, xv were stained with anti-IgM-biotin followed by Streptavidin-Alexa-568 (red) and counter-stained with DAPI (violet). Panels ii, vi, x, and xiv were stained with anti-C4-FITC (green). Panels iv, viii, xii, xvi were stained with anti-C3-FITC (green).

FIG. 11 shows the (A) nucleic acid sequence (SEQ ID NO: 47; Genbank Accession no. NM_022410) and (B) amino acid sequence (SEQ ID NO: 48; Genbank Accession no. NP_071855) of mouse non-muscle myosin heavy chain II-A (mNMHC-IIA).

FIG. 12 shows the (A) nucleic acid sequence (SEQ ID NO: 49; Genbank Accession no. NM_002473) and (B) amino acid sequence (SEQ ID NO: 50; Genbank Accession no. NP_002464) of human non-muscle myosin heavy chain II-A (hNMHC-IIA).

FIG. 13 shows the (A) nucleic acid sequence (SEQ ID NO: 51; Genbank Accession no. NM_175260) and (B) amino acid sequence (SEQ ID NO: 52; Genbank Accession no. NP_780469) of mouse non-muscle myosin heavy chain II-B (mNMHC-IIB).

FIG. 14 shows the (A) nucleic acid sequence (SEQ ID NO: 53; Genbank Accession no. NM_005964) and (B) amino acid sequence (SEQ ID NO: 54; Genbank Accession no. NP_005955) of human non-muscle myosin heavy chain II-B (hNMHC-IIB).

FIG. 15 shows the (A) nucleic acid sequence (SEQ ID NO: 55; Genbank Accession no. AY363100) and (B) amino acid sequence (SEQ ID NO: 56; Genbank Accession no. AAQ24173) of mouse non-muscle myosin heavy chain II-C (mNMHC-IIC). (C) shows the nucleic acid sequence (SEQ ID No: 57; Genbank Accession no. NM_028021) and (D) shows the amino acid sequence (SEQ ID NO: 58; Genbank Accesion no. NP_079005) of another non-muscle myosin heavy chain II-C.

FIG. 16 shows the (A) nucleic acid sequence (SEQ ID NO: 59; Genbank Accession no. NM_024729) and (B) amino acid sequence (SEQ ID NO: 60; Genbank Accession no. NP_079005) of human non-muscle myosin heavy chain II-C (hNMHC-IIC).

6. DETAILED DESCRIPTION

6.1. Definitions:

For convenience, certain terms employed in the specification, examples, and appended claims are provided. Unless defined otherwise, all technical and scientific terms used herein have the same meaning as commonly understood by one of ordinary skill in the art to which this invention belongs.

"A" and "an" are used herein to refer to one or to more than one (i.e., to at least one) of the grammatical object of the article. By way of example, "an element" means one element or more than one element.

"Amino acid" is used herein to refer to either natural or synthetic amino acids, including glycine and D or L optical isomers, and amino acid analogs and peptidomimetics.

"Antibody" is used herein to refer to binding molecules including immunoglobulin molecules and immunologically active portions of immunoglobulin molecules, i.e., molecules that contain an antigen-binding site. Immunoglobulin molecules useful in the invention can be of any class (e.g., IgG, IgE, IgM, IgD, and IgA) or subclass. Native antibodies and immunoglobulins are usually heterotetrameric glycoproteins of about 150,000 daltons, composed of two identical light chains and two identical heavy chains. Each heavy chain has at one end a variable domain followed by a number of constant domains. Each light chain has a variable domain at one end and a constant domain at its other end. Antibodies include, but are not limited to, polyclonal, monoclonal, bispecific, chimeric, partially or fully humanized antibodies, fully human antibodies (i.e., generated in a transgenic mouse expressing human immunoglobulin genes), camel antibodies, and anti-idiotypic antibodies. An antibody, or generally any molecule, "binds specifically" to an antigen (or other molecule) if the antibody binds preferentially to the antigen, and, e.g., has less than about 30%, preferably 20%, 10%, or 1% cross-reactivity with another molecule. The terms "antibody" and "immunoglobulin" are used interchangeably.

"Antibody fragment" or "antibody portion" are used herein to refer to any derivative of an antibody which is less than full-length. In exemplary embodiments, the antibody fragment retains at least a significant portion of the full-length antibody's specific binding ability. Examples of antibody fragments include, but are not limited to, Fab, Fab', $F(ab')_2$, scFv, Fv, dsFv diabody, minibody, Fd fragments, and single chain antibodies. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

"Antigen-binding site" is used herein to refer to the variable domain of a heavy chain associated with the variable domain of a light chain.

"Bind" or "binding" are used herein to refer to detectable relationships or associations (e.g. biochemical interactions) between molecules.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Comprise" and "comprising" are used in the inclusive, open sense, meaning that additional elements may be included.

"Consensus sequence" is used herein to refer to the sequence formed from the most frequently occurring amino acids (or nucleotides) in a family of related sequences (See e.g., Winnaker, From Genes to Clones, 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a natural immunoglobulin can be preferably replaced with another amino acid residue from the same side chain family. Alternatively, in another embodiment, mutations can be introduced randomly along all or part of a natural immunoglobulin coding sequence, such as by saturation mutagenesis, and the resultant mutants can be screened for biological activity.

"Detectable label" is used herein to refer to a molecule capable of detection, including, but not limited to, radioactive isotopes, fluorophores, chemiluminescent moieties, enzymes, enzyme substrates, enzyme cofactors, enzyme inhibitors, dyes, metal ions, ligands (e.g., biotin or haptens) and the like. "Fluorophore" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH, beta-galactosidase, and horseradish peroxidase.

"Inhibitor" or "IgM inhibitor" or "antagonist" as used herein refers to an agent that reduces or blocks (completely or partially) an interaction between a natural antibody and another molecule involved in an inflammatory cascade. An inhibitor may antagonize one or more of the following activities of a natural IgM: (i) inhibit or reduce an interaction (e.g., binding) between the IgM and an ischemia-specific antigen; (ii) inhibit or reduce an interaction (e.g., binding) between the natural IgM and a component of the complement pathway, e.g., Clq; (iii) neutralize the natural IgM by, e.g., sequestering the immunoglobulin and/or targeting its degradation; or (iv) inhibit or reduce production of the natural IgM e.g., blocks synthesis, assembly, and/or posttranslational modifications of the IgM. The inhibitor can be a protein or a peptide, an antibody or fragment thereof (e.g., an anti-idiotypic antibody), a modified antibody, a carbohydrate, a glycoprotein, or a small organic molecule.

"Interaction" refers to a physical association between two or more molecules, e.g., binding. The interaction may be direct or indirect.

"Inflammatory disease" is used herein to refer to a disease or disorder that is caused or contributed to by a complicated set of functional and cellular adjustments involving acute or chronic changes in microcirculation, movement of fluids, and influx and activation of inflammatory cells (e.g., leukocytes) and complement, and included autoimmune diseases. Examples of such diseases and conditions include, but are not limited to: reperfusion injury, ischemia injury, stroke, autoimmune hemolytic anemia, idiopathic thrombocytopenic purpura, rheumatoid arthritis, celiac disease, hyper-IgM immunodeficiency, arteriosclerosis, coronary artery disease, sepsis, myocarditis, encephalitis, transplant rejection, hepatitis, thyroiditis (e.g. Hashimoto's thyroiditis, Graves disease), osteoporosis, polymyositis, dermatomyositis, Type I diabetes, gout, dermatitis, alopecia greata, systemic lupus erythematosus, lichen sclerosis, ulcerative colitis, diabetic retinopathy, pelvic inflammatory disease, periodontal disease, arthritis, juvenile chronic arthritis (e.g. chronic iridocyclitis), psoriasis, osteoporosis, nephropathy in diabetes mellitus, asthma, pelvic inflammatory disease, chronic inflammatory liver disease, chronic inflammatory lung disease, lung fibrosis, liver fibrosis, rheumatoid arthritis, chronic inflammatory liver disease, chronic inflammatory lung disease, lung fibrosis, liver fibrosis, Crohn's disease, ulcerative colitis, burns, and other acute and chronic inflammatory diseases of the Central Nervous System (CNS; e.g. multiple sclerosis), gastrointestinal system, the skin and associated structures, the immune system, the hepato-biliary system, or any site in the body where pathology can occur with an inflammatory component.

An "isolated" molecule, e.g., an isolated IgM, refers to a condition of being separate or purified from other molecules present in the natural environment.

"Natural IgM" is used herein to refer to an IgM antibody that is naturally produced in a mammal (e.g., a human). They have a pentameric ring structure wherein the individual monomers resemble IgGs thereby having two light ($\kappa$ or $\lambda$) chains and two heavy ($\mu$) chains. Further, the heavy chains contain an additional $C_H4$ domain. The monomers form a pentamer by disulfide bonds between adjacent heavy chains. The pentameric ring is closed by the disulfide bonding between a J chain and two heavy chains. Because of its high number of antigen binding sites, a natural IgM antibody is an effective agglutinator of antigen. Production of natural IgM antibodies in a subject are important in the initial activation of B-cells, macrophages, and the complement system. IgM is the first immunoglobulin synthesized in an antibody response.

"Nucleic acid" is used herein to refer to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

"Operatively linked" is used herein to refer to a juxtaposition wherein the components so described are in a relationship permitting them to function in their intended manner. For example, a coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

"Patient", "subject" or "host" are used herein to refer to either a human or a non-human mammal.

"Peptide" is used herein to refer to a polymer of amino acids of relatively short length (e.g. less than 50 amino acids). The polymer may be linear or branched, it may comprise modified amino acids, and it may be interrupted by non-amino acids. The term also encompasses an amino acid polymer that has been modified; for example, disulfide bond formation, glycosylation, lipidation, acetylation, phosphorylation, or any other manipulation, such as conjugation with a labeling component.

"Promoter" is used herein to refer to a minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the of a polynucleotide sequence. Both constitutive and inducible promoters, are included in the invention (see e.g., Bitter et al., *Methods in Enzymology* 153:516-544, 1987). For example, when cloning in bacterial systems, inducible promoters such as pL of bacteriophage, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention. Tissue-specific regulatory elements may be used. Including, for example, regulatory elements from genes or viruses that are differentially expressed in different tissues.

"Specifically binds" is used herein to refer to the interaction between two molecules to form a complex that is relatively stable under physiologic conditions. The term is used herein in reference to various molecules, including, for example, the interaction of an antibody and an antigen (e.g. a peptide). Specific binding can be characterized by a dissociation constant of at least about $1\times10^{-6}$ M, generally at least about $1\times10^{-7}$ M, usually at least about $1\times10^{-8}$ M, and particularly at least about $1\times10^{-9}$ M or $1\times10^{-10}$ M or greater. Methods for determining whether two molecules specifically bind are well known and include, for example, equilibrium dialysis, surface plasmon resonance, and the like.

"Stringency hybridization" or "hybridizes under low stringency, medium stringency, high stringency, or very high stringency conditions" is used herein to describes conditions for hybridization and washing. Guidance for performing hybridization reactions can be found in Current Protocols in *Molecular Biology*, John Wiley & Sons, N.Y. (1989), 6.3.1-6:3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences and the percent homology between two sequences is a function of the number of conserved positions shared by the sequences, taking into account the number of gaps, and the length of each gap, which need to be introduced for optimal alignment of the two sequences. The comparison of sequences and determination of percent identity and/or homology between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (available on the world wide web with the extension gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available on the world wide web with the extension gcg.com), using a NWSgapdna CMP matrix and a gap weight of 40, 50, 60, 70; or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frame shift gap penalty of 5.

The percent identity and/or homology between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Treating" is used herein to refer to any treatment of, or prevention of, or inhibition of a disorder or disease in a subject and includes by way of example: (a) preventing the disease or disorder from occurring in a subject that may be predisposed to the disease or disorder, but has not yet been diagnosed as having it; (b) inhibiting the disease or disorder, i.e., arresting its progression; or (c) relieving or ameliorating the disease or disorder, i.e., causing regression. Thus, treating as used herein includes, for example, repair and regeneration of damaged or injured tissue or cells at the site of injury or prophylactic treatments to prevent damage, e.g., before surgery.

"Vector" as used herein refers to a nucleic acid molecule, which is capable of transporting another nucleic acid to which it has been operatively linked and can include a plasmid, cosmid, or viral vector. One type of preferred vector is an episome, i.e., a nucleic acid capable of extra-chromosomal replication. Preferred vectors are those capable of autonomous replication and/or expression of nucleic acids to which they are linked. Vectors may be capable of directing the expression of genes to which they are operatively linked. A vector may also be capable of integrating into the host DNA. In the present specification, "plasmid" and "vector" are used interchangeably as a plasmid (a circular arrangement of double stranded DNA) is the most commonly used form of a vector. However, the invention is intended to include such other forms of vectors which serve equivalent functions and which become known in the art subsequently hereto. Viral vectors include, e.g., replication defective retroviruses, adenoviruses and adeno-associated viruses.

6.2 Natural IgM Antibodies

The present invention is based, at least in part, on the identification of natural immunoglobulins (Ig), in particular natural IgMs. Certain IgMs may be obtained from the hybridoma that has been deposited with the American Type Culture Collection and provided Accession Number PTA-3507.

The nucleotide sequence of the heavy chain variable region of the IgM produced from hybridoma PTA-3507, $IgM^{CM-22}$ (also referred to as 22A5 IgM) is shown in FIG. 1A (SEQ ID NO: 1), and the amino acid sequence is shown in FIG. 1B (SEQ ID NO: 2). The CDR1 domain of the heavy chain variable region corresponds to amino acids 31 to 35 of SEQ ID NO: 2 (SEQ ID NO: 4), which is encoded by nucleotides 91-105 of SEQ ID NO: 1 (SEQ ID NO: 3), and the CDR2 domain of the heavy chain variable region corresponds to amino acids 50 to 66 of SEQ ID NO: 2 (SEQ ID NO: 6), which is encoded by nucleotides 148-198 of SEQ ID NO: 1 (SEQ ID NO: 5).

The nucleotide sequence of the light chain variable region of $IgM^{CM-22}$ is shown in FIG. 2A (SEQ ID NO: 7), and the amino acid sequence is shown in FIG. 2B (SEQ ID NO: 8). The CDR1 domain of the light chain variable region corresponds to amino acids 23 to 37 of SEQ ID NO: 8 (SEQ ID NO:

10), which is encoded by nucleotides 67-111 of SEQ ID NO: 7 (SEQ ID NO: 9), and the CDR2 domain of the light chain variable region corresponds to amino acids 53 to 59 of SEQ ID NO: 8 (SEQ ID NO: 12), which is encoded by nucleotides 157 to 177 of SEQ ID NO: 7 (SEQ ID NO: 11). Due to the degeneracy of the genetic code, other nucleotide sequences can encode the amino acid sequences listed herein.

The nucleic acid compositions of the present invention, while often in a native sequence (except for modified restriction sites and the like), from either cDNA, genomic or mixtures may be mutated, in accordance with standard techniques. For coding sequences, these mutations, may affect the amino acid sequence as desired. In particular, nucleotide sequences substantially identical to or derived from native V, D, J, constant, switches and other such sequences described herein are contemplated.

For example, an isolated nucleic acid can comprise an $IgM^{CM-22}$ (or 22A5 IgM) heavy chain variable region nucleotide sequence having a nucleotide sequence as shown in FIG. 1A (SEQ ID NO: 1), or a sequence, which is at least 80%, 90%, 95%, 96%, 97%, 98%, or 99% identical to SEQ ID NO: 1. A nucleic acid molecule may comprise the heavy chain CDR1 nucleotide sequence of SEQ ID NO: 3, or a portion thereof. Further, the nucleic acid molecule may comprise the heavy chain CDR2 nucleotide sequence of SEQ ID NO: 5, or a portion thereof. In an exemplary embodiment, the nucleic acid molecule comprises a heavy chain CDR1 nucleotide sequence of SEQ ID NO: 3, or portion thereof, and a heavy chain CDR2 nucleotide sequence of SEQ ID NO: 5, or portion thereof. The nucleic acid molecules of the present invention may comprise heavy chain sequences, e.g. SEQ ID NO: 1, SEQ ID NO: 3, SEQ ID NO: 5, or combinations thereof, or encompass nucleotides having at least 80%, 90%, 95%, 96%, 97%, 98%, and 99% sequence identity to SEQ ID NOs: 1, 3 or 5. Further, the nucleic acid molecules of the present invention may comprise heavy chain sequences, which hybridize under stringent conditions, e.g. low, medium, high or very high stringency conditions, to SEQ ID NOs: 1, 3 or 5.

In another embodiment, the invention features nucleic acid molecules having at least 80%, 90%, 95%, 96%, 97%, 98%, and 99% sequence identity with a nucleic acid molecule encoding a heavy chain polypeptide, e.g., a heavy chain polypeptide of SEQ ID NOs: 2, 4 or 6. The invention also features nucleic acid molecules which hybridize to nucleic acid sequences encoding a heavy chain variable region of a natural antibody or portion thereof, e.g., a heavy chain variable region of SEQ ID NO: 2, 4 or 6.

In another embodiment, the isolated nucleic acid encodes a $IgM^{CM-22}$ (22A5 IgM) light chain variable region nucleotide sequence having a nucleotide sequence as shown in FIG. 2A (SEQ ID NO: 7), or a sequence at least 80%, 90%, 95%, 96%, 97%, 98%, 99% identical to SEQ ID NO: 7. The nucleic acid molecule may comprise the light chain CDR1 nucleotide sequence of SEQ ID NO: 9, or a portion thereof. In another preferred embodiment, the nucleic acid molecule may comprise the light chain CDR2 nucleotide sequence of SEQ ID NO: 11, or a portion thereof. In an exemplary embodiment, the nucleic acid molecule comprises a light chain CDR1 nucleotide sequence of SEQ ID NO: 9, or portion thereof, and a light chain CDR2 nucleotide sequence of SEQ ID NO: 11, or portion thereof. The nucleic acid molecules of the present invention may comprise light chain sequences, e.g. SEQ ID NOs: 7, 9 or 11, or combinations thereof, or encompass nucleotides having at least 80%, 90%, 95%, 96%, 97%, 98%, and 99% sequence identity to SEQ ID NOs: 7, 9 or 11. Further nucleic acid molecules may comprise light chain sequences, which hybridize under stringent conditions, e.g. low, medium, high or very high stringency conditions, to SEQ ID NOs: 7, 9 or 11.

Nucleic acid molecules can have at least 80%, 90%, 95%, 96%, 97%, 98% or 99% sequence identity with a nucleic acid molecule encoding a light chain polypeptide, e.g., a light chain polypeptide of SEQ ID NOs: 8, 10, or 12. The invention also features nucleic acid molecules which hybridize to a nucleic acid sequence encoding a light chain variable region of a natural antibody or portion thereof, e.g., a light chain variable region of SEQ ID NOs: 8, 10 or 12.

In another embodiment, the invention provides an isolated nucleic acid encoding a heavy chain CDR1 domain comprising the amino acid sequence of SEQ ID NO: 4, or a fragment or modified form thereof. This nucleic acid can encode only the CDR1 region or can encode an entire antibody heavy chain variable region or a fragment thereof. For example, the nucleic acid can encode a heavy chain variable region having a CDR2 domain comprising the amino acid sequence of SEQ ID NO: 6. In yet another embodiment, the invention provides an isolated nucleic acid encoding a heavy chain CDR2 domain comprising the amino acid sequence of SEQ ID NO: 6, or a fragment or modified form thereof. This nucleic acid can encode only the CDR2 region or can encode an entire antibody heavy chain variable region or a fragment thereof. For example, the nucleic acid can encode a light chain variable region having a CDR1 domain comprising the amino acid sequence of SEQ ID NO: 4.

In still another embodiment, the invention provides an isolated nucleic acid encoding a light chain CDR1 domain comprising the amino acid sequence of SEQ ID NO: 10, or a fragment or modified form thereof. This nucleic acid can encode only the CDR1 region or can encode an entire antibody light chain variable region. For example, the nucleic acid can encode a light chain variable region having a CDR2 domain comprising the amino acid sequence of SEQ ID NO: 12. The isolated nucleic acid can also encode a light chain CDR2 domain comprising the amino acid sequence of SEQ ID NO: 12, or a fragment or modified form thereof. This nucleic acid can encode only the CDR2 region or can encode an entire antibody light chain variable region. For example, the nucleic acid can encode a light chain variable region having a CDR1 domain comprising the amino acid sequence of SEQ ID NO: 10.

The nucleic acid encoding the heavy or light chain variable region can be of murine or human origin, or can comprise a combination of murine and human amino acid sequences. For example, the nucleic acid can encode a heavy chain variable region comprising the CDR1 of SEQ ID NO: 2 (SEQ ID NO: 4) and/or the CDR2 of SEQ ID NO: 2 (SEQ ID NO: 6), and a human framework sequence. In addition, the nucleic acid can encode a light chain variable region comprising the CDR1 of SEQ ID NO: 8 (SEQ ID NO: 10) and/or the CDR2 of SEQ ID NO: 8 (SEQ ID NO: 12), and a human framework sequence. The invention further encompasses vectors containing the above-described nucleic acids and host cells containing the expression vectors.

The invention also features polypeptides and fragments of the $IgM^{CM-22}$ heavy chain variable regions and/or light chain variable regions. In exemplary embodiments, the isolated polypeptides comprise, for example, the amino acid sequences of SEQ ID NOs: 8, 10, or 12, or fragments or combinations thereof; or SEQ ID NO: 2, 4, or 6, or fragments or combinations thereof. The polypeptides of the present invention include polypeptides having at least, but not more than 20, 10, 5, 4, 3, 2, or 1 amino acid that differs from SEQ ID NOs: 8, 10, 12, 2, 4 or 6. Exemplary polypeptides are polypeptides that retain biological activity, e.g., the ability to bind an ischemia-specific antigen, and/or the ability to bind complement. In another embodiment, the polypeptides comprise polypeptides having at least 80%, 90%, 95%, 96%, 97%, 98%, and 99% sequence identity with a light chain variable region, or portion thereof, e.g. a light chain variable region polypeptide of SEQ ID NOs: 8, 10, or 12. In another embodiment, the polypeptides comprise polypeptides having at least 80%, 90%, 95%, 96%, 97%, 98%, and 99% sequence identity with a heavy chain variable region, or portion thereof, e.g. a heavy chain variable region polypeptide of SEQ ID NOs: 2, 4, or 6. In another embodiment, the invention features a polypeptide comprising the amino acid sequence of SEQ ID NO: 8 and SEQ ID NO: 2, further comprising an IRES sequence.

6.3 Inhibitors of Natural IgM Antibodies 6.3.1 Peptide Inhibitors of Natural IgM Antibodies The invention further features IgM inhibitors. In one embodiment, the IgM inhibitor is a peptide that specifically binds to a natural IgM and thereby blocks binding to the antigen. Such peptides can include, but are not limited to, the asparagine-rich peptides described in Table 1 below.

TABLE 1

Amino acid sequences of natural IgM antibody-binding peptides

| SEQ ID NO: | SEQUENCE | Name |
|---|---|---|
| 14 | xNNNxNNxNNNN | Asparagine-rich Consensus |
| 16 | YNNNNGNYTYRN | P1 |
| 18 | ANTRNGATNNNM | P2 |
| 20 | CDSSCDSVGNCN | P3 |
| 22 | WNNNGRNACNAN | P4 |
| 24 | HNSTSNGCNDNV | P5 |
| 26 | NSNSRYNSNSNN | P6 |
| 28 | KRNNHNNHNRSN | P7 |
| 30 | NGNNVNGNRNNN | P8 |
| 32 | NVANHNNSNHGN | P9 |
| 34 | SYNNNNHVSNRN | P10 |

The peptides can also include certain "self-peptides" as described in Table 2 below.

TABLE 2

Amino acid sequences of self-peptides

| SEQ ID NO: | SEQUENCE | Name |
|---|---|---|
| 36 | LMKNMDPLNDNI | Self-1 |
| 38 | LMKNMDPLNDNV | Self-2 ("N-2") |

As described in more detail in the Exemplification, self peptides bind to the natural IgM antibody $IgM^{CM-22}$.

In addition to the peptides described above, the present invention encompasses modified peptides whose activity may be identified and/or assayed using a variety of methods well known to the skilled artisan. For example, binding of the peptide to the IgM may be detected using biological assays, Western blotting, immunoprecipitation, or immonocytochemical techniques, such as those described below. In particular, the biological activity (e.g., the ability to a bind natural IgM antibody) of a modified peptide can be characterized relative to that of P8 (SEQ ID NO: 30) or N2 (SEQ ID NO: 38).

Such modified peptides, when designed to retain at least one activity of the naturally-occurring form of the protein, are considered "functional equivalents" of the peptides described in more detail herein. Such modified peptides may be produced, for instance, by amino acid substitution, deletion, or addition, which substitutions may consist in whole or part by conservative amino acid substitutions.

For instance, it is reasonable to expect that an isolated conservative amino acid substitution, such as replacement of a leucine with an isoleucine or valine, an aspartate with a glutamate, or a threonine with a serine, will not have a major effect on the biological activity of the resulting molecule. Whether a change in the amino acid sequence of a peptide results in a functional homolog may be readily determined by assessing the ability of the variant peptide to produce a response similar to that of the wild-type peptide (e.g. ability to bind natural IgM antibodies). Peptides in which more than one replacement has taken place may readily be tested in the same manner.

Mutagenesis of the peptide may give rise to homologs, which have improved in vivo half-lives relative to the corresponding wild-type peptide. For example, the altered peptide may be rendered more stable to proteolytic degradation or other cellular processes which result in destruction or inactivation of the protein.

The amino acid sequences for a population of peptide homologs can be aligned, preferably to promote the highest homology possible. Such a population of variants may include, for example, homologs from one or more species, or homologs from the same species but which differ due to mutation. Amino acids which appear at each position of the aligned sequences are selected to create a degenerate set of combinatorial sequences. In certain embodiments, the combinatorial library is produced by way of a degenerate library of genes encoding a library of polypeptides which each include at least a portion of potential peptide sequences. For instance, a mixture of synthetic oligonucleotides may be enzymatically ligated into gene sequences such that the degenerate set of potential nucleotide sequences are expressible as individual polypeptides, or alternatively, as a set of larger fusion proteins (e.g., for phage display).

There are many ways by which the library of potential homologs may be generated from a degenerate oligonucleotide sequence. Chemical synthesis of a degenerate gene sequence may be carried out in an automatic DNA synthesizer, and the synthetic genes may then be ligated into an appropriate vector for expression. One purpose of a degenerate set of genes is to provide, in one mixture, all of the sequences encoding the desired set of potential peptide sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp. 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-

2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis may be utilized to generate a combinatorial library. For example, peptide homologs may be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol. Biol. 1:11-19); or by random mutagenesis (Miller et al., (1992) A Short Course in Bacterial Genetics, CSHL Press, Cold Spring Harbor, N.Y.; and Greener et al., (1994) Strategies in Mol. Biol. 7:32-34).

A wide range of techniques are known in the art for screening gene products of combinatorial libraries made by point mutations and truncations, and for screening cDNA libraries for gene products having a certain property (e.g., the ability to bind a natural IgM antibody). Such techniques will be generally adaptable for rapid screening of the gene libraries generated by the combinatorial mutagenesis of peptide homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In an illustrative embodiment of a screening assay, candidate combinatorial gene products are passed over a column containing beads having attached to it the binding protein, such as an IgM or portion thereof. Those candidate combinatorial gene products that are retained on the column may be further characterized for binding to IgMs in a manner that could be useful in blocking natural IgM antibody binding and treating inflammatory diseases.

In another example, the gene library may be expressed as a fusion protein on the surface of a viral particle. For instance, in the filamentous phage system, foreign peptide sequences may be expressed on the surface of infectious phage, thereby conferring two benefits. First, because these phage may be applied to affinity matrices at very high concentrations, a large number of phage may be screened at one time. Second, because each infectious phage displays the combinatorial gene product on its surface, if a particular phage is recovered from an affinity matrix in low yield, the phage may be amplified by another round of infection. The group of almost identical *E. coli* filamentous phages M13, fd, and fl are most often used in phage display libraries, as either of the phage gIII or gVIII coat proteins may be used to generate fusion proteins without disrupting the ultimate packaging of the viral particle (Ladner et al., PCT publication WO 90/02909; Garrard et al., PCT publication WO 92/09690; Marks et al., (1992) J. Biol. Chem. 267:16007-16010; Griffiths et al., (1993) EMBO J. 12:725-734; Clackson et al., (1991) Nature 352:624-628; and Barbas et al., (1992) PNAS USA 89:4457-4461). Other phage coat proteins may be used as appropriate.

The invention also provides for mimetics (e.g., non-peptide agents) which are able to mimic binding of the authentic peptide to a natural IgM antibody. For example, the critical residues of a peptide which are involved in molecular recognition of a natural IgM antibody may be determined and used to generate peptidomimetics that bind to a natural IgM antibody. The peptidomimetic may then be used as an inhibitor of the wild-type protein by binding to the natural IgM antibodies and covering up the critical residues needed for interaction with the wild-type protein, thereby preventing interaction of the protein and the natural IgM antibody. Peptidomimetic compounds may be generated which mimic those residues in binding to the natural IgM antibody. For instance, non-hydrolyzable peptide analogs of such residues may be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), β-turn dipeptide cores (Nagai et al., (1985) Tetrahedron Lett 26:647; and Sato et al., (1986) J Chem Soc Perkin Trans 1:1231), and β-aminoalcohols (Gordon et al., (1985) Biochem Biophys Res Commun 126:419; and Dann et al., (1986) Biochem Biophys Res Commun 134:71).

6.3.2 Nucleic Acids Encoding Peptide Inhibitors

The invention also features nucleic acids, which encode the peptides discussed above. Exemplary nucleic acids are provided in Table 3.

TABLE 3

| SEQ ID NO: | Nucleic acids encoding natural IgM antibody-binding peptides SEQUENCE | Name |
|---|---|---|
| 13 | NNN AAY AAY AAY NNN AAY AAY NNN AAY AAY AAY AAY | Aparagine-rich Consensus |

TABLE 3-continued

| Nucleic acids encoding natural IgM antibody-binding peptides | | |
|---|---|---|
| SEQ ID NO: | SEQUENCE | Name |
| 15 | TAY AAY AAY AAY AAY GGN AAY TAY ACN TAY MGN AAY | P1 |
| 17 | GCN AAY ACN MGN AAY GGN GCN ACN AAY AAY AAY ATG | P2 |
| 19 | TGY GAY WSN WSN TGY GAY WSN GTN GGN AAY TGY AAY | P3 |
| 21 | TGG AAY AAY AAY GGN MGN AAY GCN TGY AAY GCN AAY | P4 |
| 23 | CAY AAY WSN ACN WSN AAY GGN TGY AAY GAY AAY GTN | P5 |
| 25 | AAY WSN AAY WSN MGN TAN AAN WSN AAY WSN AAY AAY | P6 |
| 27 | AAR MGN AAY AAY CAY AAY AAY CAY AAY MGN WSN AAY | P7 |
| 29 | AAY GGN AAY AAY GTN AAY GGN AAY MGN AAY AAY AAY | P8 |
| 31 | AAY GTN GCN AAY CAY AAY AAY WSN AAY CAY GGN AAY | P9 |
| 33 | WSN TAY AAY AAY AAY AAY CAY GTN WSN AAY MGN AAY | P10 |
| 35 | YTN ATG AAR AAY ATG GAY CCN YTN AAY GAY AAY ATH | Self-1 |
| 37 | YTN ATG AAR AAY ATG GAY CCN YTN AAY GAY AAY GTN | Self-2 |

The isolated nucleic acids in Table 3 reflect degeneracy in the genetic code. In particular, an “R” corresponds to a base that may be a A or G; a “S” corresponds to a base that may be a G or C; a “V” corresponds to a base that may be an A, C or G; a “Y” corresponds to a base that may be a C or T; a “W” corresponds to a base that may be an A or T; a “D” corresponds to a base that may be an A, G or T; a “M” corresponds to a base that may be an A or C; a “H” corresponds to a base that may be an A, C or T; a “N” corresponds to a base that may be an A, C, G or T; a “K” corresponds to a base that may be a G or T and a “B” corresponds to a base that may be a C, G or T.

It is expected that DNA sequence polymorphisms that lead to changes in the amino acid sequences of the subject proteins will exist among mammalian cells. One skilled in the art will appreciate that these variations in one or more nucleotides (from less than 1% up to about 3 or 5% or possibly more of the nucleotides) of the nucleic acids encoding a particular peptide of the invention may exist among individuals of a given species due to natural allelic variation. Any and all such nucleotide variations and resulting amino acid polymorphisms are within the scope of this invention. Preferred nucleic acids encode a peptide, which is at least about 60%, 70%, 80%, 85%, 90%, 95%, 98%, 99% homologous or more with an amino acid sequence of SEQ ID NO: 14, 16, 18, 20, 22, 24, 26, 28, 30, 32, 34, 36, 38 or another peptide of the invention. Nucleic acids which encode peptides having an activity of a peptide of the invention and having at least about 60%, 70%, 80%, 85%, 90%, 95%, 98%, 99% homology or more with SEQ ID NO: 14, 16, 18, 20, 22, 24, 26, 28, 30, 32, 34, 36, 38, or another peptide of the invention are also within the scope of the invention.

Bias in codon choice within genes in a single species appears related to the level of expression of the protein encoded by that gene. Accordingly, the invention encompasses nucleic acid sequences which have been optimized for improved expression in a host cell by altering the frequency of codon usage in the nucleic acid sequence to approach the frequency of preferred codon usage of the host cell. Due to codon degeneracy, it is possible to optimize the nucleotide sequence without effecting the amino acid sequence of an encoded polypeptide. Accordingly, the instant invention relates to any nucleotide sequence that encodes the peptides set forth in SEQ ID NO: 14, 16, 18, 20, 22, 24, 26, 28, 30, 32, 34, 36, 38 or other peptides of the invention.

Nucleic acids within the scope of the invention may also contain linker sequences, modified restriction endonuclease sites and other sequences useful for molecular cloning, expression or purification of such recombinant polypeptides.

A nucleic acid encoding a peptide of the invention may be obtained from mRNA or genomic DNA from any organism in accordance with protocols described herein, as well as those generally known to those skilled in the art. A cDNA encoding a peptide of the invention, for example, may be obtained by isolating total mRNA from an organism, e.g. a bacteria, virus, mammal, etc. Double stranded cDNAs may then be prepared from the total mRNA, and subsequently inserted into a suitable plasmid or bacteriophage vector using any one of a number of known techniques. A gene encoding a peptide of the invention may also be cloned using established polymerase chain reaction techniques in accordance with the nucleotide sequence information provided by the invention.

In another aspect of the invention, the subject nucleic acid is provided in an expression vector comprising a nucleotide sequence encoding a peptide of the invention and operably linked to at least one regulatory sequence. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

As will be apparent, the subject gene constructs may be used to cause expression of a peptide of the invention in cells propagated in culture, e.g., to produce proteins or polypeptides, including fusion proteins or polypeptides, for purification.

This invention also pertains to a host cell transfected with a recombinant gene in order to express a peptide of the invention. The host cell may be any prokaryotic or eukaryotic cell. For example, a polypeptide of the present invention may be expressed in bacterial cells, such as *E. coli*, insect cells (baculovirus), yeast, or mammalian cells. Other suitable host cells are known to those skilled in the art. Additionally, the host cell may be supplemented with tRNA molecules not typically found in the host so as to optimize expression of the peptide. Other methods suitable for maximizing expression of the peptide will be known to those in the art.

6.3.3 Methods of Producing Peptide Inhibitors

Peptide inhibitors may be synthesized, for example, chemically, ribosomally in a cell free system, or ribosomally within a cell. Chemical synthesis of peptides of the invention may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Merrifield et al. in J. Am. Chem. Soc., Volume 85, page 2149 (1964), by Houghten et al. in Proc. Natl. Acad. Sci. USA, Volume 82, page 5132 (1985), and by Stewart and Young in Solid Phase Peptide Synthesis, Pierce Chem. Co, Rockford, Ill. (1984). Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Schnolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

In another variation, peptide production may be achieved using in vitro translation systems. An in vitro translation systems is, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be carried out within in the same reaction to produce peptides from one or more isolated DNAs.

Nucleic acids encoding peptide inhibitors may be expressed in vitro by DNA transfer into a suitable host cell. Expression of peptides may be facilitated by inserting the nucleic acids encoding the peptides into a vector, such as a plasmid, virus or other vehicle known in the art that has been manipulated by insertion or incorporation of the natural antibody-binding peptide genetic sequences. Such vectors contain a promoter sequence which facilitates the efficient transcription of the inserted genetic sequence of the host. The vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Nucleic acids encoding peptide inhibitors may be expressed in either prokaryotes or eukaryotes. Hosts can include microbial, yeast, insect, and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors can incorporate DNA sequences of the invention. Methods which are well known to those skilled in the art can be used to construct vectors containing the natural antibody-binding peptide coding sequence and appropriate transcriptional/translational control signals. These methods include in vitro recombinant DNA techniques, synthetic techniques, and in vivo recombination/genetic techniques. (See, for example, the techniques described in Maniatis et al., 1989 Molecular Cloning A Laboratory Manual, Cold Spring Harbor Laboratory, N.Y.)

A variety of host-expression vector systems may be utilized. These include but are not limited to microorganisms such as bacteria transformed with recombinant bacteriophage DNA, plasmid DNA, or cosmid DNA expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); or animal cell systems infected with recombinant virus expression vectors (e.g., retroviruses, adenovirus, vaccinia virus), or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter et al., 1987, Methods in Enzymology 153:516-544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces,* 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, plasma membrane insertion of the gene product may be used as host cells.

Mammalian cell systems which utilize recombinant viruses or viral elements to direct expression may be engineered. For example, when using adenovirus expression vectors, a natural antibody-binding peptide coding sequence may be ligated to an adenovirus transcription/translation control complex, e.g., the late promoter and tripartite leader sequence. Alternatively, the vaccinia virus 7.5K promoter may be used. (e.g., see, Mackett et al., 1982, Proc. Natl. Acad. Sci. USA 79: 7415-7419; Mackett et al., 1984, J. Virol. 49: 857-864; Panicali et al., 1982, Proc. Natl. Acad. Sci. USA 79: 4927-4931). Of particular interest are vectors based on bovine papilloma virus which have the ability to replicate as extrachromosomal elements (Sarver, et al., 1981, Mol. Cell. Biol. 1: 486). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of a natural antibody-binding peptide gene in host cells (Cone & Mulligan, 1984, Proc. Natl. Acad. Sci. USA 81:6349-6353). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with a cDNA controlled by appropriate expression control elements (e.g., promoter, enhancer, sequences, transcription terminators, polyadenylation sites, etc.) and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817) genes can be employed in $tk^-$, $hgprt^-$ or $aprt^-$ cells respectively. Also, antimetabolite resistance can be used as the basis of selection for dhfr, which confers resistance to methotrexate (Wigler, et al., 1980, Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072; neo, which confers resistance to the aminoglycoside G-418 (Colberre-Garapin, et al., 1981, J. Mol. Biol. 150: 1); and hygro, which confers resistance to hygromycin (Santerre, et al., 1984, Gene 30: 147) genes. Additional selectable genes include trpB, which allows cells to utilize indole in place of tryptophan; hisD, which allows cells to utilize histinol in place of histidine (Hartman & Mulligan, 1988, Proc. Natl. Acad. Sci. USA 85: 8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

For stable recombinant cell lines, suitable cell types include but are not limited to cells of the following types: NIH 3T3 (Murine), C2C12, L6, and P19. C2C12 and L6 myoblasts will differentiate spontaneously in culture and form myotubes depending on the particular growth conditions (Yaffe and Saxel, 1977; Yaffe, 1968) P19 is an embryonic carcinoma cell line. Such cells are described, for example, in the Cell Line Catalog of the American Type Culture Collection (ATCC). These cells can be stably transformed by a method known to the skilled artisan. See, for example, Ausubel et al., Introduction of DNA Into Mammalian Cells, in CURRENT PROTOCOLS IN MOLECULAR BIOLOGY, sections 9.5.1-9.5.6 (John Wiley & Sons, Inc. 1995). "Stable" transformation in the context of the invention means that the cells are immortal to the extent of having gone through at least 50 divisions.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding natural antibody-binding peptides, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, Eukaryotic Viral Vectors, Cold Spring Harbor Laboratory, Gluzman ed., 1982).

To interact with natural antibodies or for isolation and purification, natural antibody-binding proteins may need to be secreted from the host cell. Accordingly a signal sequence may be used to direct the peptide out of the host cell where it is synthesized. Typically, the signal sequence is positioned in the coding region of nucleic acid sequence, or directly at the 5' end of the coding region. Many signal sequences have been identified, and any that are functional in the selected host cell may be used. Accordingly, the signal sequence may be homologous or heterologous to the polypeptide. Additionally, the signal sequence may be chemically synthesized using recombinant DNA techniques well known in the art.

The amount of peptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

When natural antibody-binding peptides are secreted from the host cells, the majority of the peptide will likely be found in the cell culture medium. If, however, the peptide is not secreted, it will be present in the cytoplasm (for eukaryotic, Gram-positive bacteria, and insect host cells) or in the periplasm (for Gram-negative bacteria host cells).

If the natural antibody-binding peptide remains in the intracellular space, the host cells are typically first disrupted mechanically or osmotically to release the cytoplasmic contents into a buffered solution. The peptide is then isolated from this solution. Purification of the peptide from solution can thereafter be accomplished using a variety of techniques. If the peptide has been synthesized such that it contains a tag such as hexahistidine or other small peptides at either its carboxyl or amino terminus, it may be purified in a one-step process by passing the solution through an affinity column where the column matrix has a high affinity for the tag or for the peptide directly (i.e., a monoclonal antibody). For example, polyhistidine binds with great affinity and specificity to nickel, thus an affinity column of nickel (such as the Qiagen nickel columns) can be used for purification. (See, for example, Ausubel et al., eds., Current Protocols in Molecular Biology, John Wiley & Sons, New York, 1994).

Where, on the other hand, the peptide has no tag and it is not practical to use an antibody to purify the peptide, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If it is anticipated that the peptide will be found primarily in the periplasmic space of the bacteria or the cytoplasm of eukaryotic cells, the contents of the periplasm or cytoplasm, including inclusion bodies (e.g., Gram-negative bacteria) if the processed peptide has formed such complexes, can be extracted from the host cell using any standard technique known to the skilled artisan. For example, the host cells can be lysed to release the contents of the periplasm by the use of a French press, homogenization, and/or sonication. The homogenate can then be centrifuged.

6.3.4 Antibody Inhibitors of Natural IgM Antibodies

IgM inhibitors may also be antibodies that compete with natural IgMs in binding to antigen. Methods of producing antibodies are well known in the art. For example, a monoclonal antibody against a target (e.g., a pathogenic immunoglobulin or an ischemia specific antigen on a cell) can be produced by a variety of techniques, including conventional monoclonal antibody methodology e.g., the standard somatic cell hybridization technique of Kohler and Milstein, *Nature* 256: 495 (1975). Although somatic cell hybridization procedures are preferred, in principle, other techniques for producing monoclonal antibody can be employed e.g., viral or oncogenic transformation of B lymphocytes. The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Human monoclonal antibodies can be generated using transgenic mice carrying the human immunoglobulin genes rather than mouse immunoglobulin genes. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immuno. 17:33-40; Tuaillon et al. 1993 PNAS 90:3720-3724; Bruggeman et al. 1991 Eur. J. Immunol 21:1323-1326). In one embodiment, hybridomas can be generated from human CD5+, B-1 cells. Alternatively, "humanized" murine hybridomas can be used that recognize cross-reactive "ischemic antigen".

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 PNAS 86:5,728; Huse et al. 1989 Science 246:1275; and Orlandi et al. 1989 PNAS 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al., 1991, *Biotechniques* 11:152-156). A similar strategy can also been used to amplify human heavy and light chain variable regions from human antibodies (Larrick et al., 1991, *Methods: Companion to Methods in Enzymology* 2:106-110).

In an illustrative embodiment, RNA is isolated from B lymphocytes, for example, peripheral blood cells, bone marrow, or spleen preparations, using standard protocols (e.g., U.S. Pat. No. 4,683,202; Orlandi, et al. PNAS (1989) 86:3833-3837; Sastry et al., PNAS (1989) 86:5728-5732; and Huse et al. (1989) *Science* 246:1275-1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage; to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating a variegated antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Human Antibody Hybridomas* 3:81-85; Huse et al. (1989) *Science* 246:1275-1281; Griffths et al. (1993) *EMBO J.* 12:725-734; Hawkins et al. (1992) *J. Mol. Biol.* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc. Acid Res.* 19:4133-4137; and Barbas et al. (1991) *PNAS* 88:7978-7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552-554, complete $V_H$ and $V_L$ domains of an antibody, joined by a flexible $(Gly_4\text{-}Ser)_3$ linker (SEQ ID NO: 65) can be used to produce a single chain antibody which can render the display package separable based on antigen affinity. Isolated scFV antibodies immunoreactive with the antigen can subsequently be formulated into a pharmaceutical preparation for use in the subject method.

Once displayed on the surface of a display package (e.g., filamentous phage), the antibody library is screened with the target antigen, or peptide fragment thereof, to identify and isolate packages that express an antibody having specificity for the target antigen. Nucleic acid encoding the selected antibody can be recovered from the display package (e.g., from the phage genome) and subcloned into other expression vectors by standard recombinant DNA techniques.

Specific antibody molecules with high affinities for a surface protein can be made according to methods known to those in the art, e.g., methods involving screening of libraries (Ladner, R. C., et al., U.S. Pat. No. 5,233,409; Ladner, R. C., et al., U.S. Pat. No. 5,403,484). Further, these libraries can be used in screens to obtain binding determinants that are mimetics of the structural determinants of antibodies.

In particular, the Fv binding surface of a particular antibody molecule interacts with its target ligand according to principles of protein-protein interactions, hence sequence data for $V_H$ and $V_L$ (the latter of which may be of the κ or λ chain type) can be used in protein engineering techniques known to those with skill in the art. Details of the protein surface that comprises the binding determinants can be obtained from antibody sequence information, by a modeling procedure using previously determined three-dimensional structures from other antibodies obtained from NMR studies or crystallographic data. See for example Bajorath, J. and S. Sheriff, 1996, *Proteins: Struct., Funct., and Genet.* 24 (2), 152-157; Webster, D. M. and A. R. Rees, 1995, "Molecular modeling of antibody-combining sites," in S. Paul, Ed., *Methods in Molecular Biol.* 51, Antibody Engineering Protocols, Humana Press, Totowa, N.J., pp 17-49; and Johnson, G., Wu, T. T. and E. A. Kabat, 1995, "Seqhunt: A program to screen aligned nucleotide and amino acid sequences," in *Methods in Molecular Biol.* 51, *op. cit.*, pp 1-15.

In one embodiment, a variegated peptide library is expressed by a population of display packages to form a peptide display library. Ideally, the display package comprises a system that allows the sampling of very large variegated peptide display libraries, rapid sorting after each affinity separation round, and easy isolation of the peptide-encoding gene from purified display packages. Peptide display libraries can be in, e.g., prokaryotic organisms and viruses, which can be amplified quickly, are relatively easy to manipulate, and which allow the creation of large number of clones. Preferred display packages include, for example, vegetative bacterial cells, bacterial spores, and most preferably, bacterial viruses (especially DNA viruses). However, the present invention also contemplates the use of eukaryotic cells, including yeast and their spores, as potential display packages. Phage display libraries are described above.

Other techniques include affinity chromatography with an appropriate "receptor", e.g., a target antigen, followed by identification of the isolated binding agents or ligands by conventional techniques (e.g., mass spectrometry and NMR). Preferably, the soluble receptor is conjugated to a label (e.g., fluorophores, colorimetric enzymes, radioisotopes, or luminescent compounds) that can be detected to indicate ligand binding. Alternatively, immobilized compounds can be selectively released and allowed to diffuse through a membrane to interact with a receptor.

Combinatorial libraries of compounds can also be synthesized with "tags" to encode the identity of each member of the library (see, e.g., W. C. Still et al., International Application WO 94/08051). In general, this method features the use of inert but readily detectable tags that are attached to the solid support or to the compounds. When an active compound is detected, the identity of the compound is determined by identification of the unique accompanying tag. This tagging method permits the synthesis of large libraries of compounds which can be identified at very low levels among the total set of all compounds in the library.

An antibody of the present invention can be one in which the variable region, or a portion thereof, e.g., the complementarity determining regions (CDR or CDRs), are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention. Any modification is within the scope of the invention so long as the antibody has at least one antigen binding portion.

Chimeric antibodies (e.g. mouse-human monoclonal antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) PNAS 84:3439-3443; Liu et al., 1987, J. *Immunol.* 139:3521-3526; Sun et al. (1987) PNAS 84:214-218; Nishimura et al., 1987, *Canc. Res.* 47:999-1005; Wood et al. (1985) *Nature* 314:446-449; and Shaw et al., 1988, J. *Natl. Cancer Inst.* 80:1553-1559).

A chimeric antibody can be further humanized by replacing sequences of the Fv variable region which are not directly involved in antigen binding with equivalent sequences from human Fv variable regions. General methods for generating humanized antibodies are provided by Morrison, S. L., 1985, *Science* 229:1202-1207 by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution. U.S. Pat. No. 5,225,539; Jones et al. 1986 *Nature* 321:552-525; Verhoeyan et al. 1988 *Science* 239:1534; and Beidler et al. 1988 J *Immunol.* 141:4053-4060.

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

A humanized or CDR-grafted antibody will have at least one or two but generally all recipient CDRs (of heavy and/or light immunoglobulin chains) replaced with a donor CDR. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework can be a naturally-occurring (e.g., a human) framework or a consensus framework, or a sequence about 85% or higher, preferably 90%, 95%, 99% or higher identical thereto.

All of the CDRs of a particular antibody may be replaced with at least a portion of a non-human CDR or only some of the CDRs may be replaced with non-human CDRs. It is only necessary to replace the number of CDRs required for binding of the humanized antibody to the Fc receptor.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, a humanized antibody will have framework residues identical to the donor framework residue or to another amino acid other than the recipient framework residue. As another example, in a humanized antibody having mouse CDRs, amino acids located in the human framework region can be replaced with the amino acids located at the corresponding positions in the mouse antibody. Such substitutions are known to improve binding of humanized antibodies to the antigen in some instances.

Antibody fragments of the invention are obtained using conventional procedures known to those with skill in the art. For example, digestion of an antibody with pepsin yields F(ab')2 fragments and multiple small fragments. Mercaptoethanol reduction of an antibody yields individual heavy and light chains. Digestion of an antibody with papain yields individual Fab fragments and the Fc fragment.

In another aspect, the invention also features a modified natural immunoglobulin, e.g., which functions as an agonist (mimetic) or as an antagonist. Preferably the modified natural immunoglobulin, e.g., modified pathogenic immunoglobulin, functions as an antagonist of complement activation. Variants of the pathogenic immunoglobulin can be generated by mutagenesis, e.g., discrete point mutation, the insertion or deletion of sequences or the truncation of a pathogenic immunoglobulin. An agonist of the natural immunoglobulin can retain substantially the same, or a subset, of the biological activities of the naturally occurring form of the protein. An antagonist of a natural immunoglobulin can inhibit one or more of the activities of the naturally occurring form of the pathogenic immunoglobulin by, for example, being capable of binding to an ischemic specific antigen, but incapable of activating a complement pathway. Thus, specific biological effects can be elicited by treatment with a variant of limited function.

In one embodiment, the site within the natural immunoglobulin (e.g., a pathogenic IgM) that binds Clq can be mutated such that it is no longer capable of binding Clq. For example, the CH2 domain of an IgG and the CH4 domain of an IgM, which are known to contain binding sites for Clq, can be mutated (see WO 94/29351). For example, the carboxyl terminal half of the CH2 domain of an IgG (residues 231 to 239, preferably within 234 to 239), which appear to mediate Clq binding and subsequent complement activation, can be mutated. As another example, Wright et al. have demonstrated that a single nucleotide change in the IgM constant region domain renders the antibody defective in initiating complement-dependent cytolysis. The single nucleotide change results in the encoding of a serine residue, rather than the normal proline residue, at amino acid position 436 in the third constant domain (Wright et al. 1988, *J. Biol. Chem.* 263:11221). The amino acid substitutions that can be made to antibodies in order to alter complement binding or activity are well known in the art (see for example, Wright et al. 1988, J. *Biol. Chem.* 263: 11221; Shulman et al. (1986), *Proc. Natl. Acad. Sci. USA* 83: 7678-7682; Arya et al., (1994) J. *Immunol.* 253: 1206-1212; Poon et al., (1995) J. *Biol. Chem.* 270: 8571-8577, the contents of all of which are hereby incorporated by reference). Accordingly, in one embodiment, the antibodies of the present invention have a mutation that alters complement binding or activity. Antibodies in which amino acids have been added, deleted, or substituted are referred to herein as modified antibodies or altered antibodies. As will be appreciated by the skilled artisan, the methods used for causing such changes in nucleotide or amino acid sequence will vary depending upon the desired results.

Variants of a natural immunoglobulin can be identified by screening combinatorial libraries of mutants, e.g., truncation mutants, of a natural immunoglobulin for agonist or antagonist activity.

Libraries of fragments e.g., N terminal, C terminal, or internal fragments, of a natural immunoglobulin coding sequence can be used to generate a variegated population of fragments for screening and subsequent selection of variants of this protein. Variants in which a cysteine residue is added or deleted or in which a residue that is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a technique which enhances the frequency of functional mutants in the libraries, can be used in combination with the screening assays to identify variants (Arkin and Yourvan (1992) *Proc. Natl. Acad. Sci. USA* 89:7811-7815; Delgrave et al. (1993) *Protein Engineering* 6(3):327-331).

Cell based assays can be exploited to analyze a variegated library. For example, a library of expression vectors can be transfected into a cell line, e.g., a cell line, which ordinarily responds to the protein in a substrate-dependent manner. Plasmid DNA can then be recovered from the cells which score for inhibition, or alternatively, potentiation of signaling by the pathogenic immunoglobulin-substrate, and the individual clones further characterized.

The invention also features a method of making a natural immunoglobulin, e.g., a pathogenic immunoglobulin having a non-wild type activity, e.g., an antagonist, agonist, or super agonist of a naturally occurring pathogenic immunoglobulin. The method includes: altering the sequence of a natural immunoglobulin, e.g., by substitution or deletion of one or more residues of a non-conserved region, a domain or residue disclosed herein, and testing the altered polypeptide for the desired activity.

Further, the invention features a method of making a fragment or analog of a natural immunoglobulin, e.g., a pathogenic immunoglobulin having an altered biological activity of a naturally occurring pathogenic immunoglobulin. The method includes: altering the sequence, e.g., by substitution or deletion of one or more residues, of a pathogenic immunoglobulin, e.g., altering the sequence of a non-conserved region, or a domain or residue described herein, and testing the altered polypeptide for the desired activity. In an exemplary embodiment, the modified natural immunoglobulin may have a reduced ability to activate complement. For example, one or more of the amino acid residues involved in complement binding and/or activation are mutated.

In certain embodiment, the modified natural antibody may comprise at least the CDR1 region of SEQ ID NO: 8 (SEQ ID NO: 10), or antigen binding portions thereof, and/or at least the CDR2 region of SEQ ID NO: 8 (SEQ ID NO: 12), or antigen binding portions thereof. In another embodiment, the modified antibody may comprise at least the CDR1 region of SEQ ID NO: 2 (SEQ ID NO: 4), or antigen binding portions thereof, and/or at least the CDR2 region of SEQ ID NO: 2 (SEQ ID NO: 6), or antigen binding portions thereof. In an exemplary embodiment, the modified antibody comprises the CDR1 region of SEQ ID NO: 8 (SEQ ID NO: 10) and the CDR2 region of SEQ ID NO: 8 (SEQ ID NO: 12) or antigen binding portions thereof. In another exemplary embodiment, the modified antibody comprises the CDR1 region of SEQ ID NO: 2 (SEQ ID NO: 4) and the CDR2 region of SEQ ID NO: 2 (SEQ ID NO: 6) or antigen binding portions thereof. The modified antibody may also comprise the CDR1 region of SEQ ID NO: 8 (SEQ ID NO: 10) and the CDR2 region of SEQ ID NO: 8 (SEQ ID NO: 12) and the modified antibody comprises the CDR1 region of SEQ ID NO: 2 (SEQ ID NO: 4) and the CDR2 region of SEQ ID NO: 2 (SEQ ID NO: 6) or antigen binding portions thereof.

The modified natural antibody can be a human antibody having a binding affinity to the ischemic-specific antigen, similar, e.g., greater than, less than, or equal to, the binding affinity of the antibody produced by the hybridoma deposited with the ATCC, having the accession number PTA-3507. In another embodiment, the natural antibody can be a non-human antibody, e.g., a cow, goat, mouse, rat, sheep, pig, or rabbit. In an exemplary embodiment, the non-human antibody is a murine antibody. The natural antibody may also be a recombinant antibody. In an exemplary embodiment, the natural antibody is a humanized antibody. The modified natural antibody may be an IgG or IgM antibody. In another embodiment, the isolated natural immunoglobulin possess the same antigenic specificity as the immunoglobulin produced by the hybridoma deposited with the ATCC, having accession number PTA-3507.

6.4 Screening Assay to Identify Additional Inhibitors

Other inhibitors of an interaction between a natural IgM antibody and an antigen or a component of the complement pathway may be identified from one or more (e.g., a plurality of) test compounds, comprising (i) providing a reaction mixture which includes the natural IgM antibody and the antigen or the component of the complement pathway under conditions that allow binding of the natural IgM antibody and the antigen or the component of the complement pathway to occur; (ii) contacting the natural IgM antibody and the antigen or the component of the complement pathway with one or more test compounds (e.g., members of a combinatorial library); and (iii) detecting any changes in binding of the natural IgM antibody and the antigen or the component of the complement in the presence of a given test compound relative to that detected in the absence of the test compound. A change (e.g., decrease) in the level of binding between the natural IgM antibody and the antigen or the component of the complement pathway in the presence of the test compound relative to that detected in the absence of the test compound indicates that the test compound is an inhibitor of the interaction between the natural IgM antibody and the antigen or the component of the complement pathway.

The method can further include pre-treating the natural IgM antibodies with one or more test compounds. The pre-treated natural IgM antibodies can then be injected into mice deficient in natural immunoglobulins.

In certain embodiments, the methods is performed in vitro. In an exemplary embodiment, the contacting step is effected in vivo. In an exemplary embodiment, the antigen is myosin. In other embodiments, the antigen is an endothelial tissue or lysate obtained from a subject e.g., a human patient with reperfusion or ischemic injury. In another exemplary embodiment, the component of the complement pathway is a component of the classical pathway of complement. In a further exemplary embodiment, the component of the complement pathway is a Cl molecule or a subunit thereof (e.g., Clq).

In exemplary embodiments, either the natural IgM antibody or the antigen (or both) is labeled with a detectable signal, e.g., fluorophores, calorimetric enzymes, radioisotopes, luminescent compounds, and the like. The method can further include repeating at least one step, e.g., the contacting step with a second or subsequent member or members of the library.

In an exemplary embodiment, a plurality of test compounds, e.g., library members, is tested. The plurality of test compounds, e.g., library members, can include at least 10, $10^2$, $10^3$, $10^4$, $10^5$, $10^6$, $10^7$, or $10^8$ compounds. In a preferred embodiment, the plurality of test compounds, e.g., library members, share a structural or functional characteristic. The test compound can be a peptide or a small organic molecule.

In one embodiment, the inhibitor is a small organic molecule that may be identified in a combinatorial library. In one embodiment, the invention provides libraries of inhibitors. The synthesis of combinatorial libraries is well known in the art and has been reviewed (see, e.g., E. M. Gordon et al., *J. Med. Chem.* (1994) 37:1385-1401; DeWitt, S. H.; Czarnik, A. W. Acc. *Chem. Res.* (1996) 29:114; Armstrong, R. W.; Combs, A. P.; Tempest, P. A.; Brown, S. D.; Keating, T. A. *Acc. Chem. Res.* (1996) 29:123; Ellman, J. A. *Acc. Chem. Res.* (1996) 29:132; Gordon, E. M.; Gallop, M. A.; Patel, D. V. *Acc. Chem.* Res. (1996) 29:144; Lowe, G. *Chem. Soc. Rev.* (1995) 309, Blondelle et al. *Trends Anal. Chem.* (1995) 14:83; Chen et al. J. *Am. Chem.* Soc. (1994) 116:2661; U.S. Pat. Nos. 5,359,115, 5,362,899, and 5,288,514; PCT Publication Nos. WO92/10092, WO93/09668, WO91/07087, WO93/20242, WO94/08051).

Libraries of compounds of the invention can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis", 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy results in a library of peptides, e.g., inhibitors, which can be used to prepare a library of test compounds of the invention. In another illustrative synthesis, a "diversomer library" is created by the method of Hobbs DeWitt et al. (*Proc. Natl. Acad. Sci. USA* 90:6909 (1993)). Other synthesis methods, including the "tea-bag" technique of Houghten (see, e.g., Houghten et al., *Nature* 354:84-86 (1991)) can also be used to synthesize libraries of compounds according to the subject invention. Libraries of compounds can be screened to determine whether any members of the library have a desired activity, and, if so, to identify the active species. Methods of screening combinatorial libraries have been described (see, e.g., Gordon et al., *J. Med. Chem.*, supra). Soluble compound libraries can be screened by affinity chromatography with an appropriate receptor to isolate ligands for the receptor, followed by identification of the isolated ligands by conventional techniques (e.g., mass spectrometry, NMR, and the. like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries of the invention are described below.

In one embodiment, compounds of the invention can be screened for the ability to interact with a natural immunoglobulin by assaying the activity of each compound to bind directly to the immunoglobulin or to inhibit an interaction between the immunoglobulin and an ischemic antigen, e.g., by incubating the test compound with an immunoglobulin and a lysate, e.g., an endothelial cell lysate, e.g., in one well of a multiwell plate, such as a standard 96-well microtiter plate. In this embodiment, the activity of each individual compound can be determined. A well or wells having no test compound can be used as a control. After incubation, the activity of each test compound can be determined by assaying each well. Thus, the activities of a plurality of test compounds can be determined in parallel.

6.5 Modified Inhibitors and Pharmaceutical and Diagnostic Preparations

IgM inhibitors may be modified, for example to increase solubility and/or facilitate purification, identification, detection, and/or structural characterization. Exemplary modifications, include, for example, addition of: glutathione S-transferase (GST), protein A, protein G, calmodulin-binding peptide, thioredoxin, maltose binding protein, HA, myc, poly-arginine, poly-His, poly-His-Asp or FLAG fusion proteins and tags. In various embodiments, an IgM inhibitors may comprise one or more heterologous fusions. For example, peptides may contain multiple copies of the same fusion domain or may contain fusions to two or more different domains. The fusions may occur at the N-terminus of the peptide, at the C-terminus of the peptide, or at both the N- and C-terminus of the peptide. It is also within the scope of the invention to include linker sequences between a peptide of the invention and the fusion domain in order to facilitate construction of the fusion protein or to optimize protein expression or structural constraints of the fusion protein. In another embodiment, the peptide may be constructed so as to contain protease cleavage sites between the fusion peptide and peptide of the invention in order to remove the tag after protein expression or thereafter. Examples of suitable endoproteases, include, for example, Factor Xa and TEV proteases.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments, which may subsequently be annealed to generate a chimeric gene sequence (see, for example, Current Protocols in Molecular Biology, eds. Ausubel et al., John Wiley & Sons: 1992).

IgM inhibitors may be chemically modified based on linkage to a polymer. The polymer is typically water soluble so that the inhibitor to which it is attached does not precipitate in an aqueous environment, such as a physiological environment. The polymer may have a single reactive group, such as an active ester for acylation or an aldehyde for alkylation, so that the degree of polymerization may be controlled. A preferred reactive aldehyde is polyethylene glycol propionaldehyde, which is water stable, or mono C1-C10 alkoxy or aryloxy derivatives thereof (see U.S. Pat. No. 5,252,714). The polymer may be branched or unbranched. Preferably, for therapeutic use of the end-product preparation, the polymer will be pharmaceutically acceptable. The water soluble polymer, or mixture thereof if desired, may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

IgM inhibitors may be labeled, for example with an isotopic label to facilitate its detection using nuclear magnetic resonance or another applicable technique. Exemplary isotopic labels include radioisotopic labels such as, for example, potassium-40 ($^{40}$K), carbon-14 ($^{14}C$), tritium ($^{3}$H), sulphur-35 ($^{35}$S), phosphorus-32 ($^{32}$P), technetium-99 m ($^{99m}$Tc), thallium-201 ($^{201}$Tl), gallium-67 ($^{67}$Ga), indium-111($^{111}$In), iodine-123 ($^{123}$I), iodine-131 ($^{131}$I), yttrium-90 ($^{90}$Y), samarium-153 ($^{153}$Sm), rhenium-186 ($^{186}$Re), rhenium-188 ($^{188}$Re), dysprosium-165 ($^{165}$Dy) and holmium-166 ($^{166}$Ho). The isotopic label may also be an atom with non zero nuclear spin, including, for example, hydrogen-1 ($^{1}$H), hydrogen-2 ($^{2}$H), hydrogen-3 ($^{3}$H), phosphorous-31 ($^{31}$P), sodium-23 ($^{23}$Na), nitrogen-14 ($^{14}$N), nitrogen-1 ($^{15}$N), carbon-13 ($^{13}$C) and fluorine-19 ($^{19}$F). In certain embodiments, the inhibitor is uniformly labeled with an isotopic label, for example, wherein at least 50%, 70%, 80%, 90%, 95%, or 98% of the inhibitor is labeled. In other embodiments, the isotopic label is located in one or more specific locations within the inhibitor, for example, the label may be specifically incorporated into one or more of the leucine residues of a peptide. A single inhibitor may comprise two or more different isotopic labels, for example, a peptide may comprise both $^{15}$N and $^{13}$C labeling.

Inhibitors may be labeled with a fluorescent label. In an exemplary embodiment, an inhibitor is fused to a heterologous polypeptide sequence which produces a detectable fluorescent signal, including, for example, green fluorescent protein (GFP), enhanced green fluorescent protein (EGFP), *Renilla reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Toxicity and therapeutic efficacy of natural antibody inhibitors including natural IgM antibody-binding peptides or modified natural IgM antibodies can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Natural antibody inhibitors which exhibit large therapeutic effects are preferred. While natural antibody inhibitors or natural antibody-binding peptides that exhibit toxic side effects may be used, care should be taken to design a delivery system that targets such peptides or modified antibodies to the site of affected tissue in order to minimize potential damage to uninfected cells and, thereby, reduce side effects.

The data obtained from the cell culture assays and animal studies can be used in formulating a range of dosage for use in humans. The dosage of a natural antibody inhibitor or a natural antibody-binding peptides lies preferably within a range of circulating concentrations that include the $ED_{50}$ with little or no toxicity. The dosage may vary within this range depending upon the dosage form employed and the route of administration utilized. For any inhibitor or peptide used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In another embodiment, a single bolus of a natural antibody inhibitor including a natural IgM antibody-binding peptide and modified natural IgM antibodies is administered prior to, contemporaneously with, or subsequent to a tissue injury. Typically a single dose injection will be a few hours, a few days or a few weeks after tissue injury. The present invention is based in part upon the discovery that a natural IgM antibody inhibitor prevents reperfusion injury. A single unit dosage delivery can be immediately adjacent to the site of injury or can be, for example, to a vessel that drains or flows to the site of injury.

A natural IgM antibody inhibitor such as natural IgM antibody-binding peptide or modified natural IgM antibody is administered initially at a point in time prior to the time of damage of the target organ or tissue. This may be a useful approach in subjects who are determined to be at risk for reperfusion injury, such as those with a history of reperfusion injury or those about to undergo surgery.

In yet another embodiment, a single bolus of a natural IgM antibody inhibitor can be followed by subsequence administrations of a natural IgM antibody inhibitor as continuous infusions or additional single bolus deliveries. The inhibitor may be administer in sequential exposures over a period of hours, days, weeks, months or years. In addition, it is contemplated that additional therapeutic agents can be combined with, administered prior to or subsequent to administration of a natural antibody-binding peptide or another natural antibody inhibitor. Other therapeutic agents that may be administered with an natural IgM antibody inhibitor include, but are not limited to, anti-coagulation agents and complement inhibitors.

The subject inhibitors may be provided in pharmaceutically acceptable carriers or formulated for a variety of modes of administration, including systemic and topical or localized administration. Techniques and formulations generally may be found in Remmington's Pharmaceutical Sciences, Meade Publishing Co., Easton, Pa. In certain embodiments, the inhibitor is provided for transmucosal or transdermal delivery. For such administration, penetrants appropriate to the barrier to be permeated are used in the formulation with the polypeptide. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the inhibitors of the invention are formulated into ointments, salves, gels, or creams as generally known in the art.

The pharmaceutical compositions according to the invention are prepared by bringing a natural IgM antibody inhibitors into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions are preferably prepared and administered in dose units. Solid dose units are tablets, capsules and suppositories and including, for example, alginate based pH dependent release gel caps. For treatment of a subject, depending on activity of the compound, manner of administration, nature and severity of the disorder, age and body weight of the subject, different daily doses are necessary. Under certain circumstances, however, higher or lower daily doses may be appropriate. The administration of the daily dose can be carried out both by single administration in the form of an individual dose unit or by several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. As discussed above, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Gilman et al. (eds.) (1990), each of which is herein incorporated by reference.

In one embodiment, the invention provides a pharmaceutical composition useful for administering a natural antibody-binding peptide to a subject in need of such treatment. "Administering" the pharmaceutical composition of the invention may be accomplished by any means known to the skilled artisan. Preferably a "subject" refers to a mammal, most preferably a human.

The natural IgM antibody inhibitor can be administered parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water. Where the disease or disorder is a gastrointestinal disorder oral formulations or suppository formulations are preferred.

Sterile injectable solutions can be prepared by incorporating a natural antibody-binding peptide in the required amount (e.g., about 10 μg to about 10 mg/kg) in an appropriate solvent and then sterilizing, such as by sterile filtration. Further, powders can be prepared by standard techniques such as freeze drying or vacuum drying.

In another embodiment, a natural IgM antibody inhibitor is prepared with a biodegradable carrier for sustained release characteristics for either sustained release in the GI tract or for target organ implantation with long term active agent release characteristics to the intended site of activity. Biodegradable polymers include, for example, ethylene vinyl acetate, polyanhydrides, polyglycolic acids, polylactic acids, collagen, polyorthoesters, and poly acetic acid. Liposomal formulation can also be used.

Another means of delivering natural IgM antibody inhibitor (e.g., a natural IgM antibody-binding peptide) is by delivering host cells that express natural antibody-binding peptides to a site or tissue in need of repair. Alternatively, the cells may be delivered in conjunction with various delivery vehicles, including biocompatible biodegradable or non-biodegradable sponges (e.g., collagen, or other extracellular matrix materials), cotton, polyglycolic acid, cat gut sutures, cellulose, gelatin, dextran, polyamide, a polyester, a polystyrene, a polypropylene, a polyacrylate, a polyvinyl, a polycarbonate, a polytetrafluorethylene, or a nitrocellulose compound formed into a three-dimensional structure (see, for example, U.S. Pat. No. 5,858,721 to Naughton et al., the disclosure of which is incorporated herein by reference).

Any route of administration compatible with the active principle can be used. The preferred is parenteral administration, such as subcutaneous, intramuscular or intravenous injection. The dose of the active ingredient to be administered depends on the basis of the medical prescriptions according to age, weight and the individual response of the patient.

The daily non-weighted dosage for the patient can be between about 2.5-5.0 mg/Kg, e.g., about 2.5-3.0 mg/Kg, about 3.0-3.5 mg/Kg, about 3.5-4.0 mg/Kg, about 4.0-4.5 mg/Kg, and about 4.5-5.0 mg/Kg.

The pharmaceutical composition for parenteral administration can be prepared in an injectable form comprising the active principle and a suitable vehicle. Vehicles for the parenteral administration are well known in the art and comprise, for example, water, saline solution, Ringer solution and/or dextrose.

The vehicle can contain small amounts of excipients in order to maintain the stability and isotonicity of the pharmaceutical preparation.

The preparation of the cited solutions can be carried out according to the ordinary modalities.

The present invention has been described with reference to the specific embodiments, but the content of the description comprises all modifications and substitutions which can be brought by a person skilled in the art without extending beyond the meaning and purpose of the claims. The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

6.6 Diseases and Conditions that can be Treated with Natural IgM Antibody Inhibitors IgM inhibitors, such as natural IgM antibody-binding peptides or modified natural IgM antibodies, may be used for treating a number of inflammatory diseases and conditions that are triggered by binding of natural IgM antibodies. For instance, the inhibitors may be used to treat inflammatory diseases or conditions such as reperfusion injury, ischemia injury, stroke, autoimmune hemolytic anemia, idiopathic thrombocytopenic purpura, rheumatoid arthritis, celiac disease, hyper-IgM immunodeficiency, arteriosclerosis, coronary artery disease, sepsis, myocarditis, encephalitis, transplant rejection, hepatitis, thyroiditis (e.g., Hashimoto's thyroiditis, Graves disease), osteoporosis, polymyositis, dermatomyositis, Type I diabetes, gout, dermatitis, alopecia greata, systemic lupus erythematosus, lichen sclerosis, ulcerative colitis, diabetic retinopathy, pelvic inflammatory disease, periodontal disease, arthritis, juvenile chronic arthritis (e.g., chronic iridocyclitis), psoriasis, osteoporosis, nephropathy in diabetes mellitus, asthma, pelvic inflammatory disease, chronic inflammatory liver disease, chronic inflammatory lung disease, lung fibrosis, liver fibrosis, rheumatoid arthritis, chronic inflammatory liver disease, chronic inflammatory lung disease, lung fibrosis, liver fibrosis, Crohn's disease, ulcerative colitis, burn injury (or thermal injury), and other acute and chronic inflammatory diseases of the Central Nervous System (CNS; e.g., multiple sclerosis), gastrointestinal system, the skin and associated structures, the immune system, the hepato-biliary system, or any site in the body where pathology can occur with an inflammatory component.

An inflammatory condition such as reperfusion or ischemic injury may result following a naturally occurring episode, e.g., as a stroke or myocardial infarction. Reperfusion or ischemic injury may also occur during and/or following a surgical procedure. Exemplary surgical procedures that cause can cause injury include a vessel-corrective technique selected from the group consisting of angioplasty, stenting procedure, atherectomy, and bypass surgery. In an exemplary embodiment, reperfusion or ischemic injury occurs in a cardiovascular tissue, such as the heart.

In addition, diseases or conditions that are triggered by binding of natural IgM antibodies may be treated or prevented in a subject by removing from the subject or inactivating a natural or pathogenic IgM and/or B cells producing the pathogenic immunoglobulin (e.g., B-1 cells as described herein), thereby reducing the amount of the pathogenic immunoglobulin and/or B cells present in the subject.

The methods described herein may comprise removing from the subject or inactivating a pathogenic immunoglobulin, e.g., a pathogenic IgM as described herein, and/or B-cells producing the pathogenic IgM (e.g., B-1 cells as described herein), thereby reducing the amount of the pathogenic immunoglobulin and/or B cells present in the subject.

In one embodiment, the removing or inactivating step is performed ex vivo. The pathogenic immunoglobulins or B cells can be removed by hemoperfusion. Alternatively, the B cells can be removed using a B cell-specific antibody (e.g., an anti-B-1 antibody or an anti-CD5 antibody or anti-CD 11 G/CD 18). The pathogenic immunoglobulin, e.g., an IgM, can be removed by contacting blood from a subject with an immobilized antigen (e.g., an ischemia-specific antigen) or an immobilized anti-idiotypic antibody. The removing or inactivating step of the pathogenic immunoglobulin may be performed by administering an anti-idiotypic antibody to the subject. In another embodiment, the removing or inactivating step of the B cell is performed by administering to the subject a B cell targeting moiety (e.g., an antibody or an antigen binding fragment thereof, or an antigen) coupled to a toxin, e.g., ricin or diphteria toxin. The subject is a mammal, e.g., a rodent (e.g., a mouse) or a primate (e.g., a human). In a exemplary embodiment, the subject has sustained a reperfusion or ischemic injury following a naturally occurring episode, e.g., as a stroke, and the removing step is carried out within minutes, one to five hours, five to ten hours, ten to twenty hours, one to five days, following the naturally occurring episode. In another exemplary embodiment, the reperfusion or ischemic injury occurs in a cardiovascular tissue, e.g., the heart, and the reperfusion or ischemic injury is prevented and/or decreased by, removing from the subject, the pathogenic immunoglobulin, and/or the B cells, prior to, during, and/or following the surgical procedure. For example, the removing step can be carried out at least one to five hours, five to ten hours, ten to twenty hours, or one, two or three days prior to the surgical procedure. The removing step can also be continued for appropriate time intervals during and after the surgical procedure.

6.7 Diagnostic Assays

The invention further provides a method for detecting the presence of a natural IgM antibody in a biological sample. Detection of a natural IgM antibody in a subject, particularly a mammal, and especially a human, will provide a diagnostic method for diagnosis of an inflammatory disease or condition in the subject. In general, the method involves contacting the biological sample with a compound or an agent capable of detecting natural IgM antibody of the invention or a nucleic acid of the invention in the sample. The term "biological sample" when used in reference to a diagnostic assay is intended to include tissues, cells and biological fluids isolated from a subject, as well as tissues, cells and fluids present within a subject.

The detection method of the invention may be used to detect the presence of a natural IgM antibody or a nucleic acid of the invention in a biological sample in vitro as well as in vivo. For example, in vitro techniques for detection of a nucleic acid of the invention include Northern hybridizations and in situ hybridizations. In vitro techniques for detection of polypeptides of the invention include enzyme linked immunosorbent assays (ELISAs), Western blots, immunoprecipitations, immunofluorescence, radioimmunoassays and competitive binding assays.

Nucleic acids for diagnosis may be obtained from an infected individual's cells and tissues, such as bone, blood, muscle, cartilage, and skin. Nucleic acids, e.g., DNA and RNA, may be used directly for detection or may be amplified, e.g., enzymatically by using PCR or other amplification technique, prior to analysis. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing a nucleic acid, e.g., amplified DNA, to a nucleic acid of the invention, which nucleic acid may be labeled. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g. Myers et al., Science, 230: 1242 (1985). Sequence changes at specific locations also may be revealed by nuclease protection assays, such as RNase and S1 protection or a chemical cleavage method. See, e.g., Cotton et al., Proc. Natl. Acad. Sci., USA, 85: 4397-4401 (1985).

Agents for detecting a nucleic acid of the invention, e.g., comprising the sequence set forth in a subject nucleic acid sequence, include labeled nucleic acid probes capable of hybridizing to a nucleic acid of the invention. The nucleic acid probe can comprise, for example, the full length sequence of a nucleic acid of the invention, or an equivalent thereof, or a portion thereof, such as an oligonucleotide of at least 15, 30, 50, 100, 250 or 500 nucleotides in length and sufficient to specifically hybridize under stringent conditions to a subject nucleic acid sequence, or the complement thereof. Agents for detecting a polypeptide of the invention, e.g., comprising an amino acid sequence of a subject amino acid sequence, include labeled anti-antibodies capable of binding to a natural IgM antibody of the invention. Anti-idiotypic antibodies may be polyclonal, or alternatively, monoclonal. An intact anti-idiotypic antibody, or a fragment thereof can be used. Labeling the probe or antibody also encompasses direct labeling of the probe or antibody by coupling (e.g., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In certain embodiments, detection of a nucleic acid of the invention in a biological sample involves the use of a probe/primer in a polymerase chain reaction (PCR) (see, e.g. U.S. Pat. No. 4,683,195 and U.S. Pat. No. 4,683,202), such as anchor PCR or RACE PCR, or, alternatively, in a ligation chain reaction (LCR) (see, e.g., Landegran et al. (1988) Science 241:1077-1080; and Nakazawa et al. (1994) PNAS 91:360-364), the latter of which can be particularly useful for distinguishing between orthologs of polynucleotides of the invention (see Abravaya et al. (1995) Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a nucleic acid of the invention under conditions such that hybridization and amplification of the polynucleotide (if present) occurs, and detecting the presence or absence of an amplification product, or detecting the size of the amplification product and comparing the length to a control sample.

In one aspect, the present invention contemplates a method for detecting the presence of a natural IgM antibody in a sample, the method comprising: (a) providing a sample to be tested for the presence of a natural IgM antibody; (b) contacting the sample with an anti-idiotypic antibody reactive against about eight consecutive amino acid residues of a subject amino acid sequence from such species under conditions which permit association between the anti-idiotypic antibody and its ligand; and (c) detecting interaction of the anti-idiotypic antibody with its ligand, thereby detecting the presence of a natural IgM antibody in the sample.

In another aspect, the present invention contemplates a method for detecting the presence of a natural IgM antibody in a sample, the method comprising: (a) providing a sample to be tested for the presence of a natural IgM antibody; (b) contacting the sample with an anti-idiotypic antibody that binds specifically to a polypeptide of the invention from such species under conditions which permit association between the anti-idiotypic antibody and its ligand; and (c) detecting interaction of the anti-idiotypic antibody with its ligand, thereby detecting the presence of such species in the sample.

In yet another example, the present invention contemplates a method for diagnosing a patient suffering from an inflammatory disease or condition related to the presence of a natural IgM antibody, comprising: (a) obtaining a biological sample from a patient; (b) detecting the presence or absence of a polypeptide of the invention, e.g., a natural IgM antibody, or a nucleic acid encoding a polypeptide of the invention, in the sample; and (c) diagnosing a patient suffering from such an inflammatory disease or condition based on the presence of a polypeptide of the invention, or a nucleic acid encoding a polypeptide of the invention, in the patient sample.

The diagnostic assays of the invention may also be used to monitor the effectiveness of a treatment in an individual suffering from an inflammatory disease or condition related to a natural IgM antibody. For example, the presence and/or amount of a nucleic acid of the invention or a polypeptide of the invention can be detected in an individual suffering from an inflammatory disease or condition related to a natural IgM antibody before and after treatment with a natural IgM antibody therapeutic agent. Any change in the level of a polynucleotide or polypeptide of the invention after treatment of the individual with the therapeutic agent can provide information about the effectiveness of the treatment course. In particular, no change, or a decrease, in the level of a polynucleotide or polypeptide of the invention present in the biological sample will indicate that the therapeutic is successfully combating such disease or disorder.

Alternatively, polypeptides of the invention, e.g., natural IgM antibodies, can be detected in vivo in a subject by introducing into the subject a labeled antibody specific for a polypeptide of the invention, e.g., an anti-idiotypic antibody to detect natural IgM antibodies. For example, the anti-idiotypic antibody can be labeled with a radionuclide marker whose presence and location in a subject can be detected by standard imaging techniques.

A "radionuclide" refers to molecule that is capable of generating a detectable image that can be detected either by the naked eye or using an appropriate instrument, e.g. positron emission tomography (PET), and single photon emission tomography (SPECT). Radionuclides useful within the present disclosure include penetrating photon emitters including gamma emitters and X-ray emitters. These rays accompany nuclear transformation such as electron capture, beta emission and isomeric transition. Radionuclides useful include those with photons between 80 and 400 keV and positron producers, 511 keV annihilation photons and acceptable radiation doses due to absorbed photons, particles and half life. Radionuclides include radioactive isotopes of an element. Examples of radionuclides include $^{123}$I, $^{125}$I, $^{99m}$Tc, $^{18}$F, $^{68}$ Ga, $^{62}$Cu, $^{111}$In, $^{131}$I, $^{186}$Re, $^{188}$Re, $^{90}$Y, $^{212}$Bi, $^{211}$At, $^{89}$Sr, $^{166}$Ho, $^{153}$Sm, $^{67}$Cu, $^{64}$Cu, $^{100}$Pd, $^{212}$Pb, $^{109}$Pd, $^{67}$Ga, $^{94}$Tc, $^{105}$Rh, $^{95}$Ru, $^{177}$Lu, $^{170}$Lu, $^{11}$C, and $^{76}$Br.

In one embodiment, an anti-idiotypic antibody that recognizes a natural IgM antibody of the present invention may be labeled with $^{99m}$Tc. $^{99m}$Tc, a commonly used radionuclide in Nuclear Medicine, combines desirable physical properties with a 6 hr half-life and a 140-KeV gamma energy (85% as gamma photons) and widespread availability, since it can readily be eluted from molybdenum generators.

The imaging agents of the disclosure may be used in the following manner. An effective amount of the imaging agent (from 1 to 50 mCi) may be combined with a pharmaceutically acceptable carrier for use in imaging studies. In accordance with the disclosure, "an effective amount" of the imaging agent of the disclosure is defined as an amount sufficient to yield an acceptable image using equipment which is available for clinical use. An effective amount of the imaging agent of the disclosure may be administered in more than one injection. Effective amounts of the imaging agent of the disclosure will vary according to factors such as the degree of susceptibility of the individual, the age, sex, and weight of the individual, idiosyncratic responses of the individual and dosimetry. Effective amounts of the imaging agent of the disclosure will also vary according to instrument and film-related factors. Optimization of such factors is well within the level of skill of a person skilled in the art.

The amount of imaging agent used for diagnostic purposes and the duration of the imaging study will depend upon the nature and severity of the condition being treated, on the nature of therapeutic treatments which the patient has undergone, and on the idiosyncratic responses of the patient. Ultimately, the attending physician will decide the amount of imaging agent to administer to each individual patient and the duration of the imaging study.

The pharmaceutically acceptable carrier for an imaging agent of the disclosure may include any and all solvents, dispersion media, coatings, antibacterial and antifungal agents, isotonic agents, absorption delaying agents, and the like. The use of such media and agents for pharmaceutically active substances is well known in the art. The imaging agent of the disclosure may further be administered to an individual in an appropriate diluent or adjuvant, co-administered with enzyme inhibitors or in an appropriate carrier such as human serum albumin or liposomes. Supplementary active compounds can also be incorporated into the imaging agent of the disclosure. Pharmaceutically acceptable diluents; include saline and aqueous buffer solutions. Adjuvants contemplated herein include resorcinols, non-ionic surfactants such as polyoxyethylene oleyl ether and nhexadecyl polyethylene ether. Enzyme inhibitors include pancreatic trypsin inhibitor, diethylpyrocarbonate, and trasylol. Liposomes include water-in-oil-in-water CGF emulsions as well as conventional liposomes (Strejan et al. (1984) *J. Neuroimmunol.* 7, 27).

In one embodiment, the imaging agent of the disclosure is administered parenterally as injections (intravenous, intramuscular or subcutaneous). The imaging agent may be formulated as a sterile, pyrogen-free, parenterally acceptable aqueous solution. The preparation of such parenterally acceptable solutions, having due regard to pH, isotonicity, stability, and the like, is within the skill in the art. Certain pharmaceutical compositions of this disclosure suitable for parenteral administration comprise one or more imaging agents in combination with one or more pharmaceutically acceptable sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. A formulation for injection should contain, in addition to the cardiovascular imaging agent, an isotonic vehicle such as sodium chloride solution, Ringer's solution, dextrose solution, dextrose and sodium chloride solution, lactated Ringer's solution, dextran solution, sorbitol solution, a solution containing polyvinyl alcohol, or an osmotically balanced solution comprising a surfactant and a viscosity-enhancing agent, or other vehicle as known in the art. The formulation used in the present disclosure may also contain stabilizers, preservatives, buffers, antioxidants, or other additives known to those of skill in the art.

The invention also encompasses kits for detecting the presence of a natural IgM antibody in a biological sample. For example, the kit can comprise a labeled compound or agent capable of detecting a polynucleotide or polypeptide of the invention in a biological sample; means for determining the amount of a natural IgM antibody in the sample; and means for comparing the amount of a natural IgM antibody in the sample with a standard. An unlabeled compound may also be provided with instructions for labeling the compound. The compound or agent can be packaged in a suitable container. The kit can further comprise instructions for using the kit to detect a polynucleotide or polypeptide of the invention.

EXEMPLIFICATION

The invention, having been generally described, may be more readily understood by reference to the following examples, which are included merely for purposes of illustration of certain aspects and embodiments of the present invention, and are not intended to limit the invention in any way.

Example 1

Mechanism of Ischemia-Reperfusion Injury

This Example shows that mice deficient in the complement system were resistant to ischemia-reperfusion injury.

To examine the mechanism of ischemia-reperfusion injury, mice deficient in complement C3 were treated in the hindlimb model. The C3−/− mice were partially protected from injury based on an approximate 50% reduction in permeability index (see Weiser et al. (1996) J. *Exp. Med.* 1857-1864). Thus, complement C3 is essential for induction of full injury in this murine model.

The experiments in Weiser et al. did not identify how complement was activated. The serum complement system can be activated by at least three distinct pathways, classical, lectin or alternative. Knowing which pathway is involved, is important as it suggests a mechanism for injury. For example, the classical pathways is activated very efficiently by IgM and IgG isotypes of immunoglobulin or by the serum recognition protein C-reactive protein. Whereas, the lectin pathway is activated following recognition of specific carbohydrates such as mannan by mannan binding lectin (MBL) (Epstein et al., (1996) *Immunol* 8, 29-35). In both pathways, complement C4 is required in forming an enzyme complex with C2 that catalyzes cleavage of the central component C3. By contrast, the alternative pathway activates spontaneously leading to conversion of C3 to its active form (C3b) and attachment to foreign- or self-tissues. The pathway is tightly regulated as all host cells express inhibitors of amplification of the complement pathway by inactivating, or displacing the C3 convertase (Muller-Eberhard, H. J., (1988) *Ann. Rev. Biochem.* 57, 321-347). One approach for determining the pathway involved is use of mice deficient in C4, i.e., cannot form C3 convertase via classical or lectin pathways. Comparison of mice deficient in either C3 or C4 with wild type (WT) controls in the hindlimb model, revealed that C4 was also required for induction of full injury (Weiser et al. supra). This finding was important as it suggested that antibody or MBL might be involved.

Example 2

Natural IgM Mediates Ischemia Reperfusion (I/R) Injury

This Example shows that mice deficient in immunoglobulin were resistant to ischemia-reperfusion injury.

To determine if antibody was involved in mediating I/R injury, mice totally deficient in immunoglobulin, RAG2−/− (recombinase activating gene-2 deficient) were characterized along with the complement deficient animals in the intestinal model. Significantly, the RAG-2−/− mice were protected to a similar level as observed in the complement deficient animals (Weiser et al. supra). Since the RAG2−/− animals are also missing mature lymphocytes, it was important to determine that the pathogenic effect was antibody dependent (Shinkai et al. (1992) Cell 68, 855-867). To confirm that injury was mediated by serum antibody, the deficient animals were reconstituted with either normal mouse sera (Weiser et al. supra) or purified IgM (Williams et al. (1999) J. Appl. Physiol 86; 938-42). In both cases, the reconstituted RAG-2−/− mice were no longer protected and injury was restored. In the latter experiments, a model of intestinal injury was used as in this model, injury is thought to be mediated primarily by complement.

The interpretation of these results is that during the period of ischemia, neoantigens are either expressed or exposed on the endothelial cell surface. Circulating IgMs appear to recognize the new determinant, bind and activate classical pathway of complement. While the nature of the antigen is not known, IgM rather than IgG seems to be primarily responsible for activation of complement as reconstitution of deficient mice with pooled IgG did not significantly restore injury in the mice. An alternative hypothesis is that there is another initial event such as the MBL pathway that recognizes the altered endothelial surface, induces low level complement activation which in turn exposes new antigenic sites and the pathway is amplified by binding of IgM.

Example 3

Pathogenic IgM is a Product of B-1 Cells

Since a major fraction of circulating IgM is thought to represent natural antibody, i.e. product of rearranged germline genes, it is possible that mice bearing deficiencies in the B-1 fraction of lymphocytes might also be protected. B-1 cells have a distinct phenotype from more conventional B-2 cells in that they express low levels of IgD and CD23 and a major fraction express the cell surface protein CD5 (Hardy et al., (1994) *Immunol. Rev.:* 137, 91; Kantor et al. (1993) *Annu. Rev. Immunol.* 11, 501-538, 1993. B-1 cells are also distinguished by reduced circulation in mice, limited frequency in the peripheral lymph nodes and spleen and are primarily localized within the peritoneal cavity. To examine a role for B-1 cells as a source of pathogenic IgM, antibody-deficient mice (RAG-2−/−) were reconstituted with $5\times10^5$ peritoneal B-1 cells and rested approximately 30 days before treatment. Circulating IgM levels reach a near normal range within a month following adoptive transfer. Characterization of the B-1 cell reconstituted mice in the intestinal ischemia model confirmed that B-1 cells were a major source of pathogenic IgM (see Williams et al. (1999) supra). This was an important observation because the repertoire of B-1 cell natural antibody is considerably more limited than would be expected for conventional B-2 cells. Therefore, it is possible that the pathogenic antibody represents a product of the germline.

Example 4

Cr2−/− Mice are Protected from Ischemia Reperfusion Injury

The initial characterization of Cr2−/− knockout mice revealed an approximate 50% reduction in the frequency of B-1a or CD5+B-1 cells (Ahearn et al. (1996) *Immunity* 4: 251-262). Although characterization of another strain of Cr2-deficient mice did not identify a similar reduction (Molina et al. (1996) *Proc. Natl. Acad. Sci. USA* 93, 3357-3361). Whether the difference in frequency of CD5+cells was due to variation in strain background or environmental differences is not known. Despite the reduced frequency of B-1 a cells in the Cr2−/− mice, circulating levels of IgM were within the normal range. These findings suggested that the repertoire of IgM might be different in the Cr2-deficient animals. To test this hypothesis, mice in the intestinal I/R model were characterized. Surprisingly, the Cr2−/− mice were equally protected as the complete-antibody deficient mice (FIG. 3). Comparison of survival over a five-day period following treatment in the intestinal model demonstrated a significant increase in mortality of the WT compared to Cr2-deficient animals. Consistent with an increased mortality, a dramatic reduction in injury was observed in tissue sections harvested from treated WT or Cr2−/− deficient mice.

Extensive injury to the mucosal layer of the intestine was observed in WT mice or Cr2−/− mice reconstituted with pooled IgM or B-1 cells. By contrast, tissue sections isolated from treated Cr2−/− mice were similar to that of sham controls. Thus, despite normal circulating levels of IgM, the Cr2-deficient mice were protected from injury. These results not only confirm the importance of B-1 cells as a source of pathogenic antibody but suggest that the complement system is somehow involved in formation or maintenance of the repertoire of natural antibody. For example, complement may be involved in positive selection of B-1 cells.

Example 5

Identification of Pathogenic IgMs

This Example describes the generation of a specific hybridoma clone from normal B-1 cells and the identification of one clone that produces a pathogenic IgM. The pathogenic IgM was shown to restore injury in vivo to antibody deficient mice.

Studies in mice bearing a deficiency in complement receptors CD2 I/CD35, revealed that the mice were missing the pathogenic antibody. This finding was unexpected because they have a normal level of IgM in their blood. These findings led to the hypothesis that a special population of B cells termed B-1 cells are responsible for secreting the pathogenic IgM. For example, engraftment of the receptor deficient mice (Cr2−/−) with B-1 cells from normal mice restored injury, confirming the importance of B-I cells. To identify the specific antibody or antibodies responsible for injury, a panel of hybridoma clones were constructed from an enriched pool of peritoneal B-1 cells harvested from normal mice. The general approach for preparing hybridomas from enriched fraction of peritoneal cells includes harvesting peritoneal cells from mice treated 7 days earlier with IL-10 and subsequently enriched for CD23 negative B cells by negative selection with magnetic beads. Enriched B cells are analyzed by FACS following staining with IgM, Mac-1 and CD23 specific Mab. The enriched population is further activated by culturing with LPS for 24 hours. Activated cells are hybridized with fusion partner myeloma cells in the presence of PEG and grown in HAT-selective medium. Hybridomas are screened for IgM secreting clones by ELISA, and positive wells are expanded for purification of IgM.

Twenty-two IgM-secreting hybridoma clones were analyzed by pooling an equal amount of IgM product from each of the clones. Treatment of antibody-deficient mice with the pooled IgM restored injury similar to that seen with pooled IgM from serum. This finding confirmed that the pathogenic IgM was among the twenty-two hybridomas produced. By dividing the pools into two fractions, i.e., 1-11 and 12-22, and treatment mice with the two fractions, the pathogenic antibody was found to fractionate with the pool that included clone # 22. Finally, mice were reconstituted with either clone 17 or 22. Clone 22 restored injury whereas the other clones did not (see FIG. 4).

Example 6

Complement Involvement in B-1 Cell Selection

Two different models have been proposed to explain the development of B-1 cells. The lineage hypothesis proposes that B-1 cells develop in early fetal life as a distinct population (Kantor et al. (1993) supra). Alternatively, B-1 cells develop from the same progenitors as conventional B cells but depending on their environment, i.e., encounter with antigen, they develop into B-1 or retain the B-2 cell phenotype (Wortis, H. H. (1992) Int. Rev. Immunol. 8, 235; Clarke, J. (1998) Exp. Med. 187, 1325-1334). Irrespective of their origin, it is known that B-1 cells are not replenished from adult bone marrow at the same frequency as B-2 cells and that their phenotype is more similar to that of early fetal liver B cells or neonatal bone marrow (BM) cells. Consistent with an early origin, their repertoire tends to be biased towards expression of more proximal $V_H$ genes and N-nucleotide addition is limited (Gu et al. (1990) *EMBO J* 9, 2133; Feeney, J. (1990) *Exp. Med.* 172, 1377). It seems reasonable that given the reduced replenishment by adult BM stem cells, B-1 cells are self-renewed and that antigen stimulation might be important in their renewal, expansion or even initial selection (Hayakawa et al., (1986) *Eur. J. Immunol.* 16, 1313). Indeed inherent to the conventional model, B-1 cells must be antigen selected.

Evidence in support of a B-cell receptor (BCR) signaling requirement for positive selection of B-1 cells comes from mice bearing mutations that alter BCR signaling. For example, impairment of BCR signaling through CD 19, vav, or Btk dramatically affects development of B-1 cells. By contrast, loss of negative selection such as in CD22- or SHIP-1 deficient mice can lead to an increase in B-1 cell frequency (O'Keefe et al. (1996) *Science* 274, 798-801; Shultz et al. (1993) *Cell* 73, 1445). Recent, elegant studies with mice bearing two distinct Ig transgenes, $V_H$12 (B-1 cell phenotype) or $V_H$B1-8 (B-2 cell phenotype) support the view that B-1 cells are positively selected by self-antigens. For example, B cells expressing $V_H$12 either alone or together with B1-8 developed a B-1 cell phenotype. Whereas, few if any B cells were identified that expressed the B1-8 transgene only. Thus, these results suggested that encounter of transgenic B cells with self-PtC resulted in expansion of those expressing $V_H$ 12. Selection of B-1 cells was recently reported by Hardy et al. (1994) *Immunol. Rev.* 137, 91). In their model, B cells expressing an immunoglobulin transgene specific for Thy 1.1 were selected and expanded in mice expressing the cognate antigen. By contrast, transgene+B-1 cells were not found in mice that expressed the alternative allotype Thy 1.2.

Where does complement fit into B-1 cell development? The overall reduction in B-1a cell frequency and the more specific loss of B-1 cells expressing IgM involved in I/R injury suggests a role for CD21/CD35 in either positive selection or maintenance of B-1a cells. One possible role for complement is that it enhances BCR signaling on encounter with cognate antigen. Biochemical studies and analysis of CD21/CD35 deficient mice demonstrate the importance of co-receptor signaling in activation and survival of conventional B cells (Carroll, M. C., (1998) *Ann. Rev. Immunol.* 16, 545-568; Fearon et al. (1995) *Annu. Rev. Immunol.* 13, 127-149). It is very likely that B-1 cells likewise utilize co-receptor signaling to enhance the BCR signal. For example, bacteria express typical B-1 cell antigens such as phosphoryl choline and it is not unreasonable that coating of bacteria with complement ligand C3d would enhance crosslinking of the co-receptor with the BCR and enhance overall signaling. Thus, antigens expressed at lower concentrations might require complement enhancement in order for the cognate B-cell to recognize it and expand or be positively selected. Another role for complement receptors is in localizing antigen on follicular dendritic cells (FDC) within the lymphoid compartment. However, since the major population of B-1 cells occupy the peritoneal tissues it is not clear if they would encounter FDC within lymphoid structures. The actual site or sites in which B-1 cells undergo positive selection are not known. It is possible that they must encounter cognate antigen in early fetal development or in neonatal BM. If this is the case, it might be expected that complement receptors on stromal cells within these compartments bind antigen for presentation to B cells. It is possible that complement receptors could participate in both stages of development. First, they might enhance antigens signaling in initial positive selection. Secondly, as selected B-1 cells are replenished at peripheral sites, complement receptors might again be involved in enhancement of BCR signaling.

FIG. 5 is a schematic diagram of the proposed role for complement and complement receptors in positive selection of peritoneal B-1 lymphocytes. The interaction of complement-ligand coated antigens (self- and non-self) results in co-ligation of the CD21/CD19 co-receptor and BCR on the cell surface leading to enhanced signaling and positive selection.

Example 7

Materials and Methods for Examples 8-11

Phage Display Peptide Library and Peptide Synthesis

A 12-mer M-13 phage display library (New England Biolab, Mass.) was screened by 4 rounds with MBL-beads coated with $IgM^{CM-22}$ and 2 rounds with $IgM^{CM-75}$ according to the manufacturer's recommendation. Phage clones were selected from the enriched pool and the nucleotide sequence of the relevant phage gene determined for at least ten clones. Selected peptides were synthesized with purity>95% in Harvard Proteomic Core or New England Peptide, Inc. (Gardner, Mass.).

Binding Assays

ELISA was performed as described earlier (Zhang et al. (2004) PNAS USA 101:3886-91). Briefly, IgM binding to phage or phage-specific peptides was determined by coating a 96-well plate with saturating amounts of antigen. Subsequent to blocking, IgM was added (1 or 10 μg/ml) for 2 hr at 37° C. Plates were washed and then developed with alkaline phosphatase-labeled goat anti-mouse IgM (Sigma, MO). Binding of IgM to NMHC-II was determined by culturing 96-well plates previously coated with specific rabbit antibody (NMHC-II A & B; Covance Research Products; NMHC-II C a gift from Dr. Adelstein, NHLBI, NIH, Bethesda, Md.) or pan-myosin Hc (Sigma, Mo.) with intestinal lysates prepared from $IgM^{CM-22}$ reconstituted RAG-$1^{-/-}$ mice either sham treated or treated for ischemia as described (Zhang et al. (2004) *PNAS USA* 101:3886-91). Lysates were prepared as described for immune precipitation (see below). Alkaline-phosphatase labeled goat anti-mouse IgM (Sigma, Mo.) was then used to detect bound IgM.

Intestinal RI Model

Surgical protocol for RI was performed as previously described (Zhang et al. (2004) *PNAS USA* 101:3886-91). Briefly, a laparotomy is performed, and a microclip (125 g pressure, Roboz, MD) was applied to the superior mesenteric artery and bilateral circulation limited with silk sutures flanking a 20 cm segment of the jejunum. After 40 minutes of ischemia, the microclip was removed, and reperfusion of the mesenteric vasculature was confirmed by the return of pulsation to the vascular arcade and a change to pink color. The incision was closed, and all animals kept warm for 3 hours. Reconstituted RAG-$1^{-/-}$ animals received either IgM mixed with peptide or saline in 0.2 ml volume intravenously 30 min before the initial laparotomy. WT animals were treated with saline or peptide i.v. 5 minutes prior to reperfusion. At the end of reperfusion, the ischemic segment of the jejunum was harvested and the central 4 cm was cut for pathological analysis.

Histopathology and Immuno-Histochemistry Analysis

Cryostat sections of intestinal tissues were stained by hematoxylin and eosin (H&E) and examined by light microscopy for mucosal damage. Pathology score was assessed based on procedure by Chiu (Chiu et al, *Arch Surg* 101: 484-488, 1970; Chiu, et al, *Arch Surg* 101: 478-483, 1970) that included direct inspection of all microvilli over a 4 cm stretch of jejuneum as described. Zhang et al. (2004) *PNAS USA* 101:3886-91. For immuno-fluorescence, cryosections fixed with 4% (w/v) paraformaldehyde were incubated for varying periods with either biotin-labeled anti-mouse IgM (Becton Dickinson, Calif.) followed by 1 hour with streptavidin-Alexa-568 (1:500 dilution, Molecular Probes, Oreg.). C4 deposition was detected by staining with FITC-labeled rabbit anti-huC4c (DAKO, Colo.), followed by anti-rabbit-Alexa 488 (Molecular Probes, Oreg.). The specificity of anti-C4c staining was confirmed by staining serial sections with biotin-labeled anti-mouse C4 for 1 hour followed by streptavidin-FITC (Becton Dickinson, Calif.). C3 deposition was detected by treating with FITC-labeled anti-C3 (DAKO, Colo.). Sections were mounted in Anti-fade Mounting Medium with DAPI (Molecular Probes, Oreg.).

SPR Analysis of Peptide Binding to Antibody

An IgM ($IgM^{CM-22}$ or $IgM^{CM-31}$) antibody was immobilized by amine coupling in a BiaCore SPR CM5™ chip flowcell at a density of 33,400 response units (RU) ~33 $ng/mm^2$ as described. Vorup-Jensen et al, *PNAS USA* 100: 1873-1878, 2003. Briefly, a reference flow cell was prepared by coupling of ethanolamine-HCl. Peptides, diluted in PBS running buffer, were flowed separately over the IgM-coupled surface and the reference at a rate of 10 μl/min at 25° C. and with the data collection rate at 10 Hz. The injection phase had a duration of 240 s (end of injection phases are marked by arrow heads in FIGS. 9A, B and D). Binding isotherms were derived by subtracting the response in the reference cell from the response of the IgM-coupled surface. Following each run, the surface was regenerated by injecting 40 μl 0.05% (v/v) polyoxyethylenesorbitan monolaureate/PBS.

Immune Precipitation

Frozen tissues were homogenized in a lysis buffer containing detergent and a cocktail of enzyme inhibitors. A sample of lysate is analyzed for total protein content (Bio-Rad kit) to insure similar levels of protein for analysis. Lysates are mixed with sepharose beads coated with rat anti-mouse IgM for 1 hr at 4° C. Subsequently, beads were pelleted gently, washed in lysis buffer and then boiled in SDS-sample buffer under reducing conditions to elute bound complexes. Samples were fractionated on 6% (w/v) polyacrylamide SDS gels and subsequently fixed and then stained with either coomassie blue or silver stain to identify protein bands.

Protein Identification by Tandem Mass Spectrometry

Individual Coomassie Blue-stained bands were excised from SDS-gels, destained, and subjected to enzyme digestion as described previously. Borodovsky et al, *Chem Biol* 9: 1149-1159, 2002. The peptides were separated using a nano-flow liquid coupled chromatography system (Waters Cap LC) and amino acid sequences determined by tandem mass spectrometer (Q-TOF micro, Waters, Mass.). MS/MS data were processed and subjected to database searches using Mascot (Matrixscience) against Swissprot, TREMBL/New or the NCBY non-redundant database.

Example 8

Identification of Asparagine-Rich Peptides that Bind Natural IgM Antibody

We previously identified a hybridoma clone of a natural IgM antibody ($IgM^{CM-22}$) that binds ischemic tissue in the intestinal RI model, which support our hypothesis that ischemic tissue was altered relative to normal tissue and that neo-epitopes expressed during ischemia were targets for an innate response to self. To characterize the ligand bound by pathogenic $IgM^{CM-22}$, a M-13 phage-display library of random 12-mer amino acid sequences was screened using beads coated with the specific IgM.

After four rounds of specific screening and two rounds with a control IgM (clone $IgM^{CM-75}$), ten phage clones were isolated and the nucleotide sequence of the relevant M-13 gene sequenced. Notably, all ten clones contain sequences rich in asparagine. Five of the clones were selected for a relative binding assay with $IgM^{CM-22}$ and one of these clones, P8, which bound with the highest efficiency was selected for further study (Table 4 and FIG. 6A).

TABLE 4

| Phage displayed peptides bind to $IgM^{CM-22}$ | | |
|---|---|---|
| Phage Clone | Sequence | SEQ ID NO: |
| P1 | YNNNNGNYTYRN | 16 |
| P2 | ANTRNGATNNNM | 18 |
| P3 | CDSSCDSVGNCN | 20 |
| P4 | WNNNGRNACNAN | 22 |
| P5 | HNSTSNGCNDNV | 24 |
| P6 | NSNSRYNSNSNN | 26 |
| P7 | KRNNHNNHNRSN | 28 |
| P8 | NGNNVNGNRNNN | 30 |
| P9 | NVANHNNSNHGN | 32 |
| P10 | SYNNNNHVSNRN | 34 |
| Asparagine-rich Consensus | xNNNxNNxNNNN | 14 |

A 12-amino acid peptide (P8) was synthesized based on the phage sequence and assayed for inhibition of phage P8 binding to $IgM^{CM-22}$ (FIG. 6B). Titration of increasing amounts of P8 peptide yielded 50% inhibition at an estimated concentration of 10 μmole. This assay indicates a reasonable overall avidity of binding based on multiple binding sites expressed on the phage surface. This result suggested that $IgM^{CM-22}$ binding to phage P8 was specific for the peptide region and that the synthetic peptide could be used as a mimotope for the actual antigen. To further characterize binding of P8 peptide to $IgM^{CM-22}$, ELISA plates were coated with the peptide and tested with $IgM^{CM-22}$ or control $IgM^{CM-75}$ for binding (FIG. 6C). At the lower concentration of 1 μg/ml, neither IgM bound above background. However, at 10 μg/ml, significantly more $IgM^{CM-22}$ bound than $IgM^{CM-75}$. Together, the three results suggest that peptide P8 binds specifically to $IgM^{CM-22}$ and can be used for identification of the actual antigen.

Example 9

Asparagine-Rich Peptide P8 Blocks Intestinal RI

Previous studies had demonstrated that intestinal RI in RAG-$1^{-/-}$ mice was IgM-dependent and that $IgM^{CM-22}$ alone was sufficient to restore injury. As expected, reconstitution of RAG-$1^{-/-}$ mice with $IgM^{CM-22}$ but not saline prior to reperfusion resulted in RI (FIG. 7A(i) and FIG. 7B). By contrast, mixing of $IgM^{CM-22}$ with P8 prior to injection in ischemic mice significantly blocked apparent injury (mean pathology score 6±3 versus 31±13; p<0.001) (FIG. 7Aii and FIG. 7B). Previous titration of peptide with $IgM^{CM-22}$ suggested an optimal concentration of 10 μM of P8 was sufficient to block 50-100 μg of $IgM^{CM-22}$ (0.1-0.2 μM).

Immunohistological analyses of serial sections of reperfused intestinal tissue (jejuneum) following RI identified co-localization of IgM and complement C4 and C3 within the microvilli in RAG-$1^{-/-}$ mice reconstituted with $IgM^{CM-22}$. By contrast, sections prepared from mice receiving P8 showed no evidence of IgM or complement binding. No binding of IgM or complement was observed in $IgM^{CM-22}$ reconstituted sham controls, nor RAG-$1^{-/-}$ mice reconstituted with control $IgM^{CM-31}$ or RAG-$1^{-/-}$ mice reconstituted with saline only (Zhang et al. (2004) PNAS USA 101:3886-91). Thus, P8 blocks the binding of $IgM^{CM-22}$ and the induction of injury in vivo.

The identification of a single natural IgM antibody that could initiate RI in RAG-1.sup.−/− mice led to the general question of the number of possible neo-epitopes expressed on ischemic tissues and the corresponding number of pathogenic clones of IgM in the repertoire of wild type (WT) mice. It might be predicted that the number of antibodies is limited based on the current understanding that the repertoire of natural IgMs is relatively small. Herzenberg et al, *Immunol Today* 14: 79-83, discussion 88-90, 1993; Arnold et al, *J Exp Med* 179: 1585-1595, 1994. Moreover, ligands of natural IgM antibodies are considered highly conserved structures and also are probably limited in number. To test if P8 represented a mimotope for a major self-antigen, WT mice were pretreated with P8 (approximately 10 μM) five minutes prior to reperfusion in the intestinal model. Analysis of jejuneum tissues of mice treated with saline or a control peptide prior to reperfusion identified significant injury to the microvilli as expected (FIG. 7Aiii). By contrast, pretreatment of WT mice with P8 five minutes prior to reperfusion blocked apparent injury (mean pathology score 5.+−.3 versus 24.+−.16 and 23.+−.19; p<0.005 and 0.027, respectively) (FIG. 7A(iv) and FIG. 7B). As expected, IgM, C4 and C3 co-localized within microvilli of RI treated WT mice. By contrast, no apparent deposits of IgM or complement were observed in reperfused tissues of mice administered P8. These results suggest that the number of key epitopes required to initiate RI is limited as a single peptide blocks injury and deposition of IgM and complement.

Example 10

Immunoprecipitation of Self-Peptides with $IgM^{CM-22}$

Using the amino acid sequence of P8, a homology search of the genomic database revealed no exact matches. Therefore, an immune-precipitation approach was used to identify the ischemia antigen/antigens in RAG-$1^{-/-}$ mice reconstituted with $IgM^{CM-22}$.

RAG-$1^{-/-}$ mice were reconstituted with an optimal amount of $IgM^{CM-22}$, treated for intestinal ischemia and reperfused for varying lengths of time, i.e., 0 minutes or 15 minutes before harvesting of tissues. Immune complexes of IgM-antigen were isolated from lysates of jejuneum at the varying time points and fractionated by SDS-PAGE under reducing conditions. Analysis of the stained gels indicated common bands at lower molecular weight for all time points (FIG. 8A). However, at 15 minutes, a band at high molecular weight (>200 kD) was identified (FIG. 8A).

Protein bands were excised from stained gels, enzymatically digested and peptides analyzed by Tandem Mass Spec as described. Kocks et al, *Mol Cell Proteomics* 2: 1188-1197, 2003. Analysis of eluted peptides indicated that the common bands at approximately 25, 50 and 75 kDa represented immunoglobulin light chain (Lc), and IgG heavy chain (Hc) and IgM Hc, respectively. Analysis of the high molecular weight band yielded peptide sequences homologous to non-muscle myosin heavy chain (NMHC) type II isoforms A and C (Table 5).

TABLE 5

Mass Spectrometry Results

| Matched proteins | Mass Spectroscopy sequenced peptides | |
|---|---|---|
| Mouse non muscle myosin heavy chain II-A (gi/20137006; GenBank ™ Accession NO: NP_071855) total score = 130; peptides matched = 6 | VVFQEFR | (MS-1; SEQ ID NO: 39) |
| | CNGVLEGIR | (MS-2; SEQ ID NO: 40) |
| | KFDQLLAEEK | (MS-3; SEQ ID NO: 41) |
| | KFDQLLAEEK | (SEQ ID NO: 41) |
| | EQADFAIEALAK | (MS-4; SEQ ID NO: 42) |
| | QLLQANPILEAFGNAK | (MS-5; SEQ ID NO: 43) |
| Mouse non muscle myosin heavy chain II-C (gi/33638127; GenBank ™ Accession NO: AAQ24173) total score = 133; peptides matched = 7 | CNGVLEGIR | (SEQ ID NO: 40) |
| | VKPLLQVTR | (MS-6; SEQ ID NO: 44) |
| | KFDQLLAEEK | (SEQ ID NO: 41) |
| | KFDQLLAEEK | (SEQ ID NO: 41) |
| | EQADFALEALAK | (SEQ ID NO: 42) |
| | LAQAEEQLEQESR | (MS-7; SEQ ID NO: 45) |
| | QLLQANPILEAFGNAK | (MS-8; SEQ ID NO: 46) |

*Score is -10XLog (P), where P is the probability that the observed match is a random event. Individual ion scores >53 indicate identity or extensive homology ($p < 0.05$).

In similar experiments using lysates prepared from WT mice treated for 3 hours in intestinal RI, a similar size band at 200 kD was also observed and sequence analysis identified NMHC-A and C peptides.

Three forms of type II NMHC have been identified (A, B and C) in the mouse and human genome. Golomb et al, J Biol Chem 279: 2800-2808, 2004; Kelley et al, J Cell Biol 134: 675-687, 1996. All eukaryotic cells express type II NMHC but the distribution of the three isoforms varies. NMHC-II A and B are approximately 85% homologous; whereas NMHC-II C is approximately 65% similar. Golomb et al, J Biol Chem 279: 2800-2808, 2004. The three isotypes are highly conserved among mice and humans.

To confirm the binding of $IgM^{CM-22}$ to type II NMHC, an ELISA approach was used. Plates were coated with antibody specific for each of the three forms of NMHC or with a pan-myosin antibody to capture the relevant antigen from lysates prepared from jejuneum of RAG-$1^{-/-}$ mice. Subsequently, $IgM^{CM-22}$ or $IgM^{CM-31}$ were added and then developed with a labeled anti-mouse IgM antibody. Above background binding of $IgM^{CM-22}$ but not $IgM^{CM-31}$ to all three of the isoforms of NMHC-II was observed (FIG. 8B). The combined sequence analysis and ELISA results show that $IgM^{CM-22}$ recognizes a conserved region of the type II NMHC.

To determine whether myosin is exposed to circulating antibody following ischemia, RAG-$1^{-/-}$ mice were reconstitute with a purified IgG fraction of rabbit anti-pan myosin heavy chain. Analysis of tissues of sham treated RAG-$1^{-/-}$ following reconstitution with the rabbit IgG mice showed no evidence of injury or deposition of IgG. By contrast, ischemic RAG-$1^{-/-}$ mice reconstituted with the pan-myosin IgG prior to reperfusion developed significant RI compared to saline controls (33±11 versus 11±8, $p<0.028$) (FIG. 8C). Accordingly, myosin is exposed to antibody in circulation following ischemia.

Comparison of the sequences of the three NMHC-II isoforms with the P8 peptide sequence identified one region of apparent homology (Table 6). All three isoforms include a motif of NxxxxNxNx that has similarity with the P8 sequence. A 12-amino acid self-peptide (N2) sequence (NMHC-II C isoform) was prepared for further study.

TABLE 6

Conserved homologous sequence in NMHC-II A-C

| | Sequence | |
|---|---|---|
| Phage Clone | | |
| P8 | NGNNVNGNRNNN | (SEQ ID NO:30) |
| Consensus | xNNNx(N/D)NxN(N/D)N(N/V) | (SEQ ID NO:14) |
| NMHC-II | | |
| Mouse-IIA (542-556) | LMKNMDPLNDI | (SEQ ID NO:36) |
| Human-IIA (585-596) | LMKNMDPLNDI | (SEQ ID NO:63) |
| Mouse-IIB (592-603) | LMKNMDPLNDNV | (N2; SEQ ID NO:38) |
| Human-IIB (592-603) | LMKNMDPLNDNV | (SEQ ID NO:64) |
| Mouse-IIC (607-619) | LMKNMDPLNDNV | (N2; SEQ ID NO:38) |
| Human-IIC (611-622) | LMKNMDPLNDNV | (SEQ ID NO:64) |

Figure 9:
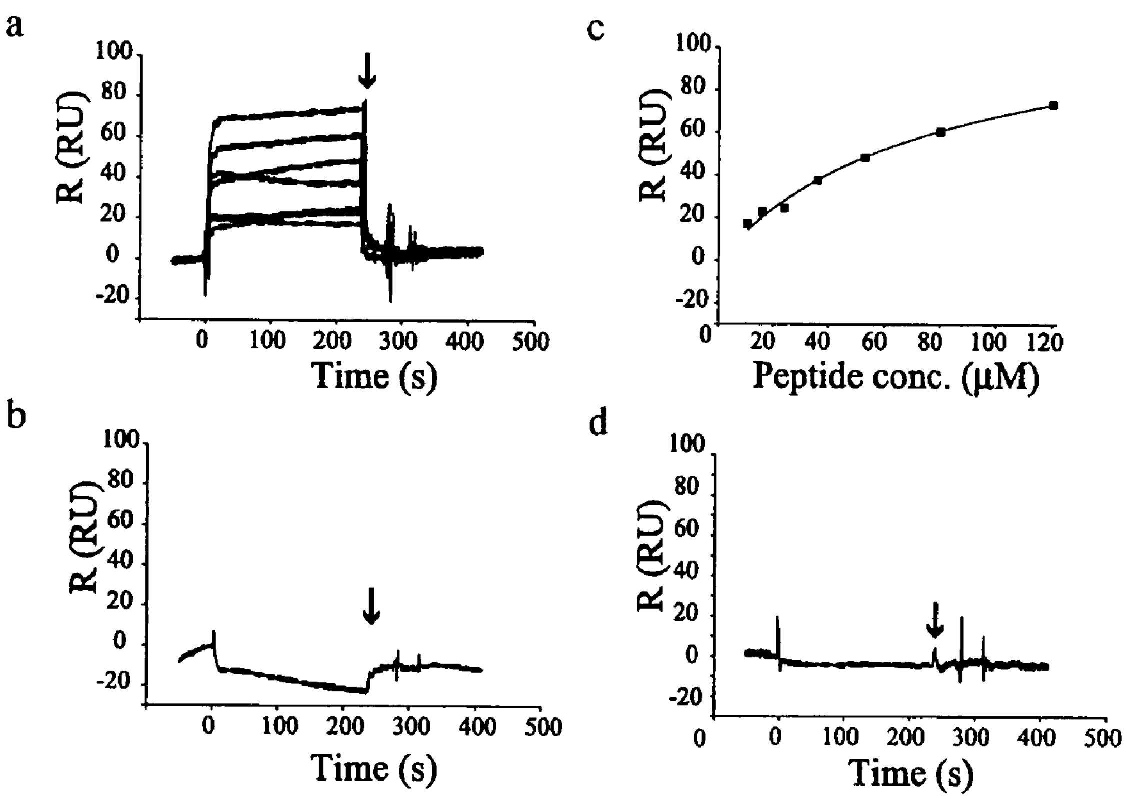

To test that this region bound $IgM^{CM-22}$ surface, plasmon resonance analysis was used (FIG. 9). N2 peptide was injected over a surface coupled with $IgM^{CM-22}$ (FIG. 9A) and generated a robust response, which corresponded to a $K_D$ of 123±61 μM (mean±SD, n=2) as calculated from the steady-state response levels (FIG. 9C). In contrast, no binding was observed when a control peptide was injected over the specific IgM-coupled surface (FIG. 9B) or when the N2 peptide was injected over a surface coupled with the $IgM^{CM-31}$ control (FIG. 9D).

Example 11

Self-Peptide N2 Blocks Intestinal RI

To test the functional binding of N2 with pathogenic IgM, approximately 100 nmoles of the peptide (or saline control) was mixed with $IgM^{CM-22}$ prior to reconstitution of RAG-$1^{-/-}$ mice and treatment in the RI model. Analysis of histology of tissue sections prepared from the reperfused jejuneum of $IgM^{CM-22}$- and saline-treated mice identified injury and deposition of IgM and complement as expected (FIGS. 5Ai and 5B). By contrast, mixing the N2 peptide with $IgM^{CM-22}$ prior to reperfusion was protective from injury (mean pathology score 13±8 versus 31±10; p<0.049) (FIGS. 10Aii and 10B). In addition, no deposition of IgM and complement was observed in reperfused jejuneum when $IgM^{CM-22}$ was mixed with the N2 peptide prior to injection in RAG-$1_{-/-}$ mice (FIG. 10Ci-viii). Thus, as observed with the synthetic peptide P8, the self-peptide N2 blocked functional binding of $IgM^{CM-22}$ in vivo.

To test if self-peptide N2 represents the major self-epitope in intestinal RI, WT mice were treated with approximately 40 μM of the synthetic peptide P8 prior to reperfusion in the intestinal model. Histological analysis of tissue sections of saline treated WT mice identified injury and deposition of IgM and complement as expected (FIGS. 10Aiii and 10Cix-xii). By contrast, treatment of WT mice with self-peptide N2 blocked both injury (mean pathology score 8±5 versus 22±17) and deposition of IgM and complement (FIG. 10Aiv; FIG. 10B; FIG. 10Cxiii-xvi). These results suggest that a conserved region within type II NMHC proteins represents the major epitope for binding of natural IgM following ischemia in the intestinal model.

INCORPORATION BY REFERENCE

All publications, patents, and patent applications mentioned herein are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequence which reference an accession number correlating to an entry in a public database, such as those maintained by The Institute for Genomic Research (TIGR) on the world wide web with the extension tigr.org and or the National Center for Biotechnology Information (NCBI) on the world wide web with the extension ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated nucleic acid molecule consisting of a nucleotide sequence encoding the peptide of SEQ ID NO: 38.

2. The isolated nucleic acid of claim 1 operably linked to a promoter.

3. A vector comprising the nucleic acid of claim 2.

4. A host cell comprising the vector of claim 3.

5. A composition consisting essentially of a peptide consisting of SEQ ID NO: 38.

6. The composition of claim 5, wherein the peptide is pegylated.

7. The composition of claim 5, wherein the peptide is labeled with a detectable label.

8. The composition of claim 5, which additionally comprises a pharmaceutically acceptable carrier.

9. An isolated nucleic acid molecule consisting of a nucleotide sequence encoding the peptide of SEQ ID NO: 36.

10. The isolated nucleic acid of claim 9 operably linked to a promoter.

11. A vector comprising the nucleic acid of claim 10.

12. A host cell comprising the vector of claim 11.

13. A composition consisting essentially of a peptide consisting of SEQ ID NO: 36.

14. The composition of claim 13, wherein the peptide is pegylated.

15. The composition of claim 13, wherein the peptide is labeled with a detectable label.

16. A composition of claim 13, which additionally comprises a pharmaceutically acceptable carrier.

* * * * *

```
                              SEQUENCE LISTING

<160> NUMBER OF SEQ ID NOS: 65

<210> SEQ ID NO 1
<211> LENGTH: 402
<212> TYPE: DNA
<213> ORGANISM: Mus musculus

<400> SEQUENCE: 1

caggttcagc tgcagcagtc tggggctgag ctggtgaagc ctggggcctc agtgaagatt      60

tcctgcaaag cttctggcta cgcattcagt agctactgga tgaactgggt gaagcagagg     120

cctggaaagg gtcttgagtg gattggacag atttatcctg gagatggtga tactaactac     180

aacggaaagt tcaagggcaa ggccacactg actgcagaca aatcctccag cacagcctac     240

atgcagctca gcagcctgac ctctgaggac tctgcggtct atttctgtgc aagagaagat     300

tactacggta gtgactggta cttcgatgtc tggggcacag ggaccacggt caccgtctcc     360

tcaggtaagc tggctttttt ctttctgcac attccattct ga                        402

<210> SEQ ID NO 2
<211> LENGTH: 133
<212> TYPE: PRT
<213> ORGANISM: Mus musculus

<400> SEQUENCE: 2

Gln Val Gln Leu Gln Gln Ser Gly Ala Glu Leu Val Lys Pro Gly Ala
```

-continued

```
  1               5                  10                  15

Ser Val Lys Ile Ser Cys Lys Ala Ser Gly Tyr Ala Phe Ser Ser Tyr
             20                  25                  30

Trp Met Asn Trp Val Lys Gln Arg Pro Gly Lys Gly Leu Glu Trp Ile
         35                  40                  45

Gly Gln Ile Tyr Pro Gly Asp Gly Asp Thr Asn Tyr Asn Gly Lys Phe
     50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Glu Asp Tyr Tyr Gly Ser Asp Trp Tyr Phe Asp Val Trp Gly
            100                 105                 110

Thr Gly Thr Thr Val Thr Val Ser Ser Gly Lys Leu Ala Phe Phe Phe
        115                 120                 125

Leu His Ile Pro Phe
    130


<210> SEQ ID NO 3
<211> LENGTH: 15
<212> TYPE: DNA
<213> ORGANISM: Mus musculus

<400> SEQUENCE: 3

agctactgga tgaac                                                    15


<210> SEQ ID NO 4
<211> LENGTH: 5
<212> TYPE: PRT
<213> ORGANISM: Mus musculus

<400> SEQUENCE: 4

Ser Tyr Trp Met Asn
  1               5


<210> SEQ ID NO 5
<211> LENGTH: 57
<212> TYPE: DNA
<213> ORGANISM: Mus musculus

<400> SEQUENCE: 5

cagatttatc ctggagatgg tgatactaac tacaacggaa agttcaaggg caaggcc      57


<210> SEQ ID NO 6
<211> LENGTH: 17
<212> TYPE: PRT
<213> ORGANISM: Mus musculus

<400> SEQUENCE: 6

Gln Ile Tyr Pro Gly Asp Gly Asp Thr Asn Tyr Asn Gly Lys Phe Lys
  1               5                  10                  15

Gly


<210> SEQ ID NO 7
<211> LENGTH: 324
<212> TYPE: DNA
<213> ORGANISM: Mus musculus

<400> SEQUENCE: 7

attgtgatga cccagtctgc tgcttcctta gctgtatctc tggggcagag ggccaccatc   60
```

-continued

```
tcatacaggg ccagcaaaag tgtcagtaca tctggctata gttatatgca ctggaaccaa    120

cagaaaccag gacagccacc cagactcctc atctatcttg tatccaacct agaatctggg    180

gtccctgcca ggttcagtgg cagtgggtct gggacagact tcaccctcaa catccatcct    240

gtggaggagg aggatgctgc aacctattac tgtcagcaca ttagggagct tacacgttcg    300

gaggggggac caagctggaa ataa                                           324


<210> SEQ ID NO 8
<211> LENGTH: 107
<212> TYPE: PRT
<213> ORGANISM: Mus musculus

<400> SEQUENCE: 8

Ile Val Met Thr Gln Ser Ala Ala Ser Leu Ala Val Ser Leu Gly Gln
  1               5                  10                  15

Arg Ala Thr Ile Ser Tyr Arg Ala Ser Lys Ser Val Ser Thr Ser Gly
             20                  25                  30

Tyr Ser Tyr Met His Trp Asn Gln Gln Lys Pro Gly Gln Pro Pro Arg
         35                  40                  45

Leu Leu Ile Tyr Leu Val Ser Asn Leu Glu Ser Gly Val Pro Ala Arg
     50                  55                  60

Phe Ser Gly Ser Gly Ser Gly Thr Asp Phe Thr Leu Asn Ile His Pro
 65                  70                  75                  80

Val Glu Glu Glu Asp Ala Ala Thr Tyr Tyr Cys Gln His Ile Arg Glu
                 85                  90                  95

Leu Thr Arg Ser Glu Gly Gly Pro Ser Trp Lys
            100                 105


<210> SEQ ID NO 9
<211> LENGTH: 45
<212> TYPE: DNA
<213> ORGANISM: Mus musculus

<400> SEQUENCE: 9

agggccagca aaagtgtcag tacatctggc tatagttata tgcac                     45


<210> SEQ ID NO 10
<211> LENGTH: 15
<212> TYPE: PRT
<213> ORGANISM: Mus musculus

<400> SEQUENCE: 10

Arg Ala Ser Lys Ser Val Ser Thr Ser Gly Tyr Ser Tyr Met His
  1               5                  10                  15


<210> SEQ ID NO 11
<211> LENGTH: 21
<212> TYPE: DNA
<213> ORGANISM: Mus musculus

<400> SEQUENCE: 11

cttgtatcca acctagaatc t                                               21


<210> SEQ ID NO 12
<211> LENGTH: 7
<212> TYPE: PRT
<213> ORGANISM: Mus musculus

<400> SEQUENCE: 12
```

-continued

```
Leu Val Ser Asn Leu Glu Ser
  1               5


<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA sequence
<220> FEATURE:
<221> NAME/KEY: modified_base
<222> LOCATION: (1)..(3)
<223> OTHER INFORMATION: a, c, g or t
<220> FEATURE:
<221> NAME/KEY: modified_base
<222> LOCATION: (13)..(15)
<223> OTHER INFORMATION: a, c, g or t
<220> FEATURE:
<221> NAME/KEY: modified_base
<222> LOCATION: (22)..(24)
<223> OTHER INFORMATION: a, c, g or t

<400> SEQUENCE: 13

nnnaayaaya aynnnaayaa ynnnaayaay aayaay                              36


<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Variable amino acid
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (8)
<223> OTHER INFORMATION: Variable amino acid

<400> SEQUENCE: 14

Xaa Asn Asn Asn Xaa Asn Asn Xaa Asn Asn Asn Asn
  1               5                  10


<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA sequence
<220> FEATURE:
<221> NAME/KEY: modified_base
<222> LOCATION: (18)
<223> OTHER INFORMATION: a, c, g or t
<220> FEATURE:
<221> NAME/KEY: modified_base
<222> LOCATION: (27)
<223> OTHER INFORMATION: a, c, g or t
<220> FEATURE:
<221> NAME/KEY: modified_base
<222> LOCATION: (33)
<223> OTHER INFORMATION: a, c, g or t

<400> SEQUENCE: 15

tayaayaaya ayaayggnaa ytayacntay mgnaay                              36
```

-continued

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Tyr Asn Asn Asn Asn Gly Asn Tyr Thr Tyr Arg Asn
1 5 10

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
DNA sequence
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (18)
<223> OTHER INFORMATION: a, c, g or t
<220> FEATURE:
<221> NAME/KEY: modified_base
<222> LOCATION: (21)
<223> OTHER INFORMATION: a, c, g or t
<220> FEATURE:
<221> NAME/KEY: modified_base
<222> LOCATION: (24)
<223> OTHER INFORMATION: a, c, g or t

<400> SEQUENCE: 17
gcnaayacnm gnaayggngc nacnaayaay aayatg 36

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Ala Asn Thr Arg Asn Gly Ala Thr Asn Asn Asn Met
1 5 10

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
DNA sequence
<220> FEATURE:
<221> NAME/KEY: modified_base
<222> LOCATION: (9)
<223> OTHER INFORMATION: a, c, g or t
<220> FEATURE:
<221> NAME/KEY: modified_base -continued
<222> LOCATION: (12)
<223> OTHER INFORMATION: a, c, g or t
<220> FEATURE:
<221> NAME/KEY: modified_base
<222> LOCATION: (21)
<223> OTHER INFORMATION: a, c, g or t
<220> FEATURE:
<221> NAME/KEY: modified_base
<222> LOCATION: (24)
<223> OTHER INFORMATION: a, c, g or t
<220> FEATURE:
<221> NAME/KEY: modified_base
<222> LOCATION: (27)
<223> OTHER INFORMATION: a, c, g or t

<400> SEQUENCE: 19
tgygaywsnw sntgygayws ngtnggnaay tgyaay 36

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Cys Asp Ser Ser Cys Asp Ser Val Gly Asn Cys Asn
1 5 10

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
DNA sequence
<220> FEATURE:
<221> NAME/KEY: modified_base
<222> LOCATION: (15)
<223> OTHER INFORMATION: a, c, g or t
<220> FEATURE:
<221> NAME/KEY: modified_base
<222> LOCATION: (18)
<223> OTHER INFORMATION: a, c, g or t
<220> FEATURE:
<221> NAME/KEY: modified_base
<222> LOCATION: (24)
<223> OTHER INFORMATION: a, c, g or t
<220> FEATURE:
<221> NAME/KEY: modified_base
<222> LOCATION: (33)
<223> OTHER INFORMATION: a, c, g or t

<400> SEQUENCE: 21
tggaayaaya ayggnmgnaa ygcntgyaay gcnaay 36

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Trp Asn Asn Asn Gly Arg Asn Ala Cys Asn Ala Asn
1 5 10

<210> SEQ ID NO 23
<211> LENGTH: 36

-continued

<212> TYPE: DNA
<213> ORGANISM: Artificial Sequence
<220> FEATURE:
<223> OTHER INFORMATION: Description of Artificial Sequence: Synthetic
DNA sequence
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (15)
<223> OTHER INFORMATION: a, c, g or t
<220> FEATURE:
<221> NAME/KEY: modified_base
<222> LOCATION: (21)
<223> OTHER INFORMATION: a, c, g or t
<220> FEATURE:
<221> NAME/KEY: modified_base
<222> LOCATION: (36)
<223> OTHER INFORMATION: a, c, g or t

<400> SEQUENCE: 23
cayaaywsna cnwsnaaygg ntgyaaygay aaygtn 36

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

His Asn Ser Thr Ser Asn Gly Cys Asn Asp Asn Val
1 5 10

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
DNA sequence
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (15)
<223> OTHER INFORMATION: a, c, g or t
<220> FEATURE:
<221> NAME/KEY: modified_base
<222> LOCATION: (18)
<223> OTHER INFORMATION: a, c, g or t
<220> FEATURE:
<221> NAME/KEY: modified_base
<222> LOCATION: (21)
<223> OTHER INFORMATION: a, c, g or t
<220> FEATURE:
<221> NAME/KEY: modified_base
<222> LOCATION: (24)
<223> OTHER INFORMATION: a, c, g or t
<220> FEATURE:
<221> NAME/KEY: modified_base
<222> LOCATION: (30)

-continued

```
<223> OTHER INFORMATION: a, c, g or t

<400> SEQUENCE: 25

aaywsnaayw snmgntanaa nwsnaaywsn aayaay                              36


<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Ser Asn Ser Arg Tyr Asn Ser Asn Ser Asn Asn
  1               5                  10


<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA sequence
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (30)
<223> OTHER INFORMATION: a, c, g or t
<220> FEATURE:
<221> NAME/KEY: modified_base
<222> LOCATION: (33)
<223> OTHER INFORMATION: a, c, g or t

<400> SEQUENCE: 27

aarmgnaaya aycayaayaa ycayaaymgn wsnaay                              36


<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Arg Asn Asn His Asn Asn His Asn Arg Ser Asn
  1               5                  10


<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA sequence
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (15)
<223> OTHER INFORMATION: a, c, g or t
<220> FEATURE:
<221> NAME/KEY: modified_base
<222> LOCATION: (21)
<223> OTHER INFORMATION: a, c, g or t
```

-continued

<220> FEATURE:
<221> NAME/KEY: modified_base
<222> LOCATION: (27)
<223> OTHER INFORMATION: a, c, g or t

<400> SEQUENCE: 29
aayggnaaya aygtnaaygg naaymgnaay aayaay 36

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Asn Gly Asn Asn Val Asn Gly Asn Arg Asn Asn Asn
1 5 10

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic DNA sequence
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (24)
<223> OTHER INFORMATION: a, c, g or t
<220> FEATURE:
<221> NAME/KEY: modified_base
<222> LOCATION: (33)
<223> OTHER INFORMATION: a, c, g or t

<400> SEQUENCE: 31
aaygtngcna aycayaayaa ywsnaaycay ggnaay 36

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Asn Val Ala Asn His Asn Asn Ser Asn His Gly Asn
1 5 10

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: Synthetic DNA sequence
<220> FEATURE:
<221> NAME/KEY: modified_base
<222> LOCATION: (3)
<223> OTHER INFORMATION: a, c, g or t
<220> FEATURE:

-continued

<221> NAME/KEY: modified_base
<222> LOCATION: (24)
<223> OTHER INFORMATION: a, c, g or t
<220> FEATURE:
<221> NAME/KEY: modified_base
<222> LOCATION: (27)
<223> OTHER INFORMATION: a, c, g or t
<220> FEATURE:
<221> NAME/KEY: modified_base
<222> LOCATION: (33)
<223> OTHER INFORMATION: a, c, g or t

<400> SEQUENCE: 33
wsntayaaya ayaayaayca ygtnwsnaay mgnaay 36

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Ser Tyr Asn Asn Asn Asn His Val Ser Asn Arg Asn
1 5 10

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic DNA sequence
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (21)
<223> OTHER INFORMATION: a, c, g or t
<220> FEATURE:
<221> NAME/KEY: modified_base
<222> LOCATION: (24)
<223> OTHER INFORMATION: a, c, g or t

<400> SEQUENCE: 35
ytnatgaara ayatggaycc nytnaaygay aayath 36

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Leu Met Lys Asn Met Asp Pro Leu Asn Asp Asn Ile
1 5 10

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic DNA sequence
<220> FEATURE:
<221> NAME/KEY: modified_base -continued
<222> LOCATION: (3)
<223> OTHER INFORMATION: a, c, g or t
<220> FEATURE:
<221> NAME/KEY: modified_base
<222> LOCATION: (21)
<223> OTHER INFORMATION: a, c, g or t
<220> FEATURE:
<221> NAME/KEY: modified_base
<222> LOCATION: (24)
<223> OTHER INFORMATION: a, c, g or t
<220> FEATURE:
<221> NAME/KEY: modified_base
<222> LOCATION: (36)
<223> OTHER INFORMATION: a, c, g or t

<400> SEQUENCE: 37
ytnatgaara ayatggaycc nytnaaygay aaygtn 36

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Leu Met Lys Asn Met Asp Pro Leu Asn Asp Asn Val
1 5 10

<210> SEQ ID NO 39
<211> LENGTH: 7
<212> TYPE: PRT
<213> ORGANISM: Mus musculus

<400> SEQUENCE: 39

Val Val Phe Gln Glu Phe Arg
1 5

<210> SEQ ID NO 40
<211> LENGTH: 9
<212> TYPE: PRT
<213> ORGANISM: Mus musculus

<400> SEQUENCE: 40

Cys Asn Gly Val Leu Glu Gly Ile Arg
1 5

<210> SEQ ID NO 41
<211> LENGTH: 10
<212> TYPE: PRT
<213> ORGANISM: Mus musculus

<400> SEQUENCE: 41

Lys Phe Asp Gln Leu Leu Ala Glu Glu Lys
1 5 10

<210> SEQ ID NO 42
<211> LENGTH: 12
<212> TYPE: PRT
<213> ORGANISM: Mus musculus

<400> SEQUENCE: 42

Glu Gln Ala Asp Phe Ala Ile Glu Ala Leu Ala Lys
1 5 10

<210> SEQ ID NO 43

-continued

<211> LENGTH: 16
<212> TYPE: PRT
<213> ORGANISM: Mus musculus

<400> SEQUENCE: 43

Gln Leu Leu Gln Ala Asn Pro Ile Leu Glu Ala Phe Gly Asn Ala Lys
1 5 10 15

<210> SEQ ID NO 44
<211> LENGTH: 9
<212> TYPE: PRT
<213> ORGANISM: Mus musculus

<400> SEQUENCE: 44

Val Lys Pro Leu Leu Gln Val Thr Arg
1 5

<210> SEQ ID NO 45
<211> LENGTH: 13
<212> TYPE: PRT
<213> ORGANISM: Mus musculus

<400> SEQUENCE: 45

Leu Ala Gln Ala Glu Glu Gln Leu Glu Gln Glu Ser Arg
1 5 10

<210> SEQ ID NO 46
<211> LENGTH: 16
<212> TYPE: PRT
<213> ORGANISM: Mus musculus

<400> SEQUENCE: 46

Gln Leu Leu Gln Ala Asn Pro Ile Leu Glu Ala Phe Gly Asn Ala Lys
1 5 10 15

<210> SEQ ID NO 47
<211> LENGTH: 7355
<212> TYPE: DNA
<213> ORGANISM: Mus musculus

<400> SEQUENCE: 47
tgggcagggc acggaaggct caagaacctg acctgctgca gcttccagtc tcgcgttcgc 60
cccaccccgc cgcgccgccc gagcgctcga gaaagtccac tcggaagaac cagcgcctgt 120
tccccgggca gacccaggtt caggtcctgg ccgcaagtca ccatggctca gcaggctgca 180
gacaagtacc tctatgtgga taaaaacttc atcaataacc cgctggccca agctgactgg 240
gctgccaaga agttggtatg ggtgccttcc agcaagaatg gctttgaacc agctagcctc 300
aaggaggagg tgggagaaga ggccattgta gagctggtag agaatgggaa gaaggtgaag 360
gtgaacaagg acgacatcca gaagatgaac ccacccaagt tctccaaggt ggaggacatg 420
gcagagctca cgtgcctcaa cgaagcttcg gtgctgcaca acctcaagga gcgatactac 480
tcagggctta tctacaccta ttcaggcctg ttctgtgtgg tcatcaaccc ttataagaac 540
ctgcccatct actcagagga gatcgtggag atgtacaagg gcaagaagag gcacgagatg 600
ccaccccaca tctacgccat cacagatact gcctaccgga gcatgatgca ggaccgggaa 660
gatcagtcca tcctgtgcac gggggagtct ggagcaggga agacagagaa caccaagaaa 720
gtcatccagt acctggcaca tgtggcctcc tcacacaaga gcaagaagga ccagggggag 780
ttggagcggc agctgctaca ggccaaccct atcctagagg cctttggaaa cgccaagacg 840
gtgaagaatg acaactcctc tcgattcggt aaattcattc gtatcaactt tgatgtcaat 900

-continued

```
ggctacattg ttggtgccaa cattgagact tatcttctgg agaaatctcg tgctatccgc    960
caagccaaag aggagcggac cttccacatc ttctactacc tgctgtctgg ggccggagaa   1020
cacctgaaga ctgatctcct gttggagcca tacaacaaat accgcttcct gtccaacggg   1080
cacgtcacca tccctgggca gcaggacaag gacatgttcc aggagacaat ggaggccatg   1140
agaattatgg gtatcccaga ggatgagcag atgggcttgc tgcgggtcat ctctggggtc   1200
cttcagcttg gcaacattgc cttcaagaag gagcggaaca ctgaccaggc gtccatgccg   1260
gacaacacag ctgctcaaaa ggtgtcccac ctcctgggga tcaatgtgac cgacttcacc   1320
agaggcatcc tcaccccacg catcaaggtg ggcagagact atgtgcagaa ggcgcagact   1380
aaagagcagg ctgactttgc cattgaggcc ttggccaagg ctacctatga gcggatgttc   1440
cgctggctgg tgcttcgcat caacaaagct ctggacaaga ccaagaggca gggcgcctca   1500
tttatcggga tcctggacat cgctggcttt gagatctttg atctgaactc cttcgagcag   1560
ctgtgcatca actacaccaa cgagaagctg cagcagctgt tcaaccacac catgttcatc   1620
ctggagcagg aggagtacca gcgagagggc atcgagtgga acttcatcga cttcggcctg   1680
gacctgcagc cctgcatcga cctcattgag aagccggcgg gtcccccagg catcctggcc   1740
ctgctagatg aggagtgctg gtttcctaag gccactgaca agagcttcgt ggagaaggtg   1800
gtgcaggagc agggcaccca ccccaagttc cagaagccca agcaactgaa ggacaaggct   1860
gatttctgca ttatccacta tgccggcaag gtggactata aagctgacga gtggctgatg   1920
aagaacatgg accccttgaa cgacaacatc gccacgctgc ttcaccagtc ctcagacaag   1980
tttgtctctg agctgtggaa ggatgtggat cggatcattg gcttggacca agtggctgga   2040
atgtccgaga cagcactacc tggtgccttc aagacccgga agggcatgtt ccgtactgtc   2100
ggacagctgt acaaggagca gctggccaag ctcatggcca cgttgaggaa taccaacccc   2160
aacttcgtgc gctgcatcat tcccaaccat gagaagaagg ccggcaaact ggacccgcac   2220
ttggtgctgg accagctgcg ctgcaatggc gtccttgagg gcatccggat ctgccgccag   2280
ggctttccca acagggtggt cttccaggag ttccggcaga ggtatgagat cctcaccccc   2340
aactccatcc cgaagggctt catggatggc aagcaagcgt gtgtgctcat gatcaaagcc   2400
ttggagcttg acagcaacct gtaccgcatc ggccagagca aagtgttctt ccgggcagga   2460
gtgctagccc acctggagga agagcgggac ctgaagatca ccgatgtcat cattggcttc   2520
caggcctgct gcaggggcta cctggccagg aaggcctttg ccaagaggca gcaacagctg   2580
accgccatga aggtcctaca gaggaactgt gctgcgtacc tcaggctgcg caactggcag   2640
tggtggaggc tcttcaccaa ggtcaagccc ctgttgaact caataagaca tgaggatgag   2700
ctgttagcca aggaggcgga actgacaaag gttcgagaga aacatctggc tgcagagaac   2760
aggctgacag agatggagac gatgcagtct cagctcatgg cagagaagct gcagcttcag   2820
gagcagctgc aggcggagac agagctgtgt gccgaggctg aggagctccg ggcccgtctg   2880
acagcgaaga agcaggagct ggaggagatc tgccatgacc tggaggccag ggtggaggag   2940
gaggaggagc gctgccagta cctgcaggcc gagaagaaga agatgcagca gaacatccag   3000
gaacttgagg agcagttgga ggaggaggag agcgcccggc agaagctgca gcttgagaag   3060
gtgaccaccg aggccaagct gaagaaactg gaggaggacc agatcatcat ggaggaccag   3120
aactgcaaac tggccaagga gaagaaactg ctggaagaca gagtagctga attcactacc   3180
aacctcatgg aagaggagga gaagtccaag agcctggcca agctcaagaa caagcacgag   3240
```

-continued

```
gcaatgatca ccgacctgga agagcgcctc cgtagggagg agaagcagag gcaggagttg   3300
gagaagaccc gtcgcaagct ggagggagac tccacagacc tcagtgacca gattgctgag   3360
ctccaggcgc agatagcaga gctcaagatg cagctggcca agaaggagga ggagttgcag   3420
gctgccttgg ccagagtgga agaagaagct gctcagaaga atatggccct gaagaagatc   3480
cgagaactgg aaactcagat ctctgagctc caggaggacc tggagtcgga gcgagcctcc   3540
aggaataaag ccgagaagca gaaacgggat ctgggagagg agctggaggc gctgaagaca   3600
gagctggagg acacgctgga ctccacggct gcccagcagg agctgaggtc gaagcgtgag   3660
caggaggtga gcatcctgaa gaagactctg gaggacgagg ccaagaccca tgaggcccag   3720
atccaggaga tgaggcagaa gcactcacag gctgtggagg agctggcaga tcagttggag   3780
cagacgaagc gggtaaaagc tacccttgag aaggcgaagc agaccctgga gaatgagcgg   3840
ggagagctgg ccaatgaggt gaaggccctg ctgcaaggca agggcgactc agagcacaag   3900
cgcaagaagg tggaggcgca gctgcaagaa ctgcaggtca agttcagcga gggagagcgc   3960
gtgcgaaccg aactggccga caaggtcacc aagctgcagg ttgaactgga cagtgtgacc   4020
ggtctcctta gccagtctga cagcaagtcc agcaagctta cgaaggactt ctctgcgctg   4080
gagtcccagc ttcaggacac acaggagttg ctccaggagg agaaccggca gaagctgagc   4140
ctgagcacca agctcaagca gatggaggat gagaaaaact ccttcaggga gcagctggag   4200
gaggaggagg aggccaagcg caacttggag aagcagatcg ccacgctcca tgcccaggtg   4260
accgacatga agaagaagat ggaggacggt gtagggtgcc tggagactgc agaggaggcg   4320
aagcggaggc ttcagaagga cttggaaggc ctgagccagc ggcttgagga gaaggtggct   4380
gcctacgata agctggagaa gaccaagaca cggctgcagc aggagctgga cgacctgctg   4440
gttgacctgg accaccagcg gcagagcgtc tccaacctgg aaaagaagca gaagaagttc   4500
gaccagctcc tagccgagga gaagaccatc tcggccaagt atgcagagga gcgtgaccga   4560
gctgaggctg aggcccgtga gaaggagaca aaggcgctat cactggcccg ggcgcttgag   4620
gaggccatgg agcagaaggc agagctggag cggctcaaca agcagttccg cacggagatg   4680
gaggacctca tgagctccaa ggatgacgtg ggcaagagtg tccacgagct ggagaagtcc   4740
aagcgggcct tggagcagca ggtggaggag atgaagaccc agctggagga gctggaggat   4800
gagctgcagg ccacggagga tgccaagctc cgcctggagg tgaacctgca ggccatgaag   4860
gcccagtttg agcgggatct gcagggccgg gatgaacaga gcgaggagaa gaagaagcag   4920
ctggtcagac aggtgcggga gatggaggcg gagctggagg atgagaggaa gcagcgctcc   4980
atggccatgg ccgcacgcaa gaaactggag atggatctga aggacctgga ggcacacatt   5040
gacacagcca ataagaaccg ggaagaggcc atcaaacagc tgcggaagct tcaggcccag   5100
atgaaggact gcatgcggga gctggacgac acgcgcgcct cccgggagga gatcctggcg   5160
caggccaagg agaatgagaa gaagctgaag agcatggagg ccgagatgat tcagctgcag   5220
gaggaactgg cagctgctga gcgtgctaag cgtcaggccc aacaggaacg ggacgagctg   5280
gctgatgaga tcgccaacag cagtggcaaa ggggccctag cattagagga gaagcggcga   5340
ctggaggccc gcattgccct gctggaggag gagctggagg aggaacaggg caacacggag   5400
ctgatcaacg atcggctgaa gaaggccaac ctgcagatcg accaaataaa caccgacctg   5460
aacctggaac gcagccacgc acagaagaat gagaatgcgc gacagcagct ggaacgccag   5520
aacaaggagc tcaaggccaa gctgcaggaa atggagagtg ctgtcaagtc caaatacaag   5580
gcctccatcg cggccttgga ggccaaaatt gcacagctgg aggaacagct ggacaacgag   5640
```

-continued

```
accaaggagc gccaggcagc ctccaagcag gtgcgccgga cggagaagaa gctgaaggac   5700
gtgctgctgc aggtggagga cgagcggagg aacgcggaac agttcaagga ccaggctgac   5760
aaggcgtcca cccgcctgaa gcagcttaaa cggcagctag aggaggctga agaggaggcc   5820
cagcgggcca atgcctcacg ccggaagctg cagcgtgagc tggaagatgc cacagagacc   5880
gctgatgcta tgaaccgcga ggtcagctcc ctgaagaaca aactgaggcg tggggacctg   5940
ccatttgtcg tgactcgccg aattgttcgg aaaggcactg gcgactgctc agacgaggag   6000
gtcgacggta aagcagatgg ggccgatgcc aaggcagctg aataggagct tctcctgcag   6060
cccaggcgga tggacaaacg gctctgcctc cctcccccaa ccctccacac ccctgccttg   6120
agactgctct gaccatgtcc ccctcctccc aaggccttcc cgagggcatt ggcttcctct   6180
gctgcagccc ttccagtcct ccataccctt tgagaatctg ataccaaaga gtccaggctg   6240
gctcaggccg gatgacccac agggtcttgt cctccttgcc tgaaagcacg ggtggtgggc   6300
aagaagggcg gccattggag taggcacaag agttttctat gaatctattt tgtcttcaga   6360
taaagatttt gatagctcag gcctctagta gtgttaccct ccccgacctc ggctgtcccc   6420
gtcccccgtc ccccctgctg ttggcaatca cacacggtaa cctcatacct gccctatggc   6480
ccccttccct gggccctatt ggtccagaag gagcctctgt ctgggtgcag aacatggggc   6540
actctgggaa tccccccact cccttctggg cagcactggt gcctctgctc ctccgactgt   6600
aaaccgtctc aagtgcaatg cccctcccct cccttgccaa ggacagaccg tcctggcacc   6660
ggggcaaacc agacagggca tcagggccac tctagaaagg ccaacagcct tccggtggct   6720
tctcccagca ctctagggga ccaaatatat ttaatggtta agggacttgc agggcctggc   6780
agccagaata tccaagggct ggagcccact gtgcgctctg gtgcctctcc taggactggg   6840
gccaagggtg gtcgagctgt gccacccact ctatagcttc aagtctgcct tccacaagga   6900
tgcttttgaa agaaaaaaaa aggttttatt tttcccttct tgtagtaagt gctctagttc   6960
tgggtgtctt cactgccttg ccctggaact gtgtttagaa gagagtagct tgccctacaa   7020
tgtctacact ggtcgctgag ttccctgcgc actgcacctc actgtttgta aatgctgtga   7080
ttaggttccc ttatggcagg aaggcttttt ttttcttttt ttttttcttt tcttttttttt  7140
ttttttaaag gaaaaccagt caaatcatga agccacatac gctagagaag ctgaatccag   7200
gtcccaaagg cgctgtcata aaggagcaag tgggacccgc acccctttttt ttatataata  7260
caagtgcctt agcatgtgtc gcagctgtca ccactacagt aagctggttt acagatgttt   7320
ccactgagcg tcacaataaa gagtaccatg tccta                              7355
```

<210> SEQ ID NO 48
<211> LENGTH: 1960
<212> TYPE: PRT
<213> ORGANISM: Mus musculus

<400> SEQUENCE: 48

```
Met Ala Gln Gln Ala Ala Asp Lys Tyr Leu Tyr Val Asp Lys Asn Phe
  1               5                  10                  15

Ile Asn Asn Pro Leu Ala Gln Ala Asp Trp Ala Ala Lys Lys Leu Val
             20                  25                  30

Trp Val Pro Ser Ser Lys Asn Gly Phe Glu Pro Ala Ser Leu Lys Glu
         35                  40                  45

Glu Val Gly Glu Glu Ala Ile Val Glu Leu Val Glu Asn Gly Lys Lys
     50                  55                  60
```

-continued

```
Val Lys Val Asn Lys Asp Asp Ile Gln Lys Met Asn Pro Pro Lys Phe
 65                 70                  75                  80

Ser Lys Val Glu Asp Met Ala Glu Leu Thr Cys Leu Asn Glu Ala Ser
                85                  90                  95

Val Leu His Asn Leu Lys Glu Arg Tyr Tyr Ser Gly Leu Ile Tyr Thr
            100                 105                 110

Tyr Ser Gly Leu Phe Cys Val Val Ile Asn Pro Tyr Lys Asn Leu Pro
        115                 120                 125

Ile Tyr Ser Glu Glu Ile Val Glu Met Tyr Lys Gly Lys Lys Arg His
    130                 135                 140

Glu Met Pro Pro His Ile Tyr Ala Ile Thr Asp Thr Ala Tyr Arg Ser
145                 150                 155                 160

Met Met Gln Asp Arg Glu Asp Gln Ser Ile Leu Cys Thr Gly Glu Ser
                165                 170                 175

Gly Ala Gly Lys Thr Glu Asn Thr Lys Lys Val Ile Gln Tyr Leu Ala
            180                 185                 190

His Val Ala Ser Ser His Lys Ser Lys Lys Asp Gln Gly Glu Leu Glu
        195                 200                 205

Arg Gln Leu Leu Gln Ala Asn Pro Ile Leu Glu Ala Phe Gly Asn Ala
    210                 215                 220

Lys Thr Val Lys Asn Asp Asn Ser Ser Arg Phe Gly Lys Phe Ile Arg
225                 230                 235                 240

Ile Asn Phe Asp Val Asn Gly Tyr Ile Val Gly Ala Asn Ile Glu Thr
                245                 250                 255

Tyr Leu Leu Glu Lys Ser Arg Ala Ile Arg Gln Ala Lys Glu Glu Arg
            260                 265                 270

Thr Phe His Ile Phe Tyr Tyr Leu Leu Ser Gly Ala Gly Glu His Leu
        275                 280                 285

Lys Thr Asp Leu Leu Leu Glu Pro Tyr Asn Lys Tyr Arg Phe Leu Ser
    290                 295                 300

Asn Gly His Val Thr Ile Pro Gly Gln Gln Asp Lys Asp Met Phe Gln
305                 310                 315                 320

Glu Thr Met Glu Ala Met Arg Ile Met Gly Ile Pro Glu Asp Glu Gln
                325                 330                 335

Met Gly Leu Leu Arg Val Ile Ser Gly Val Leu Gln Leu Gly Asn Ile
            340                 345                 350

Ala Phe Lys Lys Glu Arg Asn Thr Asp Gln Ala Ser Met Pro Asp Asn
        355                 360                 365

Thr Ala Ala Gln Lys Val Ser His Leu Leu Gly Ile Asn Val Thr Asp
    370                 375                 380

Phe Thr Arg Gly Ile Leu Thr Pro Arg Ile Lys Val Gly Arg Asp Tyr
385                 390                 395                 400

Val Gln Lys Ala Gln Thr Lys Glu Gln Ala Asp Phe Ala Ile Glu Ala
                405                 410                 415

Leu Ala Lys Ala Thr Tyr Glu Arg Met Phe Arg Trp Leu Val Leu Arg
            420                 425                 430

Ile Asn Lys Ala Leu Asp Lys Thr Lys Arg Gln Gly Ala Ser Phe Ile
        435                 440                 445

Gly Ile Leu Asp Ile Ala Gly Phe Glu Ile Phe Asp Leu Asn Ser Phe
    450                 455                 460

Glu Gln Leu Cys Ile Asn Tyr Thr Asn Glu Lys Leu Gln Gln Leu Phe
465                 470                 475                 480

Asn His Thr Met Phe Ile Leu Glu Gln Glu Glu Tyr Gln Arg Glu Gly
```

-continued

```
                485                 490                 495

Ile Glu Trp Asn Phe Ile Asp Phe Gly Leu Asp Leu Gln Pro Cys Ile
            500                 505                 510

Asp Leu Ile Glu Lys Pro Ala Gly Pro Pro Gly Ile Leu Ala Leu Leu
        515                 520                 525

Asp Glu Glu Cys Trp Phe Pro Lys Ala Thr Asp Lys Ser Phe Val Glu
    530                 535                 540

Lys Val Val Gln Glu Gln Gly Thr His Pro Lys Phe Gln Lys Pro Lys
545                 550                 555                 560

Gln Leu Lys Asp Lys Ala Asp Phe Cys Ile Ile His Tyr Ala Gly Lys
                565                 570                 575

Val Asp Tyr Lys Ala Asp Glu Trp Leu Met Lys Asn Met Asp Pro Leu
            580                 585                 590

Asn Asp Asn Ile Ala Thr Leu Leu His Gln Ser Ser Asp Lys Phe Val
        595                 600                 605

Ser Glu Leu Trp Lys Asp Val Asp Arg Ile Ile Gly Leu Asp Gln Val
    610                 615                 620

Ala Gly Met Ser Glu Thr Ala Leu Pro Gly Ala Phe Lys Thr Arg Lys
625                 630                 635                 640

Gly Met Phe Arg Thr Val Gly Gln Leu Tyr Lys Glu Gln Leu Ala Lys
                645                 650                 655

Leu Met Ala Thr Leu Arg Asn Thr Asn Pro Asn Phe Val Arg Cys Ile
            660                 665                 670

Ile Pro Asn His Glu Lys Lys Ala Gly Lys Leu Asp Pro His Leu Val
        675                 680                 685

Leu Asp Gln Leu Arg Cys Asn Gly Val Leu Glu Gly Ile Arg Ile Cys
    690                 695                 700

Arg Gln Gly Phe Pro Asn Arg Val Val Phe Gln Glu Phe Arg Gln Arg
705                 710                 715                 720

Tyr Glu Ile Leu Thr Pro Asn Ser Ile Pro Lys Gly Phe Met Asp Gly
                725                 730                 735

Lys Gln Ala Cys Val Leu Met Ile Lys Ala Leu Glu Leu Asp Ser Asn
            740                 745                 750

Leu Tyr Arg Ile Gly Gln Ser Lys Val Phe Phe Arg Ala Gly Val Leu
        755                 760                 765

Ala His Leu Glu Glu Glu Arg Asp Leu Lys Ile Thr Asp Val Ile Ile
    770                 775                 780

Gly Phe Gln Ala Cys Cys Arg Gly Tyr Leu Ala Arg Lys Ala Phe Ala
785                 790                 795                 800

Lys Arg Gln Gln Gln Leu Thr Ala Met Lys Val Leu Gln Arg Asn Cys
                805                 810                 815

Ala Ala Tyr Leu Arg Leu Arg Asn Trp Gln Trp Trp Arg Leu Phe Thr
            820                 825                 830

Lys Val Lys Pro Leu Leu Asn Ser Ile Arg His Glu Asp Glu Leu Leu
        835                 840                 845

Ala Lys Glu Ala Glu Leu Thr Lys Val Arg Glu Lys His Leu Ala Ala
    850                 855                 860

Glu Asn Arg Leu Thr Glu Met Glu Thr Met Gln Ser Gln Leu Met Ala
865                 870                 875                 880

Glu Lys Leu Gln Leu Gln Glu Gln Leu Gln Ala Glu Thr Glu Leu Cys
                885                 890                 895

Ala Glu Ala Glu Glu Leu Arg Ala Arg Leu Thr Ala Lys Lys Gln Glu
            900                 905                 910
```

-continued

```
Leu Glu Glu Ile Cys His Asp Leu Glu Ala Arg Val Glu Glu Glu
        915                 920                 925

Glu Arg Cys Gln Tyr Leu Gln Ala Glu Lys Lys Lys Met Gln Gln Asn
    930                 935                 940

Ile Gln Glu Leu Glu Glu Gln Leu Glu Glu Glu Glu Ser Ala Arg Gln
945                 950                 955                 960

Lys Leu Gln Leu Glu Lys Val Thr Thr Glu Ala Lys Leu Lys Lys Leu
                965                 970                 975

Glu Glu Asp Gln Ile Ile Met Glu Asp Gln Asn Cys Lys Leu Ala Lys
            980                 985                 990

Glu Lys Lys Leu Leu Glu Asp Arg Val Ala Glu Phe Thr Thr Asn Leu
        995                 1000                1005

Met Glu Glu Glu Glu Lys Ser Lys Ser Leu Ala Lys Leu Lys Asn Lys
    1010                1015                1020

His Glu Ala Met Ile Thr Asp Leu Glu Glu Arg Leu Arg Arg Glu Glu
1025                1030                1035                1040

Lys Gln Arg Gln Glu Leu Glu Lys Thr Arg Arg Lys Leu Glu Gly Asp
                1045                1050                1055

Ser Thr Asp Leu Ser Asp Gln Ile Ala Glu Leu Gln Ala Gln Ile Ala
            1060                1065                1070

Glu Leu Lys Met Gln Leu Ala Lys Lys Glu Glu Glu Leu Gln Ala Ala
        1075                1080                1085

Leu Ala Arg Val Glu Glu Glu Ala Ala Gln Lys Asn Met Ala Leu Lys
    1090                1095                1100

Lys Ile Arg Glu Leu Glu Thr Gln Ile Ser Glu Leu Gln Glu Asp Leu
1105                1110                1115                1120

Glu Ser Glu Arg Ala Ser Arg Asn Lys Ala Glu Lys Gln Lys Arg Asp
                1125                1130                1135

Leu Gly Glu Glu Leu Glu Ala Leu Lys Thr Glu Leu Glu Asp Thr Leu
            1140                1145                1150

Asp Ser Thr Ala Ala Gln Gln Glu Leu Arg Ser Lys Arg Glu Gln Glu
        1155                1160                1165

Val Ser Ile Leu Lys Lys Thr Leu Glu Asp Glu Ala Lys Thr His Glu
    1170                1175                1180

Ala Gln Ile Gln Glu Met Arg Gln Lys His Ser Gln Ala Val Glu Glu
1185                1190                1195                1200

Leu Ala Asp Gln Leu Glu Gln Thr Lys Arg Val Lys Ala Thr Leu Glu
                1205                1210                1215

Lys Ala Lys Gln Thr Leu Glu Asn Glu Arg Gly Glu Leu Ala Asn Glu
            1220                1225                1230

Val Lys Ala Leu Leu Gln Gly Lys Gly Asp Ser Glu His Lys Arg Lys
        1235                1240                1245

Lys Val Glu Ala Gln Leu Gln Glu Leu Gln Val Lys Phe Ser Glu Gly
    1250                1255                1260

Glu Arg Val Arg Thr Glu Leu Ala Asp Lys Val Thr Lys Leu Gln Val
1265                1270                1275                1280

Glu Leu Asp Ser Val Thr Gly Leu Leu Ser Gln Ser Asp Ser Lys Ser
                1285                1290                1295

Ser Lys Leu Thr Lys Asp Phe Ser Ala Leu Glu Ser Gln Leu Gln Asp
            1300                1305                1310

Thr Gln Glu Leu Leu Gln Glu Glu Asn Arg Gln Lys Leu Ser Leu Ser
        1315                1320                1325
```

-continued

```
Thr Lys Leu Lys Gln Met Glu Asp Glu Lys Asn Ser Phe Arg Glu Gln
    1330                1335                1340

Leu Glu Glu Glu Glu Glu Ala Lys Arg Asn Leu Glu Lys Gln Ile Ala
1345                1350                1355                1360

Thr Leu His Ala Gln Val Thr Asp Met Lys Lys Lys Met Glu Asp Gly
                1365                1370                1375

Val Gly Cys Leu Glu Thr Ala Glu Glu Ala Lys Arg Arg Leu Gln Lys
            1380                1385                1390

Asp Leu Glu Gly Leu Ser Gln Arg Leu Glu Glu Lys Val Ala Ala Tyr
        1395                1400                1405

Asp Lys Leu Glu Lys Thr Lys Thr Arg Leu Gln Gln Glu Leu Asp Asp
    1410                1415                1420

Leu Leu Val Asp Leu Asp His Gln Arg Gln Ser Val Ser Asn Leu Glu
1425                1430                1435                1440

Lys Lys Gln Lys Lys Phe Asp Gln Leu Leu Ala Glu Glu Lys Thr Ile
                1445                1450                1455

Ser Ala Lys Tyr Ala Glu Glu Arg Asp Arg Ala Glu Ala Glu Ala Arg
            1460                1465                1470

Glu Lys Glu Thr Lys Ala Leu Ser Leu Ala Arg Ala Leu Glu Glu Ala
        1475                1480                1485

Met Glu Gln Lys Ala Glu Leu Glu Arg Leu Asn Lys Gln Phe Arg Thr
    1490                1495                1500

Glu Met Glu Asp Leu Met Ser Ser Lys Asp Asp Val Gly Lys Ser Val
1505                1510                1515                1520

His Glu Leu Glu Lys Ser Lys Arg Ala Leu Glu Gln Gln Val Glu Glu
                1525                1530                1535

Met Lys Thr Gln Leu Glu Glu Leu Glu Asp Glu Leu Gln Ala Thr Glu
            1540                1545                1550

Asp Ala Lys Leu Arg Leu Glu Val Asn Leu Gln Ala Met Lys Ala Gln
        1555                1560                1565

Phe Glu Arg Asp Leu Gln Gly Arg Asp Glu Gln Ser Glu Glu Lys Lys
    1570                1575                1580

Lys Gln Leu Val Arg Gln Val Arg Glu Met Glu Ala Glu Leu Glu Asp
1585                1590                1595                1600

Glu Arg Lys Gln Arg Ser Met Ala Met Ala Ala Arg Lys Lys Leu Glu
                1605                1610                1615

Met Asp Leu Lys Asp Leu Glu Ala His Ile Asp Thr Ala Asn Lys Asn
            1620                1625                1630

Arg Glu Glu Ala Ile Lys Gln Leu Arg Lys Leu Gln Ala Gln Met Lys
        1635                1640                1645

Asp Cys Met Arg Glu Leu Asp Asp Thr Arg Ala Ser Arg Glu Glu Ile
    1650                1655                1660

Leu Ala Gln Ala Lys Glu Asn Glu Lys Lys Leu Lys Ser Met Glu Ala
1665                1670                1675                1680

Glu Met Ile Gln Leu Gln Glu Glu Leu Ala Ala Ala Glu Arg Ala Lys
                1685                1690                1695

Arg Gln Ala Gln Gln Glu Arg Asp Glu Leu Ala Asp Glu Ile Ala Asn
            1700                1705                1710

Ser Ser Gly Lys Gly Ala Leu Ala Leu Glu Glu Lys Arg Arg Leu Glu
        1715                1720                1725

Ala Arg Ile Ala Leu Leu Glu Glu Glu Leu Glu Glu Gln Gly Asn
    1730                1735                1740

Thr Glu Leu Ile Asn Asp Arg Leu Lys Lys Ala Asn Leu Gln Ile Asp
```

-continued

```
1745                1750                1755                1760

Gln Ile Asn Thr Asp Leu Asn Leu Glu Arg Ser His Ala Gln Lys Asn
                1765                1770                1775

Glu Asn Ala Arg Gln Gln Leu Glu Arg Gln Asn Lys Glu Leu Lys Ala
            1780                1785                1790

Lys Leu Gln Glu Met Glu Ser Ala Val Lys Ser Lys Tyr Lys Ala Ser
        1795                1800                1805

Ile Ala Ala Leu Glu Ala Lys Ile Ala Gln Leu Glu Glu Gln Leu Asp
    1810                1815                1820

Asn Glu Thr Lys Glu Arg Gln Ala Ala Ser Lys Gln Val Arg Arg Thr
1825                1830                1835                1840

Glu Lys Lys Leu Lys Asp Val Leu Leu Gln Val Glu Asp Glu Arg Arg
                1845                1850                1855

Asn Ala Glu Gln Phe Lys Asp Gln Ala Asp Lys Ala Ser Thr Arg Leu
            1860                1865                1870

Lys Gln Leu Lys Arg Gln Leu Glu Glu Ala Glu Glu Glu Ala Gln Arg
        1875                1880                1885

Ala Asn Ala Ser Arg Arg Lys Leu Gln Arg Glu Leu Glu Asp Ala Thr
    1890                1895                1900

Glu Thr Ala Asp Ala Met Asn Arg Glu Val Ser Ser Leu Lys Asn Lys
1905                1910                1915                1920

Leu Arg Arg Gly Asp Leu Pro Phe Val Val Thr Arg Arg Ile Val Arg
                1925                1930                1935

Lys Gly Thr Gly Asp Cys Ser Asp Glu Glu Val Asp Gly Lys Ala Asp
            1940                1945                1950

Gly Ala Asp Ala Lys Ala Ala Glu
        1955                1960


<210> SEQ ID NO 49
<211> LENGTH: 7474
<212> TYPE: DNA
<213> ORGANISM: Homo sapiens

<400> SEQUENCE: 49

atacgactca ctatagggcg atcaggtgct ggaaagaagg ctaagcaagg ctgacctgct      60

gcagctcccg cctcgtgcgc tcgccccacc cggccgccgc ccgagcgctc gagaaagtcc     120

tctcgggaga agcagcgcct gttcccgggg cagatccagg ttcaggtcct ggctataagt     180

caccatggca cagcaagctg ccgataagta tctctatgtg gataaaaact tcatcaacaa     240

tccgctggcc caggccgact gggctgccaa gaagctggta tgggtgcctt ccgacaagag     300

tggctttgag ccagccagcc tcaaggagga ggtgggcgaa gaggccatcg tggagctggt     360

ggagaatggg aagaaggtga aggtgaacaa ggatgacatc cagaagatga acccgcccaa     420

gttctccaag gtggaggaca tggcagagct cacgtgcctc aacgaagcct cggtgctgca     480

caacctcaag gagcgttact actcagggct catctacacc tattcaggcc tgttctgtgt     540

ggtcatcaat ccttacaaga acctgcccat ctactctgaa gagattgtgg aaatgtacaa     600

gggcaagaag aggcacgaga tgccccctca catctatgcc atcacagaca ccgcctacag     660

gagtatgatg caagaccgag aagatcaatc catcttgtgc actggtgaat ctggagctgg     720

caagacggag aacaccaaga aggtcatcca gtatctggcg tacgtggcgt cctcgcacaa     780

gagcaagaag gaccagggcg agctggagcg gcagctgctg caggccaacc ccatcctgga     840

ggccttcggg aacgccaaga ccgtgaagaa tgacaactcc tcccgcttcg gcaaattcat     900
```

-continued

```
tcgcatcaac tttgatgtca atggctacat tgttggagcc aacattgaga cttatctttt     960
ggagaaatct cgtgctatcc gccaagccaa ggaagaacgg accttccaca tcttctatta    1020
tctcctgtct ggggctggag agcacctgaa gaccgatctc ctgttggagc cgtacaacaa    1080
ataccgcttc ctgtccaatg gacacgtcac catccccggg cagcaggaca aggacatgtt    1140
ccaggagacc atggaggcca tgaggattat gggcatccca gaagaggagc aaatgggcct    1200
gctgcgggtc atctcagggg ttcttcagct cggcaacatc gtcttcaaga aggagcggaa    1260
cactgaccag gcgtccatgc ccgacaacac agctgcccaa aaggtgtccc atctcttggg    1320
tatcaatgtg accgatttca ccagaggaat cctcaccccg cgcatcaagg tgggacggga    1380
ttacgtccag aaggcgcaga ctaaagagca ggctgacttt gccatcgagg ccttggccaa    1440
ggcgacctat gagcggatgt tccgctggct ggtgctgcgc atcaacaagg ctctggacaa    1500
gaccaagagg cagggcgcct ccttcatcgg gatcctggac attgccggct tcgagatctt    1560
tgatctgaac tcgtttgagc agctgtgcat caattacacc aatgagaagc tgcagcagct    1620
cttcaaccac accatgttca tcctggagca ggaggagtac cagcgcgagg gcatcgagtg    1680
gaacttcatc gactttggcc tcgacctgca gccctgcatc gacctcattg agaagccagc    1740
aggccccccg ggcattctgg ccctgctgga cgaggagtgc tggttcccca aagccaccga    1800
caagagcttc gtggagaagg tgatgcagga gcagggcacc caccccaagt tccagaagcc    1860
caagcagctg aaggacaaag ctgatttctg cattatccac tatgccggca aggtggatta    1920
caaagctgac gagtggctga tgaagaacat ggatcccctg aatgacaaca tcgccacact    1980
gctccaccag tcctctgaca agtttgtctc ggagctgtgg aaggatgtgg accgcatcat    2040
cggcctggac caggtggccg gcatgtcgga gaccgcactg cccggggcct tcaagacgcg    2100
gaagggcatg ttccgcactg tggggcagct ttacaaggag cagctggcca agctgatggc    2160
tacgctgagg aacacgaacc ccaactttgt ccgctgcatc atccccaacc acgagaagaa    2220
ggccggcaag ctggacccgc atctcgtgct ggaccagctg cgctgcaacg gtgttctcga    2280
gggcatccgt atctgccgcc agggcttccc caacagggtg gtcttccagg agtttcggca    2340
gagatatgag atcctgactc caaactccat tcccaagggt ttcatggacg ggaagcaggc    2400
gtgcgtgctc atgataaaag ccctggagct cgacagcaat ctgtaccgca ttggccagag    2460
caaagtcttc ttccgtgccg gtgtgctggc ccacctggag gaggagcgag acctgaagat    2520
caccgacgtc atcatagggt tccaggcctg ctgcaggggc tacctggcca ggaaagcatt    2580
tgccaagcgg cagcagcagc ttaccgccat gaaggtcctc cagcggaact gcgctgccta    2640
cctgaagctg cggaactggc agtggtggcg gctcttcacc aaggtcaagc cgctgctgca    2700
ggtgagccgg caggaggagg agatgatggc caaggaggag gagctggtga aggtcagaga    2760
gaagcagctg gctgcggaga acaggctcac ggagatggag acgctgcagt ctcagctcat    2820
ggcagagaaa ttgcagctgc aggagcagct ccaggcagaa accgagctgt gtgccgaggc    2880
tgaggagctc cgggcccgcc tgaccgccaa gaagcaggaa ttagaagaga tctgccatga    2940
cctagaggcc agggtggagg aggaggagga gcgctgccag cacctgcagg cggagaagaa    3000
gaagatgcag cagaacatcc aggagcttga ggagcagctg gaggaggagg agagcgcccg    3060
gcagaagctg cagctggaga aggtgaccac cgaggcgaag ctgaaaaagc tggaggagga    3120
gcagatcatc ctggaggacc agaactgcaa gctggccaag gaaaagaaac tgctggaaga    3180
cagaatagct gagttcacca ccaacctcac agaagaggag gagaaatcta agagcctcgc    3240
caagctcaag aacaagcatg aggcaatgat cactgacttg gaagagcgcc tccgcaggga    3300
```

-continued

```
ggagaagcag cgacaggagc tggagaagac ccgccggaag ctggagggag actccacaga   3360
cctcagcgac cagatcgccg agctccaggc ccagatcgcg gagctcaaga tgcagctggc   3420
caagaaagag gaggagctcc aggccgccct ggccagagtg gaagaggaag ctgcccagaa   3480
gaacatggcc ctcaagaaga tccgggagct ggaatctcag atctctgaac tccaggaaga   3540
cctggagtct gagcgtgctt ccaggaataa agctgagaag cagaaacggg accttgggga   3600
agagctagag gcgctgaaaa cagagttgga ggacacgctg gattccacag ctgcccagca   3660
ggagctcagg tcaaaacgtg agcaggaggt gaacatcctg aagaagaccc tggaggagga   3720
ggccaagacc cacgaggccc agatccagga gatgaggcag aagcactcac aggccgtgga   3780
ggagctggcg gagcagctgg agcagacgaa gcgggtgaaa gcaaacctcg agaaggcaaa   3840
gcagactctg gagaacgagc ggggggagct ggccaacgag gtgaaggtgc tgctgcaggg   3900
caaaggggac tcggagcaca agcgcaagaa agtggaggcg cagctgcagg agctgcaggt   3960
caagttcaac gagggagagc gcgtgcgcac agagctggcc gacaaggtca ccaagctgca   4020
ggtggagctg gacaacgtga ccgggcttct cagccagtcc gacagcaagt ccagcaagct   4080
caccaaggac ttctccgcgc tggagtccca gctgcaggac actcaggagc tgctgcagga   4140
ggagaaccgg cagaagctga gcctgagcac caagctcaag caggtggagg acgagaagaa   4200
ttccttccgg gagcagctgg aggaggagga ggaggccaag cacaacctgg agaagcagat   4260
cgccaccctc catgcccagg tggccgacat gaaaaagaag atggaggaca gtgtggggtg   4320
cctggaaact gctgaggagg tgaagaggaa gctccagaag gacctggagg gcctgagcca   4380
gcggcacgag gagaaggtgg ccgcctacga caagctggag aagaccaaga cgcggctgca   4440
gcaggagctg gacgacctgc tggtggacct ggaccaccag cgccagagcg cgtgcaacct   4500
ggagaagaag cagaagaagt ttgaccagct cctggcggag gagaagacca tctctgccaa   4560
gtatgcagag gagcgcgacc gggctgaggc ggaggcccga gagaaggaga ccaaggctct   4620
gtcgctggcc cgggccctgg aggaagccat ggagcagaag gcggagctgg agcggctcaa   4680
caagcagttc cgcacggaga tggaggacct tatgagctcc aaggatgatg tgggcaagag   4740
tgtccacgag ctggagaagt ccaagcgggc cctagagcag caggtggagg agatgaagac   4800
gcagctggaa gagctggagg acgagctgca ggccaccgaa gatgccaagc tgcggttgga   4860
ggtcaacctg caggccatga aggcccagtt cgagcgggac ctgcagggcc gggacgagca   4920
gagcgaggag aagaagaagc agctggtcag acaggtgcgg gagatggagg cagagctgga   4980
ggacgagagg aagcagcgct cgatggcagt ggccgcccgg aagaagctgg agatggacct   5040
gaaggacctg gaggcgcaca tcgactcggc caacaagaac cgggacgaag ccatcaaaca   5100
gctgcggaag ctgcaggccc agatgaagga ctgcatgcgc gagctggatg acacccgcgc   5160
ctctcgtgag gagatcctgg cccaggccaa agagaacgag aagaagctga agagcatgga   5220
ggccgagatg atccagttgc aggaggaact ggcagccgcg gagcgtgcca agcgccaggc   5280
ccagcaggag cgggatgagc tggctgacga gatcgccaac agcagcggca aaggagccct   5340
ggcgttagag gagaagcggc gtctggaggc ccgcatcgcc cagctggagg aggagctgga   5400
ggaggagcag ggcaacacgg agctgatcaa cgaccggctg aagaaggcca acctgcagat   5460
cgaccagatc aacaccgacc tgaacctgga gcgcagccac gcccagaaga acgagaatgc   5520
tcggcagcag ctggaacgcc agaacaagga gcttaaggtc aagctgcagg agatggaggg   5580
cactgtcaag tccaagtaca aggcctccat caccgccctc gaggccaaga ttgcacagct   5640
```

-continued

```
ggaggagcag ctggacaacg agaccaagga gcgccaggca gcctgcaaac aggtgcgtcg   5700

gaccgagaag aagctgaagg atgtgctgct gcaggtggat gacgagcgga ggaacgccga   5760

gcagtacaag gaccaggccg acaaggcatc tacccgcctg aagcagctca agcggcagct   5820

ggaggaggcc gaagaggagg cccagcgggc caacgcctcc cgccggaaac tgcagcgcga   5880

gctggaggac gccactgaga cggccgatgc catgaaccgc gaagtcagct ccctaaagaa   5940

caagctcagg cgcggggacc tgccgtttgt cgtgccccgc cgaatggccc ggaaaggcgc   6000

cggggatggc tccgacgaag aggtagatgg caaagcggat ggggctgagg ccaaacctgc   6060

cgaataagcc tcttctcctg cagcctgaga tggatggaca gacagacacc acagcctccc   6120

cttcccagac cccgcagcac gcctctcccc accttcttgg gactgctgtg aacatgcctc   6180

ctcctgccct ccgccccgtc cccccatccc gtttccctcc aggtgttgtt gagggcattt   6240

ggcttcctct gctgcatccc cttccagctc cctcccctgc tcagaatctg ataccaaaga   6300

gacagggccc gggcccaggc agagagcgac cagcaggctc ctcagccctc tcttgccaaa   6360

aagcacaaga tgttgaggcg agcagggcag gcccccgggg aggggccaga gttttctatg   6420

aatctatttt tcttcagact gaggcctttt ggtagtcgga gcccccgcag tcgtcagcct   6480

ccctgacgtc tgccaccagc gcccccactc ctcctccttt ctttgctgtt tgcaatcaca   6540

cgtggtgacc tcacacacct ctgccccttg ggcctcccac tcccatggct ctgggcggtc   6600

cagaaggagc aggccctggg cctccacctc tgtgcagggc acagaaggct ggggtggggg   6660

gaggagtgga ttcctcccca ccctgtccca ggcagcgcca ctgtccgctg tctccctcct   6720

gattctaaaa tgtctcaagt gcaatgcccc ctcccctcct ttaccgagga cagcctgcct   6780

ctgccacagc aaggctgtcg gggtcaagct ggaaaggcca gcagccttcc agtggcttct   6840

cccaacactc ttggggacca aatatattta atggttaagg gacttgtccc aagtctgaca   6900

gccagagcgt tagaggggcc agcggccctc ccaggcgatc ttgtgtctac tctaggactg   6960

ggcccgaggg tggtttacct gcaccgttga ctcagtatag tttaaaaatc tgccacctgc   7020

acaggtattt ttgaaagcaa aataaggttt tctttttttcc cctttcttgt aataaatgat   7080

aaaattccga gtctttctca ctgcctttgt ttagaagaga gtagctcgtc ctcactggtc   7140

tacactggtt gccgaattta cttgtattcc taactgtttt gtatatgctg cattgagact   7200

tacggcaaga aggcattttt tttttttaaa ggaaacaaac tctcaaatca tgaagtgata   7260

taaaagctgc atatgcctac aaagctctga attcaggtcc cagttgctgt cacaaaggag   7320

tgagtgaaac tcccacccta ccccctttt tatataataa aagtgcctta gcatgtgttg   7380

cagctgtcac cactacagta agctggttta cagatgtttt ccactgagca tcacaataaa   7440

gagaaccatg tgctaaaaaa aaaaaaaaaa aaaa                              7474
```

<210> SEQ ID NO 50
<211> LENGTH: 1960
<212> TYPE: PRT
<213> ORGANISM: Homo sapiens

<400> SEQUENCE: 50

```
Met Ala Gln Gln Ala Ala Asp Lys Tyr Leu Tyr Val Asp Lys Asn Phe
  1               5                  10                  15

Ile Asn Asn Pro Leu Ala Gln Ala Asp Trp Ala Ala Lys Lys Leu Val
             20                  25                  30

Trp Val Pro Ser Asp Lys Ser Gly Phe Glu Pro Ala Ser Leu Lys Glu
         35                  40                  45
```

-continued

```
Glu Val Gly Glu Glu Ala Ile Val Glu Leu Val Glu Asn Gly Lys Lys
     50                  55                  60

Val Lys Val Asn Lys Asp Asp Ile Gln Lys Met Asn Pro Pro Lys Phe
 65                  70                  75                  80

Ser Lys Val Glu Asp Met Ala Glu Leu Thr Cys Leu Asn Glu Ala Ser
                 85                  90                  95

Val Leu His Asn Leu Lys Glu Arg Tyr Tyr Ser Gly Leu Ile Tyr Thr
            100                 105                 110

Tyr Ser Gly Leu Phe Cys Val Val Ile Asn Pro Tyr Lys Asn Leu Pro
        115                 120                 125

Ile Tyr Ser Glu Glu Ile Val Glu Met Tyr Lys Gly Lys Lys Arg His
    130                 135                 140

Glu Met Pro Pro His Ile Tyr Ala Ile Thr Asp Thr Ala Tyr Arg Ser
145                 150                 155                 160

Met Met Gln Asp Arg Glu Asp Gln Ser Ile Leu Cys Thr Gly Glu Ser
                165                 170                 175

Gly Ala Gly Lys Thr Glu Asn Thr Lys Lys Val Ile Gln Tyr Leu Ala
            180                 185                 190

Tyr Val Ala Ser Ser His Lys Ser Lys Lys Asp Gln Gly Glu Leu Glu
        195                 200                 205

Arg Gln Leu Leu Gln Ala Asn Pro Ile Leu Glu Ala Phe Gly Asn Ala
    210                 215                 220

Lys Thr Val Lys Asn Asp Asn Ser Ser Arg Phe Gly Lys Phe Ile Arg
225                 230                 235                 240

Ile Asn Phe Asp Val Asn Gly Tyr Ile Val Gly Ala Asn Ile Glu Thr
                245                 250                 255

Tyr Leu Leu Glu Lys Ser Arg Ala Ile Arg Gln Ala Lys Glu Glu Arg
            260                 265                 270

Thr Phe His Ile Phe Tyr Tyr Leu Leu Ser Gly Ala Gly Glu His Leu
        275                 280                 285

Lys Thr Asp Leu Leu Leu Glu Pro Tyr Asn Lys Tyr Arg Phe Leu Ser
    290                 295                 300

Asn Gly His Val Thr Ile Pro Gly Gln Gln Asp Lys Asp Met Phe Gln
305                 310                 315                 320

Glu Thr Met Glu Ala Met Arg Ile Met Gly Ile Pro Glu Glu Glu Gln
                325                 330                 335

Met Gly Leu Leu Arg Val Ile Ser Gly Val Leu Gln Leu Gly Asn Ile
            340                 345                 350

Val Phe Lys Lys Glu Arg Asn Thr Asp Gln Ala Ser Met Pro Asp Asn
        355                 360                 365

Thr Ala Ala Gln Lys Val Ser His Leu Leu Gly Ile Asn Val Thr Asp
    370                 375                 380

Phe Thr Arg Gly Ile Leu Thr Pro Arg Ile Lys Val Gly Arg Asp Tyr
385                 390                 395                 400

Val Gln Lys Ala Gln Thr Lys Glu Gln Ala Asp Phe Ala Ile Glu Ala
                405                 410                 415

Leu Ala Lys Ala Thr Tyr Glu Arg Met Phe Arg Trp Leu Val Leu Arg
            420                 425                 430

Ile Asn Lys Ala Leu Asp Lys Thr Lys Arg Gln Gly Ala Ser Phe Ile
        435                 440                 445

Gly Ile Leu Asp Ile Ala Gly Phe Glu Ile Phe Asp Leu Asn Ser Phe
    450                 455                 460

Glu Gln Leu Cys Ile Asn Tyr Thr Asn Glu Lys Leu Gln Gln Leu Phe
```

-continued

```
465                 470                 475                 480

Asn His Thr Met Phe Ile Leu Glu Gln Glu Glu Tyr Gln Arg Glu Gly
                485                 490                 495

Ile Glu Trp Asn Phe Ile Asp Phe Gly Leu Asp Leu Gln Pro Cys Ile
            500                 505                 510

Asp Leu Ile Glu Lys Pro Ala Gly Pro Pro Gly Ile Leu Ala Leu Leu
        515                 520                 525

Asp Glu Glu Cys Trp Phe Pro Lys Ala Thr Asp Lys Ser Phe Val Glu
    530                 535                 540

Lys Val Met Gln Glu Gln Gly Thr His Pro Lys Phe Gln Lys Pro Lys
545                 550                 555                 560

Gln Leu Lys Asp Lys Ala Asp Phe Cys Ile Ile His Tyr Ala Gly Lys
                565                 570                 575

Val Asp Tyr Lys Ala Asp Glu Trp Leu Met Lys Asn Met Asp Pro Leu
            580                 585                 590

Asn Asp Asn Ile Ala Thr Leu Leu His Gln Ser Ser Asp Lys Phe Val
        595                 600                 605

Ser Glu Leu Trp Lys Asp Val Asp Arg Ile Ile Gly Leu Asp Gln Val
    610                 615                 620

Ala Gly Met Ser Glu Thr Ala Leu Pro Gly Ala Phe Lys Thr Arg Lys
625                 630                 635                 640

Gly Met Phe Arg Thr Val Gly Gln Leu Tyr Lys Glu Gln Leu Ala Lys
                645                 650                 655

Leu Met Ala Thr Leu Arg Asn Thr Asn Pro Asn Phe Val Arg Cys Ile
            660                 665                 670

Ile Pro Asn His Glu Lys Lys Ala Gly Lys Leu Asp Pro His Leu Val
        675                 680                 685

Leu Asp Gln Leu Arg Cys Asn Gly Val Leu Glu Gly Ile Arg Ile Cys
    690                 695                 700

Arg Gln Gly Phe Pro Asn Arg Val Val Phe Gln Glu Phe Arg Gln Arg
705                 710                 715                 720

Tyr Glu Ile Leu Thr Pro Asn Ser Ile Pro Lys Gly Phe Met Asp Gly
                725                 730                 735

Lys Gln Ala Cys Val Leu Met Ile Lys Ala Leu Glu Leu Asp Ser Asn
            740                 745                 750

Leu Tyr Arg Ile Gly Gln Ser Lys Val Phe Phe Arg Ala Gly Val Leu
        755                 760                 765

Ala His Leu Glu Glu Glu Arg Asp Leu Lys Ile Thr Asp Val Ile Ile
    770                 775                 780

Gly Phe Gln Ala Cys Cys Arg Gly Tyr Leu Ala Arg Lys Ala Phe Ala
785                 790                 795                 800

Lys Arg Gln Gln Gln Leu Thr Ala Met Lys Val Leu Gln Arg Asn Cys
                805                 810                 815

Ala Ala Tyr Leu Lys Leu Arg Asn Trp Gln Trp Trp Arg Leu Phe Thr
            820                 825                 830

Lys Val Lys Pro Leu Leu Gln Val Ser Arg Gln Glu Glu Glu Met Met
        835                 840                 845

Ala Lys Glu Glu Glu Leu Val Lys Val Arg Glu Lys Gln Leu Ala Ala
    850                 855                 860

Glu Asn Arg Leu Thr Glu Met Glu Thr Leu Gln Ser Gln Leu Met Ala
865                 870                 875                 880

Glu Lys Leu Gln Leu Gln Glu Gln Leu Gln Ala Glu Thr Glu Leu Cys
                885                 890                 895
```

-continued

```
Ala Glu Ala Glu Glu Leu Arg Ala Arg Leu Thr Ala Lys Lys Gln Glu
            900                 905                 910

Leu Glu Glu Ile Cys His Asp Leu Glu Ala Arg Val Glu Glu Glu Glu
        915                 920                 925

Glu Arg Cys Gln His Leu Gln Ala Glu Lys Lys Lys Met Gln Gln Asn
    930                 935                 940

Ile Gln Glu Leu Glu Glu Gln Leu Glu Glu Glu Glu Ser Ala Arg Gln
945                 950                 955                 960

Lys Leu Gln Leu Glu Lys Val Thr Thr Glu Ala Lys Leu Lys Lys Leu
                965                 970                 975

Glu Glu Glu Gln Ile Ile Leu Glu Asp Gln Asn Cys Lys Leu Ala Lys
            980                 985                 990

Glu Lys Lys Leu Leu Glu Asp Arg Ile Ala Glu Phe Thr Thr Asn Leu
        995                 1000                1005

Thr Glu Glu Glu Glu Lys Ser Lys Ser Leu Ala Lys Leu Lys Asn Lys
    1010                1015                1020

His Glu Ala Met Ile Thr Asp Leu Glu Glu Arg Leu Arg Arg Glu Glu
1025                1030                1035                1040

Lys Gln Arg Gln Glu Leu Glu Lys Thr Arg Arg Lys Leu Glu Gly Asp
                1045                1050                1055

Ser Thr Asp Leu Ser Asp Gln Ile Ala Glu Leu Gln Ala Gln Ile Ala
            1060                1065                1070

Glu Leu Lys Met Gln Leu Ala Lys Lys Glu Glu Glu Leu Gln Ala Ala
        1075                1080                1085

Leu Ala Arg Val Glu Glu Glu Ala Ala Gln Lys Asn Met Ala Leu Lys
    1090                1095                1100

Lys Ile Arg Glu Leu Glu Ser Gln Ile Ser Glu Leu Gln Glu Asp Leu
1105                1110                1115                1120

Glu Ser Glu Arg Ala Ser Arg Asn Lys Ala Glu Lys Gln Lys Arg Asp
                1125                1130                1135

Leu Gly Glu Glu Leu Glu Ala Leu Lys Thr Glu Leu Glu Asp Thr Leu
            1140                1145                1150

Asp Ser Thr Ala Ala Gln Gln Glu Leu Arg Ser Lys Arg Glu Gln Glu
        1155                1160                1165

Val Asn Ile Leu Lys Lys Thr Leu Glu Glu Glu Ala Lys Thr His Glu
    1170                1175                1180

Ala Gln Ile Gln Glu Met Arg Gln Lys His Ser Gln Ala Val Glu Glu
1185                1190                1195                1200

Leu Ala Glu Gln Leu Glu Gln Thr Lys Arg Val Lys Ala Asn Leu Glu
                1205                1210                1215

Lys Ala Lys Gln Thr Leu Glu Asn Glu Arg Gly Glu Leu Ala Asn Glu
            1220                1225                1230

Val Lys Val Leu Leu Gln Gly Lys Gly Asp Ser Glu His Lys Arg Lys
        1235                1240                1245

Lys Val Glu Ala Gln Leu Gln Glu Leu Gln Val Lys Phe Asn Glu Gly
    1250                1255                1260

Glu Arg Val Arg Thr Glu Leu Ala Asp Lys Val Thr Lys Leu Gln Val
1265                1270                1275                1280

Glu Leu Asp Asn Val Thr Gly Leu Leu Ser Gln Ser Asp Ser Lys Ser
                1285                1290                1295

Ser Lys Leu Thr Lys Asp Phe Ser Ala Leu Glu Ser Gln Leu Gln Asp
            1300                1305                1310
```

-continued

```
Thr Gln Glu Leu Leu Gln Glu Glu Asn Arg Gln Lys Leu Ser Leu Ser
        1315                1320                1325

Thr Lys Leu Lys Gln Val Glu Asp Glu Lys Asn Ser Phe Arg Glu Gln
    1330                1335                1340

Leu Glu Glu Glu Glu Glu Ala Lys His Asn Leu Glu Lys Gln Ile Ala
1345                1350                1355                1360

Thr Leu His Ala Gln Val Ala Asp Met Lys Lys Lys Met Glu Asp Ser
                1365                1370                1375

Val Gly Cys Leu Glu Thr Ala Glu Glu Val Lys Arg Lys Leu Gln Lys
            1380                1385                1390

Asp Leu Glu Gly Leu Ser Gln Arg His Glu Glu Lys Val Ala Ala Tyr
        1395                1400                1405

Asp Lys Leu Glu Lys Thr Lys Thr Arg Leu Gln Gln Glu Leu Asp Asp
    1410                1415                1420

Leu Leu Val Asp Leu Asp His Gln Arg Gln Ser Ala Cys Asn Leu Glu
1425                1430                1435                1440

Lys Lys Gln Lys Lys Phe Asp Gln Leu Leu Ala Glu Glu Lys Thr Ile
                1445                1450                1455

Ser Ala Lys Tyr Ala Glu Glu Arg Asp Arg Ala Glu Ala Glu Ala Arg
            1460                1465                1470

Glu Lys Glu Thr Lys Ala Leu Ser Leu Ala Arg Ala Leu Glu Glu Ala
        1475                1480                1485

Met Glu Gln Lys Ala Glu Leu Glu Arg Leu Asn Lys Gln Phe Arg Thr
    1490                1495                1500

Glu Met Glu Asp Leu Met Ser Ser Lys Asp Asp Val Gly Lys Ser Val
1505                1510                1515                1520

His Glu Leu Glu Lys Ser Lys Arg Ala Leu Glu Gln Gln Val Glu Glu
                1525                1530                1535

Met Lys Thr Gln Leu Glu Glu Leu Glu Asp Glu Leu Gln Ala Thr Glu
            1540                1545                1550

Asp Ala Lys Leu Arg Leu Glu Val Asn Leu Gln Ala Met Lys Ala Gln
        1555                1560                1565

Phe Glu Arg Asp Leu Gln Gly Arg Asp Glu Gln Ser Glu Glu Lys Lys
    1570                1575                1580

Lys Gln Leu Val Arg Gln Val Arg Glu Met Glu Ala Glu Leu Glu Asp
1585                1590                1595                1600

Glu Arg Lys Gln Arg Ser Met Ala Val Ala Ala Arg Lys Lys Leu Glu
                1605                1610                1615

Met Asp Leu Lys Asp Leu Glu Ala His Ile Asp Ser Ala Asn Lys Asn
            1620                1625                1630

Arg Asp Glu Ala Ile Lys Gln Leu Arg Lys Leu Gln Ala Gln Met Lys
        1635                1640                1645

Asp Cys Met Arg Glu Leu Asp Asp Thr Arg Ala Ser Arg Glu Glu Ile
    1650                1655                1660

Leu Ala Gln Ala Lys Glu Asn Glu Lys Lys Leu Lys Ser Met Glu Ala
1665                1670                1675                1680

Glu Met Ile Gln Leu Gln Glu Glu Leu Ala Ala Ala Glu Arg Ala Lys
                1685                1690                1695

Arg Gln Ala Gln Gln Glu Arg Asp Glu Leu Ala Asp Glu Ile Ala Asn
            1700                1705                1710

Ser Ser Gly Lys Gly Ala Leu Ala Leu Glu Glu Lys Arg Arg Leu Glu
        1715                1720                1725

Ala Arg Ile Ala Gln Leu Glu Glu Glu Leu Glu Glu Glu Gln Gly Asn
```

-continued

```
    1730                1735                1740

Thr Glu Leu Ile Asn Asp Arg Leu Lys Lys Ala Asn Leu Gln Ile Asp
1745                1750                1755                1760

Gln Ile Asn Thr Asp Leu Asn Leu Glu Arg Ser His Ala Gln Lys Asn
                1765                1770                1775

Glu Asn Ala Arg Gln Gln Leu Glu Arg Gln Asn Lys Glu Leu Lys Val
            1780                1785                1790

Lys Leu Gln Glu Met Glu Gly Thr Val Lys Ser Lys Tyr Lys Ala Ser
        1795                1800                1805

Ile Thr Ala Leu Glu Ala Lys Ile Ala Gln Leu Glu Glu Gln Leu Asp
    1810                1815                1820

Asn Glu Thr Lys Glu Arg Gln Ala Ala Cys Lys Gln Val Arg Arg Thr
1825                1830                1835                1840

Glu Lys Lys Leu Lys Asp Val Leu Leu Gln Val Asp Asp Glu Arg Arg
                1845                1850                1855

Asn Ala Glu Gln Tyr Lys Asp Gln Ala Asp Lys Ala Ser Thr Arg Leu
            1860                1865                1870

Lys Gln Leu Lys Arg Gln Leu Glu Glu Ala Glu Glu Glu Ala Gln Arg
        1875                1880                1885

Ala Asn Ala Ser Arg Arg Lys Leu Gln Arg Glu Leu Glu Asp Ala Thr
    1890                1895                1900

Glu Thr Ala Asp Ala Met Asn Arg Glu Val Ser Ser Leu Lys Asn Lys
1905                1910                1915                1920

Leu Arg Arg Gly Asp Leu Pro Phe Val Val Pro Arg Arg Met Ala Arg
                1925                1930                1935

Lys Gly Ala Gly Asp Gly Ser Asp Glu Glu Val Asp Gly Lys Ala Asp
            1940                1945                1950

Gly Ala Glu Ala Lys Pro Ala Glu
        1955                1960
```

<210> SEQ ID NO 51
<211> LENGTH: 7666
<212> TYPE: DNA
<213> ORGANISM: Mus musculus

<400> SEQUENCE: 51

```
gtctttcctg ggagatgggc gcgcaaaccg accagtgggt ctgggggcgg cagtgatggg      60

cgtggagatg gcccaatgag ggtgggagtg ggtggggcag gcgcgagcag cagtgctaaa     120

ggagcccggc ggaggcagcg gtgggtttgg aattgagacg ctggatctgt ggtcgctgct     180

ggggacgtgt gccggcgcca ccatcttcgg ctgaagaggc aattactttt gggtccttct     240

gtttacaatg gcccagagaa ctggactgga ggatcccgag aggtatctct ttgtggacag     300

ggctgtcatc tacaaccctg ccactcaagc tgactggaca gctaaaaagc tggtgtggat     360

tccatcggaa cgccatggtt ttgaggcagc tagtattaaa gaagagcggg gcgatgaggt     420

tatggtggag ctggcagaga atgggaagaa agcaatggtc aacaaagatg acattcagaa     480

gatgaaccca ccaaagttct ccaaggtgga ggatatggca gagctgacat gcttgaacga     540

agcctctgtc ttacataatt tgaaggaccg ctactattca ggacttatct atacttactc     600

tggactcttc tgtgtggtga taaatcctta caagaacctt ccaatttact ctgagaatat     660

tattgaaatg tatagaggga agaaacgcca tgagatgcca cccacatct acgccatatc     720

agagtctgct tacagatgca tgcttcaaga tcgtgaggac cagtcaattc tatgcacggg     780

tgaatcgggt gccgggaaga cagaaaatac caagaaagtc attcagtacc ttgcccacgt     840
```

-continued

```
tgcttcttct cacaaaggaa gaaaggacca taatattcct ggggaacttg aacggcagct    900
tttacaagca aatccaattc tggaatcctt tggaaatgcg aagactgtga aaaatgataa    960
ctcatctcgc tttggcaagt ttatccggat caactttgat gtaactggct atattgttgg   1020
ggccaacatt gaaacatacc ttctggaaaa gtctcgtgct gttcgtcaag ctaaagatga   1080
gcgtacattt catatctttt atcagttgct ctctggagca ggggaacacc tgaaatccga   1140
cttactcctg gaaggtttca acaactacag attcctctcc aatggctata ttcctattcc   1200
tggacagcaa gacaaggata acttccagga gaccatggaa gccatgcaca tcatgggctt   1260
ctctcacgaa gagatcctct caatgcttaa agtcgtatct tcagtgctgc agtttggaaa   1320
catctctttc aaaaaggaga gaaacactga ccaagcctcc atgccggaga acacagtcgc   1380
acagaagctc tgccacctgc tcgggatgaa tgtgatggag ttcactcggg ctatcctcac   1440
gcccaggatc aaggttggcc gggattacgt acagaaagcc cagaccaaag agcaggctga   1500
ttttgcagtg gaagcattgg caaaagctac ctatgagcgg ttgtttcgct ggctcgttca   1560
ccgcatcaat aaagcgctgg ataggaccaa acgccaggga gcttccttca ttgggatcct   1620
ggatattgct ggttttgaaa tttttgagct gaactccttc gagcagctgt gcatcaacta   1680
caccaacgag aagctgcagc agctgttcaa ccacaccatg ttcatcctgg agcaggagga   1740
gtaccagcga gagggcatcg agtggaactt tatcgacttc ggcctggacc tgcagccctg   1800
catcgacctg atagagagac ctgccaatcc ccctggcgtg ctggccctcc tggatgaaga   1860
atgctggttc cccaaagcta cagataaaac atttgttgaa aagctggttc aggagcaagg   1920
ttcccactcc aagtttcaga agccgcgcca actgaaagac aaagccgact tctgcatcat   1980
ccactacgcg gggaaggtgg actataaggc agatgagtgg ctgatgaaga acatggaccc   2040
gctgaatgac aacgtggcca ccctcctgca ccagtcctcg gacagatttg tggctgagct   2100
ttggaaggac gtggaccgaa ttgtaggtct ggatcaagtc actgggatga ctgagaccgc   2160
gtttggctct gcatacaaaa ccaagaaggg catgttccga accgtcgggc agctctacaa   2220
ggagtctctc accaagctga tggcaactct ccgcaacacc aaccccaact tcgtccgctg   2280
catcattcca aatcacgaga agcgggctgg gaaactggac ccgcacctcg tgctcgatca   2340
gcttcgctgt aacggcgtcc tggaagggat ccggatctgt cgccaggggt tccccaaccg   2400
gatagttttc caggaattca gacagagata tgagatccta actcccaatg ctattcctaa   2460
aggcttcatg gatggcaaac aggcgtgtga gcgaatgatc cgagctttag aactggaccc   2520
aaacctgtat agaattggac agagcaagat atttttccga gctggagttt tggcgcactt   2580
agaagaagaa agagatttaa aaatcactga tatcatcatc tttttccaag ctgtatgcag   2640
aggctacctc gcccgaaagg cctttgccaa gaaacagcaa caactaagtg ccttaaaggt   2700
cttgcagcgg aactgtgcgg cgtacctgaa gctgcgacac tggcagtggt ggcgtgtctt   2760
cacgaaggtg aagcctctcc tccaagtgac ccgccaggag gaagaactcc aggcaaaaga   2820
tgaggagctg ctgaaggtga aagagaagca gacaaaagtg gaaggggagc ttgaggagat   2880
ggagcggaag caccagcagc tgctggaaga gaagaatatc ctggcagaac aactgcaagc   2940
cgagaccgag ctcttcgctg aagcagaaga gatgagagca aggcttgctg ccaaaaagca   3000
ggaactggag gagattctcc atgacctcga gtccagggtg gaggaggagg aagagcggaa   3060
ccagatccta cagaatgaga agaagaagat gcaggcgcac attcaggacc tagaagaaca   3120
actggatgag gaggaggggg cccggcaaaa gctgcagctg gagaaggtga cagcagaggc   3180
```

-continued

```
taaaatcaag aagatggaag aggaggttct gcttctcgaa gaccagaatt ccaaatttat   3240
caaagaaaag aaactcatgg aagaccgaat tgctgagtgt tcctctcagc tggctgaaga   3300
ggaagaaaag gcaaaaaact tggccaaaat caggaataag caagaagtga tgatctcgga   3360
cttagaagaa cgcttgaaga aggaggagaa aactcgacag gaactggaaa aggccaaacg   3420
gaagctggat ggggaaacaa ccgatctgca ggaccagatc gctgagctgc aggcacaggt   3480
cgatgagctc aaagtccagt tgaccaagaa ggaggaggag cttcaggggg cgctggccag   3540
aggagatgat gagacactgc acaagaataa tgcacttaaa gttgcacggg agctgcaggc   3600
ccaaatcgca gagctccagg aagactttga gtctgaaaag gcttcaagga acaaggctga   3660
gaaacaaaaa cgggacttga gtgaggagct ggaagctctg aagacagagc tggaggacac   3720
cctagacacc acagcagctc agcaggaact ccgcacaaaa cgtgagcagg aagtggcaga   3780
gctgaagaag gctcttgagg atgaaactaa gaaccacgaa gctcagatcc aggacatgag   3840
acagaggcat gccacagcgc tggaggagct ttccgagcag ctggagcaag cgaaaaggtt   3900
caaagccaac ctggagaaga acaaacaggg cctggagaca gacaacaagg agctggcgtg   3960
tgaggtgaag gtgctgcagc aggtgaaggc ggagtcagag cacaagagga agaagctgga   4020
tgcccaggtc caggagctcc atgccaaggt gtcagagggt gacaggctca gggtagagct   4080
ggccgagaaa gcaaacaagc tacagaatga gctggataat gtgtcaaccc tgctggaaga   4140
agctgagaag aaaggtatta agtttgcgaa ggatgcagct ggtctcgagt ctcaactaca   4200
ggacacacag gagctccttc aggaagagac acggcagaaa ctgaacctga gcagtcggat   4260
ccggcagctg gaggaggaga agaacagcct tcaggagcag caggaggagg aggaggaggc   4320
caggaagaac ctggagaagc aggtgttggc tctgcagtcc cagctggctg acaccaagaa   4380
gaaagtggac gatgacctgg ggacaatcga gagtttggag gaagccaaaa agaaactgct   4440
caaggatgtg gaggcgctga gccagcggct ggaggagaag gtcctggcgt atgacaagct   4500
ggagaagacc aagaaccggc tgcaacaaga actggatgac ctgacggtgg acctggacca   4560
ccagcgccag atcgtctcca acttggagaa gaaacagaag aagttcgacc agctgttggc   4620
agaagaaaag ggcatctctg ctcgctatgc agaagagcgg gaccgggctg aagctgaggc   4680
cagagagaaa gaaaccaaag cgctctccct ggcgcgggcc cttgaggagg ccttggaggc   4740
gaaggaggaa ttcgagaggc agaacaagca gcttcgagca gacatggaag acctgatgag   4800
ctctaaagac gatgtgggga agaacgtcca cgagcttgag aaatccaagc gagccttgga   4860
gcagcaggtg gaggagatgc ggacccagct ggaggagctg gaggacgagc tgcaggccac   4920
tgaggatgcc aagctccgcc tggaagtcaa catgcaggcc atgaaggccc agtttgagag   4980
ggacctgcaa acccgagatg agcagaatga agaaaagaag cggctgctgc ttaagcaggt   5040
gcgggagctc gaggcagagc tggaggatga gcggaaacag cgggcactgg ctgtggcgtc   5100
aaagaagaag atggagatag acctgaagga cctggaggct cagatcgagg ctgcgaacaa   5160
agcccgggat gaagtgatca agcagcttcg caaacttcag gcacagatga aggattacca   5220
gcgtgaacta gaagaggctc gagcatctag agatgagatt tttgctcaat ccaaagaaag   5280
tgaaaagaaa ctgaagagtc tagaagcaga aattcttcag ctgcaagagg agctggcctc   5340
atccgagcga gcccgccgac acgcagagca ggagcgagac gagctggctg atgagatcgc   5400
caacagcgcc tctggaaagt ctgcgctgtt ggatgagaag cggcgcctgg aagcgcggat   5460
cgcacagctg gaagaggagc tggaggagga gcagagcaac atggagctgc tcaatgaccg   5520
cttccgcaag accacgctgc aggtggacac actgaacaca gagctggcag cagagcgcag   5580
```

-continued

```
cgctgcccag aagagtgaca atgcccgcca gcagctggag cgacaaaaca aggagctgaa   5640
ggccaagctg caggagctgg agggggcagt caagtccaag ttcaaggcta ccatctcagc   5700
cctggaagcc aagattgggc agctggagga gcagcttgag caggaagcca aggagcgagc   5760
agctgccaac aaactagtcc gtcgaacaga gaagaaactg aaagaaatct tcatgcaggt   5820
tgaagacgag cgtcggcatg cggatcagta taaggagcag atggagaagg ctaatgccag   5880
gatgaagcag cttaaacgac agttggaaga ggctgaggaa gaggccacac gtgccaacgc   5940
atctcggcgt aaactccaaa gggagctgga cgacgccact gaggccaatg aaggcctgag   6000
ccgcgaggtc agcactctca agaaccggct caggcggggc ggtccaatca gcttttcttc   6060
aagccgatct ggccggcgcc agctgcacat tgagggggca tcgctagagc tgtcagatga   6120
cgacacagaa agtaagacca gtgatgtcaa tgacacacag ccaccccaat cagaataggc   6180
acaggaggtc agaggtgatg ctgaggacag gccagaactc atcccagcac cagtctgctt   6240
gagccctgca ctcactgctc gggaatggca agctcccaga ttccttccag gaaagtcaac   6300
tgtgtcttaa ggctttgcgg cctgcgcaga ctatatcctg cttcagacta gatacaattg   6360
ccccttttta tatatacacc tccacaagac atgcgtatta aacagattgt ctcatcgttg   6420
catctatttt ccatgtattc atcaagagac cattttatga cacattaaga agaaagaacc   6480
tttttgaaac aaactccagg ccctttgttg ccagtggctg ggcctaaggg ttgccccggg   6540
accgtgctca gctgctctgc atgccctgtc ctactgacag gtaccttagt tctgtgttca   6600
tgtggccctg acccttcctt caaccacacc tggtctctta gaacattgtg aacctaacct   6660
gcacttgtgt ctctcatttc ctgtgaatag tgatcactgt ctcagtgagc aaactgggag   6720
aggggctttg gcggcttagg ggtgggtttg gattggggaa gcagcatcca tttggggttc   6780
tcctgcccat ctcccaaggg gtgaccctgc ccctcaaatt catggtgtcc ccaccgtctc   6840
aatgtgaata gtctcagagc tctgtgcaca gagaggacag tggccacaac acataaggtg   6900
ccccgggtgg cagccatcac agtaacttcc aggtggtctc ctgagtgtct ggcttgataa   6960
tgccctcaat tcaggagtga gcctctgtga ccccttgggt gctcgcagaa ggcctctcca   7020
agcagtcaag ccctcttgca aattcagcca ctgctttgag cccaaaacgg gaatattagt   7080
tttatgtcgg aggtgtgttc caagtttgtc aatgaggcta tagcctcaag aagatgccat   7140
ctgcctgaat gttgacatgc cagcgggcgt gtgacccttc attttccctt tcccttcctt   7200
tggacagtgt tacaatgaac acttagcatt ctgtttttgg ttgatagttg agcaaactga   7260
cattacagaa agtgccttag acactacagt actaagacaa tgttaaatat attatttgcc   7320
tctataacaa cttaatgtat taagttctga ctgtgcttca tatcatgtac ctctctagtg   7380
aagtagatgc gcaaacattc agtgacagca aatcagtgtt agtgacaagc cccgaccgtg   7440
gcgatgtgct ggaaaacacg gaccttttgg gttaaaagct ttaacatctg tgaggaagaa   7500
ctggtcacat gggtttggaa tctttgattt cccctgtatg aattgtactg gctgttgacc   7560
accagacacc tgactgcaaa tatcttttct tgtattccca tatttctaga caatgatttt   7620
tgtaagacaa taaatttatt cattatagaa aaaaaaaaaa aaaaaa                 7666
```

<210> SEQ ID NO 52
<211> LENGTH: 1976
<212> TYPE: PRT
<213> ORGANISM: Mus musculus

<400> SEQUENCE: 52

-continued

```
Met Ala Gln Arg Thr Gly Leu Glu Asp Pro Glu Arg Tyr Leu Phe Val
1               5                   10                  15

Asp Arg Ala Val Ile Tyr Asn Pro Ala Thr Gln Ala Asp Trp Thr Ala
            20                  25                  30

Lys Lys Leu Val Trp Ile Pro Ser Glu Arg His Gly Phe Glu Ala Ala
        35                  40                  45

Ser Ile Lys Glu Glu Arg Gly Asp Glu Val Met Val Glu Leu Ala Glu
    50                  55                  60

Asn Gly Lys Lys Ala Met Val Asn Lys Asp Asp Ile Gln Lys Met Asn
65                  70                  75                  80

Pro Pro Lys Phe Ser Lys Val Glu Asp Met Ala Glu Leu Thr Cys Leu
                85                  90                  95

Asn Glu Ala Ser Val Leu His Asn Leu Lys Asp Arg Tyr Tyr Ser Gly
            100                 105                 110

Leu Ile Tyr Thr Tyr Ser Gly Leu Phe Cys Val Val Ile Asn Pro Tyr
        115                 120                 125

Lys Asn Leu Pro Ile Tyr Ser Glu Asn Ile Ile Glu Met Tyr Arg Gly
    130                 135                 140

Lys Lys Arg His Glu Met Pro Pro His Ile Tyr Ala Ile Ser Glu Ser
145                 150                 155                 160

Ala Tyr Arg Cys Met Leu Gln Asp Arg Glu Asp Gln Ser Ile Leu Cys
                165                 170                 175

Thr Gly Glu Ser Gly Ala Gly Lys Thr Glu Asn Thr Lys Lys Val Ile
            180                 185                 190

Gln Tyr Leu Ala His Val Ala Ser Ser His Lys Gly Arg Lys Asp His
        195                 200                 205

Asn Ile Pro Gly Glu Leu Glu Arg Gln Leu Leu Gln Ala Asn Pro Ile
    210                 215                 220

Leu Glu Ser Phe Gly Asn Ala Lys Thr Val Lys Asn Asp Asn Ser Ser
225                 230                 235                 240

Arg Phe Gly Lys Phe Ile Arg Ile Asn Phe Asp Val Thr Gly Tyr Ile
                245                 250                 255

Val Gly Ala Asn Ile Glu Thr Tyr Leu Leu Glu Lys Ser Arg Ala Val
            260                 265                 270

Arg Gln Ala Lys Asp Glu Arg Thr Phe His Ile Phe Tyr Gln Leu Leu
        275                 280                 285

Ser Gly Ala Gly Glu His Leu Lys Ser Asp Leu Leu Leu Glu Gly Phe
    290                 295                 300

Asn Asn Tyr Arg Phe Leu Ser Asn Gly Tyr Ile Pro Ile Pro Gly Gln
305                 310                 315                 320

Gln Asp Lys Asp Asn Phe Gln Glu Thr Met Glu Ala Met His Ile Met
                325                 330                 335

Gly Phe Ser His Glu Glu Ile Leu Ser Met Leu Lys Val Val Ser Ser
            340                 345                 350

Val Leu Gln Phe Gly Asn Ile Ser Phe Lys Lys Glu Arg Asn Thr Asp
        355                 360                 365

Gln Ala Ser Met Pro Glu Asn Thr Val Ala Gln Lys Leu Cys His Leu
    370                 375                 380

Leu Gly Met Asn Val Met Glu Phe Thr Arg Ala Ile Leu Thr Pro Arg
385                 390                 395                 400

Ile Lys Val Gly Arg Asp Tyr Val Gln Lys Ala Gln Thr Lys Glu Gln
                405                 410                 415

Ala Asp Phe Ala Val Glu Ala Leu Ala Lys Ala Thr Tyr Glu Arg Leu
```

-continued

```
            420                 425                 430

Phe Arg Trp Leu Val His Arg Ile Asn Lys Ala Leu Asp Arg Thr Lys
        435                 440                 445

Arg Gln Gly Ala Ser Phe Ile Gly Ile Leu Asp Ile Ala Gly Phe Glu
    450                 455                 460

Ile Phe Glu Leu Asn Ser Phe Glu Gln Leu Cys Ile Asn Tyr Thr Asn
465                 470                 475                 480

Glu Lys Leu Gln Gln Leu Phe Asn His Thr Met Phe Ile Leu Glu Gln
                485                 490                 495

Glu Glu Tyr Gln Arg Glu Gly Ile Glu Trp Asn Phe Ile Asp Phe Gly
            500                 505                 510

Leu Asp Leu Gln Pro Cys Ile Asp Leu Ile Glu Arg Pro Ala Asn Pro
        515                 520                 525

Pro Gly Val Leu Ala Leu Leu Asp Glu Glu Cys Trp Phe Pro Lys Ala
    530                 535                 540

Thr Asp Lys Thr Phe Val Glu Lys Leu Val Gln Glu Gln Gly Ser His
545                 550                 555                 560

Ser Lys Phe Gln Lys Pro Arg Gln Leu Lys Asp Lys Ala Asp Phe Cys
                565                 570                 575

Ile Ile His Tyr Ala Gly Lys Val Asp Tyr Lys Ala Asp Glu Trp Leu
            580                 585                 590

Met Lys Asn Met Asp Pro Leu Asn Asp Asn Val Ala Thr Leu Leu His
        595                 600                 605

Gln Ser Ser Asp Arg Phe Val Ala Glu Leu Trp Lys Asp Val Asp Arg
    610                 615                 620

Ile Val Gly Leu Asp Gln Val Thr Gly Met Thr Glu Thr Ala Phe Gly
625                 630                 635                 640

Ser Ala Tyr Lys Thr Lys Lys Gly Met Phe Arg Thr Val Gly Gln Leu
                645                 650                 655

Tyr Lys Glu Ser Leu Thr Lys Leu Met Ala Thr Leu Arg Asn Thr Asn
            660                 665                 670

Pro Asn Phe Val Arg Cys Ile Ile Pro Asn His Glu Lys Arg Ala Gly
        675                 680                 685

Lys Leu Asp Pro His Leu Val Leu Asp Gln Leu Arg Cys Asn Gly Val
    690                 695                 700

Leu Glu Gly Ile Arg Ile Cys Arg Gln Gly Phe Pro Asn Arg Ile Val
705                 710                 715                 720

Phe Gln Glu Phe Arg Gln Arg Tyr Glu Ile Leu Thr Pro Asn Ala Ile
                725                 730                 735

Pro Lys Gly Phe Met Asp Gly Lys Gln Ala Cys Glu Arg Met Ile Arg
            740                 745                 750

Ala Leu Glu Leu Asp Pro Asn Leu Tyr Arg Ile Gly Gln Ser Lys Ile
        755                 760                 765

Phe Phe Arg Ala Gly Val Leu Ala His Leu Glu Glu Glu Arg Asp Leu
    770                 775                 780

Lys Ile Thr Asp Ile Ile Ile Phe Phe Gln Ala Val Cys Arg Gly Tyr
785                 790                 795                 800

Leu Ala Arg Lys Ala Phe Ala Lys Lys Gln Gln Gln Leu Ser Ala Leu
                805                 810                 815

Lys Val Leu Gln Arg Asn Cys Ala Ala Tyr Leu Lys Leu Arg His Trp
            820                 825                 830

Gln Trp Trp Arg Val Phe Thr Lys Val Lys Pro Leu Leu Gln Val Thr
        835                 840                 845
```

-continued

```
Arg Gln Glu Glu Glu Leu Gln Ala Lys Asp Glu Glu Leu Leu Lys Val
    850                 855                 860

Lys Glu Lys Gln Thr Lys Val Glu Gly Glu Leu Glu Glu Met Glu Arg
865                 870                 875                 880

Lys His Gln Gln Leu Leu Glu Glu Lys Asn Ile Leu Ala Glu Gln Leu
                885                 890                 895

Gln Ala Glu Thr Glu Leu Phe Ala Glu Ala Glu Glu Met Arg Ala Arg
            900                 905                 910

Leu Ala Ala Lys Lys Gln Glu Leu Glu Glu Ile Leu His Asp Leu Glu
        915                 920                 925

Ser Arg Val Glu Glu Glu Glu Glu Arg Asn Gln Ile Leu Gln Asn Glu
    930                 935                 940

Lys Lys Lys Met Gln Ala His Ile Gln Asp Leu Glu Glu Gln Leu Asp
945                 950                 955                 960

Glu Glu Glu Gly Ala Arg Gln Lys Leu Gln Leu Glu Lys Val Thr Ala
                965                 970                 975

Glu Ala Lys Ile Lys Lys Met Glu Glu Glu Val Leu Leu Leu Glu Asp
            980                 985                 990

Gln Asn Ser Lys Phe Ile Lys Glu Lys Lys Leu Met Glu Asp Arg Ile
        995                 1000                1005

Ala Glu Cys Ser Ser Gln Leu Ala Glu Glu Glu Glu Lys Ala Lys Asn
    1010                1015                1020

Leu Ala Lys Ile Arg Asn Lys Gln Glu Val Met Ile Ser Asp Leu Glu
1025                1030                1035                1040

Glu Arg Leu Lys Lys Glu Glu Lys Thr Arg Gln Glu Leu Glu Lys Ala
                1045                1050                1055

Lys Arg Lys Leu Asp Gly Glu Thr Thr Asp Leu Gln Asp Gln Ile Ala
            1060                1065                1070

Glu Leu Gln Ala Gln Val Asp Glu Leu Lys Val Gln Leu Thr Lys Lys
        1075                1080                1085

Glu Glu Glu Leu Gln Gly Ala Leu Ala Arg Gly Asp Asp Glu Thr Leu
    1090                1095                1100

His Lys Asn Asn Ala Leu Lys Val Ala Arg Glu Leu Gln Ala Gln Ile
1105                1110                1115                1120

Ala Glu Leu Gln Glu Asp Phe Glu Ser Glu Lys Ala Ser Arg Asn Lys
                1125                1130                1135

Ala Glu Lys Gln Lys Arg Asp Leu Ser Glu Glu Leu Glu Ala Leu Lys
            1140                1145                1150

Thr Glu Leu Glu Asp Thr Leu Asp Thr Thr Ala Ala Gln Gln Glu Leu
        1155                1160                1165

Arg Thr Lys Arg Glu Gln Glu Val Ala Glu Leu Lys Lys Ala Leu Glu
    1170                1175                1180

Asp Glu Thr Lys Asn His Glu Ala Gln Ile Gln Asp Met Arg Gln Arg
1185                1190                1195                1200

His Ala Thr Ala Leu Glu Glu Leu Ser Glu Gln Leu Glu Gln Ala Lys
                1205                1210                1215

Arg Phe Lys Ala Asn Leu Glu Lys Asn Lys Gln Gly Leu Glu Thr Asp
            1220                1225                1230

Asn Lys Glu Leu Ala Cys Glu Val Lys Val Leu Gln Gln Val Lys Ala
        1235                1240                1245

Glu Ser Glu His Lys Arg Lys Lys Leu Asp Ala Gln Val Gln Glu Leu
    1250                1255                1260
```

-continued

```
His Ala Lys Val Ser Glu Gly Asp Arg Leu Arg Val Glu Leu Ala Glu
1265                1270                1275                1280

Lys Ala Asn Lys Leu Gln Asn Glu Leu Asp Asn Val Ser Thr Leu Leu
                1285                1290                1295

Glu Glu Ala Glu Lys Lys Gly Ile Lys Phe Ala Lys Asp Ala Ala Gly
            1300                1305                1310

Leu Glu Ser Gln Leu Gln Asp Thr Gln Glu Leu Leu Gln Glu Glu Thr
        1315                1320                1325

Arg Gln Lys Leu Asn Leu Ser Ser Arg Ile Arg Gln Leu Glu Glu Glu
    1330                1335                1340

Lys Asn Ser Leu Gln Glu Gln Gln Glu Glu Glu Glu Glu Ala Arg Lys
1345                1350                1355                1360

Asn Leu Glu Lys Gln Val Leu Ala Leu Gln Ser Gln Leu Ala Asp Thr
                1365                1370                1375

Lys Lys Lys Val Asp Asp Asp Leu Gly Thr Ile Glu Ser Leu Glu Glu
            1380                1385                1390

Ala Lys Lys Lys Leu Leu Lys Asp Val Glu Ala Leu Ser Gln Arg Leu
        1395                1400                1405

Glu Glu Lys Val Leu Ala Tyr Asp Lys Leu Glu Lys Thr Lys Asn Arg
    1410                1415                1420

Leu Gln Gln Glu Leu Asp Asp Leu Thr Val Asp Leu Asp His Gln Arg
1425                1430                1435                1440

Gln Ile Val Ser Asn Leu Glu Lys Lys Gln Lys Lys Phe Asp Gln Leu
                1445                1450                1455

Leu Ala Glu Glu Lys Gly Ile Ser Ala Arg Tyr Ala Glu Glu Arg Asp
            1460                1465                1470

Arg Ala Glu Ala Glu Ala Arg Glu Lys Glu Thr Lys Ala Leu Ser Leu
        1475                1480                1485

Ala Arg Ala Leu Glu Glu Ala Leu Glu Ala Lys Glu Glu Phe Glu Arg
    1490                1495                1500

Gln Asn Lys Gln Leu Arg Ala Asp Met Glu Asp Leu Met Ser Ser Lys
1505                1510                1515                1520

Asp Asp Val Gly Lys Asn Val His Glu Leu Glu Lys Ser Lys Arg Ala
                1525                1530                1535

Leu Glu Gln Gln Val Glu Glu Met Arg Thr Gln Leu Glu Glu Leu Glu
            1540                1545                1550

Asp Glu Leu Gln Ala Thr Glu Asp Ala Lys Leu Arg Leu Glu Val Asn
        1555                1560                1565

Met Gln Ala Met Lys Ala Gln Phe Glu Arg Asp Leu Gln Thr Arg Asp
    1570                1575                1580

Glu Gln Asn Glu Glu Lys Lys Arg Leu Leu Leu Lys Gln Val Arg Glu
1585                1590                1595                1600

Leu Glu Ala Glu Leu Glu Asp Glu Arg Lys Gln Arg Ala Leu Ala Val
                1605                1610                1615

Ala Ser Lys Lys Lys Met Glu Ile Asp Leu Lys Asp Leu Glu Ala Gln
            1620                1625                1630

Ile Glu Ala Ala Asn Lys Ala Arg Asp Glu Val Ile Lys Gln Leu Arg
        1635                1640                1645

Lys Leu Gln Ala Gln Met Lys Asp Tyr Gln Arg Glu Leu Glu Glu Ala
    1650                1655                1660

Arg Ala Ser Arg Asp Glu Ile Phe Ala Gln Ser Lys Glu Ser Glu Lys
1665                1670                1675                1680

Lys Leu Lys Ser Leu Glu Ala Glu Ile Leu Gln Leu Gln Glu Glu Leu
```

-continued

```
                1685                1690                1695

Ala Ser Ser Glu Arg Ala Arg Arg His Ala Glu Gln Glu Arg Asp Glu
            1700                1705                1710

Leu Ala Asp Glu Ile Ala Asn Ser Ala Ser Gly Lys Ser Ala Leu Leu
        1715                1720                1725

Asp Glu Lys Arg Arg Leu Glu Ala Arg Ile Ala Gln Leu Glu Glu Glu
    1730                1735                1740

Leu Glu Glu Glu Gln Ser Asn Met Glu Leu Leu Asn Asp Arg Phe Arg
1745                1750                1755                1760

Lys Thr Thr Leu Gln Val Asp Thr Leu Asn Thr Glu Leu Ala Ala Glu
                1765                1770                1775

Arg Ser Ala Ala Gln Lys Ser Asp Asn Ala Arg Gln Gln Leu Glu Arg
            1780                1785                1790

Gln Asn Lys Glu Leu Lys Ala Lys Leu Gln Glu Leu Glu Gly Ala Val
        1795                1800                1805

Lys Ser Lys Phe Lys Ala Thr Ile Ser Ala Leu Glu Ala Lys Ile Gly
    1810                1815                1820

Gln Leu Glu Glu Gln Leu Glu Gln Glu Ala Lys Glu Arg Ala Ala Ala
1825                1830                1835                1840

Asn Lys Leu Val Arg Arg Thr Glu Lys Lys Leu Lys Glu Ile Phe Met
                1845                1850                1855

Gln Val Glu Asp Glu Arg Arg His Ala Asp Gln Tyr Lys Glu Gln Met
            1860                1865                1870

Glu Lys Ala Asn Ala Arg Met Lys Gln Leu Lys Arg Gln Leu Glu Glu
        1875                1880                1885

Ala Glu Glu Glu Ala Thr Arg Ala Asn Ala Ser Arg Arg Lys Leu Gln
    1890                1895                1900

Arg Glu Leu Asp Asp Ala Thr Glu Ala Asn Glu Gly Leu Ser Arg Glu
1905                1910                1915                1920

Val Ser Thr Leu Lys Asn Arg Leu Arg Arg Gly Gly Pro Ile Ser Phe
                1925                1930                1935

Ser Ser Ser Arg Ser Gly Arg Arg Gln Leu His Ile Glu Gly Ala Ser
            1940                1945                1950

Leu Glu Leu Ser Asp Asp Asp Thr Glu Ser Lys Thr Ser Asp Val Asn
        1955                1960                1965

Asp Thr Gln Pro Pro Gln Ser Glu
    1970                1975


<210> SEQ ID NO 53
<211> LENGTH: 7619
<212> TYPE: DNA
<213> ORGANISM: Homo sapiens

<400> SEQUENCE: 53

actgaggcgc tggatctgtg gtcgcggctg gggacgtgcg cccgcgccac catcttcggc      60

tgaagaggca attgcttttg gatcgttcca tttacaatgg cgcagagaac tggactcgag     120

gatccagaga ggtatctctt tgtggacagg gctgtcatct acaaccctgc cactcaagct     180

gattggacag ctaaaaagct agtgtggatt ccatcagaac gccatggttt tgaggcagct     240

agtatcaaag aagaacgggg agatgaagtt atggtggagt tggcagagaa tggaaagaaa     300

gcaatggtca acaaagatga tattcagaag atgaacccac ctaagttttc caaggtggag     360

gatatggcag aattgacatg cttgaatgaa gcttccgttt tacataatct gaaggatcgc     420

tactattcag gactaatcta tacttattct ggactcttct gtgtagttat aaacccttac     480
```

-continued

```
aagaatcttc caatttactc tgagaatatt attgaaatgt acagagggaa gaagcgtcat    540
gagatgcctc cacacatcta tgctatatct gaatctgctt acagatgcat gcttcaagat    600
cgtgaggacc agtcaattct ttgcacgggt gagtcaggtg ctgggaagac agaaaataca    660
aagaaagtta ttcagtacct tgcccatgtt gcttcttcac ataaaggaag aaaggaccat    720
aatattcctg gggaacttga acggcagctt ttgcaagcaa atccaattct ggaatcattt    780
ggaaatgcga agactgtgaa aaatgataac tcatctcgtt ttggcaaatt tattcggatc    840
aactttgatg taactggcta tatcgttggg gccaacattg aaacatacct tctggaaaag    900
tctcgtgctg ttcgtcaagc aaaagatgaa cgtacttttc atatctttta ccagttgtta    960
tctggagcag gagaacacct aaagtctgat ttgcttcttg aaggatttaa taactacagg   1020
tttctctcca atggctatat tcctattccg ggacagcaag acaaagataa tttccaggag   1080
accatggaag caatgcacat aatgggcttc tcccatgaag agattctgtc aatgcttaaa   1140
gtagtatctt cagtgctaca gtttggaaat atttctttca aaaaggagag aaatactgat   1200
caagcttcca tgccagaaaa tacagttgcg cagaagctct gccatcttct tgggatgaat   1260
gtgatggagt ttactcgggc catcctgact ccccggatca aggtcggccg agactatgtg   1320
caaaaagccc agaccaaaga acaggcagat tttgcagtag aagcattggc aaaagctacc   1380
tatgagcggc tctttcgctg gctcgttcat cgcatcaata aagctctgga taggaccaaa   1440
cgtcagggag catctttcat tggaatcctg gatattgctg gatttgaaat ttttgagctg   1500
aactcctttg aacaactttg catcaactac accaatgaga agctgcagca gctgttcaac   1560
cacaccatgt ttatcctaga acaagaggaa taccagcgcg aaggcatcga gtggaacttc   1620
atcgatttcg ggctggatct gcagccatgc atcgacctaa tagagagacc tgcgaaccct   1680
cctggtgtac tggccctttt ggatgaagaa tgctggttcc ctaaagccac agataaaacc   1740
tttgttgaaa aactggttca agagcaaggt tcccactcca agtttcagaa acctcgacaa   1800
ttaaaagaca aagctgattt ttgcattata cattatgcag ggaaggtgga ctataaggca   1860
gatgagtggc tgatgaagaa tatggacccc ctgaatgaca acgtggccac ccttttgcac   1920
cagtcatcag acagatttgt ggcagagctt tggaaagatg tggaccgtat cgtgggtctg   1980
gatcaagtca ctggtatgac tgagacagct tttggctccg catataaaac caagaagggc   2040
atgtttcgta ccgttgggca actctacaaa gaatctctca ccaagctgat ggcaactctc   2100
cgaaacacca accctaactt tgttcgttgt atcattccaa atcacgagaa gagggctgga   2160
aaattggatc cacacctagt cctagatcag cttcgctgta atggtgtcct ggaagggatc   2220
cgaatctgtc gccagggctt ccctaaccga atagttttcc aggaattcag acagagatat   2280
gagatcctaa ctccaaatgc tattcctaaa ggttttatgg atggtaaaca ggcctgtgaa   2340
cgaatgatcc gggctttaga attggaccca aacttgtaca gaattggaca gagcaagata   2400
tttttcagag ctggagttct ggcacactta gaggaagaaa gagatttaaa aatcaccgat   2460
atcattatct tcttccaggc cgtttgcaga ggttacctgg ccagaaaggc ctttgccaag   2520
aagcagcagc aactaagtgc cttaaaggtc ttgcagcgga actgtgccgc gtacctgaaa   2580
ttacggcact ggcagtggtg gcgagtcttc acaaaggtga agccgcttct acaagtgact   2640
cgccaggagg aagaacttca ggccaaagat gaagagctgt tgaaggtgaa ggagaagcag   2700
acgaaggtgg aaggagagct ggaggagatg gagcggaagc accagcagct tttagaagag   2760
aagaatatcc ttgcagaaca actacaagca gagactgagc tctttgctga agcagaagag   2820
```

-continued

```
atgagggcaa gacttgctgc taaaaagcag gaattagaag agattctaca tgacttggag   2880
tctagggttg aagaagaaga agaaagaaac caaatcctcc aaaatgaaaa gaaaaaaatg   2940
caagcacata ttcaggacct ggaagaacag ctagacgagg aggaaggggc tcggcaaaag   3000
ctgcagctgg aaaaggtgac agcagaggcc aagatcaaga agatggaaga ggagattctg   3060
cttctcgagg accaaaattc caagttcatc aaagaaaaga aactcatgga agatcgcatt   3120
gctgagtgtt cctctcagct ggctgaagag gaagaaaagg cgaaaaactt ggccaaaatc   3180
aggaataagc aagaagtgat gatctcagat ttagaagaac gcttaaagaa ggaagaaaag   3240
actcgtcagg aactggaaaa ggccaaaaga aaactcgacg gggagacgac cgacctgcag   3300
gaccagatcg cagagctgca ggcgcagatt gatgagctca agctgcagct ggccaagaag   3360
gaggaggagc tgcagggcgc actggccaga ggtgatgatg aaacactcca taagaacaat   3420
gcccttaaag ttgtgcgaga gctacaagcc caaattgctg aacttcagga agactttgaa   3480
tccgagaagg cttcacggaa caaggccgaa aagcagaaaa gggacttgag tgaggaactg   3540
gaagctctga aaacagagct ggaggacacg ctggacacca cggcagccca gcaggaacta   3600
cgtacaaaac gtgaacaaga agtggcagag ctgaagaaag ctcttgagga ggaaactaag   3660
aaccatgaag ctcaaatcca ggacatgaga caaagacacg caacagccct ggaggagctc   3720
tcagagcagc tggaacaggc caagcggttc aaagcaaatc tagagaagaa caagcagggc   3780
ctggagacag ataacaagga gctggcgtgt gaggtgaagg tcctgcagca ggtcaaggct   3840
gagtctgagc acaagaggaa gaagctcgac gcgcaggtcc aggagctcca tgccaaggtc   3900
tctgaaggcg acaggctcag ggtggagctg gcggagaaag caagtaagct gcagaatgag   3960
ctagataatg tctccaccct tctggaagaa gcagagaaga agggtattaa atttgctaag   4020
gatgcagcta gtcttgagtc tcaactacag gatacacagg agcttcttca ggaggagaca   4080
cgccagaaac taaacctgag cagtcggatc cggcagctgg aagaggagaa gaacagtctt   4140
caggagcagc aggaggagga ggaggaggcc aggaagaacc tggagaagca agtgctggcc   4200
ctgcagtccc agttggctga taccaagaag aaagtagatg acgacctggg aacaattgaa   4260
agtctggaag aagccaagaa gaagcttctg aaggacgcgg aggccctgag ccagcgcctg   4320
gaggagaagg cactggcgta tgacaaactg gagaagacca agaaccgcct gcagcaggag   4380
ctggacgacc tcacggtgga cctggaccac cagcgccagg tcgcctccaa cttggagaag   4440
aagcagaaga agtttgacca gctgttagca gaagagaaga gcatctctgc tcgctatgcc   4500
gaagagcggg accgggccga agccgaggcc agagagaaag aaaccaaagc cctgtcactg   4560
gcccgggccc tcgaggaagc cctggaggcc aaggaggagt ttgagaggca gaacaagcag   4620
ctccgagcag acatggaaga cctcatgagc tccaaagatg atgtgggaaa aaacgttcac   4680
gaacttgaaa aatccaaacg ggccctagag cagcaggtgg aggaaatgag gacccagctg   4740
gaggagctgg aagacgaact ccaggccacg gaagatgcca agcttcgtct ggaggtcaac   4800
atgcaggcca tgaaggcgca gttcgagaga gacctgcaaa ccagggatga gcagaatgaa   4860
gagaagaagc ggctgctgat caaacaggtg cgggagctcg aggcggagct ggaggatgag   4920
aggaaacagc gggcgcttgc tgtagcttca aagaaaaaga tggagataga cctgaaggac   4980
ctcgaagccc aaatcgaggc tgcgaacaaa gctcgggatg aggtgattaa gcagctccgc   5040
aagctccagg ctcagatgaa ggattaccaa cgtgaattag aagaagctcg tgcatccaga   5100
gatgagattt ttgctcaatc caaagagagt gaaaagaaat tgaagagtct ggaagcagaa   5160
atccttcaat tgcaggagga acttgcctca tctgagcgag cccgccgaca cgccgagcag   5220
```

-continued

```
gagagagatg agctggcgga cgagatcacc aacagcgcct ctggcaagtc cgcgctgctg   5280
gatgagaagc ggcgtctgga agctcggatc gcacagctgg aggaggagct ggaagaggag   5340
cagagcaaca tggagctgct caacgaccgc ttccgcaaga ccactctaca ggtggacaca   5400
ctgaacgccg agctagcagc cgagcgcagc gccgcccaga agagtgacaa tgcacgccag   5460
caactggagc ggcagaacaa ggagctgaag gccaagctgc aggaactcga gggtgctgtc   5520
aagtctaagt tcaaggccac catctcagcc ctggaggcca agattgggca gctggaggag   5580
cagcttgagc aggaagccaa ggaacgagca gccgccaaca aattagtccg tcgcactgag   5640
aagaagctga aagaaatctt catgcaggtt gaggatgagc gtcgacacgc ggaccagtat   5700
aaagagcaga tggagaaggc caacgctcgg atgaagcagc ttaaacgcca gctggaggaa   5760
gcagaagaag aagcgacgcg tgccaacgca tctcggcgta aactccagcg ggaactggat   5820
gatgccaccg aggccaacga gggcctgagc cgcgaggtca gcaccctgaa gaaccggctg   5880
aggcggggtg gccccatcag cttctcttcc agccgatctg gccggcgcca gctgcacctt   5940
gaaggagctt ccctggagct ctccgacgat gacacagaaa gtaagaccag tgatgtcaac   6000
gagacgcagc caccccagtc agagtaaagt tgcaggaagc cagaggaggc aatacagtgg   6060
gacagttagg aatgcacccg gggcctcctg cagatttcgg aaattggcaa gctacgggat   6120
tccttcctga aagatcaact gtgtcttaag gctctccagc ctatgcatac tgtatcctgc   6180
ttcagactta ggtacaattg ctcccctttt tatatataga cacacacagg acacatatat   6240
taaacagatt gtttcatcat tgcatctatt ttccatatag tcatcaagag accattttat   6300
aaaacatggt aagacccttt ttaaaacaaa ctccaggccc ttggttgcgg gtcgctgggt   6360
tattggggca gcgccgtggt cgtcactcag tcgctctgca tgctctctgt catacagaca   6420
ggtaacctag ttctgtgttc acgtggcccc cgactcctca gccacatcaa gtctcctaga   6480
ccactgtgga ctctaaactg cacttgtctc tctcatttcc ttcaaataat gatcaatgct   6540
atttcagtga gcaaactgtg aaaggggctt tggaaagagt aggaggggtg ggctggatcg   6600
gaagcaacac ccatttgggg ttaccatgtc catcccccaa ggggggccct gcccctcgag   6660
tcgatggtgt cccgcatcta ctcatgtgaa ctggccttgg cgagggctgg tctgtgcata   6720
gaagggatag tggccacact gcagctgagg ccccaggtgg cagccatgga tcatgtagac   6780
ttccagatgg tctcccgaac cgcctggctc tgccggcgcc ctcctcacgt caggagcaag   6840
cagccgtgga cccctaagcc gagctggtgg aaggcccctc cctgtcgcca gccgggccct   6900
catgctgacc ttgcaaattc agccgctgct ttgagcccaa aatgggaata ttggttttgt   6960
gtccgaggct tgttccaagt ttgtcaatga ggtttatgga gcctccagaa cagatgccat   7020
cttcctgaat gttgacatgc cagtgggtgt gactccttca tttttccttc tcccttccct   7080
ttggacagtg ttacagtgaa cacttagcat cctgtttttg gttggtagtt aagcaaactg   7140
acattacgga aagtgcctta gacactacag tactaagaca atgttgaata tatcattcgc   7200
ctctataaca atttaatgta ttcagttttg actgtgcttc atatcatgta cctctctagt   7260
caaagtggta ttacagacat tcagtgacaa tgaatcagtg ttaattctaa atccttgatc   7320
ctctgcaatg tgcttgaaaa cacaaacctt ttgggttaaa agctttaaca tctattagga   7380
agaatttgtc ctgtgggttt ggaatcttgg attttccccc tttatgaact gtactggctg   7440
ttgaccacca gacacctgac cgcaaatatc ttttcttgta ttcccatatt tctagacaat   7500
gatttttgta agacaataaa tttattcatt atagatattt gcgcctgctc tgtttacttg   7560
```

-continued aagaaaaaag cacccgtgga gaataaagag acctcaataa acaagaataa tcatgtgaa 7619

<210> SEQ ID NO 54
<211> LENGTH: 1976
<212> TYPE: PRT
<213> ORGANISM: Homo sapiens

<400> SEQUENCE: 54

```
Met Ala Gln Arg Thr Gly Leu Glu Asp Pro Glu Arg Tyr Leu Phe Val
  1               5                  10                  15

Asp Arg Ala Val Ile Tyr Asn Pro Ala Thr Gln Ala Asp Trp Thr Ala
             20                  25                  30

Lys Lys Leu Val Trp Ile Pro Ser Glu Arg His Gly Phe Glu Ala Ala
         35                  40                  45

Ser Ile Lys Glu Glu Arg Gly Asp Glu Val Met Val Glu Leu Ala Glu
     50                  55                  60

Asn Gly Lys Lys Ala Met Val Asn Lys Asp Asp Ile Gln Lys Met Asn
 65                  70                  75                  80

Pro Pro Lys Phe Ser Lys Val Glu Asp Met Ala Glu Leu Thr Cys Leu
                 85                  90                  95

Asn Glu Ala Ser Val Leu His Asn Leu Lys Asp Arg Tyr Tyr Ser Gly
            100                 105                 110

Leu Ile Tyr Thr Tyr Ser Gly Leu Phe Cys Val Val Ile Asn Pro Tyr
        115                 120                 125

Lys Asn Leu Pro Ile Tyr Ser Glu Asn Ile Ile Glu Met Tyr Arg Gly
    130                 135                 140

Lys Lys Arg His Glu Met Pro Pro His Ile Tyr Ala Ile Ser Glu Ser
145                 150                 155                 160

Ala Tyr Arg Cys Met Leu Gln Asp Arg Glu Asp Gln Ser Ile Leu Cys
                165                 170                 175

Thr Gly Glu Ser Gly Ala Gly Lys Thr Glu Asn Thr Lys Lys Val Ile
            180                 185                 190

Gln Tyr Leu Ala His Val Ala Ser Ser His Lys Gly Arg Lys Asp His
        195                 200                 205

Asn Ile Pro Gly Glu Leu Glu Arg Gln Leu Leu Gln Ala Asn Pro Ile
    210                 215                 220

Leu Glu Ser Phe Gly Asn Ala Lys Thr Val Lys Asn Asp Asn Ser Ser
225                 230                 235                 240

Arg Phe Gly Lys Phe Ile Arg Ile Asn Phe Asp Val Thr Gly Tyr Ile
                245                 250                 255

Val Gly Ala Asn Ile Glu Thr Tyr Leu Leu Glu Lys Ser Arg Ala Val
            260                 265                 270

Arg Gln Ala Lys Asp Glu Arg Thr Phe His Ile Phe Tyr Gln Leu Leu
        275                 280                 285

Ser Gly Ala Gly Glu His Leu Lys Ser Asp Leu Leu Leu Glu Gly Phe
    290                 295                 300

Asn Asn Tyr Arg Phe Leu Ser Asn Gly Tyr Ile Pro Ile Pro Gly Gln
305                 310                 315                 320

Gln Asp Lys Asp Asn Phe Gln Glu Thr Met Glu Ala Met His Ile Met
                325                 330                 335

Gly Phe Ser His Glu Glu Ile Leu Ser Met Leu Lys Val Val Ser Ser
            340                 345                 350

Val Leu Gln Phe Gly Asn Ile Ser Phe Lys Lys Glu Arg Asn Thr Asp
        355                 360                 365
```

-continued

```
Gln Ala Ser Met Pro Glu Asn Thr Val Ala Gln Lys Leu Cys His Leu
    370                 375                 380

Leu Gly Met Asn Val Met Glu Phe Thr Arg Ala Ile Leu Thr Pro Arg
385                 390                 395                 400

Ile Lys Val Gly Arg Asp Tyr Val Gln Lys Ala Gln Thr Lys Glu Gln
                405                 410                 415

Ala Asp Phe Ala Val Glu Ala Leu Ala Lys Ala Thr Tyr Glu Arg Leu
            420                 425                 430

Phe Arg Trp Leu Val His Arg Ile Asn Lys Ala Leu Asp Arg Thr Lys
        435                 440                 445

Arg Gln Gly Ala Ser Phe Ile Gly Ile Leu Asp Ile Ala Gly Phe Glu
    450                 455                 460

Ile Phe Glu Leu Asn Ser Phe Glu Gln Leu Cys Ile Asn Tyr Thr Asn
465                 470                 475                 480

Glu Lys Leu Gln Gln Leu Phe Asn His Thr Met Phe Ile Leu Glu Gln
                485                 490                 495

Glu Glu Tyr Gln Arg Glu Gly Ile Glu Trp Asn Phe Ile Asp Phe Gly
            500                 505                 510

Leu Asp Leu Gln Pro Cys Ile Asp Leu Ile Glu Arg Pro Ala Asn Pro
        515                 520                 525

Pro Gly Val Leu Ala Leu Leu Asp Glu Glu Cys Trp Phe Pro Lys Ala
    530                 535                 540

Thr Asp Lys Thr Phe Val Glu Lys Leu Val Gln Glu Gln Gly Ser His
545                 550                 555                 560

Ser Lys Phe Gln Lys Pro Arg Gln Leu Lys Asp Lys Ala Asp Phe Cys
                565                 570                 575

Ile Ile His Tyr Ala Gly Lys Val Asp Tyr Lys Ala Asp Glu Trp Leu
            580                 585                 590

Met Lys Asn Met Asp Pro Leu Asn Asp Asn Val Ala Thr Leu Leu His
        595                 600                 605

Gln Ser Ser Asp Arg Phe Val Ala Glu Leu Trp Lys Asp Val Asp Arg
    610                 615                 620

Ile Val Gly Leu Asp Gln Val Thr Gly Met Thr Glu Thr Ala Phe Gly
625                 630                 635                 640

Ser Ala Tyr Lys Thr Lys Lys Gly Met Phe Arg Thr Val Gly Gln Leu
                645                 650                 655

Tyr Lys Glu Ser Leu Thr Lys Leu Met Ala Thr Leu Arg Asn Thr Asn
            660                 665                 670

Pro Asn Phe Val Arg Cys Ile Ile Pro Asn His Glu Lys Arg Ala Gly
        675                 680                 685

Lys Leu Asp Pro His Leu Val Leu Asp Gln Leu Arg Cys Asn Gly Val
    690                 695                 700

Leu Glu Gly Ile Arg Ile Cys Arg Gln Gly Phe Pro Asn Arg Ile Val
705                 710                 715                 720

Phe Gln Glu Phe Arg Gln Arg Tyr Glu Ile Leu Thr Pro Asn Ala Ile
                725                 730                 735

Pro Lys Gly Phe Met Asp Gly Lys Gln Ala Cys Glu Arg Met Ile Arg
            740                 745                 750

Ala Leu Glu Leu Asp Pro Asn Leu Tyr Arg Ile Gly Gln Ser Lys Ile
        755                 760                 765

Phe Phe Arg Ala Gly Val Leu Ala His Leu Glu Glu Glu Arg Asp Leu
    770                 775                 780

Lys Ile Thr Asp Ile Ile Ile Phe Phe Gln Ala Val Cys Arg Gly Tyr
```

-continued

```
785                 790                 795                 800

Leu Ala Arg Lys Ala Phe Ala Lys Lys Gln Gln Gln Leu Ser Ala Leu
                805                 810                 815

Lys Val Leu Gln Arg Asn Cys Ala Ala Tyr Leu Lys Leu Arg His Trp
            820                 825                 830

Gln Trp Trp Arg Val Phe Thr Lys Val Lys Pro Leu Leu Gln Val Thr
        835                 840                 845

Arg Gln Glu Glu Glu Leu Gln Ala Lys Asp Glu Glu Leu Leu Lys Val
    850                 855                 860

Lys Glu Lys Gln Thr Lys Val Glu Gly Glu Leu Glu Glu Met Glu Arg
865                 870                 875                 880

Lys His Gln Gln Leu Leu Glu Glu Lys Asn Ile Leu Ala Glu Gln Leu
                885                 890                 895

Gln Ala Glu Thr Glu Leu Phe Ala Glu Ala Glu Glu Met Arg Ala Arg
            900                 905                 910

Leu Ala Ala Lys Lys Gln Glu Leu Glu Glu Ile Leu His Asp Leu Glu
        915                 920                 925

Ser Arg Val Glu Glu Glu Glu Glu Arg Asn Gln Ile Leu Gln Asn Glu
    930                 935                 940

Lys Lys Lys Met Gln Ala His Ile Gln Asp Leu Glu Glu Gln Leu Asp
945                 950                 955                 960

Glu Glu Glu Gly Ala Arg Gln Lys Leu Gln Leu Glu Lys Val Thr Ala
                965                 970                 975

Glu Ala Lys Ile Lys Lys Met Glu Glu Glu Ile Leu Leu Leu Glu Asp
            980                 985                 990

Gln Asn Ser Lys Phe Ile Lys Glu Lys Lys Leu Met Glu Asp Arg Ile
        995                 1000                1005

Ala Glu Cys Ser Ser Gln Leu Ala Glu Glu Glu Glu Lys Ala Lys Asn
    1010                1015                1020

Leu Ala Lys Ile Arg Asn Lys Gln Glu Val Met Ile Ser Asp Leu Glu
1025                1030                1035                1040

Glu Arg Leu Lys Lys Glu Glu Lys Thr Arg Gln Glu Leu Glu Lys Ala
                1045                1050                1055

Lys Arg Lys Leu Asp Gly Glu Thr Thr Asp Leu Gln Asp Gln Ile Ala
            1060                1065                1070

Glu Leu Gln Ala Gln Ile Asp Glu Leu Lys Leu Gln Leu Ala Lys Lys
        1075                1080                1085

Glu Glu Glu Leu Gln Gly Ala Leu Ala Arg Gly Asp Asp Glu Thr Leu
    1090                1095                1100

His Lys Asn Asn Ala Leu Lys Val Val Arg Glu Leu Gln Ala Gln Ile
1105                1110                1115                1120

Ala Glu Leu Gln Glu Asp Phe Glu Ser Glu Lys Ala Ser Arg Asn Lys
                1125                1130                1135

Ala Glu Lys Gln Lys Arg Asp Leu Ser Glu Glu Leu Glu Ala Leu Lys
            1140                1145                1150

Thr Glu Leu Glu Asp Thr Leu Asp Thr Thr Ala Ala Gln Gln Glu Leu
        1155                1160                1165

Arg Thr Lys Arg Glu Gln Glu Val Ala Glu Leu Lys Lys Ala Leu Glu
    1170                1175                1180

Glu Glu Thr Lys Asn His Glu Ala Gln Ile Gln Asp Met Arg Gln Arg
1185                1190                1195                1200

His Ala Thr Ala Leu Glu Glu Leu Ser Glu Gln Leu Glu Gln Ala Lys
                1205                1210                1215
```

-continued

```
Arg Phe Lys Ala Asn Leu Glu Lys Asn Lys Gln Gly Leu Glu Thr Asp
            1220                1225                1230

Asn Lys Glu Leu Ala Cys Glu Val Lys Val Leu Gln Gln Val Lys Ala
        1235                1240                1245

Glu Ser Glu His Lys Arg Lys Lys Leu Asp Ala Gln Val Gln Glu Leu
    1250                1255                1260

His Ala Lys Val Ser Glu Gly Asp Arg Leu Arg Val Glu Leu Ala Glu
1265                1270                1275                1280

Lys Ala Ser Lys Leu Gln Asn Glu Leu Asp Asn Val Ser Thr Leu Leu
                1285                1290                1295

Glu Glu Ala Glu Lys Lys Gly Ile Lys Phe Ala Lys Asp Ala Ala Ser
            1300                1305                1310

Leu Glu Ser Gln Leu Gln Asp Thr Gln Glu Leu Leu Gln Glu Glu Thr
        1315                1320                1325

Arg Gln Lys Leu Asn Leu Ser Ser Arg Ile Arg Gln Leu Glu Glu Glu
    1330                1335                1340

Lys Asn Ser Leu Gln Glu Gln Gln Glu Glu Glu Glu Glu Ala Arg Lys
1345                1350                1355                1360

Asn Leu Glu Lys Gln Val Leu Ala Leu Gln Ser Gln Leu Ala Asp Thr
                1365                1370                1375

Lys Lys Lys Val Asp Asp Asp Leu Gly Thr Ile Glu Ser Leu Glu Glu
            1380                1385                1390

Ala Lys Lys Lys Leu Leu Lys Asp Ala Glu Ala Leu Ser Gln Arg Leu
        1395                1400                1405

Glu Glu Lys Ala Leu Ala Tyr Asp Lys Leu Glu Lys Thr Lys Asn Arg
    1410                1415                1420

Leu Gln Gln Glu Leu Asp Asp Leu Thr Val Asp Leu Asp His Gln Arg
1425                1430                1435                1440

Gln Val Ala Ser Asn Leu Glu Lys Lys Gln Lys Lys Phe Asp Gln Leu
                1445                1450                1455

Leu Ala Glu Glu Lys Ser Ile Ser Ala Arg Tyr Ala Glu Glu Arg Asp
            1460                1465                1470

Arg Ala Glu Ala Glu Ala Arg Glu Lys Glu Thr Lys Ala Leu Ser Leu
        1475                1480                1485

Ala Arg Ala Leu Glu Glu Ala Leu Glu Ala Lys Glu Glu Phe Glu Arg
    1490                1495                1500

Gln Asn Lys Gln Leu Arg Ala Asp Met Glu Asp Leu Met Ser Ser Lys
1505                1510                1515                1520

Asp Asp Val Gly Lys Asn Val His Glu Leu Glu Lys Ser Lys Arg Ala
                1525                1530                1535

Leu Glu Gln Gln Val Glu Glu Met Arg Thr Gln Leu Glu Glu Leu Glu
            1540                1545                1550

Asp Glu Leu Gln Ala Thr Glu Asp Ala Lys Leu Arg Leu Glu Val Asn
        1555                1560                1565

Met Gln Ala Met Lys Ala Gln Phe Glu Arg Asp Leu Gln Thr Arg Asp
    1570                1575                1580

Glu Gln Asn Glu Glu Lys Lys Arg Leu Leu Ile Lys Gln Val Arg Glu
1585                1590                1595                1600

Leu Glu Ala Glu Leu Glu Asp Glu Arg Lys Gln Arg Ala Leu Ala Val
                1605                1610                1615

Ala Ser Lys Lys Lys Met Glu Ile Asp Leu Lys Asp Leu Glu Ala Gln
            1620                1625                1630
```

-continued

```
Ile Glu Ala Ala Asn Lys Ala Arg Asp Glu Val Ile Lys Gln Leu Arg
        1635                1640                1645

Lys Leu Gln Ala Gln Met Lys Asp Tyr Gln Arg Glu Leu Glu Glu Ala
    1650                1655                1660

Arg Ala Ser Arg Asp Glu Ile Phe Ala Gln Ser Lys Glu Ser Glu Lys
1665                1670                1675                1680

Lys Leu Lys Ser Leu Glu Ala Glu Ile Leu Gln Leu Gln Glu Glu Leu
                1685                1690                1695

Ala Ser Ser Glu Arg Ala Arg Arg His Ala Glu Gln Glu Arg Asp Glu
            1700                1705                1710

Leu Ala Asp Glu Ile Thr Asn Ser Ala Ser Gly Lys Ser Ala Leu Leu
        1715                1720                1725

Asp Glu Lys Arg Arg Leu Glu Ala Arg Ile Ala Gln Leu Glu Glu Glu
    1730                1735                1740

Leu Glu Glu Glu Gln Ser Asn Met Glu Leu Leu Asn Asp Arg Phe Arg
1745                1750                1755                1760

Lys Thr Thr Leu Gln Val Asp Thr Leu Asn Ala Glu Leu Ala Ala Glu
                1765                1770                1775

Arg Ser Ala Ala Gln Lys Ser Asp Asn Ala Arg Gln Gln Leu Glu Arg
            1780                1785                1790

Gln Asn Lys Glu Leu Lys Ala Lys Leu Gln Glu Leu Glu Gly Ala Val
        1795                1800                1805

Lys Ser Lys Phe Lys Ala Thr Ile Ser Ala Leu Glu Ala Lys Ile Gly
    1810                1815                1820

Gln Leu Glu Glu Gln Leu Glu Gln Glu Ala Lys Glu Arg Ala Ala Ala
1825                1830                1835                1840

Asn Lys Leu Val Arg Arg Thr Glu Lys Lys Leu Lys Glu Ile Phe Met
                1845                1850                1855

Gln Val Glu Asp Glu Arg Arg His Ala Asp Gln Tyr Lys Glu Gln Met
            1860                1865                1870

Glu Lys Ala Asn Ala Arg Met Lys Gln Leu Lys Arg Gln Leu Glu Glu
        1875                1880                1885

Ala Glu Glu Glu Ala Thr Arg Ala Asn Ala Ser Arg Arg Lys Leu Gln
    1890                1895                1900

Arg Glu Leu Asp Asp Ala Thr Glu Ala Asn Glu Gly Leu Ser Arg Glu
1905                1910                1915                1920

Val Ser Thr Leu Lys Asn Arg Leu Arg Arg Gly Gly Pro Ile Ser Phe
                1925                1930                1935

Ser Ser Ser Arg Ser Gly Arg Arg Gln Leu His Leu Glu Gly Ala Ser
            1940                1945                1950

Leu Glu Leu Ser Asp Asp Asp Thr Glu Ser Lys Thr Ser Asp Val Asn
        1955                1960                1965

Glu Thr Gln Pro Pro Gln Ser Glu
    1970                1975


<210> SEQ ID NO 55
<211> LENGTH: 6442
<212> TYPE: DNA
<213> ORGANISM: Mus musculus

<400> SEQUENCE: 55

ccttttctgt ccaggccgag gcctctggac cgccctgggc gccgaccatg gctgcagtga      60

ccatgtccgt gtctgggagg aaggtagcct ccaggccagg cccggtgcct gaggcagccc     120

aatcgttcct ctacgcgccc cggacgccaa atgtaggtgg ccctggaggg ccacaggtgg     180
```

-continued

```
agtggacagc ccggcgcatg gtgtgggtgc cctcggaact gcatgggttc gaggcagcag    240
ccctgcggga tgaaggggag gaggaggcag aagtggagct ggcggagagt gggcgccgcc    300
tgcggctgcc cagggaccag atccagcgca tgaacccacc caagttcagc aaggcagaag    360
atatggctga gctcacctgc ctcaacgagg cctcggtcct gcacaacctg cgagaacgct    420
actactccgg gctcatttat acctactctg gcctcttctg tgtggtcatt aacccataca    480
agcagctgcc catctacacg gaggccattg ttgaaatgta ccggggcaag aagcgccatg    540
aggtgccacc tcacgtgtat gctgtgacgg agggcgcgta ccgcagcatg cttcaggatc    600
gtgaggatca atccattctc tgcacgggag agtctggcgc tgggaagacg gagaacacca    660
agaaggtcat ccagtacctg gcccatgtgg catcatctcc aaagggcagg aaggagcctg    720
gtgtccctgc ctccgtcagc accatgtctt atggggagct agagcgtcag cttcttcaag    780
ccaaccccat cctagaggcc tttggcaatg ccaagacagt gaagaacgac aactcttccc    840
gatttggcaa attcatccgc atcaactttg atattgctgg ctacatcgtg ggagcaaaca    900
tcgagaccta tctgttggag aagtcccggg ccatcagaca ggccaaggat gaatgcagct    960
tccatatctt ctaccagctg ctagggggcg ctggggagca gctaaaagct gacctccttc   1020
tggagccctg ttcccattat cgcttcctga ccaatgggcc ctcatcgtcc ccgggccagg   1080
agcgtgagtt attccaggag accctggagt ccctgcgtgt gctgggcctc ctcccagaag   1140
agatcactgc catgctgcgc actgtctctg ctgtcctcca gtttggcaac attgtcctga   1200
agaaagagcg caatacggac caagccacca tgcctgacaa cacagctgcc cagaagcttt   1260
gccgcctctt gggactcgga gtgaccgact tctccagagc ccttctcaca ccccgcatca   1320
aagtgggccg agattatgtt cagaaagcac aaaccaagga gcaggctgac tttgcgctgg   1380
aggctctggc caaagctacc tatgagcgcc tgttccgctg gctggttctg cggctcaacc   1440
gtgccctgga cagaagcccg cggcagggtg cctccttcct gggcatcctg gacatcgcgg   1500
gctttgagat cttccagctg aactccttcg agcagctgtg catcaactac accaacgaga   1560
agctacagca gctattcaac cacaccatgt tcgtgctgga gcaggaggag taccagcgag   1620
agggcatccc ctggaccttc ctagacttcg ggttggacct gcaaccttgc atcgacctca   1680
ttgagcgtcc ggccaacccct ccaggtctcc tggccctgct ggacgaggag tgctggttcc   1740
ccaaggccac ggacaagtct tttgtggaga aggtcgccca ggagcagggc agccacccca   1800
aattccagcg ccccaggaac ctgcgagatc aggccgactt cagcgtcctg cactatgccg   1860
gcaaggttga ctacaaagcc agtgagtggc tgatgaagaa catggaccca ctgaatgaca   1920
atgtggccgc cttgcttcac cagagcacgg atcgtctcac agctgagatc tggaaggatg   1980
tggagggcat cgtggggctg gagcaagtaa gcagccttgg agatggccca ccgggaggcc   2040
gcccccgccg tggaatgttc cggactgtgg ggcagctcta caaagaatcc ctgagccgcc   2100
tcatggccac gctcagcaac accaacccta gttttgtccg ctgcatcgtt cccaatcatg   2160
agaagagggc tggaaagctg gagccgcgcc tggtgctgga ccaactccgt tgtaacgggg   2220
tcctcgaggg tatacgcatc tgtcgccaag gcttccccaa ccgcatcctc ttccaggagt   2280
tccgacagcg ctatgaaatc ctcaccccga acgctattcc caagggcttc atggacggca   2340
aacaggcctg tgagaagatg atccaggccc tggagctaga ccccaacctg taccgtgttg   2400
gccaaagcaa gatcttcttc cgggcagggg tcctggccca gctggaggag gagcgggacc   2460
tgaaagtcac cgacatcata gtgtctttcc aggcagcggc acggggctac ctggcccgta   2520
```

-continued

```
gggctttcca gagacggcag cagcagcaga gtgctctgag ggtgatgcag agaaactgtg   2580
ctgcctacct caagctcagg aactggcagt ggtggaggct gttcatcaag gtgaagcccc   2640
tgctgcaggt gacacggcag gatgaggtgc tgcaggcgcg cgcccaggag ctgcagaaag   2700
ttcaggagct gcagcagcag agcgctcgtg aagtggggga actgcagggt cgagtggcac   2760
agctagagga ggagcgcacg cgcctggctg agcagcttcg agcagaagcc gagctctgct   2820
ctgaggccga ggagacgcgg gcgcgactgg ctgcccggaa gcaggagctg gagctggtgg   2880
tgacagagct ggaggcacga gtgggcgagg aagaagagtg cagccggcag ctgcagagtg   2940
agaagaagag gctgcagcag catatccagg agctagagag ccacctggaa gctgaggagg   3000
gtgcccggca gaagctacag ctggagaagg tgaccacaga ggccaagatg aagaaatttg   3060
aggaggacct gctgctcctg gaggaccaga attccaagct gagcaaggag cggaggctgc   3120
tggaggagcg gctggctgag ttctcctcac aggcagcaga agaggaagag aaagtcaaaa   3180
gtctcaacaa gctgaggctc aaatatgaag ccacaatctc agacatggaa gaccggctga   3240
agaaggagga gaagggacgc caggaactag agaagctgaa gcgacggctg gacggggaga   3300
gctcagagct tcaggagcag atggtggagc agaagcagag ggcagaggaa ctgctcgcac   3360
agctgggccg caaggaggat gagctgcagg ccgccctgct cagggcagag gaagagggtg   3420
gtgcccgtgc ccagttgctc aagtccctgc gagaggcaca ggctggcctt gctgaggctc   3480
aggaggacct ggaagctgag cgggtagcca gggccaaggc ggagaagcag cgccgggacc   3540
tgggcgagga gttggaggcc ctacgtgggg agctcgagga cactctggat tccaccaacg   3600
cccagcagga gctgcggtcc aagagggagc aggaggtgac agagctgaag aaagcattgg   3660
aagaggagtc ccgtgcccat gaggtgtcca tgcaggagct gagacagagg catagccagg   3720
cactggtgga gatggccgag cagttggagc aagcccggag gggcaaaggt gtgtgggaga   3780
agactcggct atccctggag gctgaggtgt ccgagctgaa ggccgagctg agcagcctgc   3840
agacctcgag acaggagggt gagcagaaga ggcgccgcct ggagtcccag ctacaggagg   3900
tccagggccg atccagtgat tcggagcggg ctcggtctga ggctgctgag aagctgcaga   3960
gagcccaggc ggaacttgag agcgtgtcca cagccctgag tgaggcggag tccaaagcca   4020
tcaggctggg caaggagctg agcagtgcag agtcccagct gcatgacacc caggaactgc   4080
ttcaggagga gaccagggca aagctggcct tggggtcccg tgtgcgtgcc ctagaggccg   4140
aggcggcggg gcttcgggag cagatggaag aggaggtggt tgccagggaa cgggctggcc   4200
gggagctgca gagcacgcag gcccagctct ctgaatggcg gcgccgccag gaagaagagg   4260
ctgcggtgct ggaggctggg gaggaggctc ggcgccgtgc agcccgggag gcagagaccc   4320
tgacccagcg cctggcagaa aagactgagg ctgtagaacg actggagcga gcccggcgcc   4380
gactgcagca ggagttggac gatgccactg tggatctggg gcagcagaag cagctcctga   4440
gcacactgga gaagaagcag cggaaatttg accagctcct ggcagaggag aaggctgcag   4500
ttctacgggc tgtggaagac cgtgaacgga tagaggccga aggccgggag cgagaggccc   4560
gggccctgtc gctgacccgg gccctggaag aggagcagga ggcccgggag gagctggaga   4620
ggcagaaccg tgctctgagg gctgagctgg aagcactgct gagcagcaag gatgacgtgg   4680
gcaagaacgt gcacgagctg gagcgagccc gtaaggcggc tgaacaggca gccagtgacc   4740
tgcggacaca ggtgacagaa ttggaggatg agctgacagc cgcagaggat gccaagctgc   4800
gcctggaggt gactgtgcag gctctgaagg ctcaacatga acgcgacctg cagggccgcg   4860
atgatgccgg tgaggagagg cggaggcagc tggccaagca gctaagagac gcagaggtag   4920
```

-continued

```
agcgcgatga ggaacggaag cagagggcac tggctatggc tgcccgcaag aagctggagc   4980

tggaactgga ggagttgaag gcgcagacat ctgctgctgg gcagggcaag gaagaggcag   5040

tgaagcagct gaagaagatg caggtccaga tgaaggagct gtggcgggag gtagaggaga   5100

cgcgtagctc ccgcgacgag atgtttaccc tgagcaggga aaatgagaag aagctcaagg   5160

ggctggaagc tgaggtgctg cgtctgcaag aggaacttgc tgcctcagac cgagcccgga   5220

ggcaggccca gcaagacaga gacgagatgg cagaggaggt ggccagtggc aatcttagca   5280

aggcagccac cctggaggaa aaacggcagc tggaggggcg actgagccag ttggaagagg   5340

agctggagga agaacagaac aactcggagc tgctcaagga ccattaccga aagctagtgc   5400

tacaggtcga gtccctcacc acagaactgt ctgccgaacg aagtttctca gccaaggccg   5460

agagtggacg gcagcagctg gagcggcaga tccaggaact gcgggcccgc ttgggtgaag   5520

aggatgctgg agcccgagcc aggcagaaaa tgctgatcgc tgctctggag tctaaactgg   5580

cccaggcaga ggagcagctg gagcaggaga gcagggagcg catcctctct ggcaagctgg   5640

tacgcagagc tgagaagcgg ctgaaggagg tagttcttca ggtggatgaa gagcgcaggg   5700

tggctgacca ggtccgggac cagctggaga aaagcaacct ccggctgaag cagctcaaga   5760

ggcagctgga ggaggcagag gaggaggcat ctcgggcaca ggctggtcgg aggcggctgc   5820

agcgggagct ggaggacgtc actgagtctg cagaatccat gaaccgggag gtgaccacgc   5880

tgaggaacag gctccggcgt ggcccactta cattcaccac acggactgtg cgccaggtgt   5940

tccggctgga agagggcgtg gcttctgacg aggaagaggc tgaaggagct gaacctggct   6000

ctgcaccagg ccaggagccg gaggctccgc cccctgccac accccaatga tccagtctgt   6060

cctagatgcc ccaaggacag agccctttcc agtgcccctc ctggtttgca ctttgaaatg   6120

gcactgtcct ctggcacttt ctggcattga tgaaccctcc tgggacccca ggacccctgc   6180

ccactggggg ccccaaacca aggagctggg tgggagggag gccatgatgg tctctcttgt   6240

tagagaaaca aaattgaacg tggatgtcaa gaatgtcctg tctgcaccta ttttcagcag   6300

gcctgtcccc tggagagggc aggcagggtg cttccatccc ctctcagtat cttgccctct   6360

tttttggggg gaagtggggt gtctgtgtgc tcatagggta atgctcatgg cccctcatgc   6420

tccagacact aaagaaataa aa                                            6442
```

<210> SEQ ID NO 56
<211> LENGTH: 2000
<212> TYPE: PRT
<213> ORGANISM: Mus musculus

<400> SEQUENCE: 56

```
Met Ala Ala Val Thr Met Ser Val Ser Gly Arg Lys Val Ala Ser Arg
  1               5                  10                  15

Pro Gly Pro Val Pro Glu Ala Ala Gln Ser Phe Leu Tyr Ala Pro Arg
             20                  25                  30

Thr Pro Asn Val Gly Gly Pro Gly Gly Pro Gln Val Glu Trp Thr Ala
         35                  40                  45

Arg Arg Met Val Trp Val Pro Ser Glu Leu His Gly Phe Glu Ala Ala
     50                  55                  60

Ala Leu Arg Asp Glu Gly Glu Glu Glu Ala Glu Val Glu Leu Ala Glu
 65                  70                  75                  80

Ser Gly Arg Arg Leu Arg Leu Pro Arg Asp Gln Ile Gln Arg Met Asn
                 85                  90                  95
```

-continued

```
Pro Pro Lys Phe Ser Lys Ala Glu Asp Met Ala Glu Leu Thr Cys Leu
            100                 105                 110

Asn Glu Ala Ser Val Leu His Asn Leu Arg Glu Arg Tyr Tyr Ser Gly
        115                 120                 125

Leu Ile Tyr Thr Tyr Ser Gly Leu Phe Cys Val Val Ile Asn Pro Tyr
    130                 135                 140

Lys Gln Leu Pro Ile Tyr Thr Glu Ala Ile Val Glu Met Tyr Arg Gly
145                 150                 155                 160

Lys Lys Arg His Glu Val Pro Pro His Val Tyr Ala Val Thr Glu Gly
                165                 170                 175

Ala Tyr Arg Ser Met Leu Gln Asp Arg Glu Asp Gln Ser Ile Leu Cys
            180                 185                 190

Thr Gly Glu Ser Gly Ala Gly Lys Thr Glu Asn Thr Lys Lys Val Ile
        195                 200                 205

Gln Tyr Leu Ala His Val Ala Ser Ser Pro Lys Gly Arg Lys Glu Pro
    210                 215                 220

Gly Val Pro Ala Ser Val Ser Thr Met Ser Tyr Gly Glu Leu Glu Arg
225                 230                 235                 240

Gln Leu Leu Gln Ala Asn Pro Ile Leu Glu Ala Phe Gly Asn Ala Lys
                245                 250                 255

Thr Val Lys Asn Asp Asn Ser Ser Arg Phe Gly Lys Phe Ile Arg Ile
            260                 265                 270

Asn Phe Asp Ile Ala Gly Tyr Ile Val Gly Ala Asn Ile Glu Thr Tyr
        275                 280                 285

Leu Leu Glu Lys Ser Arg Ala Ile Arg Gln Ala Lys Asp Glu Cys Ser
    290                 295                 300

Phe His Ile Phe Tyr Gln Leu Leu Gly Gly Ala Gly Glu Gln Leu Lys
305                 310                 315                 320

Ala Asp Leu Leu Leu Glu Pro Cys Ser His Tyr Arg Phe Leu Thr Asn
                325                 330                 335

Gly Pro Ser Ser Ser Pro Gly Gln Glu Arg Glu Leu Phe Gln Glu Thr
            340                 345                 350

Leu Glu Ser Leu Arg Val Leu Gly Leu Leu Pro Glu Glu Ile Thr Ala
        355                 360                 365

Met Leu Arg Thr Val Ser Ala Val Leu Gln Phe Gly Asn Ile Val Leu
    370                 375                 380

Lys Lys Glu Arg Asn Thr Asp Gln Ala Thr Met Pro Asp Asn Thr Ala
385                 390                 395                 400

Ala Gln Lys Leu Cys Arg Leu Leu Gly Leu Gly Val Thr Asp Phe Ser
                405                 410                 415

Arg Ala Leu Leu Thr Pro Arg Ile Lys Val Gly Arg Asp Tyr Val Gln
            420                 425                 430

Lys Ala Gln Thr Lys Glu Gln Ala Asp Phe Ala Leu Glu Ala Leu Ala
        435                 440                 445

Lys Ala Thr Tyr Glu Arg Leu Phe Arg Trp Leu Val Leu Arg Leu Asn
    450                 455                 460

Arg Ala Leu Asp Arg Ser Pro Arg Gln Gly Ala Ser Phe Leu Gly Ile
465                 470                 475                 480

Leu Asp Ile Ala Gly Phe Glu Ile Phe Gln Leu Asn Ser Phe Glu Gln
                485                 490                 495

Leu Cys Ile Asn Tyr Thr Asn Glu Lys Leu Gln Gln Leu Phe Asn His
            500                 505                 510

Thr Met Phe Val Leu Glu Gln Glu Glu Tyr Gln Arg Glu Gly Ile Pro
```

-continued

```
        515                 520                 525

Trp Thr Phe Leu Asp Phe Gly Leu Asp Leu Gln Pro Cys Ile Asp Leu
    530                 535                 540

Ile Glu Arg Pro Ala Asn Pro Pro Gly Leu Leu Ala Leu Leu Asp Glu
545                 550                 555                 560

Glu Cys Trp Phe Pro Lys Ala Thr Asp Lys Ser Phe Val Glu Lys Val
                565                 570                 575

Ala Gln Glu Gln Gly Ser His Pro Lys Phe Gln Arg Pro Arg Asn Leu
            580                 585                 590

Arg Asp Gln Ala Asp Phe Ser Val Leu His Tyr Ala Gly Lys Val Asp
        595                 600                 605

Tyr Lys Ala Ser Glu Trp Leu Met Lys Asn Met Asp Pro Leu Asn Asp
    610                 615                 620

Asn Val Ala Ala Leu Leu His Gln Ser Thr Asp Arg Leu Thr Ala Glu
625                 630                 635                 640

Ile Trp Lys Asp Val Glu Gly Ile Val Gly Leu Glu Gln Val Ser Ser
                645                 650                 655

Leu Gly Asp Gly Pro Pro Gly Gly Arg Pro Arg Arg Gly Met Phe Arg
            660                 665                 670

Thr Val Gly Gln Leu Tyr Lys Glu Ser Leu Ser Arg Leu Met Ala Thr
        675                 680                 685

Leu Ser Asn Thr Asn Pro Ser Phe Val Arg Cys Ile Val Pro Asn His
    690                 695                 700

Glu Lys Arg Ala Gly Lys Leu Glu Pro Arg Leu Val Leu Asp Gln Leu
705                 710                 715                 720

Arg Cys Asn Gly Val Leu Glu Gly Ile Arg Ile Cys Arg Gln Gly Phe
                725                 730                 735

Pro Asn Arg Ile Leu Phe Gln Glu Phe Arg Gln Arg Tyr Glu Ile Leu
            740                 745                 750

Thr Pro Asn Ala Ile Pro Lys Gly Phe Met Asp Gly Lys Gln Ala Cys
        755                 760                 765

Glu Lys Met Ile Gln Ala Leu Glu Leu Asp Pro Asn Leu Tyr Arg Val
    770                 775                 780

Gly Gln Ser Lys Ile Phe Phe Arg Ala Gly Val Leu Ala Gln Leu Glu
785                 790                 795                 800

Glu Glu Arg Asp Leu Lys Val Thr Asp Ile Ile Val Ser Phe Gln Ala
                805                 810                 815

Ala Ala Arg Gly Tyr Leu Ala Arg Arg Ala Phe Gln Arg Arg Gln Gln
            820                 825                 830

Gln Gln Ser Ala Leu Arg Val Met Gln Arg Asn Cys Ala Ala Tyr Leu
        835                 840                 845

Lys Leu Arg Asn Trp Gln Trp Trp Arg Leu Phe Ile Lys Val Lys Pro
    850                 855                 860

Leu Leu Gln Val Thr Arg Gln Asp Glu Val Leu Gln Ala Arg Ala Gln
865                 870                 875                 880

Glu Leu Gln Lys Val Gln Glu Leu Gln Gln Gln Ser Ala Arg Glu Val
                885                 890                 895

Gly Glu Leu Gln Gly Arg Val Ala Gln Leu Glu Glu Glu Arg Thr Arg
            900                 905                 910

Leu Ala Glu Gln Leu Arg Ala Glu Ala Glu Leu Cys Ser Glu Ala Glu
        915                 920                 925

Glu Thr Arg Ala Arg Leu Ala Ala Arg Lys Gln Glu Leu Glu Leu Val
    930                 935                 940
```

-continued

```
Val Thr Glu Leu Glu Ala Arg Val Gly Glu Glu Glu Glu Cys Ser Arg
945                 950                 955                 960

Gln Leu Gln Ser Glu Lys Lys Arg Leu Gln Gln His Ile Gln Glu Leu
                965                 970                 975

Glu Ser His Leu Glu Ala Glu Glu Gly Ala Arg Gln Lys Leu Gln Leu
            980                 985                 990

Glu Lys Val Thr Thr Glu Ala Lys Met Lys Lys Phe Glu Glu Asp Leu
        995                 1000                1005

Leu Leu Leu Glu Asp Gln Asn Ser Lys Leu Ser Lys Glu Arg Arg Leu
    1010                1015                1020

Leu Glu Glu Arg Leu Ala Glu Phe Ser Ser Gln Ala Ala Glu Glu Glu
1025                1030                1035                1040

Glu Lys Val Lys Ser Leu Asn Lys Leu Arg Leu Lys Tyr Glu Ala Thr
                1045                1050                1055

Ile Ser Asp Met Glu Asp Arg Leu Lys Lys Glu Glu Lys Gly Arg Gln
            1060                1065                1070

Glu Leu Glu Lys Leu Lys Arg Arg Leu Asp Gly Glu Ser Ser Glu Leu
        1075                1080                1085

Gln Glu Gln Met Val Glu Gln Lys Gln Arg Ala Glu Glu Leu Leu Ala
    1090                1095                1100

Gln Leu Gly Arg Lys Glu Asp Glu Leu Gln Ala Ala Leu Leu Arg Ala
1105                1110                1115                1120

Glu Glu Glu Gly Gly Ala Arg Ala Gln Leu Leu Lys Ser Leu Arg Glu
                1125                1130                1135

Ala Gln Ala Gly Leu Ala Glu Ala Gln Glu Asp Leu Glu Ala Glu Arg
            1140                1145                1150

Val Ala Arg Ala Lys Ala Glu Lys Gln Arg Arg Asp Leu Gly Glu Glu
        1155                1160                1165

Leu Glu Ala Leu Arg Gly Glu Leu Glu Asp Thr Leu Asp Ser Thr Asn
    1170                1175                1180

Ala Gln Gln Glu Leu Arg Ser Lys Arg Glu Gln Glu Val Thr Glu Leu
1185                1190                1195                1200

Lys Lys Ala Leu Glu Glu Glu Ser Arg Ala His Glu Val Ser Met Gln
                1205                1210                1215

Glu Leu Arg Gln Arg His Ser Gln Ala Leu Val Glu Met Ala Glu Gln
            1220                1225                1230

Leu Glu Gln Ala Arg Arg Gly Lys Gly Val Trp Glu Lys Thr Arg Leu
        1235                1240                1245

Ser Leu Glu Ala Glu Val Ser Glu Leu Lys Ala Glu Leu Ser Ser Leu
    1250                1255                1260

Gln Thr Ser Arg Gln Glu Gly Glu Gln Lys Arg Arg Arg Leu Glu Ser
1265                1270                1275                1280

Gln Leu Gln Glu Val Gln Gly Arg Ser Ser Asp Ser Glu Arg Ala Arg
                1285                1290                1295

Ser Glu Ala Ala Glu Lys Leu Gln Arg Ala Gln Ala Glu Leu Glu Ser
            1300                1305                1310

Val Ser Thr Ala Leu Ser Glu Ala Glu Ser Lys Ala Ile Arg Leu Gly
        1315                1320                1325

Lys Glu Leu Ser Ser Ala Glu Ser Gln Leu His Asp Thr Gln Glu Leu
    1330                1335                1340

Leu Gln Glu Glu Thr Arg Ala Lys Leu Ala Leu Gly Ser Arg Val Arg
1345                1350                1355                1360
```

-continued

```
Ala Leu Glu Ala Glu Ala Ala Gly Leu Arg Glu Gln Met Glu Glu Glu
                1365                1370                1375

Val Val Ala Arg Glu Arg Ala Gly Arg Glu Leu Gln Ser Thr Gln Ala
            1380                1385                1390

Gln Leu Ser Glu Trp Arg Arg Arg Gln Glu Glu Glu Ala Ala Val Leu
        1395                1400                1405

Glu Ala Gly Glu Glu Ala Arg Arg Arg Ala Ala Arg Glu Ala Glu Thr
    1410                1415                1420

Leu Thr Gln Arg Leu Ala Glu Lys Thr Glu Ala Val Glu Arg Leu Glu
1425                1430                1435                1440

Arg Ala Arg Arg Arg Leu Gln Gln Glu Leu Asp Asp Ala Thr Val Asp
                1445                1450                1455

Leu Gly Gln Gln Lys Gln Leu Leu Ser Thr Leu Glu Lys Lys Gln Arg
            1460                1465                1470

Lys Phe Asp Gln Leu Leu Ala Glu Glu Lys Ala Ala Val Leu Arg Ala
        1475                1480                1485

Val Glu Asp Arg Glu Arg Ile Glu Ala Glu Gly Arg Glu Arg Glu Ala
    1490                1495                1500

Arg Ala Leu Ser Leu Thr Arg Ala Leu Glu Glu Glu Gln Glu Ala Arg
1505                1510                1515                1520

Glu Glu Leu Glu Arg Gln Asn Arg Ala Leu Arg Ala Glu Leu Glu Ala
                1525                1530                1535

Leu Leu Ser Ser Lys Asp Asp Val Gly Lys Asn Val His Glu Leu Glu
            1540                1545                1550

Arg Ala Arg Lys Ala Ala Glu Gln Ala Ala Ser Asp Leu Arg Thr Gln
        1555                1560                1565

Val Thr Glu Leu Glu Asp Glu Leu Thr Ala Ala Glu Asp Ala Lys Leu
    1570                1575                1580

Arg Leu Glu Val Thr Val Gln Ala Leu Lys Ala Gln His Glu Arg Asp
1585                1590                1595                1600

Leu Gln Gly Arg Asp Asp Ala Gly Glu Glu Arg Arg Arg Gln Leu Ala
                1605                1610                1615

Lys Gln Leu Arg Asp Ala Glu Val Glu Arg Asp Glu Glu Arg Lys Gln
            1620                1625                1630

Arg Ala Leu Ala Met Ala Ala Arg Lys Lys Leu Glu Leu Glu Leu Glu
        1635                1640                1645

Glu Leu Lys Ala Gln Thr Ser Ala Ala Gly Gln Gly Lys Glu Glu Ala
    1650                1655                1660

Val Lys Gln Leu Lys Lys Met Gln Val Gln Met Lys Glu Leu Trp Arg
1665                1670                1675                1680

Glu Val Glu Glu Thr Arg Ser Ser Arg Asp Glu Met Phe Thr Leu Ser
                1685                1690                1695

Arg Glu Asn Glu Lys Lys Leu Lys Gly Leu Glu Ala Glu Val Leu Arg
            1700                1705                1710

Leu Gln Glu Glu Leu Ala Ala Ser Asp Arg Ala Arg Arg Gln Ala Gln
        1715                1720                1725

Gln Asp Arg Asp Glu Met Ala Glu Glu Val Ala Ser Gly Asn Leu Ser
    1730                1735                1740

Lys Ala Ala Thr Leu Glu Glu Lys Arg Gln Leu Glu Gly Arg Leu Ser
1745                1750                1755                1760

Gln Leu Glu Glu Glu Leu Glu Glu Glu Gln Asn Asn Ser Glu Leu Leu
                1765                1770                1775

Lys Asp His Tyr Arg Lys Leu Val Leu Gln Val Glu Ser Leu Thr Thr
```

-continued

```
            1780                1785                1790

Glu Leu Ser Ala Glu Arg Ser Phe Ser Ala Lys Ala Glu Ser Gly Arg
        1795                1800                1805

Gln Gln Leu Glu Arg Gln Ile Gln Glu Leu Arg Ala Arg Leu Gly Glu
    1810                1815                1820

Glu Asp Ala Gly Ala Arg Ala Arg Gln Lys Met Leu Ile Ala Ala Leu
1825                1830                1835                1840

Glu Ser Lys Leu Ala Gln Ala Glu Glu Gln Leu Glu Gln Glu Ser Arg
                1845                1850                1855

Glu Arg Ile Leu Ser Gly Lys Leu Val Arg Arg Ala Glu Lys Arg Leu
            1860                1865                1870

Lys Glu Val Val Leu Gln Val Asp Glu Glu Arg Arg Val Ala Asp Gln
        1875                1880                1885

Val Arg Asp Gln Leu Glu Lys Ser Asn Leu Arg Leu Lys Gln Leu Lys
    1890                1895                1900

Arg Gln Leu Glu Glu Ala Glu Glu Glu Ala Ser Arg Ala Gln Ala Gly
1905                1910                1915                1920

Arg Arg Arg Leu Gln Arg Glu Leu Glu Asp Val Thr Glu Ser Ala Glu
                1925                1930                1935

Ser Met Asn Arg Glu Val Thr Thr Leu Arg Asn Arg Leu Arg Arg Gly
            1940                1945                1950

Pro Leu Thr Phe Thr Thr Arg Thr Val Arg Gln Val Phe Arg Leu Glu
        1955                1960                1965

Glu Gly Val Ala Ser Asp Glu Glu Glu Ala Glu Gly Ala Glu Pro Gly
    1970                1975                1980

Ser Ala Pro Gly Gln Glu Pro Glu Ala Pro Pro Pro Ala Thr Pro Gln
1985                1990                1995                2000


<210> SEQ ID NO 57
<211> LENGTH: 6377
<212> TYPE: DNA
<213> ORGANISM: Mus musculus

<400> SEQUENCE: 57

ccgaccatgg ctgcagtgac catgtccgtg tctgggagga aggtagcctc caggccaggc      60

ccggtgcctg aggcagccca atcgttcctc tacgcgcccc ggacgccaaa tgtaggtggc     120

cctggagggc cacaggtgga gtggacagcc cggcgcatgg tgtgggtgcc ctcggaactg     180

catgggttcg aggcagcagc cctgcgggat gaaggggagg aggaggcaga agtggagctg     240

gcggagagtg ggcgccgcct gcggctgccc agggaccaga tccagcgcat gaacccaccc     300

aagttcagca aggcagaaga tatggctgag ctcacctgcc tcaacgaggc ctcggtcctg     360

cacaacctgc gagaacgcta ctactccggg ctcatttata cctactctgg cctcttctgt     420

gtggtcatta acccatacaa gcagctgccc atctacacgg aggccattgt tgaaatgtac     480

cggggcaaga agcgccatga ggtgccacct cacgtgtatg ctgtgacgga gggcgcgtac     540

cgcagcatgc ttcaggatcg tgaggatcaa tccattctct gcacgggaga gtctggcgct     600

gggaagacgg agaacaccaa gaaggtcatc cagtacctgg cccatgtggc atcatctcca     660

aagggcagga aggagcctgg tgtccctggg gagctagagc gtcagcttct tcaagccaac     720

cccatcctag aggcctttgg caatgccaag acagtgaaga acgacaactc ttcccgattt     780

ggcaaattca tccgcatcaa ctttgatatt gctggctaca tcgtgggagc aaacatcgag     840

acctatctgt tggagaagtc ccgggccatc agacaggcca aggatgaatg cagcttccat     900
```

-continued

```
atcttctacc agctgctagg gggcgctggg gagcagctaa aagctgacct ccttctggag    960
ccctgttccc attatcgctt cctgaccaat gggccctcat cgtccccggg ccaggagcgt   1020
gagttattcc aggagaccct ggagtccctg cgtgtgctgg gcctcctccc agaagagatc   1080
actgccatgc tgcgcactgt ctctgctgtc ctccagtttg gcaacattgt cctgaagaaa   1140
gagcgcaata cggaccaagc caccatgcct gacaacacag ctgcccagaa gctttgccgc   1200
ctcttgggac tcggagtgac cgacttctcc agagcccttc tcacaccccg catcaaagtg   1260
ggccgagatt atgttcagaa agcacaaacc aaggagcagg ctgactttgc gctggaggct   1320
ctggccaaag ctacctatga gcgcctgttc cgctggctgg ttctgcggct caaccgtgcc   1380
ctggacagaa gcccgcggca gggtgcctcc ttcctgggca tcctggacat cgcgggcttt   1440
gagatcttcc agctgaactc cttcgagcag ctgtgcatca actacaccaa cgagaagcta   1500
cagcagctat tcaaccacac catgttcgtg ctggagcagg aggagtacca gcgagagggc   1560
atcccctgga ccttcctaga cttcgggttg gacctgcaac cttgcatcga cctcattgag   1620
cgtccggcca accctccagg tctcctggcc ctgctggacg aggagtgctg gttccccaag   1680
gccacggaca agtcttttgt ggagaaggtc gcccaggagc agggcagcca ccccaaattc   1740
cagcgcccca ggaacctgcg agatcaggcc gacttcagcg tcctgcacta tgccggcaag   1800
gttgactaca aagccagtga gtggctgatg aagaacatgg acccactgaa tgacaatgtg   1860
gccgccttgc ttcaccagag cacggatcgt ctcacagctg agatctggaa ggatgtggag   1920
ggcatcgtgg ggctggagca agtaagcagc cttggagatg gcccaccggg aggccgcccc   1980
cgccgtggaa tgttccggac tgtggggcag ctctacaaag aatccctgag ccgcctcatg   2040
gccacgctca gcaacaccaa ccctagtttt gtccgctgca tcgttcccaa tcatgagaag   2100
agggctggaa agctggagcc gcgcctggtg ctggaccaac tccgttgtaa cggggtcctc   2160
gagggtatac gcatctgtcg ccaaggcttc cccaaccgca tcctcttcca ggagttccga   2220
cagcgctatg aaatcctcac cccgaacgct attcccaagg gcttcatgga cggcaaacag   2280
gcctgtgaga agatgatcca ggccctggag ctagacccca acctgtaccg tgttggccaa   2340
agcaagatct tcttccgggc aggggtcctg gcccagctgg aggaggagcg ggacctgaaa   2400
gtcaccgaca tcatagtgtc tttccaggca gcggcacggg gctacctggc ccgtagggct   2460
ttccagagac ggcagcagca gcagagtgct ctgagggtga tgcagagaaa ctgtgctgcc   2520
tacctcaagc tcaggaactg gcagtggtgg aggctgttca tcaaggtgaa gcccctgctg   2580
caggtgacac ggcaggatga ggtgctgcag gcgcgcgccc aggagctgca gaaagttcag   2640
gagctgcagc agcagagcgc tcgtgaagtg ggggaactgc agggtcgagt ggcacagcta   2700
gaggaggagc gcacgcgcct ggctgagcag cttcgagcag aagccgagct ctgctctgag   2760
gccgaggaga cgcgggcgcg actggctgcc cggaagcagg agctggagct ggtggtgaca   2820
gagctggagg cacgagtggg cgaggaagaa gagtgcagcc ggcagctgca gagtgagaag   2880
aagaggctgc agcagcatat ccaggagcta gagagccacc tggaagctga ggagggtgcc   2940
cggcagaagc tacagctgga gaaggtgacc acagaggcca agatgaagaa atttgaggag   3000
gacctgctgc tcctggagga ccagaattcc aagctgagca aggagcggag gctgctggag   3060
gagcggctgg ctgagttctc ctcacaggca gcagaagagg aagagaaagt caaaagtctc   3120
aacaagctga ggctcaaata tgaagccaca atctcagaca tggaagaccg gctgaagaag   3180
gaggagaagg gacgccagga actagagaag ctgaagcgac ggctggacgg ggagagctca   3240
gagcttcagg agcagatggt ggagcagaag cagagggcag aggaactgct cgcacagctg   3300
```

-continued

```
ggccgcaagg aggatgagct gcaggccgcc ctgctcaggg cagaggaaga gggtggtgcc   3360
cgtgcccagt tgctcaagtc cctgcgagag gcacaggctg gccttgctga ggctcaggag   3420
gacctggaag ctgagcgggt agccagggcc aaggcggaga agcagcgccg ggacctgggc   3480
gaggagttgg aggccctacg tggggagctc gaggacactc tggattccac caacgcccag   3540
caggagctgc ggtccaagag ggagcaggag gtgacagagc tgaagaaagc attggaagag   3600
gagtcccgtg cccatgaggt gtccatgcag gagctgagac agaggcatag ccaggcactg   3660
gtggagatgg ccgagcagtt ggagcaagcc cggagggggca aaggtgtgtg ggagaagact   3720
cggctatccc tggaggctga ggtgtccgag ctgaaggccg agctgagcag cctgcagacc   3780
tcgagacagg agggtgagca gaagaggcgc cgcctggagt cccagctaca ggaggtccag   3840
ggccgatcca gtgattcgga gcgggctcgg tctgaggctg ctgagaagct gcagagagcc   3900
caggcggaac ttgagagcgt gtccacagcc ctgagtgagg cggagtccaa agccatcagg   3960
ctgggcaagg agctgagcag tgcagagtcc cagctgcatg acacccagga actgcttcag   4020
gaggagacca gggcaaagct ggccttgggg tcccgtgtgc gtgccctaga ggccgaggcg   4080
gcggggcttc gggagcagat ggaagaggag gtggttgcca gggaacgggc tggccgggag   4140
ctgcagagca cgcaggccca gctctctgaa tggcggcgcc gccaggaaga agaggccgcg   4200
gtgctggagg ctggggagga ggctcggcgc cgtgcagccc gggaggcaga gaccctgacc   4260
cagcgcctgg cagaaaagac tgaggctgta gaacgactgg agcgagcccg gcgccgactg   4320
cagcaggagt tggacgatgc cactgtggat ctggggcagc agaagcagct cctgagcaca   4380
ctggagaaga agcagcggaa atttgaccag ctcctggcag aggagaaggc tgcagttcta   4440
cgggctgtgg aagaccgtga acggatagag gccgaaggcc gggagcgaga ggcccgggcc   4500
ctgtcgctga cccgggccct ggaagaggag caggaggccc gggaggagct ggagaggcag   4560
aaccgtgctc tgagggctga gctggaagca ctgctgagca gcaaggatga cgtgggcaag   4620
aacgtgcacg agctggagcg agcccgtaag gcggctgaac aggcagccag tgacctgcgg   4680
acacaggtga cagaattgga ggatgagctg acagccgcag aggatgccaa gctgcgcctg   4740
gaggtgactg tgcaggctct gaaggctcaa catgaacgcg acctgcaggg ccgcgatgat   4800
gccggtgagg agaggcggag gcagctggcc aagcagctaa gagacgcaga ggtagagcgc   4860
gatgaggaac ggaagcagag ggcactggct atggctgccc gcaagaagct ggagctggaa   4920
ctggaggagt tgaaggcgca gacatctgct gctgggcagg gcaaggaaga ggcagtgaag   4980
cagctgaaga agatgcaggt ccagatgaag gagctgtggc gggaggtaga ggagacgcgt   5040
agctcccgcg acgagatgtt taccctgagc agggaaaatg agaagaagct caaggggctg   5100
gaagctgagg tgctgcgtct gcaagaggaa cttgctgcct cagaccgagc ccggaggcag   5160
gcccagcaag acagagacga gatggcagag gaggtggcca gtggcaatct tagcaaggca   5220
gccaccctgg aggaaaaacg gcagctggag gggcgactga gccagttgga agaggagctg   5280
gaggaagaac agaacaactc ggagctgctc aaggaccatt accgaaagct agtgctacag   5340
gtcgagtccc tcaccacaga actgtctgcc gaacgaagtt tctcagccaa ggccgagagt   5400
ggacggcagc agctggagcg gcagatccag gaactgcggg cccgcttggg tgaagaggat   5460
gctggagccc gagccaggca gaaaatgctg atcgctgctc tggagtctaa actggcccag   5520
gcagaggagc agctggagca ggagagcagg gagcgcatcc tctctggcaa gctggtacgc   5580
agagctgaga agcggctgaa ggaggtagtt cttcaggtgg atgaagagcg cagggtggct   5640
```

-continued

```
gaccaggtcc gggaccagct ggagaaaagc aacctccggc tgaagcagct caagaggcag   5700

ctggaggagg cagaggagga ggcatctcgg gcacaggctg gtcggaggcg gctgcagcgg   5760

gagctggagg acgtcactga gtctgcagaa tccatgaacc gggaggtgac cacgctgagg   5820

aacaggctcc ggcgtggccc acttacattc accacacgga ctgtgcgcca ggtgttccgg   5880

ctggaagagg gcgtggcttc tgacgaggaa gaggctgaag gagctgaacc tggctctgca   5940

ccaggccagg agccggaggc tccgcccccct gccacacccc aatgatccag tctgtcctag   6000

atgccccaag gacagagccc tttccagtgc cctcctggt ttgcactttg aaatggcact   6060

gtcctctggc actttctggc attgatgaac cctcctggga ccccaggacc cctgcccact   6120

gggggcccca aaccaaggag ctgggtggga gggaggccat gatggtctct cttgttagag   6180

aaacaaaatt gaacgtggat gtcaagaatg tcctgtctgc acctattttc agcaggcctg   6240

tcccctggag agggcaggca gggtgcttcc atcccctctc agtatcttgc cctcttttt   6300

ggggggaagt ggggtgtctg tgtgctcata gggtaatgct catggcccct catgctccag   6360

acactaaaga aataaaa                                                  6377


<210> SEQ ID NO 58
<211> LENGTH: 1992
<212> TYPE: PRT
<213> ORGANISM: Mus musculus

<400> SEQUENCE: 58

Met Ala Ala Val Thr Met Ser Val Ser Gly Arg Lys Val Ala Ser Arg
1               5                   10                  15

Pro Gly Pro Val Pro Glu Ala Ala Gln Ser Phe Leu Tyr Ala Pro Arg
            20                  25                  30

Thr Pro Asn Val Gly Gly Pro Gly Gly Pro Gln Val Glu Trp Thr Ala
        35                  40                  45

Arg Arg Met Val Trp Val Pro Ser Glu Leu His Gly Phe Glu Ala Ala
    50                  55                  60

Ala Leu Arg Asp Glu Gly Glu Glu Glu Ala Glu Val Glu Leu Ala Glu
65                  70                  75                  80

Ser Gly Arg Arg Leu Arg Leu Pro Arg Asp Gln Ile Gln Arg Met Asn
                85                  90                  95

Pro Pro Lys Phe Ser Lys Ala Glu Asp Met Ala Glu Leu Thr Cys Leu
            100                 105                 110

Asn Glu Ala Ser Val Leu His Asn Leu Arg Glu Arg Tyr Tyr Ser Gly
        115                 120                 125

Leu Ile Tyr Thr Tyr Ser Gly Leu Phe Cys Val Val Ile Asn Pro Tyr
    130                 135                 140

Lys Gln Leu Pro Ile Tyr Thr Glu Ala Ile Val Glu Met Tyr Arg Gly
145                 150                 155                 160

Lys Lys Arg His Glu Val Pro Pro His Val Tyr Ala Val Thr Glu Gly
                165                 170                 175

Ala Tyr Arg Ser Met Leu Gln Asp Arg Glu Asp Gln Ser Ile Leu Cys
            180                 185                 190

Thr Gly Glu Ser Gly Ala Gly Lys Thr Glu Asn Thr Lys Lys Val Ile
        195                 200                 205

Gln Tyr Leu Ala His Val Ala Ser Ser Pro Lys Gly Arg Lys Glu Pro
    210                 215                 220

Gly Val Pro Gly Glu Leu Glu Arg Gln Leu Leu Gln Ala Asn Pro Ile
225                 230                 235                 240
```

-continued

```
Leu Glu Ala Phe Gly Asn Ala Lys Thr Val Lys Asn Asp Asn Ser Ser
                245                 250                 255

Arg Phe Gly Lys Phe Ile Arg Ile Asn Phe Asp Ile Ala Gly Tyr Ile
            260                 265                 270

Val Gly Ala Asn Ile Glu Thr Tyr Leu Leu Glu Lys Ser Arg Ala Ile
        275                 280                 285

Arg Gln Ala Lys Asp Glu Cys Ser Phe His Ile Phe Tyr Gln Leu Leu
    290                 295                 300

Gly Gly Ala Gly Glu Gln Leu Lys Ala Asp Leu Leu Leu Glu Pro Cys
305                 310                 315                 320

Ser His Tyr Arg Phe Leu Thr Asn Gly Pro Ser Ser Ser Pro Gly Gln
                325                 330                 335

Glu Arg Glu Leu Phe Gln Glu Thr Leu Glu Ser Leu Arg Val Leu Gly
            340                 345                 350

Leu Leu Pro Glu Glu Ile Thr Ala Met Leu Arg Thr Val Ser Ala Val
        355                 360                 365

Leu Gln Phe Gly Asn Ile Val Leu Lys Lys Glu Arg Asn Thr Asp Gln
    370                 375                 380

Ala Thr Met Pro Asp Asn Thr Ala Ala Gln Lys Leu Cys Arg Leu Leu
385                 390                 395                 400

Gly Leu Gly Val Thr Asp Phe Ser Arg Ala Leu Leu Thr Pro Arg Ile
                405                 410                 415

Lys Val Gly Arg Asp Tyr Val Gln Lys Ala Gln Thr Lys Glu Gln Ala
            420                 425                 430

Asp Phe Ala Leu Glu Ala Leu Ala Lys Ala Thr Tyr Glu Arg Leu Phe
        435                 440                 445

Arg Trp Leu Val Leu Arg Leu Asn Arg Ala Leu Asp Arg Ser Pro Arg
    450                 455                 460

Gln Gly Ala Ser Phe Leu Gly Ile Leu Asp Ile Ala Gly Phe Glu Ile
465                 470                 475                 480

Phe Gln Leu Asn Ser Phe Glu Gln Leu Cys Ile Asn Tyr Thr Asn Glu
                485                 490                 495

Lys Leu Gln Gln Leu Phe Asn His Thr Met Phe Val Leu Glu Gln Glu
            500                 505                 510

Glu Tyr Gln Arg Glu Gly Ile Pro Trp Thr Phe Leu Asp Phe Gly Leu
        515                 520                 525

Asp Leu Gln Pro Cys Ile Asp Leu Ile Glu Arg Pro Ala Asn Pro Pro
    530                 535                 540

Gly Leu Leu Ala Leu Leu Asp Glu Glu Cys Trp Phe Pro Lys Ala Thr
545                 550                 555                 560

Asp Lys Ser Phe Val Glu Lys Val Ala Gln Glu Gln Gly Ser His Pro
                565                 570                 575

Lys Phe Gln Arg Pro Arg Asn Leu Arg Asp Gln Ala Asp Phe Ser Val
            580                 585                 590

Leu His Tyr Ala Gly Lys Val Asp Tyr Lys Ala Ser Glu Trp Leu Met
        595                 600                 605

Lys Asn Met Asp Pro Leu Asn Asp Asn Val Ala Ala Leu Leu His Gln
    610                 615                 620

Ser Thr Asp Arg Leu Thr Ala Glu Ile Trp Lys Asp Val Glu Gly Ile
625                 630                 635                 640

Val Gly Leu Glu Gln Val Ser Ser Leu Gly Asp Gly Pro Pro Gly Gly
                645                 650                 655

Arg Pro Arg Arg Gly Met Phe Arg Thr Val Gly Gln Leu Tyr Lys Glu
```

-continued

```
                660                 665                 670

Ser Leu Ser Arg Leu Met Ala Thr Leu Ser Asn Thr Asn Pro Ser Phe
            675                 680                 685

Val Arg Cys Ile Val Pro Asn His Glu Lys Arg Ala Gly Lys Leu Glu
    690                 695                 700

Pro Arg Leu Val Leu Asp Gln Leu Arg Cys Asn Gly Val Leu Glu Gly
705                 710                 715                 720

Ile Arg Ile Cys Arg Gln Gly Phe Pro Asn Arg Ile Leu Phe Gln Glu
                725                 730                 735

Phe Arg Gln Arg Tyr Glu Ile Leu Thr Pro Asn Ala Ile Pro Lys Gly
            740                 745                 750

Phe Met Asp Gly Lys Gln Ala Cys Glu Lys Met Ile Gln Ala Leu Glu
        755                 760                 765

Leu Asp Pro Asn Leu Tyr Arg Val Gly Gln Ser Lys Ile Phe Phe Arg
    770                 775                 780

Ala Gly Val Leu Ala Gln Leu Glu Glu Glu Arg Asp Leu Lys Val Thr
785                 790                 795                 800

Asp Ile Ile Val Ser Phe Gln Ala Ala Ala Arg Gly Tyr Leu Ala Arg
                805                 810                 815

Arg Ala Phe Gln Arg Arg Gln Gln Gln Gln Ser Ala Leu Arg Val Met
            820                 825                 830

Gln Arg Asn Cys Ala Ala Tyr Leu Lys Leu Arg Asn Trp Gln Trp Trp
        835                 840                 845

Arg Leu Phe Ile Lys Val Lys Pro Leu Leu Gln Val Thr Arg Gln Asp
    850                 855                 860

Glu Val Leu Gln Ala Arg Ala Gln Glu Leu Gln Lys Val Gln Glu Leu
865                 870                 875                 880

Gln Gln Gln Ser Ala Arg Glu Val Gly Glu Leu Gln Gly Arg Val Ala
                885                 890                 895

Gln Leu Glu Glu Glu Arg Thr Arg Leu Ala Glu Gln Leu Arg Ala Glu
            900                 905                 910

Ala Glu Leu Cys Ser Glu Ala Glu Glu Thr Arg Ala Arg Leu Ala Ala
        915                 920                 925

Arg Lys Gln Glu Leu Glu Leu Val Val Thr Glu Leu Glu Ala Arg Val
    930                 935                 940

Gly Glu Glu Glu Glu Cys Ser Arg Gln Leu Gln Ser Glu Lys Lys Arg
945                 950                 955                 960

Leu Gln Gln His Ile Gln Glu Leu Glu Ser His Leu Glu Ala Glu Glu
                965                 970                 975

Gly Ala Arg Gln Lys Leu Gln Leu Glu Lys Val Thr Thr Glu Ala Lys
            980                 985                 990

Met Lys Lys Phe Glu Glu Asp Leu Leu Leu Leu Glu Asp Gln Asn Ser
        995                 1000                1005

Lys Leu Ser Lys Glu Arg Arg Leu Leu Glu Glu Arg Leu Ala Glu Phe
   1010                 1015                1020

Ser Ser Gln Ala Ala Glu Glu Glu Glu Lys Val Lys Ser Leu Asn Lys
1025                1030                1035                1040

Leu Arg Leu Lys Tyr Glu Ala Thr Ile Ser Asp Met Glu Asp Arg Leu
                1045                1050                1055

Lys Lys Glu Glu Lys Gly Arg Gln Glu Leu Glu Lys Leu Lys Arg Arg
            1060                1065                1070

Leu Asp Gly Glu Ser Ser Glu Leu Gln Glu Gln Met Val Glu Gln Lys
        1075                1080                1085
```

-continued

```
Gln Arg Ala Glu Glu Leu Leu Ala Gln Leu Gly Arg Lys Glu Asp Glu
    1090                1095                1100

Leu Gln Ala Ala Leu Leu Arg Ala Glu Glu Glu Gly Gly Ala Arg Ala
1105                1110                1115                1120

Gln Leu Leu Lys Ser Leu Arg Glu Ala Gln Ala Gly Leu Ala Glu Ala
                1125                1130                1135

Gln Glu Asp Leu Glu Ala Glu Arg Val Ala Arg Ala Lys Ala Glu Lys
            1140                1145                1150

Gln Arg Arg Asp Leu Gly Glu Glu Leu Glu Ala Leu Arg Gly Glu Leu
        1155                1160                1165

Glu Asp Thr Leu Asp Ser Thr Asn Ala Gln Gln Glu Leu Arg Ser Lys
    1170                1175                1180

Arg Glu Gln Glu Val Thr Glu Leu Lys Lys Ala Leu Glu Glu Glu Ser
1185                1190                1195                1200

Arg Ala His Glu Val Ser Met Gln Glu Leu Arg Gln Arg His Ser Gln
                1205                1210                1215

Ala Leu Val Glu Met Ala Glu Gln Leu Glu Gln Ala Arg Arg Gly Lys
            1220                1225                1230

Gly Val Trp Glu Lys Thr Arg Leu Ser Leu Glu Ala Glu Val Ser Glu
        1235                1240                1245

Leu Lys Ala Glu Leu Ser Ser Leu Gln Thr Ser Arg Gln Glu Gly Glu
    1250                1255                1260

Gln Lys Arg Arg Arg Leu Glu Ser Gln Leu Gln Glu Val Gln Gly Arg
1265                1270                1275                1280

Ser Ser Asp Ser Glu Arg Ala Arg Ser Glu Ala Ala Glu Lys Leu Gln
                1285                1290                1295

Arg Ala Gln Ala Glu Leu Glu Ser Val Ser Thr Ala Leu Ser Glu Ala
            1300                1305                1310

Glu Ser Lys Ala Ile Arg Leu Gly Lys Glu Leu Ser Ser Ala Glu Ser
        1315                1320                1325

Gln Leu His Asp Thr Gln Glu Leu Leu Gln Glu Glu Thr Arg Ala Lys
    1330                1335                1340

Leu Ala Leu Gly Ser Arg Val Arg Ala Leu Glu Ala Glu Ala Ala Gly
1345                1350                1355                1360

Leu Arg Glu Gln Met Glu Glu Glu Val Val Ala Arg Glu Arg Ala Gly
                1365                1370                1375

Arg Glu Leu Gln Ser Thr Gln Ala Gln Leu Ser Glu Trp Arg Arg Arg
            1380                1385                1390

Gln Glu Glu Glu Ala Ala Val Leu Glu Ala Gly Glu Glu Ala Arg Arg
        1395                1400                1405

Arg Ala Ala Arg Glu Ala Glu Thr Leu Thr Gln Arg Leu Ala Glu Lys
    1410                1415                1420

Thr Glu Ala Val Glu Arg Leu Glu Arg Ala Arg Arg Arg Leu Gln Gln
1425                1430                1435                1440

Glu Leu Asp Asp Ala Thr Val Asp Leu Gly Gln Gln Lys Gln Leu Leu
                1445                1450                1455

Ser Thr Leu Glu Lys Lys Gln Arg Lys Phe Asp Gln Leu Leu Ala Glu
            1460                1465                1470

Glu Lys Ala Ala Val Leu Arg Ala Val Glu Asp Arg Glu Arg Ile Glu
        1475                1480                1485

Ala Glu Gly Arg Glu Arg Glu Ala Arg Ala Leu Ser Leu Thr Arg Ala
    1490                1495                1500
```

-continued

Leu Glu Glu Glu Gln Glu Ala Arg Glu Glu Leu Glu Arg Gln Asn Arg
1505 1510 1515 1520

Ala Leu Arg Ala Glu Leu Glu Ala Leu Leu Ser Ser Lys Asp Asp Val
1525 1530 1535

Gly Lys Asn Val His Glu Leu Glu Arg Ala Arg Lys Ala Ala Glu Gln
1540 1545 1550

Ala Ala Ser Asp Leu Arg Thr Gln Val Thr Glu Leu Glu Asp Glu Leu
1555 1560 1565

Thr Ala Ala Glu Asp Ala Lys Leu Arg Leu Glu Val Thr Val Gln Ala
1570 1575 1580

Leu Lys Ala Gln His Glu Arg Asp Leu Gln Gly Arg Asp Asp Ala Gly
1585 1590 1595 1600

Glu Glu Arg Arg Arg Gln Leu Ala Lys Gln Leu Arg Asp Ala Glu Val
1605 1610 1615

Glu Arg Asp Glu Glu Arg Lys Gln Arg Ala Leu Ala Met Ala Ala Arg
1620 1625 1630

Lys Lys Leu Glu Leu Glu Leu Glu Glu Leu Lys Ala Gln Thr Ser Ala
1635 1640 1645

Ala Gly Gln Gly Lys Glu Glu Ala Val Lys Gln Leu Lys Lys Met Gln
1650 1655 1660

Val Gln Met Lys Glu Leu Trp Arg Glu Val Glu Glu Thr Arg Ser Ser
1665 1670 1675 1680

Arg Asp Glu Met Phe Thr Leu Ser Arg Glu Asn Glu Lys Lys Leu Lys
1685 1690 1695

Gly Leu Glu Ala Glu Val Leu Arg Leu Gln Glu Glu Leu Ala Ala Ser
1700 1705 1710

Asp Arg Ala Arg Arg Gln Ala Gln Gln Asp Arg Asp Glu Met Ala Glu
1715 1720 1725

Glu Val Ala Ser Gly Asn Leu Ser Lys Ala Ala Thr Leu Glu Glu Lys
1730 1735 1740

Arg Gln Leu Glu Gly Arg Leu Ser Gln Leu Glu Glu Glu Leu Glu Glu
1745 1750 1755 1760

Glu Gln Asn Asn Ser Glu Leu Leu Lys Asp His Tyr Arg Lys Leu Val
1765 1770 1775

Leu Gln Val Glu Ser Leu Thr Thr Glu Leu Ser Ala Glu Arg Ser Phe
1780 1785 1790

Ser Ala Lys Ala Glu Ser Gly Arg Gln Gln Leu Glu Arg Gln Ile Gln
1795 1800 1805

Glu Leu Arg Ala Arg Leu Gly Glu Glu Asp Ala Gly Ala Arg Ala Arg
1810 1815 1820

Gln Lys Met Leu Ile Ala Ala Leu Glu Ser Lys Leu Ala Gln Ala Glu
1825 1830 1835 1840

Glu Gln Leu Glu Gln Glu Ser Arg Glu Arg Ile Leu Ser Gly Lys Leu
1845 1850 1855

Val Arg Arg Ala Glu Lys Arg Leu Lys Glu Val Val Leu Gln Val Asp
1860 1865 1870

Glu Glu Arg Arg Val Ala Asp Gln Val Arg Asp Gln Leu Glu Lys Ser
1875 1880 1885

Asn Leu Arg Leu Lys Gln Leu Lys Arg Gln Leu Glu Glu Ala Glu Glu
1890 1895 1900

Glu Ala Ser Arg Ala Gln Ala Gly Arg Arg Arg Leu Gln Arg Glu Leu
1905 1910 1915 1920

Glu Asp Val Thr Glu Ser Ala Glu Ser Met Asn Arg Glu Val Thr Thr

-continued

```
                1925                1930                1935

Leu Arg Asn Arg Leu Arg Arg Gly Pro Leu Thr Phe Thr Thr Arg Thr
            1940                1945                1950

Val Arg Gln Val Phe Arg Leu Glu Glu Gly Val Ala Ser Asp Glu Glu
        1955                1960                1965

Glu Ala Glu Gly Ala Glu Pro Gly Ser Ala Pro Gly Gln Glu Pro Glu
    1970                1975                1980

Ala Pro Pro Pro Ala Thr Pro Gln
1985                1990
```

<210> SEQ ID NO 59
<211> LENGTH: 6786
<212> TYPE: DNA
<213> ORGANISM: Homo sapiens

<400> SEQUENCE: 59

```
ctctttctcc ccaggccgaa gcctcgggac ggccctggaa gccgaccatg gcagccgtga     60
ccatgtcggt gcccgggcgg aaggcgcccc ccaggccggg cccagtgccc gaggcggccc    120
agccgttcct gttcacgccc cgcgggccca gcgcgggtgg cgggcctggc tcgggcacct    180
ccccgcaggt ggagtggacg gcccggcgtc tcgtgtgggt gccttcggag cttcacgggt    240
tcgaggcggc ggcgctgcgg gacgaaggcg aggaggaggc ggaggtggag ctggcggaga    300
gcgggaggcg gctgcgactg ccgcgggacc agatccagcg catgaacccg cccaagttca    360
gcaaggccga ggacatggcc gagctgacct gcctcaacga ggcctcggtc ctgcacaacc    420
tccgggagcg gtactactcc ggcctcatct acacgtactc cggccttttc tgtgtggtca    480
tcaacccgta caagcagctt cccatctaca cagaagccat tgtggagatg taccggggca    540
agaagcgcca cgaggtgcca ccccacgtgt acgcagtgac cgaggggccc tatcggagca    600
tgctgcagga tcgtgaggac cagtccattc tctgcactgg agagtctgga gctgggaaga    660
cggaaaacac caagaaggtc atccagtacc tcgcccacgt ggcatcgtct ccaaagggca    720
ggaaggagcc gggtgtcccc ggtgagctgg agcggcagct gcttcaggcc aaccccatcc    780
tagaggcctt tggcaatgcc aagacagtga agaatgacaa ctcctcccga ttcggcaaat    840
tcatccgcat caactttgat gttgccgggt acatcgtggg cgccaacatt gagacctacc    900
tgctggagaa gtcgcgggcc atccgccagg ccaaggacga gtgcagcttc cacatcttct    960
accagctgct gggggggcgct ggagagcagc tcaaagccga cctcctcctc gagccctgct   1020
cccactaccg gttcctgacc aacgggccgt catcctctcc cggccaggag cgggaactct   1080
tccaggagac gctggagtcg ctgcgggtcc tgggattcag ccacgaggaa atcatctcca   1140
tgctgcggat ggtctcagca gttctccagt ttggcaacat tgccttgaag agagaacgga   1200
acaccgatca agccaccatg cctgacaaca cagctgcaca gaagctctgc cgcctcttgg   1260
gactgggggt gacggatttc tcccgagcct tgctcacccc tcgcatcaaa gttggccgag   1320
actatgtgca gaaagcccag actaaggaac aggctgactt cgcgctggag gccctggcca   1380
aggccaccta cgagcgcctc ttccgctggc tggttctgcg cctcaaccgg gccttggacc   1440
gcagcccccg ccaaggcgcc tccttcctgg gcatcctgga catcgcgggc tttgagatct   1500
tccagctgaa ctccttcgag cagctctgca tcaactacac caacgagaag ctgcagcagc   1560
tcttcaacca caccatgttc gtgctggagc aggaggagta ccagcgtgag ggcatcccct   1620
ggaccttcct cgactttggc ctcgacctgc agccctgcat cgacctcatc gagcggccgg   1680
ccaacccccc tggactcctg gccctgctgg atgaggagtg ctggttcccg aaggccacag   1740
```

-continued acaagtcgtt tgtggagaag gtagcccagg agcagggcgg ccaccccaag ttccagcggc 1800
cgaggcacct gcgggatcag gccgacttca gtgttctcca ctacgcgggc aaggtcgact 1860
acaaggccaa cgagtggctg atgaaaaaca tggaccctct gaatgacaac gtcgcagcct 1920
tgctccacca gagcacagac cggctgacgg cagagatctg gaaagacgtg gagggcatcg 1980
tggggctgga acaggtgagc agcctgggcg acggcccacc aggtggccgc ccccgtcggg 2040
gtatgttccg gacagtggga cagctctaca aggagtccct gagccgcctc atggccacac 2100
tcagcaacac caaccccagt tttgtccggt gcattgtccc caaccacgag aagagggccg 2160
ggaagctgga gccacggctg gtgctggacc agcttcgctg caacggggtc ctggagggca 2220
tccgcatctg tcgccagggc ttccccaacc gcatcctctt ccaggagttc cggcagcgat 2280
acgagatcct gacacccaat gccatcccca agggcttcat ggatgggaag caggcctgtg 2340
aaaagatgat ccaggcgctg gaactggacc ccaacctcta ccgcgtggga cagagcaaga 2400
tcttcttccg ggctggggtc ctggcccagc tggaagagga gcgagacctg aaggtcaccg 2460
acatcatcgt ctccttccag gcagctgccc ggggatacct ggctcgcagg gccttccaga 2520
agcgccagca gcagcagagc gccctgaggg tgatgcagcg gaactgcgcg gcctacctca 2580
agctgagaca ctggcagtgg tggcggctgt ttaccaaggt gaagccactg ctgcaggtga 2640
cgcggcagga tgaggtgctg caggcacggg cccaggagct gcagaaagtg caggagctac 2700
agcagcagag cgcccgcgaa gttggggagc tccagggccg agtggcacag ctggaagagg 2760
agcgcgcccg cctggcagag caattgcgag cagaggcaga actgtgtgca gaggccgagg 2820
agacgcgggg gaggctggca gcccgcaagc aggagctgga gctggtggtg tcagagctgg 2880
aggctcgcgt gggcgaggag gaggagtgca gccgtcaaat gcaaaccgag aagaagaggc 2940
tacagcagca catacaggag ctagaggccc accttgaggc tgaggagggt gcgcggcaga 3000
agctgcagct ggagaaggtg acgacagagg caaaaatgaa gaaatttgaa gaggacctgc 3060
tgctcctgga agaccagaat tccaagctga gcaagagcgg aagctgctgg aagatcgtct 3120
ggccgagttc tcatcccagg cagctgagga ggaggagaag gtcaagagcc tcaataagct 3180
acggctcaaa tatgaggcca caatcgcaga catggaggga ccgcctacgg aaggaggaga 3240
agggtcgcca ggagctggag aagctgaagc ggaggctgga tggggagagc tcagagctgc 3300
aggagcagat ggtggagcag caacagcggg cagaggagct gcgggcccag ctgggccgga 3360
aggaggagga gctgcaggct gccctggcca gggcagaaga cgagggtggg gcccgggccc 3420
agctgctgaa atccctgcgg gaggctcaag cagccctggc cgaggcccag gaggacctgg 3480
agtctgagcg tgtggccagg accaaggcgg agaagcagcg ccgggacctg ggcgaggagc 3540
tggaggcgct gcggggcgag ctggaggaca cgctggactc caccaacgca cagcaggagc 3600
tccggtccaa gagggaacag gaggtgacgg agctgaagaa gactctggag gaggagactc 3660
gcatccacga ggcggcagtg caggagctga ggcagcgcca cggccaggcc ctgggggagc 3720
tggcggagca gctggagcag gcccggaggg gcaaaggtgc atgggagaag acccggctgg 3780
ccctggaggc cgaggtgtcc gagctgcggg cagaactgag cagcctgcag actgcacgtc 3840
aggagggtga gcagcggagg cgccgcctgg agttacagct gcaggaggtg cagggccggg 3900
ctggtgatgg ggagagggca cgagcggagg ctgctgagaa gctgcagcga gcccaggctg 3960
aactggagaa tgtgtctggg gcgctgaacg aggctgagtc caaaaccatc cgtcttagca 4020
aggagctgag cagcacagaa gcccagctgc acgatgccca ggagctgctg caggaggaga 4080

-continued

```
ccagggcgaa attggccttg gggtcccggg tgcgagccat ggaggctgag gcagccgggc   4140
tgcgtgagca gctggaggag gaggcagctg ccagggaacg ggcgggccgt gaactgcaga   4200
ctgcccaggc ccagctttcc gagtggcggc ggcgccagga ggaggaggca ggggcactgg   4260
aggcagggga ggaggcacgg cgccgggcag cccgggaggc cgaggccctg acccagcgcc   4320
tggcagaaaa gacagagacc gtggatcggc tggagcgggg ccgccgccgg ctgcagcagg   4380
agctggacga cgccaccatg gacctggagc agcagcggca gcttgtgagc accctggaga   4440
agaagcagcg caagtttgac cagcttctgg cagaggagaa ggcagctgta cttcgggcag   4500
tggaggaacg tgagcgggcc gaggcagagg gccgggagcg tgaggctcgg gccctgtcac   4560
tgacacgggc actggaggag gagcaggagg cacgtgagga gctggagcgg cagaaccggg   4620
ccctgcgggc tgagctggag gcactgctga gcagcaagga tgacgtcggc aagagcgtgc   4680
atgagctgga acgagcctgc cgggtagcag aacaggcagc caatgatctg cgagcacagg   4740
tgacagaact ggaggatgag ctgacagcgg ccgaggatgc caagctgcgt ctggaggtga   4800
ctgtgcaggc tctcaagact cagcatgagc gtgacctgca gggccgtgat gaggctggtg   4860
aagagaggcg gaggcagctg gccaagcagc tgagagatgc agaggtggag cgggatgagg   4920
agcggaagca gcgcactctg gccgtggctg cccgcaagaa gctggaggga gagctggagg   4980
agctgaaggc tcagatggcc tctgccggcc agggcaagga ggaggcggtg aagcagcttc   5040
gcaagatgca ggcccagatg aaggagctat ggcgggaggt ggaggagaca cgcacctccc   5100
gggaggagat cttctcccag aatcgggaaa gtgaaaagcg cctcaagggc ctggaggctg   5160
aggtgctgcg gctgcaggag gaactggccg cctcggaccg tgctcggcgg caggcccagc   5220
aggaccggga tgagatggca gatgaggtgg ccaatggtaa ccttagcaag gcagccattc   5280
tggaggagaa gcgtcagctg gaggggcgcc tggggcagtt ggaggaagag ctggaggagg   5340
agcagagcaa ctcagagctg ctcaatgacc gctaccgcaa gctgctcctg caggtagagt   5400
cactgaccac agagctgtca gctgagcgca gtttctcagc caaggcagag agcgggcggc   5460
agcagctgga acggcagatc caggagctac ggggacgcct gggtgaggag gatgctgggg   5520
cccgtgcccg ccacaagatg accattgctg cccttgagtc taagttggcc caggctgagg   5580
agcagctaga gcaagagacc agagagcgca tcctctctgg aaagctggtg cgcagagctg   5640
agaagcggct taaagaggtg gtgctccagg tggaggagga gcggagggtg gctgaccagc   5700
tccgggacca gctggagaag ggaaaccttc gagtcaagca gctgaagcgg cagctggagg   5760
aggccgagga ggaggcatcc cgggctcagg ctggccgccg gaggctgcag cgtgagctgg   5820
aagatgtcac agagtcggcc gagtccatga accgtgaagt gaccacactg aggaaccggc   5880
ttcgacgcgg cccccctcacc ttcaccaccc gcacggtgcg ccaggtcttc cgactagagg   5940
agggcgtggc atccgacgag gaggcagagg aagcacagcc tgggtctggg ccatccccgg   6000
agcctgaggg gtccccacca gcccaccccc agtgacccta ccctgtcccc agatgcacta   6060
acagatgggg cccagccccc ttcctccctg gaccccacgg gcccctgtcc caggaacccc   6120
gccctctgac ttcttgccct ttggaaatgg tgcagcactc tggcatttat cacccccacc   6180
tgggtcccct gcaacctccc atcaaaggat gacccctaaa cacagaggag cggggcaggc   6240
agggaggcaa ggactggagc taccttgctt gttgggggac tgggtacagt tggcaagctg   6300
tgtttccatc agctccctgt cctcctttct tccctcgtta ttgatctata gacattagga   6360
agggagtgag acggctcctc caccatcctc agccagtgca acccattccc tctgcttctc   6420
tctctctctc tctctctccc tccctctcct tccctaccct ctcaccatct ttcttggcct   6480
```

-continued

```
ctctgagggt ctctctgtgc atctttttag gaatctcgct ctcactctct acgtagccac   6540

tctccttccc ccatttctgc gtccacccct gaactcctga gcgacagaag ccccaggcct   6600

ccaccagcct tgaacccttg caaaggggca ggacaagggg acccctctca ctcctgctgc   6660

tgcccatgct ctgccctccc ttctggttgc tctgagggtt cggagcttcc ctctgggact   6720

aaaggagtgt cctttaccct cccagcctcc aggctctggc agaaataaac tccaacccga   6780

ctggac                                                              6786


<210> SEQ ID NO 60
<211> LENGTH: 1995
<212> TYPE: PRT
<213> ORGANISM: Homo sapiens

<400> SEQUENCE: 60

Met Ala Ala Val Thr Met Ser Val Pro Gly Arg Lys Ala Pro Pro Arg
  1               5                  10                  15

Pro Gly Pro Val Pro Glu Ala Ala Gln Pro Phe Leu Phe Thr Pro Arg
             20                  25                  30

Gly Pro Ser Ala Gly Gly Gly Pro Gly Ser Gly Thr Ser Pro Gln Val
         35                  40                  45

Glu Trp Thr Ala Arg Arg Leu Val Trp Val Pro Ser Glu Leu His Gly
     50                  55                  60

Phe Glu Ala Ala Ala Leu Arg Asp Glu Gly Glu Glu Glu Ala Glu Val
 65                  70                  75                  80

Glu Leu Ala Glu Ser Gly Arg Arg Leu Arg Leu Pro Arg Asp Gln Ile
                 85                  90                  95

Gln Arg Met Asn Pro Pro Lys Phe Ser Lys Ala Glu Asp Met Ala Glu
            100                 105                 110

Leu Thr Cys Leu Asn Glu Ala Ser Val Leu His Asn Leu Arg Glu Arg
        115                 120                 125

Tyr Tyr Ser Gly Leu Ile Tyr Thr Tyr Ser Gly Leu Phe Cys Val Val
    130                 135                 140

Ile Asn Pro Tyr Lys Gln Leu Pro Ile Tyr Thr Glu Ala Ile Val Glu
145                 150                 155                 160

Met Tyr Arg Gly Lys Lys Arg His Glu Val Pro Pro His Val Tyr Ala
                165                 170                 175

Val Thr Glu Gly Ala Tyr Arg Ser Met Leu Gln Asp Arg Glu Asp Gln
            180                 185                 190

Ser Ile Leu Cys Thr Gly Glu Ser Gly Ala Gly Lys Thr Glu Asn Thr
        195                 200                 205

Lys Lys Val Ile Gln Tyr Leu Ala His Val Ala Ser Ser Pro Lys Gly
    210                 215                 220

Arg Lys Glu Pro Gly Val Pro Gly Glu Leu Glu Arg Gln Leu Leu Gln
225                 230                 235                 240

Ala Asn Pro Ile Leu Glu Ala Phe Gly Asn Ala Lys Thr Val Lys Asn
                245                 250                 255

Asp Asn Ser Ser Arg Phe Gly Lys Phe Ile Arg Ile Asn Phe Asp Val
            260                 265                 270

Ala Gly Tyr Ile Val Gly Ala Asn Ile Glu Thr Tyr Leu Leu Glu Lys
        275                 280                 285

Ser Arg Ala Ile Arg Gln Ala Lys Asp Glu Cys Ser Phe His Ile Phe
    290                 295                 300

Tyr Gln Leu Leu Gly Gly Ala Gly Glu Gln Leu Lys Ala Asp Leu Leu
```

-continued

```
305                 310                 315                 320

Leu Glu Pro Cys Ser His Tyr Arg Phe Leu Thr Asn Gly Pro Ser Ser
                325                 330                 335

Ser Pro Gly Gln Glu Arg Glu Leu Phe Gln Glu Thr Leu Glu Ser Leu
            340                 345                 350

Arg Val Leu Gly Phe Ser His Glu Glu Ile Ile Ser Met Leu Arg Met
        355                 360                 365

Val Ser Ala Val Leu Gln Phe Gly Asn Ile Ala Leu Lys Arg Glu Arg
    370                 375                 380

Asn Thr Asp Gln Ala Thr Met Pro Asp Asn Thr Ala Ala Gln Lys Leu
385                 390                 395                 400

Cys Arg Leu Leu Gly Leu Gly Val Thr Asp Phe Ser Arg Ala Leu Leu
                405                 410                 415

Thr Pro Arg Ile Lys Val Gly Arg Asp Tyr Val Gln Lys Ala Gln Thr
            420                 425                 430

Lys Glu Gln Ala Asp Phe Ala Leu Glu Ala Leu Ala Lys Ala Thr Tyr
        435                 440                 445

Glu Arg Leu Phe Arg Trp Leu Val Leu Arg Leu Asn Arg Ala Leu Asp
    450                 455                 460

Arg Ser Pro Arg Gln Gly Ala Ser Phe Leu Gly Ile Leu Asp Ile Ala
465                 470                 475                 480

Gly Phe Glu Ile Phe Gln Leu Asn Ser Phe Glu Gln Leu Cys Ile Asn
                485                 490                 495

Tyr Thr Asn Glu Lys Leu Gln Gln Leu Phe Asn His Thr Met Phe Val
            500                 505                 510

Leu Glu Gln Glu Glu Tyr Gln Arg Glu Gly Ile Pro Trp Thr Phe Leu
        515                 520                 525

Asp Phe Gly Leu Asp Leu Gln Pro Cys Ile Asp Leu Ile Glu Arg Pro
    530                 535                 540

Ala Asn Pro Pro Gly Leu Leu Ala Leu Leu Asp Glu Glu Cys Trp Phe
545                 550                 555                 560

Pro Lys Ala Thr Asp Lys Ser Phe Val Glu Lys Val Ala Gln Glu Gln
                565                 570                 575

Gly Gly His Pro Lys Phe Gln Arg Pro Arg His Leu Arg Asp Gln Ala
            580                 585                 590

Asp Phe Ser Val Leu His Tyr Ala Gly Lys Val Asp Tyr Lys Ala Asn
        595                 600                 605

Glu Trp Leu Met Lys Asn Met Asp Pro Leu Asn Asp Asn Val Ala Ala
    610                 615                 620

Leu Leu His Gln Ser Thr Asp Arg Leu Thr Ala Glu Ile Trp Lys Asp
625                 630                 635                 640

Val Glu Gly Ile Val Gly Leu Glu Gln Val Ser Ser Leu Gly Asp Gly
                645                 650                 655

Pro Pro Gly Gly Arg Pro Arg Arg Gly Met Phe Arg Thr Val Gly Gln
            660                 665                 670

Leu Tyr Lys Glu Ser Leu Ser Arg Leu Met Ala Thr Leu Ser Asn Thr
        675                 680                 685

Asn Pro Ser Phe Val Arg Cys Ile Val Pro Asn His Glu Lys Arg Ala
    690                 695                 700

Gly Lys Leu Glu Pro Arg Leu Val Leu Asp Gln Leu Arg Cys Asn Gly
705                 710                 715                 720

Val Leu Glu Gly Ile Arg Ile Cys Arg Gln Gly Phe Pro Asn Arg Ile
                725                 730                 735
```

-continued

```
Leu Phe Gln Glu Phe Arg Gln Arg Tyr Glu Ile Leu Thr Pro Asn Ala
            740                 745                 750

Ile Pro Lys Gly Phe Met Asp Gly Lys Gln Ala Cys Glu Lys Met Ile
        755                 760                 765

Gln Ala Leu Glu Leu Asp Pro Asn Leu Tyr Arg Val Gly Gln Ser Lys
    770                 775                 780

Ile Phe Phe Arg Ala Gly Val Leu Ala Gln Leu Glu Glu Glu Arg Asp
785                 790                 795                 800

Leu Lys Val Thr Asp Ile Ile Val Ser Phe Gln Ala Ala Ala Arg Gly
            805                 810                 815

Tyr Leu Ala Arg Arg Ala Phe Gln Lys Arg Gln Gln Gln Gln Ser Ala
            820                 825                 830

Leu Arg Val Met Gln Arg Asn Cys Ala Ala Tyr Leu Lys Leu Arg His
        835                 840                 845

Trp Gln Trp Trp Arg Leu Phe Thr Lys Val Lys Pro Leu Leu Gln Val
    850                 855                 860

Thr Arg Gln Asp Glu Val Leu Gln Ala Arg Ala Gln Glu Leu Gln Lys
865                 870                 875                 880

Val Gln Glu Leu Gln Gln Gln Ser Ala Arg Glu Val Gly Glu Leu Gln
            885                 890                 895

Gly Arg Val Ala Gln Leu Glu Glu Glu Arg Ala Arg Leu Ala Glu Gln
            900                 905                 910

Leu Arg Ala Glu Ala Glu Leu Cys Ala Glu Ala Glu Glu Thr Arg Gly
        915                 920                 925

Arg Leu Ala Ala Arg Lys Gln Glu Leu Glu Leu Val Val Ser Glu Leu
    930                 935                 940

Glu Ala Arg Val Gly Glu Glu Glu Glu Cys Ser Arg Gln Met Gln Thr
945                 950                 955                 960

Glu Lys Lys Arg Leu Gln Gln His Ile Gln Glu Leu Glu Ala His Leu
            965                 970                 975

Glu Ala Glu Glu Gly Ala Arg Gln Lys Leu Gln Leu Glu Lys Val Thr
            980                 985                 990

Thr Glu Ala Lys Met Lys Lys Phe Glu Glu Asp Leu Leu Leu Leu Glu
        995                 1000                1005

Asp Gln Asn Ser Lys Leu Ser Lys Ser Gly Ser Cys Trp Lys Ile Val
    1010                1015                1020

Trp Pro Ser Ser His Pro Arg Gln Leu Arg Arg Arg Arg Ser Arg
1025                1030                1035                1040

Ala Ser Ile Ser Tyr Gly Ser Asn Met Arg Pro Gln Ser Gln Thr Trp
            1045                1050                1055

Arg Asp Arg Leu Arg Lys Glu Glu Lys Gly Arg Gln Glu Leu Glu Lys
            1060                1065                1070

Leu Lys Arg Arg Leu Asp Gly Glu Ser Ser Glu Leu Gln Glu Gln Met
        1075                1080                1085

Val Glu Gln Gln Gln Arg Ala Glu Glu Leu Arg Ala Gln Leu Gly Arg
    1090                1095                1100

Lys Glu Glu Glu Leu Gln Ala Ala Leu Ala Arg Ala Glu Asp Glu Gly
1105                1110                1115                1120

Gly Ala Arg Ala Gln Leu Leu Lys Ser Leu Arg Glu Ala Gln Ala Ala
            1125                1130                1135

Leu Ala Glu Ala Gln Glu Asp Leu Glu Ser Glu Arg Val Ala Arg Thr
            1140                1145                1150
```

-continued

```
Lys Ala Glu Lys Gln Arg Arg Asp Leu Gly Glu Glu Leu Glu Ala Leu
        1155                1160                1165

Arg Gly Glu Leu Glu Asp Thr Leu Asp Ser Thr Asn Ala Gln Gln Glu
    1170                1175                1180

Leu Arg Ser Lys Arg Glu Gln Glu Val Thr Glu Leu Lys Lys Thr Leu
1185                1190                1195                1200

Glu Glu Glu Thr Arg Ile His Glu Ala Ala Val Gln Glu Leu Arg Gln
                1205                1210                1215

Arg His Gly Gln Ala Leu Gly Glu Leu Ala Glu Gln Leu Glu Gln Ala
            1220                1225                1230

Arg Arg Gly Lys Gly Ala Trp Glu Lys Thr Arg Leu Ala Leu Glu Ala
        1235                1240                1245

Glu Val Ser Glu Leu Arg Ala Glu Leu Ser Ser Leu Gln Thr Ala Arg
    1250                1255                1260

Gln Glu Gly Glu Gln Arg Arg Arg Arg Leu Glu Leu Gln Leu Gln Glu
1265                1270                1275                1280

Val Gln Gly Arg Ala Gly Asp Gly Glu Arg Ala Arg Ala Glu Ala Ala
                1285                1290                1295

Glu Lys Leu Gln Arg Ala Gln Ala Glu Leu Glu Asn Val Ser Gly Ala
            1300                1305                1310

Leu Asn Glu Ala Glu Ser Lys Thr Ile Arg Leu Ser Lys Glu Leu Ser
        1315                1320                1325

Ser Thr Glu Ala Gln Leu His Asp Ala Gln Glu Leu Leu Gln Glu Glu
    1330                1335                1340

Thr Arg Ala Lys Leu Ala Leu Gly Ser Arg Val Arg Ala Met Glu Ala
1345                1350                1355                1360

Glu Ala Ala Gly Leu Arg Glu Gln Leu Glu Glu Glu Ala Ala Ala Arg
                1365                1370                1375

Glu Arg Ala Gly Arg Glu Leu Gln Thr Ala Gln Ala Gln Leu Ser Glu
            1380                1385                1390

Trp Arg Arg Arg Gln Glu Glu Glu Ala Gly Ala Leu Glu Ala Gly Glu
        1395                1400                1405

Glu Ala Arg Arg Arg Ala Ala Arg Glu Ala Glu Ala Leu Thr Gln Arg
    1410                1415                1420

Leu Ala Glu Lys Thr Glu Thr Val Asp Arg Leu Glu Arg Gly Arg Arg
1425                1430                1435                1440

Arg Leu Gln Gln Glu Leu Asp Asp Ala Thr Met Asp Leu Glu Gln Gln
                1445                1450                1455

Arg Gln Leu Val Ser Thr Leu Glu Lys Lys Gln Arg Lys Phe Asp Gln
            1460                1465                1470

Leu Leu Ala Glu Glu Lys Ala Ala Val Leu Arg Ala Val Glu Glu Arg
        1475                1480                1485

Glu Arg Ala Glu Ala Glu Gly Arg Glu Arg Glu Ala Arg Ala Leu Ser
    1490                1495                1500

Leu Thr Arg Ala Leu Glu Glu Glu Gln Glu Ala Arg Glu Glu Leu Glu
1505                1510                1515                1520

Arg Gln Asn Arg Ala Leu Arg Ala Glu Leu Glu Ala Leu Leu Ser Ser
                1525                1530                1535

Lys Asp Asp Val Gly Lys Ser Val His Glu Leu Glu Arg Ala Cys Arg
            1540                1545                1550

Val Ala Glu Gln Ala Ala Asn Asp Leu Arg Ala Gln Val Thr Glu Leu
        1555                1560                1565

Glu Asp Glu Leu Thr Ala Ala Glu Asp Ala Lys Leu Arg Leu Glu Val
```

-continued

```
    1570                1575                1580

Thr Val Gln Ala Leu Lys Thr Gln His Glu Arg Asp Leu Gln Gly Arg
1585                1590                1595                1600

Asp Glu Ala Gly Glu Glu Arg Arg Arg Gln Leu Ala Lys Gln Leu Arg
                1605                1610                1615

Asp Ala Glu Val Glu Arg Asp Glu Glu Arg Lys Gln Arg Thr Leu Ala
            1620                1625                1630

Val Ala Ala Arg Lys Lys Leu Glu Gly Glu Leu Glu Glu Leu Lys Ala
        1635                1640                1645

Gln Met Ala Ser Ala Gly Gln Gly Lys Glu Glu Ala Val Lys Gln Leu
    1650                1655                1660

Arg Lys Met Gln Ala Gln Met Lys Glu Leu Trp Arg Glu Val Glu Glu
1665                1670                1675                1680

Thr Arg Thr Ser Arg Glu Glu Ile Phe Ser Gln Asn Arg Glu Ser Glu
                1685                1690                1695

Lys Arg Leu Lys Gly Leu Glu Ala Glu Val Leu Arg Leu Gln Glu Glu
            1700                1705                1710

Leu Ala Ala Ser Asp Arg Ala Arg Arg Gln Ala Gln Gln Asp Arg Asp
        1715                1720                1725

Glu Met Ala Asp Glu Val Ala Asn Gly Asn Leu Ser Lys Ala Ala Ile
    1730                1735                1740

Leu Glu Glu Lys Arg Gln Leu Glu Gly Arg Leu Gly Gln Leu Glu Glu
1745                1750                1755                1760

Glu Leu Glu Glu Glu Gln Ser Asn Ser Glu Leu Leu Asn Asp Arg Tyr
                1765                1770                1775

Arg Lys Leu Leu Leu Gln Val Glu Ser Leu Thr Thr Glu Leu Ser Ala
            1780                1785                1790

Glu Arg Ser Phe Ser Ala Lys Ala Glu Ser Gly Arg Gln Gln Leu Glu
        1795                1800                1805

Arg Gln Ile Gln Glu Leu Arg Gly Arg Leu Gly Glu Glu Asp Ala Gly
    1810                1815                1820

Ala Arg Ala Arg His Lys Met Thr Ile Ala Ala Leu Glu Ser Lys Leu
1825                1830                1835                1840

Ala Gln Ala Glu Glu Gln Leu Glu Gln Glu Thr Arg Glu Arg Ile Leu
                1845                1850                1855

Ser Gly Lys Leu Val Arg Arg Ala Glu Lys Arg Leu Lys Glu Val Val
            1860                1865                1870

Leu Gln Val Glu Glu Glu Arg Arg Val Ala Asp Gln Leu Arg Asp Gln
        1875                1880                1885

Leu Glu Lys Gly Asn Leu Arg Val Lys Gln Leu Lys Arg Gln Leu Glu
    1890                1895                1900

Glu Ala Glu Glu Glu Ala Ser Arg Ala Gln Ala Gly Arg Arg Arg Leu
1905                1910                1915                1920

Gln Arg Glu Leu Glu Asp Val Thr Glu Ser Ala Glu Ser Met Asn Arg
                1925                1930                1935

Glu Val Thr Thr Leu Arg Asn Arg Leu Arg Arg Gly Pro Leu Thr Phe
            1940                1945                1950

Thr Thr Arg Thr Val Arg Gln Val Phe Arg Leu Glu Glu Gly Val Ala
        1955                1960                1965

Ser Asp Glu Glu Ala Glu Glu Ala Gln Pro Gly Ser Gly Pro Ser Pro
    1970                1975                1980

Glu Pro Glu Gly Ser Pro Pro Ala His Pro Gln
1985                1990                1995
```

-continued

```
<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Cys Gly Met Pro Tyr Val Arg Ile Pro Thr Ala
  1               5                  10


<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Gly Cys Met Pro Tyr Val Arg Ile Pro Thr Ala
  1               5                  10


<210> SEQ ID NO 63
<211> LENGTH: 11
<212> TYPE: PRT
<213> ORGANISM: Homo sapiens

<400> SEQUENCE: 63

Leu Met Lys Asn Met Asp Pro Leu Asn Asp Ile
  1               5                  10


<210> SEQ ID NO 64
<211> LENGTH: 12
<212> TYPE: PRT
<213> ORGANISM: Homo sapiens

<400> SEQUENCE: 64

Leu Met Lys Asn Met Asp Pro Leu Asn Asp Asn Val
  1               5                  10


<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 65

Gly Gly Gly Gly Ser Gly Gly Gly Gly Ser Gly Gly Gly Gly Ser
  1               5                  10                  15
```